US011369679B2

(12) United States Patent
Wong et al.

(10) Patent No.: US 11,369,679 B2
(45) Date of Patent: *Jun. 28, 2022

(54) MULTIMERIC IL-15-BASED MOLECULES

(71) Applicant: Altor Bioscience, LLC., Culver City, CA (US)

(72) Inventors: Hing C. Wong, Weston, FL (US); Warren Marcus, Miramar, FL (US); Bai Liu, Cooper City, FL (US); Wenxin Xu, Pembroke Pines, FL (US); Robert Newman, Miramar, FL (US); Karen Kage, Miramar, FL (US); Lijing You, Miramar, FL (US); Peter Rhode, Miami, FL (US); Patrick Soon-Shiong, Culver City, CA (US)

(73) Assignee: Altor Bioscience, LLC, Culver City, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 16/752,606

(22) Filed: Jan. 24, 2020

(65) Prior Publication Data
US 2020/0261575 A1 Aug. 20, 2020

Related U.S. Application Data

(63) Continuation of application No. 15/789,985, filed on Oct. 21, 2017, now abandoned.

(60) Provisional application No. 62/513,964, filed on Jun. 1, 2017, provisional application No. 62/411,216, filed on Oct. 21, 2016.

(51) Int. Cl.
A61K 39/395 (2006.01)
C07K 16/28 (2006.01)
C07K 14/54 (2006.01)
A61K 38/20 (2006.01)
A61P 31/18 (2006.01)
A61P 35/00 (2006.01)
A61K 38/00 (2006.01)
C07K 16/10 (2006.01)
C07K 14/715 (2006.01)
C07K 16/36 (2006.01)
A61K 39/00 (2006.01)
A61K 38/17 (2006.01)

(52) U.S. Cl.
CPC ........ A61K 39/3955 (2013.01); A61K 38/005 (2013.01); A61K 38/2086 (2013.01); A61P 31/18 (2018.01); A61P 35/00 (2018.01); C07K 14/5443 (2013.01); C07K 14/7155 (2013.01); C07K 16/1045 (2013.01); C07K 16/2803 (2013.01); C07K 16/2818 (2013.01); C07K 16/2827 (2013.01); C07K 16/36 (2013.01); A61K 38/17 (2013.01); A61K 2039/505 (2013.01); C07K 2317/60 (2013.01); C07K 2317/622 (2013.01); C07K 2319/035 (2013.01); C07K 2319/30 (2013.01); C07K 2319/70 (2013.01)

(58) Field of Classification Search
None
See application file for complete search history.

(56) References Cited

U.S. PATENT DOCUMENTS

| 5,116,964 | A  | 5/1992  | Capon et al. |
| 5,541,087 | A  | 7/1996  | Lo et al. |
| 5,620,939 | A  | 4/1997  | Halasa et al. |
| 6,344,192 | B1 | 2/2002  | Grooten et al. |
| 8,124,084 | B2 | 2/2012  | Lefrancois et al. |
| 8,163,879 | B2 | 4/2012  | Wong et al. |
| 8,492,118 | B2 | 7/2013  | Wong et al. |
| 8,507,222 | B2 | 8/2013  | Wong et al. |
| 8,940,288 | B2 | 1/2015  | Lefrancois et al. |
| 8,940,289 | B2 | 1/2015  | Wong et al. |
| 9,255,141 | B2 | 2/2016  | Wong et al. |
| 9,365,630 | B2 | 6/2016  | Lefrancois et al. |
| 9,428,573 | B2 | 8/2016  | Wong et al. |
| 9,464,127 | B2 | 10/2016 | Wong et al. |
| 9,593,152 | B2 | 3/2017  | Wong et al. |
| 10,047,146 | B2 | 8/2018  | Mouquet et al. |
| 10,150,805 | B2 | 12/2018 | Wong |
| 10,358,478 | B2 | 7/2019  | Wong et al. |
| 10,450,359 | B2 | 10/2019 | Wong et al. |
| 10,537,615 | B2 | 1/2020  | Klu et al. |
| 10,865,230 | B2 | 12/2020 | Liu et al. |
| 10,899,821 | B2 | 1/2021  | Wong et al. |
| 11,046,747 | B2 | 6/2021  | Wong et al. |
| 11,053,299 | B2 | 7/2021  | Soon-Shiong et al. |
| 2003/0144474 | A1 | 7/2003 | Weidanz et al. |
| 2003/0180888 | A1 | 9/2003 | Fraser |
| 2004/0156826 | A1 | 8/2004 | Dangond et al. |

(Continued)

FOREIGN PATENT DOCUMENTS

| AU | 2008/253720 | 1/2014 |
| AU | 2013/273643 | 1/2016 |

(Continued)

OTHER PUBLICATIONS

Official Action for European Patent Application No. 17861811.2, dated Aug. 5, 2021 4 pages.

(Continued)

Primary Examiner — Bridget E Bunner
Assistant Examiner — Fozia M Hamud
(74) Attorney, Agent, or Firm — Sheridan Ross P.C.

(57) ABSTRACT

The invention features multi-specific protein complexes with one domain comprising IL-15 or a functional variant and a binding domain specific to a disease antigen, immune checkpoint or signaling molecule.

16 Claims, 34 Drawing Sheets
Specification includes a Sequence Listing.

(56) References Cited

U.S. PATENT DOCUMENTS

| | | |
|---|---|---|
| 2004/0242025 A1 | 12/2004 | Angerpointner et al. |
| 2004/0253587 A1 | 12/2004 | Grabstein et al. |
| 2006/0263857 A1 | 11/2006 | LeFrancois et al. |
| 2009/0010966 A1 | 1/2009 | Davis et al. |
| 2009/0117618 A1 | 5/2009 | Hermann et al. |
| 2011/0081311 A1 | 4/2011 | Pavlakis et al. |
| 2013/0121960 A1 | 5/2013 | Sadelain et al. |
| 2014/0099254 A1 | 4/2014 | Chang et al. |
| 2014/0134128 A1 | 5/2014 | Wong et al. |
| 2014/0205560 A1 | 7/2014 | Wong et al. |
| 2015/0023938 A1 | 1/2015 | Yee |
| 2015/0152188 A1 | 6/2015 | Morisseau et al. |
| 2015/0183835 A1 | 7/2015 | Carfi et al. |
| 2015/0374790 A1 | 12/2015 | Liu et al. |
| 2017/0088597 A1 | 3/2017 | Wong et al. |
| 2018/0200366 A1 | 7/2018 | Wong et al. |
| 2020/0002425 A1 | 1/2020 | Li et al. |
| 2020/0016239 A1 | 1/2020 | Klu et al. |
| 2020/0140513 A1 | 5/2020 | Wong et al. |
| 2020/0181237 A1 | 6/2020 | Wong et al. |
| 2021/0030844 A1 | 2/2021 | Liu et al. |

FOREIGN PATENT DOCUMENTS

| | | |
|---|---|---|
| AU | 2011/305476 | 12/2016 |
| AU | 2016/326575 | 4/2018 |
| AU | 2017/201056 | 12/2018 |
| AU | 2017345791 A1 | 5/2019 |
| AU | 2015/284248 | 4/2020 |
| BR | 112019007920 A2 | 10/2019 |
| CA | 2811734 | 3/2012 |
| CA | 2953816 | 1/2016 |
| CA | 2999294 | 3/2017 |
| CA | 3 041 310 A1 | 4/2018 |
| CA | 2690825 | 2/2019 |
| CN | 1441675 | 9/2003 |
| CN | 1478098 | 2/2004 |
| CN | 1493687 | 5/2004 |
| CN | 1760209 | 4/2006 |
| CN | 1780856 | 5/2006 |
| CN | 1942481 | 4/2007 |
| CN | 101360827 | 2/2009 |
| CN | 101484472 | 7/2009 |
| CN | 101743249 A | 6/2010 |
| CN | 104672325 | 6/2015 |
| CN | 105017429 | 11/2015 |
| CN | 106659775 | 5/2017 |
| CN | 101743249 B | 8/2017 |
| CN | 103370339 | 12/2017 |
| CN | 104109200 | 3/2018 |
| CN | 107880136 | 4/2018 |
| CN | 108463239 | 8/2018 |
| CN | 108948177 | 12/2018 |
| CN | 110799528 A | 2/2020 |
| EP | 0971728 | 1/2000 |
| EP | 1777294 | 4/2007 |
| EP | 1934353 | 6/2008 |
| EP | 2388266 A2 | 11/2011 |
| EP | 2537933 | 12/2012 |
| EP | 2388266 B1 | 4/2014 |
| EP | 2160401 | 9/2014 |
| EP | 2619229 | 4/2016 |
| EP | 3160498 | 5/2017 |
| EP | 2769984 | 8/2017 |
| EP | 2918607 | 11/2017 |
| EP | 3305805 | 4/2018 |
| EP | 3327040 | 5/2018 |
| EP | 3352779 | 8/2018 |
| EP | 3 529 263 A1 | 8/2019 |
| EP | 3673915 | 7/2020 |
| IN | 201917020025 A | 8/2019 |
| JP | H06-87898 | 3/1994 |
| JP | H09-512165 | 12/1997 |
| JP | H11-500908 | 1/1999 |
| JP | 2001-502521 | 2/2001 |
| JP | 2008-545397 | 12/2008 |
| JP | 2009-512433 | 3/2009 |
| JP | 2010-527919 | 8/2010 |
| JP | 6251570 | 9/2011 |
| JP | 2013-541335 | 11/2013 |
| JP | 5501222 | 3/2014 |
| JP | 2014-524737 | 9/2014 |
| JP | 5841623 | 11/2015 |
| JP | 6152156 | 6/2017 |
| JP | 2017-521410 | 8/2017 |
| JP | 2018-046831 | 3/2018 |
| JP | 6408039 | 9/2018 |
| JP | 2018-174697 | 11/2018 |
| JP | 2018-532729 | 11/2018 |
| JP | 2019-033754 | 3/2019 |
| JP | 2019-533449 A | 11/2019 |
| KR | 10-2007-0000252 | 1/2007 |
| KR | 10-2907-0002052 | 1/2007 |
| KR | 20-2014-0020228 | 2/2014 |
| KR | 10-2017-0047221 | 5/2017 |
| KR | 20180125435 | 11/2018 |
| KR | 2019-0091264 A | 8/2019 |
| KR | 10-2070098 | 1/2020 |
| MX | 2017000116 | 5/2017 |
| MX | 2019004681 A | 10/2019 |
| WO | WO-94/04689 A1 | 3/1994 |
| WO | WO-94/29350 A2 | 12/1994 |
| WO | WO 95/27722 | 10/1995 |
| WO | WO 96/26274 | 8/1996 |
| WO | WO-96/32478 A1 | 10/1996 |
| WO | WO-97/34631 A1 | 9/1997 |
| WO | WO 97/41232 | 11/1997 |
| WO | WO 98/36768 | 8/1998 |
| WO | WO 0187330 | 11/2001 |
| WO | WO 03080672 | 10/2003 |
| WO | WO-2005/046449 A2 | 5/2005 |
| WO | WO 2005/085282 | 9/2005 |
| WO | WO 2006/063974 | 6/2006 |
| WO | WO 2007/001677 | 1/2007 |
| WO | WO 2007/046006 | 4/2007 |
| WO | 2008/143794 A1 | 11/2008 |
| WO | WO 2009/002562 | 12/2008 |
| WO | WO 2009/117117 | 9/2009 |
| WO | WO 2012/040323 | 3/2012 |
| WO | WO 2012/175222 | 12/2012 |
| WO | WO 2013/076183 | 5/2013 |
| WO | WO 2013/163427 | 10/2013 |
| WO | WO 2014/028776 | 2/2014 |
| WO | WO 2014/066527 | 5/2014 |
| WO | 2015/109124 A2 | 7/2015 |
| WO | WO 2016/004060 | 1/2016 |
| WO | WO 2016/154003 | 9/2016 |
| WO | WO-2017/053649 A1 | 3/2017 |
| WO | WO 2017/205726 | 11/2017 |
| WO | WO-2018/075989 A1 | 4/2018 |

OTHER PUBLICATIONS

Official Action for Canadian Patent Application No. 3041310, dated Mar. 31, 2020 4 pages.
U.S. Appl. No. 17/385,714, filed Jul. 26, 2021, Wong et al.
Official Action (with English translation) for Korean Patent Application No. 10-2021-7015704, dated Aug. 27, 2021 14 pages.
Official Action for U.S. Appl. No. 15/789,985, dated Mar. 13, 2019 9 pages, Restriction Requirement.
Official Action for U.S. Appl. No. 15/789,985, dated Oct. 1, 2019 13 pages.
Notice of Allowance for U.S. Appl. No. 17/163,239, dated Feb. 20, 2020 9 pages.
Notice of Allowance for U.S. Appl. No. 17/163,239, dated Sep. 15, 2021, 8 pages.
Official Action (English translation) for Japanese Patent Application No. 2019-521081, dated Sep. 27, 2021 13 pages.
U.S. Appl. No. 16/659,311, filed Oct. 21, 2019, Wong et al.
U.S. Appl. No. 17/163,239, filed Jan. 29, 2021, Wong et al.
Gene Characterization Kits (1988), Strategene Catalog, 2 pages.

(56) References Cited

OTHER PUBLICATIONS

"N-803 Plus BCG Elicits 72% CR in BCG-Unresponsive, High-Grade Non-Muscle Invasive Bladder Cancer" Dec. 2020, Onclive. Accessed Apr. 15, 2021, 15 pages.
Press Release, Feb. 16, 2021, ImmunityBio, Inc.: ASCO Genitourinary Cancer symposium 2021 presentation: Phase 11/111 clinical results of IL-15RaFc superagonist N-803 with BCG in BCG-unresponsive non-muscle invasive bladder cancer (NMIBC) carcinoma in situ (CIS) patients. Accessed Apr. 15, 2021, 5 pages.
Alam et al. (Feb. 1999) "Qualitative and Quantitative Differences in T Cell Receptor Binding of Agonist and Antagonist Ligands", Immunity, 10(2):227-237.
Alpdogan et al. (Jan. 2005) "IL-7 and IL-15: Therapeutic Cytokines for Immunodeficiency", Trends in Immunology, 25-26(1):56-64.
Anderson et al. (1995) "Functional Characterization of the Human Interleukin-15 Receptor a Chain and Close Linkage of IL 15RA and IL2RA Genes", The Journal of Biological Chemistry, 270(50):29862-29869.
Anonymous (May 15, 2014) "A Study of Intravesical BCG in Combination With ALT-803 in Patients with Non-Muscle Invasive Bladder Cancer", ClinicalTrials.gov, NTC02138734, 9 Pages.
Arcaro et al. (Nov. 19, 2001) "CD8~ Endows CD8 with Efficient Coreceptor Function by Coupling T Cell Receptor/CD3 to Raft-associated CD8/p56Ick Complexes", Journal of Experimental Medicine, 194(10):1485-1495.
Baeuerle et al. (Feb. 2009) "BiTE: Teaching Antibodies to Engage T-Cells for Cancer Therapy", Current Opinion in Molecular Therapeutics, 11(1):22-30.
Bailey et al. (2013) "New Interleukin-15 Superagonist (IL-15 SA) Significantly Enhances Graft-Versus-Tumor Activity After Allogeneic Hematopoietic Stem Cell Transplantation", Blood, 122(21):05 pages.
Bailey et al. (Jul. 4, 2017) "New Interleukin-15 Superagonist (IL-15SA) Significantly Enhances Graft-versus-tumor Activity", Oncotarget, 8(27):44366-44378.
Bazan et al. (Dec. 2012) "Phage display—A Powerful Technique for Immunotherapy", Human Vaccines & Immunotherapeutics, 8(12):1817-1828.
Beers et al. (1999) "The Merck Manual of Diagnosis and Therapy", 17th Edition, 986-995.
Belmont et al. (Oct. 2006) "Potent Antitumor Activity of a Tumor-specific Soluble TCR/IL-2 Fusion Protein", Journal of Clinical Immunology, 121(1):29-39.
Bergamaschi et al. (Feb. 15, 2008) "Intracellular Interaction of Interleukin-15 with its Receptor Alpha during Production Leads to Mutual Stabilization and Increased Bioactivity", Journal of Biological Chemistry, 28(7):4189-4199.
Bernard et al. (Jun. 4, 2004) "Identification of an Interleukin-15α Receptor-binding Site on Human Interleukin-15", Journal of Biological Chemistry, 279(23):24313-24322.
Bessard et al. (Sep. 2009) "High Antitumor Activity of RLI, An Interleukin-15 (IL-15)-IL-15 Receptor a Fusion Protein, in Metastatic Melanoma and Colorectal Cancer", Molecular Cancer Therapeutics, 8(9):2736-2745.
Bevan (Aug. 1997) "In Thymic Selection, Peptide Diversity Gives and Takes Away", Immunity, 7(2): 175-178.
Bjorkman (Apr. 18, 1997) "MHC Restriction in Three Dimensions: A View of T Cell Receptor/Ligand Interactions", Cell, 89(2):167-170.
Bork, Peer, "Powers and Pitfalls in Sequence Analysis: The 70% Hurdle," Genome Research, vol. 10 (2000):398-400.
Borras et al. (Mar. 19, 2010) "Generic Approach for the Generation of Stable Humanized Single-chain Fv Fragments from Rabbit Monoclonal Antibodies", The Journal of Biological Chemistry, 285(12):9054-9066.
Bouchaud et al., "The Exon-3-Encoded Domain of IL-15Rα Contributes to IL-15 High-Affinity Binding and Is Crucial for the IL-15 Antagonistic Effect of Soluble IL-15Rα", Journal of Molecular Biology, Sep. 26, 2008, vol. 382(1), pp. 1-12.

Bruhns (Apr. 16, 2009) "Specificity and Affinity of Human Fcγ Receptors and their Polymorphic Variants for human IgG Subclasses", Blood, 113(16):3716-3725.
Busch et al. (May 1, 2002) "Stabilization of Soluble, Low-Affinity HLA-DM/HLA-DR1 Complexes by Leucine Zippers", Journal of Immunological Methods, 263(1-2):111-121.
Cany et al. (Jan. 11, 2018) "Decitabine Enhances Targeting of AML Cells by CD34+ Progenitor-Derived NK Cells in NOD/SCID/IL2Rgnull Mice", Blood, 131(2):202-214.
Card et al. (Nov. 11, 2003) "A Soluble Single-Chain T-Cell Receptor IL-2 Fusion Protein Retains MHC-Restricted Peptide Specificity and IL-2 Bioactivity", Cancer Immunology, Immunotherapy, 53(4):345-357.
Chae et al. (1996) "Mutant IL-15 Protein Exerting Antagonistic Effects on IL-15 Triggered Cell Proliferation", Journal of the American Society of Nephrology, 7(9):1654.
Chan et al. (May 2010) "Therapeutic Antibodies for Autoimmunity and Inflammation", Nature Reviews Immunology, 10(5):301-316.
Cheever (Apr. 2008) "Twelve Immunotherapy Drugs That Could Cure Cancers", Immunological Reviews, 222(1):357-368.
Chirifu et al. (Jul. 22, 2007) "Crystal Structure of the IL-15-IL-15Rα Complex, a Cytokine-Receptor Unit Presented in Trans", Nature Immunology, 8:1001-1007.
Chu et al. (Mar. 2016) "Therapeutic Effects of AL T-803, an IL-15 Superagonist, in Combination with Anti-CD20 Chimeric Antigen Receptor Modified Expanded Natural Killer Cells Against Burkitt Lymphoma (BL)", Biology of Blood and Marrow Transplantation, 22(3):1 page.
Cole et al. (Feb. 19, 2008) "T Cell Receptor Engagement of Peptide-Major Histocompatibility Complex Class I Does Not Modify CD8 Binding", Molecular Immunology, 45(9):2700-2709.
Conlon et al. (Jan. 1, 2005) "Redistribution, Hyperproliferation, Activation of Natural Killer Cells and CD8 T Cells, and Cytokine Production During First-In-Human Clinical Trial of Recombinant Human Interleukin-15 in Patients With Cancer", Journal of Clinical Oncology, 33(1):74-82.
Cragg et al. (Apr. 1, 2004) "Antibody Specificity Controls in Vivo Effector Mechanisms of Anti-Cd20 Reagents", Blood, 103(7):2738-274 3.
Cuesta et al. (Apr. 2009) "In Vivo Tumor Targeting and Imaging with Engineered Trivalent Antibody Fragments Containing Collagen-Derived Sequences", Plos One, 4(4):(e5381):9 pages.
Daniels et al. (2000) "Critical Role for Cd8 in T Cell Receptor Binding and Activation by Peptide/Major Histocompatibility Complex Multimers", Journal of Experimental Medicine, 191(2):335-346.
Database UniProt Sequence, retrieved from EBI, Database Accession No. 097687, XP002659759 (1999), 1 page, 1999.
Database UniProt Sequence, retrieved from EBI, Database Accession No. Q6B416, XP002659761, 1 page, 2004.
Database UniProt Sequence, retrieved from EBI, Database Accession No. Q8SPYO, XP002659760, 1 page, 2002.
Davis (1998) "Ligand Recognition by αβ T Cell Receptors", Annual Reviews Immunology, 16:523-544.
Davis et al. (Aug. 4, 1988) "T-cell Antigen Receptor Genes and T-cell Recognition", Nature, 334(6181):395-402.
Deer et al. (2004) "High-Level Expression of Proteins in Mammalian Cells Using Transcription Regulatory Sequences from the Chinese Hamster EF-1α Gene", Cell Culture and Tissue Engineering, 20(3):880-889.
Doerks, Tobias et al., "Protein annotation: detective work for function prediction," TIG, vol. 14, Issue 6(1998):248-250.
Dubois et al. (2008) "Preassociation of IL-15 with IL-15Rα-IgG1-Fc Enhances Its Activity on Proliferation of NK and CD8+/CD44high T Cells and Its Antitumor Action", Journal of Immunology, 180(4):2099-2106.
Dubois et al. (Sep. 17, 1999) "Natural Splicing of Exon 2 of Human Interleukin-15 Receptor α-Chain mRNA Results in a Shortened Form with a Distinct Pattern of Expression", The Journal of Biological Chemistry, 274(38):26978-26984.
Dudley et al. (Sep. 2003) "Adoptive-Cell-Transfer Therapy for the Treatment of Patients with Cancer", Nature Review Cancer, 3:665-695.

(56) References Cited

OTHER PUBLICATIONS

Eisen et al. (1996) "Antigen-Specific T-Cell Receptors and Their Reactions with Complexes Formed by Peptides with Major Histocompatibility Complex Proteins", Advances in Protein Chemistry, 49:1-56.
Epardaud et al. (Apr. 15, 2008) "Interleukin-15/Interleukin-15Rα Complexes Promote Destruction of Established Tumors by Reviving Tumor-Resident CD8+ T Cells", Cancer Research, 68(8):2972-2983.
Fabbi et al. (2016) "Dual Roles of IL-15 in Cancer Biology", Journal of Cytokine Biology, 1(2):103, 7 pages.
Feldmann (May 1, 2002) "Development of Anti-TNF Therapy for Rheumatoid Arthritis", Nature Reviews Immunology 2:364-371.
Felices et al. (Dec. 2016) "CD16-IL 15-CD33 Trispecific Killer Engager (TriKE) Overcomes Cancer-Induced Immune Suppression and Induces Natural Killer Cell-Mediated Control of MDS and AML Via Enhanced Killing Kinetics", Blood, 128(22):4 pages.
Ferrari-Lacraz et al. (Dec. 15, 2006) "CD8+ T Cells Resistant to Costimulatory Blockade Are Controlled by an Antagonist Interleukin-I5/Fc Protein", Transplantation, 82(11):14 pages.
Ferrari-Lacraz et al. (Nov. 1, 2004) "Targeting IL-15 Receptor-Bearing Cells with an Antagonist Mutant IL-15/Fc Protein Prevents Disease Development and Progression in Murine Collagen-Induced Arthritis", The Journal of Immunology, 173(9):5818-5826.
Ferrari-Lacraz et al. (Sep. 15, 2001) "An antagonist IL-15/Fc protein prevents costimulation blockade-resistant rejection", Journal of Immunology, 167(6): 3478-3485.
Gakamsky et al. (Sep. 2005) "CD8 Kinetically Promotes Ligand Binding to the T-Cell Antigen Receptor", Biophysical Journal, 89(3):2121-2133.
Galfre, et al., (1981) "Preparation of Monoclonal Antibodies: Strategies and Procedures", Methods in Enzymology, 73(Pt B):3-46, publication nummary, 2 pages.
Garboczi et al. (Apr. 15, 1989) "HLA-A2-Peptide Complexes: Refolding and Crystallization of Molecules Expressed in *Escherichia coli* and Complexed with Single Antigenic Peptides", PNAS, 89(8):3429-3433.
Garboczi et al. (Nov. 14, 1996) "Pillars Article: Structure of the Complex Between Human T-cell Receptor, Viral Peptide and HLA-A2", Nature, 384:134-141.
Gillies et al. (May 15, 2005) "An Anti-CD20-IL-2 Immunocytokine is Highly Efficacious in A SCIO Mouse Model of Established Human B Lymphoma", Blood, 105(10):3972-3978.
Golay et al. (Nov. 14, 2013) "Glycoengineered CD20 Antibody Obinutuzumab Activates Neutrophils and Mediates Phagocytosis Through CD16B More Efficiently Than Rituximab", Blood, 122(20):3482-3491.
Gomes et al. (May 5, 2013) "IL-15 Analogue (ALT-803) Targeting T Regulatory Cells Causes Tomor Burden Reduction in an Orthotopic Non-Muscle Invasive Bladder Cancer Model," The Journal of Urology, 189(4S):e238-e239.
Gomes-Giacoia et al. (Jun. 4, 2014) "Intravesical ALT-803 and BCG Treatment Reduces Tumor Burden in a Carcinogen Induced Bladder Cancer Rat Model; a Role for Cytokine Production and NK Cell Expansion", PLoS One, e96705, 9(6):11 pages.
Guglielmi et al. (Jul. 15, 2002) "Donor lymphocyte infusion for relapsed chronic myelogenous leuken1 ia: prognostic relevance of the initial cell dose", Blood, 100(2):295-307.
Hara et al. (Nov. 1, 1995) "Implicating a Role for Immune Recognition of Self in Tumor Rejection: Passive Immunization Against the Brown Locus Protein", Journal of Experimental Medicine, 182(5):1609-1614.
Hatzimichael et al. (2010) "Hematopoietic stem cell transplantation", Stem Cells and Cloning: Advances and Applications, 3:105-117.
Hayden-Ledbetter et al. (Apr. 2009) "CD20-Directed Small Modular Immunopharmaceutical, TRU-015, Depletes Normal and Malignant B Cells", Clinical Cancer Research, 15(8):2739-2746.

Hessell et al. (Sep. 6, 2007) "Fc Receptor but Not Complement Binding is Important in Antibody Protection Against HIV", Nature, 449(7158):101-104.
Hezareh et al. (Dec. 2001) "Effector Function Activities of a Panel of Mutants of a Broadly Neutralizing Antibody against Human Immunodeficiency Virus Type 1", Journal of Virology, 75(24):12161-12168.
Huang, J., et al.Intravesical ALT-803 for BCG-unresponsive Bladder Cancer—A Case Report. Urology Case Reports 14 (2017) 15-17.
Hogquist et al. (Jan. 1994) "T Cell Receptor Antagonist Peptides Induce Positive Selection", Cell, 76(1): 17-27.
Holliger et al. (Sep. 2005) "Engineered Antibody Fragments and the Rise of Single Domains", Nature Biotechnology, 23(9):1126-1136.
Hughes et al. (Apr. 2005) "Transfer of a TCR Gene Derived from a Patient with a marked Antitumor Response Conveys Highly Active T-Cell Effector Functions", Human Gene Therapy, 16(4):457-472.
Jakobisiak et al., Interleukin 15 as a promising candidate for tumor immunotherapy. Cytokine & Growth Factor Reviews. 2011; 22:99-108.
Kaspar et al. (May 15, 2007) "The antibody-mediated targeted delivery of interleukin-15 and GM-CSF to the tumor neovasculature inhibits tumor growth and metastasis Cancer Research", American Association for Cancer Research, US 67(10): 4940-4948.
Kern et al. (Sep. 17, 1999) "Expression, Purification, and Functional Analysis of Murine Ectodomain Fragments of CD8αα and CD8αβ Dimers", The Journal of Biological Chemistry, 274:27237-27243.
Khantasup et al. (Dec. 1, 2015) "Design and Generation of Humanized Single-chain Fv Derived from Mouse Hybridoma for Potential Targeting Application", Monoclonal Antibodies in Immunodiagnosis and Immunotherapy, 34(6):404-417.
Kim et al. (2012) "Humanization by CDR Grafting and Specificity-Determining Residue Grafting", Methods in molecular biology, 907:237-245.
Kim, Yon Su et al., "Targeting the IL-15 Receptor with an Antagonist IL-15 Mutant/Fcγ 2a Protein Blocks Delayed-Type Hypersensitivity," The Journal of Immunology, vol. 160(1998):5742-5748.
Klebanoff et al. (Feb. 17, 2004) "IL-15 Enhances the in Vivo Antitumor Activity of Tumor-Reactive CD8+ T Cells", Proceedings of the National Academy of Sciences of the United States of America, 101(7):1969-1974.
Kobayashi et al. (Dec. 15, 1994) "Tyrosinase Related Protein 1 (TRP1) Functions as a DHICA Oxidase in Melanin Biosynthesis", The EMBO Journal, 13(24):5818-5825.
Kostelny et al. (Mar. 1, 1992) "Formation of A Bispecific Antibody by the Use of Leucine Zippers", Journal of Immunology, 148(5):1547-1553.
Kouzarides et al. (Aug. 17, 1989) "Leucine zippers of fos, jun and GCN4 dictate dimerization specificity and hereby control DNA binding", Nature, 340:568-571.
Kouzarides et al. (Dec. 15, 1988) "The role of the leucine zipper in the fos-jun Interaction", Nature, 336:646-651.
Kruif et al. (Mar. 29, 1996) "Leucine Zipper Dimerized Bivalent and Bispecific scFv Antibodies from a Semi-synthetic Antibody Phage Display Library", The Journal of Biological Chemistry, 271:7630-7634.
Kubetzko et al. (Nov. 17, 2006) "PEGylation and Multimerization of the Anti-p185HER-2 Single Chain Fv Fragment 4D5-Effects on Tumor Targeting", The Journal of Biological Chemistry, 281:35186-35201.
Laugel et al. (Aug. 17, 2007) "Different T Cell Receptor Affinity Thresholds and CD8 Coreceptor Dependence 43 Govern Cytotoxic T Lymphocyte Activation and Tetramer Binding Properties", The Journal of Biological Chemistry, 282:23799-23810.
Lawrencia et al. (May 2001) "Transfection of Urothelial Cells using Methyl-β-Cyclodextrin Solubilized Cholesterol and Dotap", Gene Therapy, 8(10):760-768.
Lazar et al. (Mar. 14, 2006) "Engineered Antibody Fc Variants with Enhanced Effector Function", Proceedings of the National Academy of Sciences, 103(11):4005-4010.

(56) References Cited

OTHER PUBLICATIONS

Lazar et al. (Mar. 1988) "Transforming Growth Factor α: Mutation of Aspartic Acid 47 and Leucine 48 Results in Different Biological Activities", Molecular and Cellular Biology, 8(3):1247-1252.
Lin et al. (Aug. 10, 1990) "Expression of T Cell Antigen Receptor Heterodimers in a Lipid-Linked Form", Science, 249(4969) :677-679.
Liu et al. (Dec. 2014) "Evaluation of a Novel CD20-Targeted IL-15 Immunotherapeutic with Potent Activity Against B Cell Lymphoma", Journal for ImmunoTherapy of Cancer, 2(Suppl 3):1 page.
Lu et al. (2009) "Construction and Production of an IgG-like Tetravalent Bispecific Antibody for Enhanced Therapeutic Efficacy", Methods in Molecular Biology, 525:377-404.
Matsumoto et al., Intravesical Interleukin-15 Gene Therapy in an Orthotopic Bladder Cancer Model. Human Gene Therapy. Nov. 2011; 22:1423-1432.
Mclaughlin et al. (2015) "Adoptive T-cell therapies for refractory/relapsed leukemia and lymphoma: current strategies and recent advances", Therapy Advance Hematology, 6(6):295-307.
Mohler et al. (Aug. 1, 1993) "Soluble Tumor Necrosis Factor (TNF) Receptors Are Effective Therapeutic Agents in 3 Lethal Endotoxemia and Function Simultaneously as Both TNF Carriers and TNF Antagonists", The Journal of Immunology, 151(3):1548-1561.
Mortier et al. (Jan. 20, 2006) "Soluble Interleukin-15 Receptor α (IL-15Rα)-sushi as a Selective and Potent Agonist of IL-15 Action through IL-15β/γ", The Journal of Biological Chemistry, 281(3):1612-1619.
Mosquera et al. (April, 1 2005) "In Vitro And In Vivo Characterization Of A Novel Antibody-Like Single-Chain TCR Human IgG1 Fusion Protein", Journal of Immunology, 174(7):4381-4388.
Neveu et al. (Jul. 2006) "Impact of CD8-MHC Class I Interaction in Detection and Sorting Efficiencies of Antigen-7 Specific T Cells Using MHC Class I/peptide Multimers: Contribution of pMHC Valency", International Immunology, 18(7):1139-1145.
Ng et al. (2005) "Liposomal Polyene Antibiotics", Methods in Enzymology, 391 :304-313.
Nogawa et al. (Apr. 2005) "Intravesical Administration of Small Interfering RNA Targeting PLK-1 Successfully Prevents the Growth of Bladder Cancer", Journal of Clinical Investigation, 115(4):978-985.
Nugent et al. (May 15, 2005) "Low Binding Capacity of Murine Tetramers Mutated at Residue 227 Does Not Preclude the Ability to Efficiently Activate CD8+ T Lymphocytes", Immunology Letters, 98(2):208-215.
Orti et al. (2017) "Donor lymphocyte infusions in AML and MOS: Enhancing the graft-versus-leuke1nia effect", Experimental Hematology, 48:1-11.
Ortiz-Sanchez et al. (May 2008) "Antibody-cytokine Fusion Proteins: Applications in Cancer Therapy", Expert Opinion on Biological Therapy, 8(5):609-632.
Otegbeye et al. (Dec. 3, 2015) "The IL-15 Super-Agonist AL T-803 Promotes Superior Activation and Cytotoxicity of Ex Vivo Expanded NK Cells Against AML", Blood, 3090, 126(23):4 Pages.
Penichet et al. (1997) "Antibody-IL-2 Fusion Proteins: A Novel Strategy for Immune Protection", Human Antibodies, 8(3):106-118.
Pettit et al. (Jan. 24, 1997) "Structure-Function Studies of Interleukin 15 Using Site-Specific Mutagenesis, Polyethylene Glycol Conjugation, and Homology Modeling", Journal of Biological Chemistry, 272(4):2312-2318.
Quemener, Agnes et al., "Docking of Human Interleukin-15 to its Specific Receptor alpha Chain: Correlation Between Molecular Modeling and Mutagenesis Experimental Data," Proteins: Structure, Function and Bioinfonrnatics, vol. 65 (2006):623-636.
Rabinowitz et al. (Feb. 20, 1996) "Kinetic Discrimination in T-cell Activation", Proceedings of the National Academy of Sciences of the United States of America, 93(4):1401-1405.
Ramos et al. (Apr. 10, 2015) "Current Approaches in the Treatment of Relapsed and Refractory Acute Myeloid Leukemia", Journal of Clinical Medicine, 4:665-695.

Richards et al. (Aug. 2008) "Optimization of Antibody Binding to FcγRIIa Enhances Macrophage Phagocytosis of Tumor Cells", Molecular Cancer Therapeutics, 7(8):2517-2527.
Rieker et al. (2000) "Molecular Applications of Fusions to Leucine Zippers", Methods in Enzymology, 328:282-296.
Rossi et al. (Oct. 29, 2009) "CD20-Targeted Tetrameric Interferon-α, A Novel and Potent Immunocytokine for the Therapy of B-Cell Lymphomas", Blood, 114(18):3864-3871.
Roychowdhury et al. (Nov. 1, 2004) "Failed 1-15 Adoptive Immunotherapy with Tumor-Specific T Cells: Reversal with Low-Dose Interleukin 15 but not Low-Dose Interleukin 2", Cancer Research, 64(21):8062-8067.
Rubinstein et al. (Jun. 13, 2006) "Converting IL-15 to a Superagonist by Binding to Soluble IL-15Rα", Proceedings of the National Academy of Sciences of the United States of America, 103(24):9166-9171.
Rudikoff et al., "Single amino acid substitution altering antigen-binding specificity," PNAS, Mar. 1982, vol. 79, pp. 1979-1983.
Sauter et al. (Apr. 29, 2013) "Interleukin-15 Administration Increases Graft-Versus-Tumor Activity in Recipients of Haploidentical Hematopoietic SCT", Bone Marrow Transplantation, 48(9):1237-1242.
Savio, Alicia Santos, "IL-15: a relevant cytokine for lymphoid homeostasis and autoimmune diseases," Biotecnologia Aplicada, vol. 23 (2006):87-93.
Schmohl et al. (Jul. 2016) "Enhanced ADCC and NK Cell Activation of an Anticarcinoma Bispecific Antibody by Genetic Insertion of a Modified IL-15 Cross-linker", TriKE Facilitates ADCC and Sustaining of NK Cells, Molecular Therapy, 24(7):1312-1322.
Schott et al. (Dec. 2002) "Mouse MHC Class I Tetramers That Are Unable to Bind to CD8 Reveal the Need for CD8 Engagement in Order to Activate Naive CD8 T Cells", European Journal of Immunology, 32(12):3425-3434.
Shen et al. (Feb. 15, 2006) "Single Variable Domain-IgG Fusion A Novel Recombinant Approach To Fe Domain-Containing Bispecific Antibodies", The Journal of Biological Chemistry, 281:10706-10714.
Skolnick, Jeffrey et al., "From genes to protein structure and function: novel applications of computational approaches in the genomic era," Trends Biotechnol., vol. 18 Issue 1 (2000):34-39.
Sloan et al. (Jun. 29, 1995) "Mediation by HLA-DM of Dissociation of Peptides from HLA-DR", Nature, 375:802-806.
Sprent et al. (Mar. 29, 2000) "T-cell proliferation in vivo and the role of cytokines", Philosophical Transactions of the Royal Society of London, Series B, Biological Sciences, 355(1395):317-322.
Steel, Interleukin-15 and its Receptor Augment Dendritic Cell Vaccination Against the neu Oncogene Through the Induction of Antibodies Partially Independent of CD4-help. Cancer Res. Feb. 1, 2010; 70(3): 1-19.
Stern et al. (Feb. 7, 1992) "The Human Class II MHC Protein HLA-DR1 Assembles as Empty αβ Heterodimers in the Absence of Antigenic Peptide", Cell, 68(3):465-477.
Stoklasek et al. (Nov. 1, 2006) "Combined IL-15/IL-15Rα Immunotherapy Maximizes IL-15 Activity in Vivo", Journal of Immunology, 177(9):6072-6080.
Sukumar (Nov. 4, 2015) "Modulating Immunometabolism of Tumor Specific Mouse and Human Lymphocytes to Enhance T Cell Based Therapy for Cancer", Journal for ImmunoTherapy of Cancer, 02, 2(Suppl 3): 2 pages.
Tai et al. (Sep. 15, 2010) "The Role of HER2 In Cancer Therapy and Targeted Drug Delivery", Journal of Controlled Release, 146(3):264-275.
Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, Feb. 2000, vol. 164, pp. 1432-1441.
Tay et al. (Jul. 26, 2016) "TriKEs and BiKEs Join CARs on the Cancer Immunotherapy Highway", Human Vaccines & Immunotherapeutics, 12(11):2790-2796.
Terawaki et al. (Jul. 2007) "Specific and High-affinity Binding of Tetramerized PD-L 1 Extracellular Domain to PD-1-expressing

(56) References Cited

OTHER PUBLICATIONS

Cells: Possible Application to Enhance T Cell Function", International Immunology, 19(7):881-890.
Theobald et al. (Dec. 19, 1995) "Targeting P53 as a General Tumor Antigen", PNAS, 92(26)11993-11997.
Thomson et al. (Aug. 1985) "Pigmentation-associated Glycoprotein of Human Melanomas and Melanocytes: Definition With a Mouse Monoclonal Antibody", Journal of Investigative Dermatology, 85(2):169-174.
Tietze et al. (Mar. 29, 2012) "Delineation of Antigen-Specific and Antigen-Nonspecific CD8+ Memory T-Cell Responses after Cytokine-Based Cancer Immunotherapy", Blood, 119(13):3073-3083.
Tokuriki, Nobuhiko et al., "Stability effects of mutations and protein evolvabilily," Current Opinion in Structural Biology, vol. 19 (2009):596-604.
Tonegawa (Apr. 14, 1983) "Somatic Generation of Immune Diversity", Bioscience Reports, 8(1):3-26.
Tough et al. (May 15, 2001) "An IFN-γ-Dependent Pathway Controls Stimulation of Memory Phenotype CD8+ T Cell Turnover in Vivo by IL-12, IL-18, and IFN-γ", Journal of Immunology, 166(10):6007-6011.
Traunecker et al. (Jan. 1989) "Solubilizing the T-Cell Receptor-Problems in Solution", Immunology Today, 10(1):29-32.
Trevisani et al. (Jun. 2004) "Ethanol Causes Inflammation in the Airways by a Neurogenic and TRPV1-Dependent Mechanism", Journal of Pharmacology and Experimental Therapeutics, 309(3):1167-1173.
Trevisani et al., (Jun. 2002) "Ethanol Elicits and Potentiates Nociceptor Responses via the Vanilloid Receptor-1", Nature Neuroscience, 5(6):546-551.
Tyagi et al. (Jan. 2004) "Urodynamic and Immunohistochemical Evaluation of Intravesical Capsaicin Delivery using Thermosensitive Hydrogel and Liposomes", The Journal of Urology, 171 (1):483-489.
Valencia et al. (Mar. 15, 2013) "In Vitro Selection of Proteins with Desired Characteristics Using mRNA-dispiay", Methods, 60(1):32 pages.
Valitutti (May 11, 1995) "Serial Triggering of Many T-Cell Receptors by a Few Peptide-MHC Complexes", Nature, 375(6527):148-151.
Van Den Bergh et al. (2015) "Interleukin-15: New Kid on the Block for Antitumor Combination Therapy", Cytokine and Growth Factor Reviews, 26:15-24.
Verbist et al., Functions of IL-15 in Anti-Viral Immunity: Multiplicity and Variety. Cytokine. Sep. 2012; 59(3):467-478.
Villinger et al. (Sep. 3, 2004) "IL-15 is Superior to IL-2 in the Generation of Long-Lived Antigen Specific Memory CD4 And CD8 T Cells in Rhesus Macaques", Vaccine, 22(25-26):3510-3521.
Vincent et al. (Aug. 1, 2013) "Tumor Targeting of the IL-15 Superagonist RU by an anti-GD2 Antibody Strongly Enhances Its Antitumor Potency", International Journal of Cancer, 133(3):757-765.
Vincent et al., (Nov. 2013) "Antitumor Activity of an Immunocytokine Composed of an Anti-GD2 Antibody and the IL-15 Superagonist RLI", Oncolmmunology, e26441, 2(11):3 pages.
Vincent et al. (Oct. 2011) "Development of Two IL 15 Immunocytokines Targeting Either GD2—or CD20-tumoral Bearing Cells", Cytokine, 56(1):1 Page.
Waldmann et al., IL-15 Receptor, 2000, pp. 1521-1528.
Wang et al. (Aug. 15, 2009) "Structural Basis of the CD8αβ/MHC Class I Interaction: Focused Recognition Orients CD8β to a T Cell Proximal Position", The Journal of Immunology, 183(4):2554-2564.
Ward et al. (Nov. 2009) "*E. coli* Expression and Purification of Human and Cynomolgus IL-15", Protein Expression and Purification, 68(1):42-48.
Wei et al. (2001) "The Sushi Domain of Soluble IL-15 Receptor a Is Essential for Binding IL-15 and Inhibiting Inflammatory and Allogenic Responses In Vitro and In Vivo", The Journal of Immunology, 167:277-282.

Weidanz et al. (Dec. 1, 1996) "Display of Functional αβ Single-Chain T-Cell Receptor Molecules on the Surface of Bacteriophage", Journal of Immunological Methods, 221 (1-2):59-76.
Weiner (Sep. 2007) "Building Better Magic Bullets—Improving Unconjugated Monoclonal Antibody Therapy for Cancer", Nature Reviews Cancer, 7:701-706.
Wells (Sep. 18, 1990) "Additivity of Mutational Effects in Proteins", Biochemistry, 29(37):8509-8517.
Wen et al. (2008) "Targeting Activity of a TCR/IL-2 Fusion Protein Against Established Tumors", Cancer Immunology Immunother, 57(12):1781-1794.
Wong et al. (2011) "Interleukin-15:Interleukin-15 Receptor α Scaffold for Creation of Multivalent Targeted Immune Molecules", Protein Engineering, Design & Selection, 24(4):373-383.
Wong et al. (May 1, 2012) "Efficacy and mechanism-of-action of a novel superagonist IL-15:IL-15Rα/Fc fusion complex in murine multiple myeloma syngeneic mouse models (46.44)", The Journal of Immunology, 188(Suppl 1):04 pages.
Wong et al. (Nov. 1, 2013) "The IL-15-based superagonist ALT-803 promotes the antigen-independent conversion of memory CD8+ T cells into innate-like effector cells with antitumor activity", Oncoimmunology, 2(11): e26442—3 pages.
Wooldridge et al. (Jul. 29, 2005) "Interaction between the CD8 Coreceptor and Major Histocompatibility Complex Class I Stabilizes T Cell Receptor-Antigen Complexes at the Cell Surface", The Journal of Biological Chemistry, 280:27491-27501.
Wu, IL-15 Agonists: The Cancer Cure Cytokine. J Mol Genet Med. Feb. 28, 2014; 7(85):1-6.
Xu et al. (May 15, 2013) "Efficacy and Mechanism-of-Action of a Novel Superagonist Interleukin-15: Interieukin-15 Receptor αSu/Fc Fusion Complex in Syngeneic Murine Models of Multiple Myeloma", Therapeutics, Targets and Chemical Biology, 73(10):3075-3085.
Xuan et al. (Apr. 8, 2010) "Targeted Delivery of Interferon-Alpha via Fusion to Anti-CD20 Results in Potent Antitumor Activity against B-Cell Lymphoma", Blood, 115(14):2864-2871.
Yang et al. (Nov.-Dec. 2008) "Clinical-Scale Lentiviral Vector Transduction of PBL for TCR Gene Therapy and Potential for Expression in Less Differentiated Cells", Journal of Immunotherapy, 31 (9):830-839.
Yu et al. (Apr. 17, 2012) "Simultaneous Inhibition of Two Regulatory T-Cell Subsets Enhanced Interleukin-15 Efficacy in a Prostate Tumor Model", Proceedings of the National Academy of Sciences of the United States of America, 109(16):6187-6192.
Zah et al. (Jun. 2016) "T Cells Expressing CD19/CD20 Bispecific Chimeric Antigen Receptors Prevent Antigen Escape by Malignant B Cells", Cancer Immunology Research, 4(6):498-508.
Zhang et al. (May 1998) "Potent and Selective Stimulation of Memory-Phenotype CD8+ T Cells in Vivo by IL-15", Immunity, 8(5):591-599.
Zhang et al. (May 5, 2009) "Interleukin-15 Combined with an Anti-CD40 Antibody Provides Enhanced Therapeutic Efficacy for Murine Models of Colon Cancer", Proceedings of the National Academy of Sciences of the United States of America, 106(18):7513-7518.
Zhao et al. (Nov. 1, 2007) "High-Affinity TCRs Generated by Phage Display Provide CD4+ T Cells with the Ability to Recognize and Kill Tumor Cell Lines", The Journal of Immunology, 179(9):5845-5854.
Zheng et al. (Jan. 15, 2006) "An Antagonist Mutant IL-15/Fc Promotes Transplant Tolerance", Transplantation, 81(1):109-116.
Zhu et al. (Mar. 1, 2006) "Visualization of p53264-272/HLA-A 0201 Complexes Naturally Presented on Tumor Cell Surface by a Multimeric Soluble Single-Chain T Cell Receptor", Journal of Immunology, 176(5):3223-3232.
International Search Report and Written Opinion for PCT International Application No. PCT/US2008/005916, dated Sep. 4, 2008, 6 pages.
International Preliminary Report on Patentability for International (PCT) Patent Application No. PCT/US2008/005918, dated Nov. 17, 2009 5 pages.
International Search Report and Written Opinion for PCT International Application No. PCT/US2011/052545, dated May 2, 2012, 16 pages.

(56) References Cited

OTHER PUBLICATIONS

International Preliminary Report on Patentability for Application No. PCT/US2011/052545, dated Apr. 4, 2013, 12 pages.
International Search Report and Written Opinion received for PCT Patent International Application No. PCT/US2015/038587, dated Oct. 15, 2015, 9 pages.
International Preliminary Report on Patentability received for PCT International Application No. PCT/US2015/038587, dated Jan. 12, 2017, 8 pages.
International Search Report and Written Opinion received for PCT Patent International Application No. PCT/US2017/057757, dated Mar. 1, 2018, 14 pages.
International Preliminary Report on Patentability received for PCT International Application No. PCT/US2017/057757, dated May 2, 2019, 10 pages.
Official Action for Canadian Patent Application No. 3041310, dated Apr. 9, 2021 5 pages.
Official Action (English translation) for India Patent Application No. 201917020025, dated Jun. 17, 2021 7 pages.
Official Action (with English translation) for Korean Patent Application No. 10-2019-7014404, dated Jul. 7, 2021 7 pages.
International Search Report and Written Opinion received for PCT Patent International Application No. PCT/US2016/053230, dated Dec. 30, 2016, 11 pages.
International Preliminary Report on Patentability received for PCT International Application No. PCT/US2016/053230, dated Apr. 5, 2018, 8 pages.
International Preliminary Report on Patentability received for PCT International Application No. PCT/US17/57757, dated May 2, 2019, 10 pages.
International Search Report and Written Opinion received for PCT Patent International Application No. PCT/US17/57757, dated Mar. 1, 2018, 14 pages.
Benton et al. (Apr. 8, 1977) "Screening λgt Recombinant Clones by Hybridization to Single Plaques in Situ", Science, 196(4286):180-182.
Capon et al. (Feb. 9, 1989) "Designing CD4 Immunoadhesins for AIDS Therapy", Nature, 337(6207):525-531.
Chamow et al. (Feb. 1996) "Immunoadhesins: Principles and Applications", Trends Biotechnoloqy, 14:52-60.
Database Genbank (Sep. 21, 1994; retrieved from online on Apr. 1, 2020) "Human Interleukin 15 (IL15) mRNA, Complete cds", Genbank Accession No. U14407.1, 2 pages.
Database Genbank (Dec. 19, 1995; retrieved from online on Apr. 1, 2020) "Human Interleukin-15 Receptor Alpha Chain Precursor (IL15RA) mRNA, Complete cds", Genbank Accession No. U31628.1, 2 pages.
Database Genbank (Sep. 14, 1995; retrieved from online on Apr. 1, 2020) "Mus Musculus Interleukin 15 (IL15) mRNA, Complete cds", Genbank Accession No. U14332.1, 2 pages.
Database Genbank (May 20, 2005; retrieved from online on Apr. 1, 2020) "Mus Musculus Interleukin 15 Receptor, Alpha Chain, mRNA (cDNA clone IMAGE:4457379), Complete cds", Genbank Accession No. BC095982.1, 2 pages.
Davis (1985) "Molecular Genetics of the T Cell-receptor Beta Chain", Annual Review of Immunology, 3:537-560.
Desbois et al. (May 23, 2016) "IL-15 Trans-Signaling with the Superagonist RLI Promotes Effector/Memory CD8+ T Cell Responses and Enhances Antitumor Activity of PD-1 Antagonists", The Journal of Immunology, 97(1):168-178.
Ellison et al. (Jul. 10, 1982) "The Nucleotide Sequence of a Human Immunoglobulin Cγl Gene", Nucleic Acids Research, 10(13):4071-4079.
Fleer (Oct. 1992) "Engineering Yeast for High Level Expression", Current Opinion in Biotechnology, 3(5):486-496.
Frankel et al. (Oct. 2000) "Cell Surface Receptor-Targeted Therapy of Acute Myeloid Leukemia: A Review", Cancer Biotherapy & Radiopharmaceuticals, 15(5):459-476.

Gerber et al. (May/Jun. 2009) "Antibody Drug-Conjugates Targeting the Tumor Vasculature: Current and Future Developments", mAbs, 1(3):247-253.
Graham et al. (Jul. 1977) "Characteristics of a Human Cell Line Transformed by DNA from Human Adenovirus Type 5", Journal of General Virology, 36(1):59-72.
Grunstein et al. (Oct. 1975) "Colony Hybridization: A Method for the Isolation of Cloned DNAs That Contain a Specific Gene", Proceedings of the National Academy of Sciences of the United States of America, 72(10):3961-3965.
Guo et al. (2013) "Therapeutic Cancer Vaccines: Past, Present and Future", Advances in Cancer Research, 119:421-475.
Han et al. (Oct. 22, 2011) "IL-15: IL-15 Receptor Alpha Superagonist Complex: High-Level Co-Expression in Recombinant Mammalian Cells, Purification and Characterization", Cytokine, 56(3):804-810.
Kim et al. (Feb. 18, 2016) "IL-15 Superagonist/IL-15RαSushi-Fc Fusion Complex (IL-15SA/IL-15RαSu—Fc; ALT-803) Markedly Enhances Specific Subpopulations of NK and Memory CD8+ T Cells, and Mediates Potent Anti-Tumor Activity Against Murine Breast and Colon Carcinomas", Oncotarget, 7(13):16130-16145.
Kimmel (1987) "Identification and Characterization of Specific Clones: Strategy for Confirming the Validity of Presumptive Clones", Methods in Enzymology, 152:507-511.
Mathios et al. (Jan. 1, 2016) "Therapeutic Administration of IL-15 Superagonist Complex ALT-803 Leads to Long-term Survival and Durable Antitumor Immune Response in a Murine Glioblastoma Model", International Journal of Cancer, 138(1):187-194.
Morton et al. (Nov. 1, 2016) "Humanized Mouse Xenograft Models: Narrowing the Tumor-Microenvironment Gap", Cancer Research, 76(21):6153-6158.
Moskaug et al. (Sep. 15, 1989) "Translocation of Diphtheria Toxin A-Fragment to the Cytosol. Role of The Site of Interfragment Cleavage", Journal of Biological Chemistry, 264(26):15709-15713.
Novellino et al. (Mar. 2005; e-published on Aug. 7, 2004) "A Listing of Human Tumor Antigens Recognized by T Cells: Mar. 2004 Update", Cancer Immunology, Immunotherapy, 54(3):187-207.
Oleksiewicz et al. (Jun. 13, 2012) "Anti-bacterial Monoclonal Antibodies: Back to the Future?", Archives of Biochemistry and Biophysics, 526(2):124-131.
Olsnes et al. (1982) "Chimeric Toxins", Pharmacology and Therapeutics, 15(3):355-381.
Pardoll (Apr. 2012) "The Blockade of Immune Checkpoints in Cancer Immunotherapy", Nature Reviews Cancer, 12(4):252-264.
Parmiani et al. (2007) "Unique Human Tumor Antigens: Immunobiology and Use in Clinical Trials", The Journal of Immunology, 178(4):1975-1979.
Pastan et al. (Dec. 5, 1986) "Immunotoxins", Cell, 47(5):641-648.
Pastan et al. (1992) "Recombinant Toxins as Novel Therapeutic Agents", Annual Review Biochemistry, 61:331-354.
Sliwkowski et al. (Sep. 13, 2013) "Antibody Therapeutics in Cancer", Science, 341(6151):1192-1198.
Sockolosky et al. (Apr. 18, 2016) "Durable Antitumor Responses to CD47 Blockade Require Adaptive Immune Stimulation", Proceedings of the National Academy of Sciences of the United States of America, May 10, 2016, 113(19): E2646-E2654.
Stewart et al. (Sep. 2015; e-published on May 5, 2015) "Identification and Characterization of MEDI4736, An Antagonistic Anti-PD-L1 Monoclonal Antibody", Cancer Immunology Research, 3(9):1052-1062.
Thaventhiran et al. (2012) "T Cell Co-Inhibitory Receptors: Functions and Signalling Mechanisms", Journal of Clinical & Cellular Immunology, S12:12 pages.
Tomalia (1993) "Starburst/Cascade Dendrimers: Fundamental Building Blocks for a New Nanoscopic Chemistry Set", Aldrichimica Acta, 26(4):89-101.
Urlaub et al. (Jul. 1980) "Isolation of Chinese Hamster Cell Mutants Deficient in Dihydrofolate Reductase Activity", PNAS, 77(7):4216-4220.
Wahl et al. (1987) "Molecular Hybridization of Immobilized Nucleic Acids: Theoretical Concepts and Practical Considerations", Methods in Enzymology, 152:399-407.

(56) References Cited

OTHER PUBLICATIONS

Waldmann (Aug. 2006) "The Biology of Interleukin-2 and Interleukin-15: Implications for Cancer Therapy and Vaccine Design", Nature Reviews Immunology, 6(8):595-601.
Weidle et al. (2013) "The Emerging Role of New Protein Scaffold-based Agents for Treatment of Cancer", Cancer Genomics and Proteomics, 10(4):155-168.
Whitlow et al. (Apr. 1991) "Single-Chain Fv Proteins and their Fusion Proteins", Methods: A Companion to Methods in Enzymology, 2(2):97-105.
Zhu et al. (Sep. 15, 2009) "Novel Human Interleukin-15 Agonists", Journal of Immunology, 183(6):3598-3607.
Felices et al. (Feb. 21, 2017) "IL-15 Super-Agonist (ALT-803) Enhances Natural Killer (NK) Cell Function Against Ovarian Cancer", Gynecologic Oncology, 145(3):19 pages.
Liu et al. (Nov. 11, 2016) "A Novel Fusion of ALT-803 (Interleukin (IL)-15 Superagonist) with an Antibody Demonstrates Antigen-specific Antitumor Responses", The Journal of Biological Chemistry, 291(46):23869-23881.
Official Action (English translation) for Singapore Patent Application No. 11201903306S, dated Feb. 23, 2022 8 pages.
Ozdemir et al. "Mechanisms of Superior Anti-Tumor Cytotoxic Response of Interleukin 15-Induced Lymphokine-Activated Killer Cells," Journal of Immunotherapy, Jan./Feb. 2005, vol. 28(1), pp. 44-52.
Official Action (English translation) for Israel Patent Application No. 266100, dated Jan. 20, 2022 4 pages.
Notice of Allowance for U.S. Appl. No. 17/163,239, dated Feb. 10, 2022, 7 pages.
Disis et al., "Avelumab (MSB0010718C; anti-PD-L1) in patients with recurrent/refractory ovarian cancer from the Javelin Solid Tumor phase lb trial: Safety and clinical activity," Journal of Clinical Oncology, 2016 ASCO Annual Meeting, vol. 34(15 supp.), 4 pages.
Rowles et al., "MPDL3280A (anti-PD-L1) treatment leads to clinical activity in metastatic bladder cancer," Nature, Letter, Nov. 27, 2014, vol. 515(7528), 12 pages.
Official Action (with English machine translation) for Japanese Patent Application No. 2019-521081, dated Apr. 5, 2022 15 pages.
Notice of Allowance (with English translation) for Korean Patent Application No. 10-2021-7015704, dated Mar. 30, 2022 5 pages.
Official Action for Canadian Patent Application No. 3041310, dated Apr. 14, 2022 5 pages.

FIG. 9A
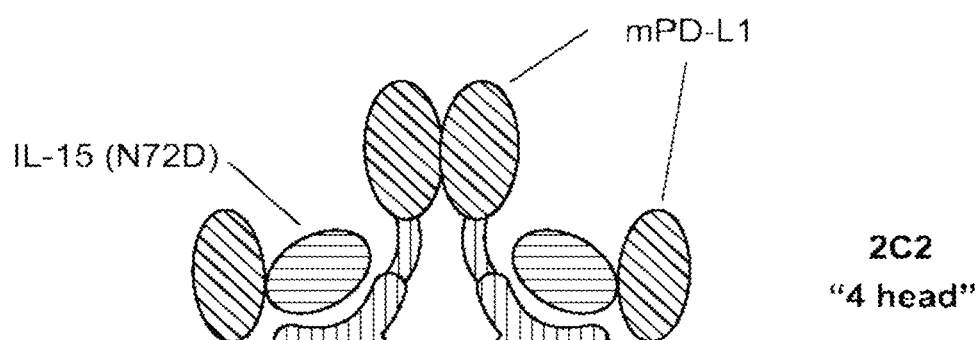
2C2
"4 head"
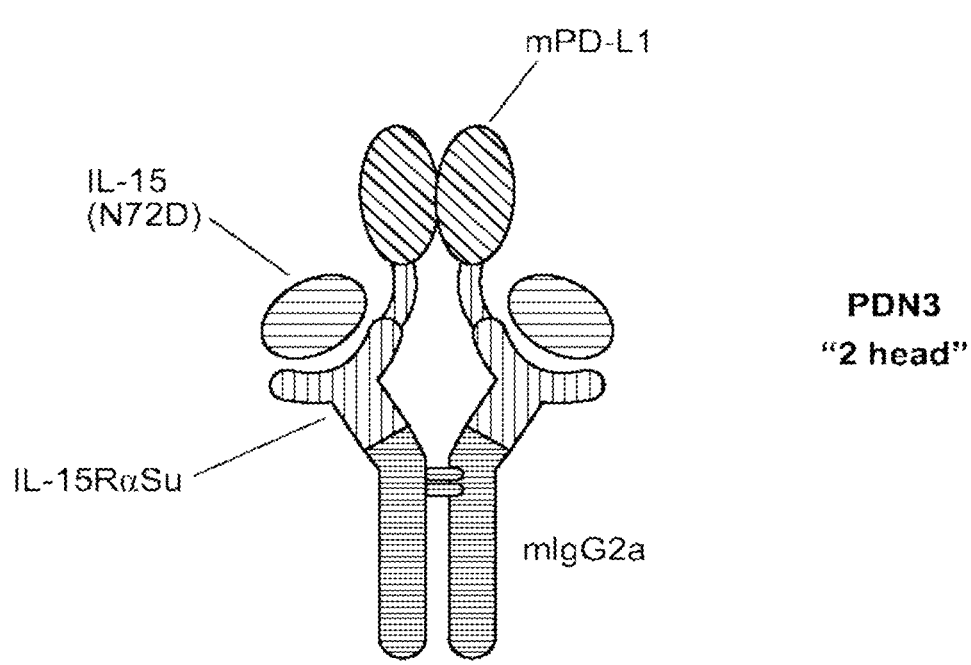
PDN3
"2 head"

PDN3

2C2 note: 10x concentration of 2C2 was used

EC50 value of h2*PDL1/TxM is
~1-1.5 fold higher than ALT-803

EC50 value of h4*PDL1/TxM is
~ 5 fold higher than ALT-803

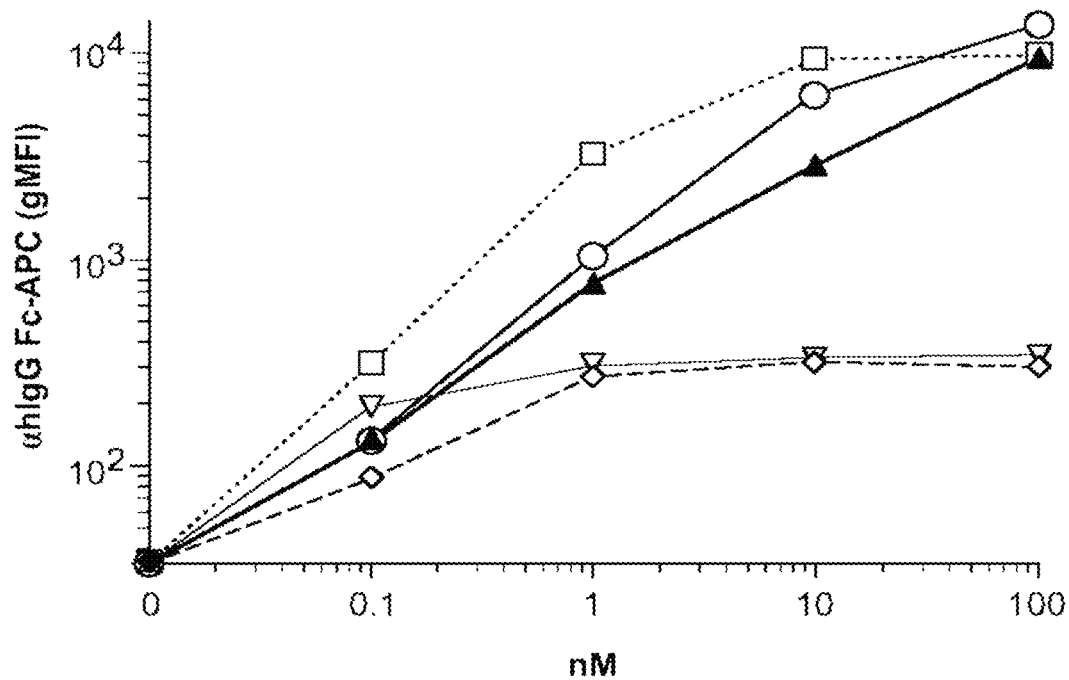

SEQUENCE LISTING

<160> NUMBER OF SEQ ID NOS: 58

<210> SEQ ID NO 1
<211> LENGTH: 1125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgaagtggg tgaccttcat cagcctgctg ttcctgttct ccagcgccta ctccaacatc      60
cagatgaccc agtcccctag ctccgtgtcc gcctccgtgg gagatcgggt gaccatcacc     120
tgtagggcct cccaggacat ctccaggtgg ctggcctggt accagcagaa gcccggcaag     180
gcccccaagc tgctgatcta cgccgcctcc tccctgcagt ccggagtgcc tagcaggttc     240
tccggctccg gatccggcac agacttcgcc ctgaccatct cctccctgca gcccgaggac     300
ttcgccacct actactgcca gcaggccgac tccaggttct ccatcacctt cggccagggc     360
accaggctgg agatcaagag ggggaggtggc ggatccggag gtggaggttc tggtggaggt     420
gggagtgagg tgcagctggt gcagtccgga ggaggactgg tgcagcctgg cggatccctg     480
aggctgtcct gtgccgcttc cggcttcacc ttcagctcct actccatgaa ctgggtgagg     540
caggcccctg gaaagggcct ggagtgggtg tcctacatct ccagctcctc ctccaccatc     600
cagtacgccg actccgtgaa gggcaggttc accatctcca gggacaacgc caagaactcc     660
ctgtacctgc agatgaacag cctgagggac gaggacaccg ccgtgtacta ctgcgccagg     720
ggcgactatt actacggcat ggacgtgtgg ggccagggaa ccaccgtgac cgtgtcctcc     780
aactgggtta acgtaataag tgatttgaaa aaaattgaag atcttattca atctatgcat     840
attgatgcta ctttatatac ggaaagtgat gttcacccca gttgcaaagt aacagcaatg     900
aagtgctttc tcttggagtt acaagttatt tcacttgagt ccggagatgc aagtattcat     960
gatacagtag aaaatctgat catcctagca aacgacagtt tgtcttctaa tgggaatgta    1020
acagaatctg gatgcaaaga atgtgaggaa ctggaggaaa aaaatattaa agaatttttg    1080
cagagttttg tacatattgt ccaaatgttc atcaacactt cttaa                    1125
```

<210> SEQ ID NO 2

<211> LENGTH: 374
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 2

Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ser Val Ser Ala Ser
            20                  25                  30

Val Gly Asp Arg Val Thr Ile Thr Cys Arg Ala Ser Gln Asp Ile Ser
        35                  40                  45

Arg Trp Leu Ala Trp Tyr Gln Gln Lys Pro Gly Lys Ala Pro Lys Leu
    50                  55                  60

Leu Ile Tyr Ala Ala Ser Ser Leu Gln Ser Gly Val Pro Ser Arg Phe
65                  70                  75                  80

Ser Gly Ser Gly Ser Gly Thr Asp Phe Ala Leu Thr Ile Ser Ser Leu
                85                  90                  95

Gln Pro Glu Asp Phe Ala Thr Tyr Tyr Cys Gln Gln Ala Asp Ser Arg
            100                 105                 110

Phe Ser Ile Thr Phe Gly Gln Gly Thr Arg Leu Glu Ile Lys Arg Gly
        115                 120                 125

Gly Gly Gly Ser Gly Gly Gly Ser Gly Gly Gly Gly Ser Glu Val
130                 135                 140

Gln Leu Val Gln Ser Gly Gly Gly Leu Val Gln Pro Gly Gly Ser Leu
145                 150                 155                 160

Arg Leu Ser Cys Ala Ala Ser Gly Phe Thr Phe Ser Ser Tyr Ser Met
                165                 170                 175

Asn Trp Val Arg Gln Ala Pro Gly Lys Gly Leu Glu Trp Val Ser Tyr
            180                 185                 190

Ile Ser Ser Ser Ser Ser Thr Ile Gln Tyr Ala Asp Ser Val Lys Gly
        195                 200                 205

Arg Phe Thr Ile Ser Arg Asp Asn Ala Lys Asn Ser Leu Tyr Leu Gln
    210                 215                 220

Met Asn Ser Leu Arg Asp Glu Asp Thr Ala Val Tyr Tyr Cys Ala Arg
225                 230                 235                 240

Gly Asp Tyr Tyr Tyr Gly Met Asp Val Trp Gly Gln Gly Thr Thr Val
                245                 250                 255

Thr Val Ser Ser Asn Trp Val Asn Val Ile Ser Asp Leu Lys Lys Ile
            260                 265                 270

Glu Asp Leu Ile Gln Ser Met His Ile Asp Ala Thr Leu Tyr Thr Glu
        275                 280                 285

Ser Asp Val His Pro Ser Cys Lys Val Thr Ala Met Lys Cys Phe Leu
    290                 295                 300

Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
                325                 330                 335

Asn Gly Asn Val Thr Glu Ser Gly Cys Lys Glu Cys Glu Glu Leu Glu
            340                 345                 350

Glu Lys Asn Ile Lys Glu Phe Leu Gln Ser Phe Val His Ile Val Gln
        355                 360                 365

Met Phe Ile Asn Thr Ser

<210> SEQ ID NO 3
<211> LENGTH: 1674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgaagtggg tgaccttcat cagcctgctg ttcctgttct ccagcgccta ctccaacatc      60
cagatgaccc agtcccctag ctccgtgtcc gcctccgtgg gagatcgggt gaccatcacc     120
tgtagggcct cccaggacat ctccaggtgg ctggcctggt accagcagaa gcccggcaag     180
gcccccaagc tgctgatcta cgccgcctcc tccctgcagt ccggagtgcc tagcaggttc     240
tccggctccg gatccggcac agacttcgcc ctgaccatct cctccctgca gcccgaggac     300
ttcgccacct actactgcca gcaggccgac tccaggttct ccatcacctt cggccagggc     360
accaggctgg agatcaagag ggaggtggc ggatccggag gtggaggttc tggtggaggt     420
gggagtgagg tgcagctggt gcagtccgga ggaggactgg tgcagcctgg cggatccctg     480
aggctgtcct gtgccgcttc cggcttcacc ttcagctcct actccatgaa ctgggtgagg     540
caggcccctg gaaagggcct ggagtgggtg tcctacatct ccagctcctc ctccaccatc     600
cagtacgccg actccgtgaa gggcaggttc accatctcca gggacaacgc caagaactcc     660
ctgtacctgc agatgaacag cctgagggac gaggacaccg ccgtgtacta ctgcgccagg     720
ggcgactatt actacggcat ggacgtgtgg ggccagggaa ccaccgtgac cgtgtcctcc     780
atcacgtgcc ctccccccat gtccgtggaa cacgcagaca tctgggtcaa gagctacagc     840
ttgtactcca gggagcggta catttgtaac tctggtttca gcgtaaagc cggcacgtcc     900
agcctgacgg agtgcgtgtt gaacaaggcc acgaatgtcg cccactggac acccccagt     960
ctcaaatgca ttagagagcc gaaatcttgt gacaaaactc acacatgccc accgtgccca    1020
gcacctgaac tcctgggggg accgtcagtc ttcctcttcc cccaaaaacc caaggacacc    1080
ctcatgatct cccggacccc tgaggtcaca tgcgtggtgg tggacgtgag ccacgaagac    1140
cctgaggtca agttcaactg gtacgtggac ggcgtggagg tgcataatgc caagacaaag    1200
ccgcgggagg agcagtacaa cagcacgtac cgtgtggtca gcgtcctcac cgtcctgcac    1260
caggactggc tgaatggcaa ggagtacaag tgcaaggtct ccaacaaagc cctcccagcc    1320
cccatcgaga aaaccatctc caaagccaaa gggcagcccc gagaaccaca ggtgtacacc    1380
ctgcccccat cccgggatga gctgaccaag aaccaggtca gcctgacctg cctggtcaaa    1440
ggcttctatc ccagcgacat cgccgtggag tgggagagca atgggcagcc ggagaacaac    1500
tacaagacca cgcctcccgt gctggactcc gacggctcct tcttcctcta cagcaagctc    1560
accgtggaca gagcaggtg gcagcagggg aacgtcttct catgctccgt gatgcatgag    1620
gctctgcaca accactacac gcagaagagc ctctccctgt ctcctggtaa ataa          1674
```

<210> SEQ ID NO 4
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ser Val Ser Ala Ser
            20                  25                  30

Val Gly Asp Arg Val Thr Ile Thr Cys Arg Ala Ser Gln Asp Ile Ser
            35                  40                  45

Arg Trp Leu Ala Trp Tyr Gln Gln Lys Pro Gly Lys Ala Pro Lys Leu
        50                  55                  60

Leu Ile Tyr Ala Ala Ser Ser Leu Gln Ser Gly Val Pro Ser Arg Phe
65                  70                  75                  80

Ser Gly Ser Gly Ser Gly Thr Asp Phe Ala Leu Thr Ile Ser Ser Leu
                85                  90                  95

Gln Pro Glu Asp Phe Ala Thr Tyr Tyr Cys Gln Gln Ala Asp Ser Arg
            100                 105                 110

Phe Ser Ile Thr Phe Gly Gln Gly Thr Arg Leu Glu Ile Lys Arg Gly
        115                 120                 125

Gly Gly Gly Ser Gly Gly Gly Gly Ser Gly Gly Gly Gly Ser Glu Val
130                 135                 140

Gln Leu Val Gln Ser Gly Gly Gly Leu Val Gln Pro Gly Gly Ser Leu
145                 150                 155                 160

Arg Leu Ser Cys Ala Ala Ser Gly Phe Thr Phe Ser Ser Tyr Ser Met
            165                 170                 175

Asn Trp Val Arg Gln Ala Pro Gly Lys Gly Leu Glu Trp Val Ser Tyr
        180                 185                 190

Ile Ser Ser Ser Ser Ser Thr Ile Gln Tyr Ala Asp Ser Val Lys Gly
            195                 200                 205

Arg Phe Thr Ile Ser Arg Asp Asn Ala Lys Asn Ser Leu Tyr Leu Gln
        210                 215                 220

Met Asn Ser Leu Arg Asp Glu Asp Thr Ala Val Tyr Tyr Cys Ala Arg
225                 230                 235                 240

Gly Asp Tyr Tyr Tyr Gly Met Asp Val Trp Gly Gln Gly Thr Thr Val
            245                 250                 255

Thr Val Ser Ser Ile Thr Cys Pro Pro Pro Met Ser Val Glu His Ala
        260                 265                 270

Asp Ile Trp Val Lys Ser Tyr Ser Leu Tyr Ser Arg Glu Arg Tyr Ile
        275                 280                 285

Cys Asn Ser Gly Phe Lys Arg Lys Ala Gly Thr Ser Ser Leu Thr Glu
    290                 295                 300

Cys Val Leu Asn Lys Ala Thr Asn Val Ala His Trp Thr Thr Pro Ser
305                 310                 315                 320

Leu Lys Cys Ile Arg Glu Pro Lys Ser Cys Asp Lys Thr His Thr Cys
            325                 330                 335

Pro Pro Cys Pro Ala Pro Glu Leu Leu Gly Gly Pro Ser Val Phe Leu
        340                 345                 350

Phe Pro Pro Lys Pro Lys Asp Thr Leu Met Ile Ser Arg Thr Pro Glu
        355                 360                 365

Val Thr Cys Val Val Val Asp Val Ser His Glu Asp Pro Glu Val Lys
        370                 375                 380

Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
            405                 410                 415
```

Thr Val Leu His Gln Asp Trp Leu Asn Gly Lys Glu Tyr Lys Cys Lys
            420                 425                 430

Val Ser Asn Lys Ala Leu Pro Ala Pro Ile Glu Lys Thr Ile Ser Lys
        435                 440                 445

Ala Lys Gly Gln Pro Arg Glu Pro Gln Val Tyr Thr Leu Pro Pro Ser
    450                 455                 460

Arg Asp Glu Leu Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
    530                 535                 540

His Tyr Thr Gln Lys Ser Leu Ser Leu Ser Pro Gly Lys
545                 550                 555

<210> SEQ ID NO 5
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaagtggg tgaccttcat cagcctgctg ttcctgttct ccagcgccta ctcccagtcc      60
gctctgaccc agcctgcttc cgtgtccggc tcccctggac agtccatcac catctcctgt     120
accggcacct cctccgatgt gggcggctac aactacgtgt cctggtacca gcagcacccc     180
ggcaaagccc ccaagctgat gatctatgac gtgtccaacc ggcccctccgg cgtgtccaac     240 aggttctccg gctccaagtc cggcaacacc gcctccctga caatctccgg cctgcaggcc     300
gaggatgagg ctgactacta ctgctcctcc tacacctcct cctccaccag ggtgttcggc     360
accggcacca aggtgaccgt gctgggaggt ggcggatccg aggtggagg ttctggtgga     420 ggtgggagtg aggtgcagct gctggagtcc ggaggcggac tggtgcagcc tggaggatcc     480
ctgaggctgt cctgcgctgc ctccggcttc accttctcct cctacatcat gatgtgggtg     540
aggcaggctc ctggcaaggg cctggagtgg gtgtcctcca tctacccctc ggcggcatc     600 accttctacg ccgataccgt gaagggcagg ttcaccatct cccgggacaa ctccaagaac     660
accctgtacc tgcagatgaa ctccctgagg gctgaggaca ccgccgtgta ctactgcgcc     720
aggatcaagc tgggcaccgt gaccacagtg gactactggg gacagggcac cctggtgacc     780
gtgtcctcca actgggttaa cgtaataagt gatttgaaaa aaattgaaga tcttattcaa     840
tctatgcata ttgatgctac tttatatacg gaaagtgatg ttcaccccag ttgcaaagta     900
acagcaatga agtgctttct cttggagtta caagttattt cacttgagtc cggagatgca     960
agtattcatg atacagtaga aaatctgatc atcctagcaa cgacagttt gtcttctaat    1020 gggaatgtaa cagaatctgg atgcaaagaa tgtgaggaac tggaggaaaa aaatattaaa    1080 gaattttgc agagttttgt acatattgtc caaatgttca tcaacacttc ttaa          1134

<210> SEQ ID NO 6
<211> LENGTH: 377

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Lys Trp Val Thr Phe Ile Ser Leu Leu Phe Leu Phe Ser Ser Ala
1               5                   10                  15

Tyr Ser Gln Ser Ala Leu Thr Gln Pro Ala Ser Val Ser Gly Ser Pro
            20                  25                  30

Gly Gln Ser Ile Thr Ile Ser Cys Thr Gly Thr Ser Ser Asp Val Gly
        35                  40                  45

Gly Tyr Asn Tyr Val Ser Trp Tyr Gln Gln His Pro Gly Lys Ala Pro
    50                  55                  60

Lys Leu Met Ile Tyr Asp Val Ser Asn Arg Pro Ser Gly Val Ser Asn
65                  70                  75                  80

Arg Phe Ser Gly Ser Lys Ser Gly Asn Thr Ala Ser Leu Thr Ile Ser
                85                  90                  95

Gly Leu Gln Ala Glu Asp Glu Ala Asp Tyr Tyr Cys Ser Ser Tyr Thr
            100                 105                 110

Ser Ser Ser Thr Arg Val Phe Gly Thr Gly Thr Lys Val Thr Val Leu
        115                 120                 125

Gly Gly Gly Gly Ser Gly Gly Gly Ser Gly Gly Gly Gly Ser Glu
130                 135                 140

Val Gln Leu Leu Glu Ser Gly Gly Leu Val Gln Pro Gly Gly Ser
145                 150                 155                 160

Leu Arg Leu Ser Cys Ala Ala Ser Gly Phe Thr Phe Ser Ser Tyr Ile
                165                 170                 175

Met Met Trp Val Arg Gln Ala Pro Gly Lys Gly Leu Glu Trp Val Ser
            180                 185                 190

Ser Ile Tyr Pro Ser Gly Gly Ile Thr Phe Tyr Ala Asp Thr Val Lys
        195                 200                 205

Gly Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Arg Ile Lys Leu Gly Thr Val Thr Thr Val Asp Tyr Trp Gly Gln Gly
                245                 250                 255

Thr Leu Val Thr Val Ser Ser Asn Trp Val Asn Val Ile Ser Asp Leu
            260                 265                 270

Lys Lys Ile Glu Asp Leu Ile Gln Ser Met His Ile Asp Ala Thr Leu
        275                 280                 285

Tyr Thr Glu Ser Asp Val His Pro Ser Cys Lys Val Thr Ala Met Lys
    290                 295                 300

Cys Phe Leu Leu Glu Leu Gln Val Ile Ser Leu Glu Ser Gly Asp Ala
305                 310                 315                 320

Ser Ile His Asp Thr Val Glu Asn Leu Ile Ile Leu Ala Asn Asp Ser
                325                 330                 335

Leu Ser Ser Asn Gly Asn Val Thr Glu Ser Gly Cys Lys Glu Cys Glu
            340                 345                 350

Glu Leu Glu Glu Lys Asn Ile Lys Glu Phe Leu Gln Ser Phe Val His
        355                 360                 365

Ile Val Gln Met Phe Ile Asn Thr Ser
    370                 375
```

<210> SEQ ID NO 7
<211> LENGTH: 1683
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 7

```
atgaagtggg tgaccttcat cagcctgctg ttcctgttct ccagcgccta ctcccagtcc      60
gctctgaccc agcctgcttc cgtgtccggc tcccctggac agtccatcac catctcctgt     120
accggcacct cctccgatgt gggcggctac aactacgtgt cctggtacca gcagcacccc     180
ggcaaagccc ccaagctgat gatctatgac gtgtccaacc ggccctccgg cgtgtccaac     240
aggttctccg gctccaagtc cggcaacacc gcctccctga caatctccgg cctgcaggcc     300
gaggatgagg ctgactacta ctgctcctcc tacacctcct cctccaccag ggtgttcggc     360
accggcacca aggtgaccgt gctgggaggt ggcggatccg aggtggaggt ttctggtgga     420
ggtgggagtg aggtgcagct gctggagtcc ggaggcggac tggtgcagcc tggaggatcc     480
ctgaggctgt cctgcgctgc ctccggcttc accttctcct cctacatcat gatgtgggtg     540
aggcaggctc ctggcaaggg cctggagtgg gtgtcctcca tctacccctc cggcggcatc     600
accttctacg ccgataccgt gaagggcagg ttcaccatct cccggacaa ctccaagaac     660
accctgtacc tgcagatgaa ctccctgagg gctgaggaca ccgccgtgta ctactgcgcc     720
aggatcaagc tgggcaccgt gaccacagtg gactactggg gacagggcac cctggtgacc     780
gtgtcctcca tcacgtgccc tccccccatg tccgtggaac acgcagacat ctgggtcaag     840
agctacagct gtactccag ggagcggtac atttgtaact ctggtttcaa gctaaagcc     900
ggcacgtcca gcctgacgga gtgcgtgttg aacaaggcca cgaatgtcgc ccactggaca     960
acccccagtc tcaaatgcat tagagagccg aaatcttgtg acaaaactca cacatgccca    1020
ccgtgcccag cacctgaact cctgggggga ccgtcagtct tcctcttccc cccaaaaccc    1080
aaggacaccc tcatgatctc ccggacccct gaggtcacat gcgtggtggt ggacgtgagc    1140
cacgaagacc ctgaggtcaa gttcaactgg tacgtggacg gcgtggaggt gcataatgcc    1200
aagacaaagc cgcgggagga gcagtacaac agcacgtacc gtgtggtcag cgtcctcacc    1260
gtcctgcacc aggactggct gaatggcaag gagtacaagt gcaaggtctc caacaaagcc    1320
ctcccagccc ccatcgagaa aaccatctcc aaagccaaag gcagccccg agaaccacag    1380
gtgtacaccc tgcccccatc ccgggatgag ctgaccaaga accaggtcag cctgacctgc    1440
ctggtcaaag gcttctatcc cagcgacatc gccgtggagt gggagagcaa tgggcagccg    1500
gagaacaact acaagaccac gcctcccgtg ctggactccg acggctcctt cttcctctac    1560
agcaagctca ccgtggacaa gagcaggtgg cagcagggga acgtcttctc atgctccgtg    1620
atgcatgagg ctctgcacaa ccactacacg cagaagagcc tctccctgtc tcctggtaaa    1680
taa                                                                  1683
```

<210> SEQ ID NO 8
<211> LENGTH: 560
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

```
Met Lys Trp Val Thr Phe Ile Ser Leu Leu Phe Leu Phe Ser Ser Ala
1               5                   10                  15

Tyr Ser Gln Ser Ala Leu Thr Gln Pro Ala Ser Val Ser Gly Ser Pro
            20                  25                  30

Gly Gln Ser Ile Thr Ile Ser Cys Thr Gly Thr Ser Ser Asp Val Gly
        35                  40                  45

Gly Tyr Asn Tyr Val Ser Trp Tyr Gln Gln His Pro Gly Lys Ala Pro
    50                  55                  60

Lys Leu Met Ile Tyr Asp Val Ser Asn Arg Pro Ser Gly Val Ser Asn
65                  70                  75                  80

Arg Phe Ser Gly Ser Lys Ser Gly Asn Thr Ala Ser Leu Thr Ile Ser
                85                  90                  95

Gly Leu Gln Ala Glu Asp Glu Ala Asp Tyr Tyr Cys Ser Ser Tyr Thr
            100                 105                 110

Ser Ser Ser Thr Arg Val Phe Gly Thr Gly Thr Lys Val Thr Val Leu
        115                 120                 125

Gly Gly Gly Gly Ser Gly Gly Gly Ser Gly Gly Gly Gly Ser Glu
    130                 135                 140

Val Gln Leu Leu Glu Ser Gly Gly Gly Leu Val Gln Pro Gly Gly Ser
145                 150                 155                 160

Leu Arg Leu Ser Cys Ala Ala Ser Gly Phe Thr Phe Ser Ser Tyr Ile
                165                 170                 175

Met Met Trp Val Arg Gln Ala Pro Gly Lys Gly Leu Glu Trp Val Ser
            180                 185                 190

Ser Ile Tyr Pro Ser Gly Gly Ile Thr Phe Tyr Ala Asp Thr Val Lys
        195                 200                 205

Gly Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Arg Ile Lys Leu Gly Thr Val Thr Thr Val Asp Tyr Trp Gly Gln Gly
                245                 250                 255

Thr Leu Val Thr Val Ser Ser Ile Thr Cys Pro Pro Pro Met Ser Val
            260                 265                 270

Glu His Ala Asp Ile Trp Val Lys Ser Tyr Ser Leu Tyr Ser Arg Glu
        275                 280                 285

Arg Tyr Ile Cys Asn Ser Gly Phe Lys Arg Lys Ala Gly Thr Ser Ser
    290                 295                 300

Leu Thr Glu Cys Val Leu Asn Lys Ala Thr Asn Val Ala His Trp Thr
305                 310                 315                 320

Thr Pro Ser Leu Lys Cys Ile Arg Glu Pro Lys Ser Cys Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415
```

```
Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Ser Arg Asp Glu Leu Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560
```

```
<210> SEQ ID NO 9
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgacatgga ctctactatt ccttgccttc cttcatcact taacagggtc atgtgcccag      60
tttgtgctta ctcagccaaa ctctgtgtct acgaatctcg gaagcacagt caagctgtct    120
tgcaaccgca gcactggtaa cattggaaac aattatgtga actggtacca gcagcatgaa    180
ggaagatctc ccaccactct gatttattgg gatgatagga gaccagatgg agttcctgac    240
aggttctctg gctccattga cagatcttcc aactcagccc tcctgacaat caataatgtg    300
cagactgagg atgaaactga ctacttctgt cagtcttaca gtagtggtat gtatattttc    360
ggcggtggaa ccaagctcac tgtcctagga ggtggcggat ccggaggtgg aggttctggt    420
ggaggtggga gtgaggttca gctgcagcag tctggggctg agctggtgaa gcctggggct    480
tcagtaaagt tgtcctgcaa aacttctggt tacaccttca gcaattacta tatgagttgg    540
ttgaagcaga tgcctggaca gaatattgag tggatcggaa acatttatgg tggaaatggt    600
ggtgctggct ataatcagaa gttcaagggc aaggccacac tgacagtgga caaatcttcc    660
agcacagcgt acatggatct cagcagcctg acatctgagg cctctgcagt ctattttgt    720 gcaagggtcg gacttcccgg ccttttgat tactggggcc agggagtcat ggtcacagtc    780
tcctcaaact gggtgaatgt aataagtgat ttgaaaaaaa ttgaagatct tattcaatct    840
atgcatattg atgctacttt atatacggaa agtgatgttc accccagttg caaagtaaca    900
gcaatgaagt gctttctctt ggagttacaa gttatttcac ttgagtccgg agatgcaagt    960
attcatgata cagtagaaaa tctgatcatc ctagcaaacg acagtttgtc ttctaatggg   1020
aatgtaacag aatctggatg caaagaatgt gaggaactgg aggaaaaaaa tattaaagaa   1080
tttttgcaga gttttgtaca tattgtccaa atgttcatca acacttctta a            1131
```

```
<210> SEQ ID NO 10
```

<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Thr Trp Thr Leu Leu Phe Leu Ala Phe Leu His His Leu Thr Gly
1               5                   10                  15

Ser Cys Ala Gln Phe Val Leu Thr Gln Pro Asn Ser Val Ser Thr Asn
            20                  25                  30

Leu Gly Ser Thr Val Lys Leu Ser Cys Asn Arg Ser Thr Gly Asn Ile
        35                  40                  45

Gly Asn Asn Tyr Val Asn Trp Tyr Gln Gln His Glu Gly Arg Ser Pro
    50                  55                  60

Thr Thr Leu Ile Tyr Trp Asp Asp Arg Arg Pro Asp Gly Val Pro Asp
65                  70                  75                  80

Arg Phe Ser Gly Ser Ile Asp Arg Ser Ser Asn Ser Ala Leu Leu Thr
                85                  90                  95

Ile Asn Asn Val Gln Thr Glu Asp Glu Thr Asp Tyr Phe Cys Gln Ser
            100                 105                 110

Tyr Ser Ser Gly Met Tyr Ile Phe Gly Gly Gly Thr Lys Leu Thr Val
        115                 120                 125

Leu Gly Gly Gly Gly Ser Gly Gly Gly Ser Gly Gly Gly Ser
    130                 135                 140

Glu Val Gln Leu Gln Gln Ser Gly Ala Glu Leu Val Lys Pro Gly Ala
145                 150                 155                 160

Ser Val Lys Leu Ser Cys Lys Thr Ser Gly Tyr Thr Phe Ser Asn Tyr
                165                 170                 175

Tyr Met Ser Trp Leu Lys Gln Met Pro Gly Gln Asn Ile Glu Trp Ile
            180                 185                 190

Gly Asn Ile Tyr Gly Gly Asn Gly Gly Ala Gly Tyr Asn Gln Lys Phe
        195                 200                 205

Lys Gly Lys Ala Thr Leu Thr Val Asp Lys Ser Ser Ser Thr Ala Tyr
    210                 215                 220

Met Asp Leu Ser Ser Leu Thr Ser Glu Ala Ser Ala Val Tyr Phe Cys
225                 230                 235                 240

Ala Arg Val Gly Leu Pro Gly Leu Phe Asp Tyr Trp Gly Gln Gly Val
                245                 250                 255

Met Val Thr Val Ser Ser Asn Trp Val Asn Val Ile Ser Asp Leu Lys
            260                 265                 270

Lys Ile Glu Asp Leu Ile Gln Ser Met His Ile Asp Ala Thr Leu Tyr
        275                 280                 285

Thr Glu Ser Asp Val His Pro Ser Cys Lys Val Thr Ala Met Lys Cys
    290                 295                 300

Phe Leu Leu Glu Leu Gln Val Ile Ser Leu Glu Ser Gly Asp Ala Ser
305                 310                 315                 320

Ile His Asp Thr Val Glu Asn Leu Ile Ile Leu Ala Asn Asp Ser Leu
                325                 330                 335

Ser Ser Asn Gly Asn Val Thr Glu Ser Gly Cys Lys Glu Cys Glu Glu
            340                 345                 350

Leu Glu Glu Lys Asn Ile Lys Glu Phe Leu Gln Ser Phe Val His Ile
        355                 360                 365

Val Gln Met Phe Ile Asn Thr Ser
```

<210> SEQ ID NO 11
<211> LENGTH: 1683
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
atgacatgga ctctactatt ccttgccttc cttcatcact taacagggtc atgtgcccag      60
tttgtgctta ctcagccaaa ctctgtgtct acgaatctcg aagcacagt caagctgtct     120
tgcaaccgca gcactggtaa cattggaaac aattatgtga actggtacca gcagcatgaa    180
ggaagatctc ccaccactct gatttattgg gatgatagga gaccagatgg agttcctgac    240
aggttctctg gctccattga cagatcttcc aactcagccc tcctgacaat caataatgtg    300
cagactgagg atgaaactga ctacttctgt cagtcttaca gtagtggtat gtatattttc    360
ggcggtggaa ccaagctcac tgtcctagga ggtggcggat ccggaggtgg aggttctggt    420
ggaggtggga gtgaggttca gctgcagcag tctggggctg agctggtgaa gcctggggct    480
tcagtaaagt tgtcctgcaa acttctggt tacaccttca gcaattacta tatgagttgg    540
ttgaagcaga tgcctggaca gaatattgag tggatcggaa acatttatgg tggaaatggt    600
ggtgctggct ataatcagaa gttcaagggc aaggccacac tgacagtgga caaatcttcc    660
agcacagcgt acatggatct cagcagcctg acatctgagg cctctgcagt ctatttttgt    720
gcaagggtcg gacttcccgg ccttttttgat tactggggcc agggagtcat ggtcacagtc    780
tcctcaatca cgtgccctcc ccccatgtcc gtggaacacg cagacatctg ggtcaagagc    840
tacagcttgt actccaggga gcggtacatt tgtaactctg gtttcaagcg taaagccggc    900
acgtccagcc tgacggagtg cgtgttgaac aaggccacga atgtcgccca ctggacaacc    960
cccagtctca aatgcattag agaaccaaga gggcccacaa tcaagccctg tcctccatgc   1020
aaatgcccag cacctaacct cttgggtgga ccatccgtct tcatcttccc tccaaagatc   1080
aaggatgtac tcatgatctc cctgagcccc atagtcacat gtgtggtggt ggatgtgagc   1140
gaggatgacc cagatgtcca gatcagctgg tttgtgaaca acgtggaagt acacacagct   1200
cagacacaaa cccatagaga ggattacaac agtactctcc gggtggtcag tgccctcccc   1260
atccagcacc aggactggat gagtggcaag gagttcaaat gcaaggtcaa caacaaagac   1320
ctcccagcgc ccatcgagag aaccatctca aaacccaaag gtcagtaag agctccacag   1380
gtatatgtct tgcctccacc agaagaagag atgactaaga acaggtcac tctgacctgc   1440
atggtcacag acttcatgcc tgaagacatt tacgtggagt ggaccaacaa cgggaaaaca   1500
gagctaaact acaagaacac tgaaccagtc ctggactctg atggttctta cttcatgtac   1560
agcaagctga gagtggaaaaa gaagaactgg gtggaaagaa atagctactc ctgttcagtg   1620
gtccacgagg gtctgcacaa tcaccacacg actaagagct ctcccggac tccaggtaaa   1680
taa                                                                  1683
```

<210> SEQ ID NO 12
<211> LENGTH: 560
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 12

Met Thr Trp Thr Leu Leu Phe Leu Ala Phe Leu His His Leu Thr Gly
1               5                   10                  15

Ser Cys Ala Gln Phe Val Leu Thr Gln Pro Asn Ser Val Ser Thr Asn
            20                  25                  30

Leu Gly Ser Thr Val Lys Leu Ser Cys Asn Arg Ser Thr Gly Asn Ile
        35                  40                  45

Gly Asn Asn Tyr Val Asn Trp Tyr Gln Gln His Glu Gly Arg Ser Pro
    50                  55                  60

Thr Thr Leu Ile Tyr Trp Asp Asp Arg Arg Pro Asp Gly Val Pro Asp
65                  70                  75                  80

Arg Phe Ser Gly Ser Ile Asp Arg Ser Ser Asn Ser Ala Leu Leu Thr
                85                  90                  95

Ile Asn Asn Val Gln Thr Glu Asp Glu Thr Asp Tyr Phe Cys Gln Ser
            100                 105                 110

Tyr Ser Ser Gly Met Tyr Ile Phe Gly Gly Gly Thr Lys Leu Thr Val
        115                 120                 125

Leu Gly Gly Gly Ser Gly Gly Gly Ser Gly Gly Gly Gly Ser
130                 135                 140

Glu Val Gln Leu Gln Gln Ser Gly Ala Glu Leu Val Lys Pro Gly Ala
145                 150                 155                 160

Ser Val Lys Leu Ser Cys Lys Thr Ser Gly Tyr Thr Phe Ser Asn Tyr
                165                 170                 175

Tyr Met Ser Trp Leu Lys Gln Met Pro Gly Gln Asn Ile Glu Trp Ile
            180                 185                 190

Gly Asn Ile Tyr Gly Gly Asn Gly Gly Ala Gly Tyr Asn Gln Lys Phe
        195                 200                 205

Lys Gly Lys Ala Thr Leu Thr Val Asp Lys Ser Ser Thr Ala Tyr
210                 215                 220

Met Asp Leu Ser Ser Leu Thr Ser Glu Ala Ser Ala Val Tyr Phe Cys
225                 230                 235                 240

Ala Arg Val Gly Leu Pro Gly Leu Phe Asp Tyr Trp Gly Gln Gly Val
                245                 250                 255

Met Val Thr Val Ser Ser Ile Thr Cys Pro Pro Met Ser Val Glu
            260                 265                 270

His Ala Asp Ile Trp Val Lys Ser Tyr Ser Leu Tyr Ser Arg Glu Arg
            275                 280                 285

Tyr Ile Cys Asn Ser Gly Phe Lys Arg Lys Ala Gly Thr Ser Ser Leu
            290                 295                 300

Thr Glu Cys Val Leu Asn Lys Ala Thr Asn Val Ala His Trp Thr Thr
305                 310                 315                 320

Pro Ser Leu Lys Cys Ile Arg Glu Pro Arg Gly Pro Thr Ile Lys Pro
                325                 330                 335

Cys Pro Pro Cys Lys Cys Pro Ala Pro Asn Leu Leu Gly Gly Pro Ser
            340                 345                 350

Val Phe Ile Phe Pro Pro Lys Ile Lys Asp Val Leu Met Ile Ser Leu
        355                 360                 365

Ser Pro Ile Val Thr Cys Val Val Asp Val Ser Glu Asp Asp Pro
            370                 375                 380

Asp Val Gln Ile Ser Trp Phe Val Asn Asn Val Glu Val His Thr Ala
385                 390                 395                 400

Gln Thr Gln Thr His Arg Glu Asp Tyr Asn Ser Thr Leu Arg Val Val
```

```
                    405                 410                 415
Ser Ala Leu Pro Ile Gln His Gln Asp Trp Met Ser Gly Lys Glu Phe
                420                 425                 430

Lys Cys Lys Val Asn Asn Lys Asp Leu Pro Ala Pro Ile Glu Arg Thr
            435                 440                 445

Ile Ser Lys Pro Lys Gly Ser Val Arg Ala Pro Gln Val Tyr Val Leu
        450                 455                 460

Pro Pro Pro Glu Glu Glu Met Thr Lys Lys Gln Val Thr Leu Thr Cys
465                 470                 475                 480

Met Val Thr Asp Phe Met Pro Glu Asp Ile Tyr Val Glu Trp Thr Asn
                485                 490                 495

Asn Gly Lys Thr Glu Leu Asn Tyr Lys Asn Thr Glu Pro Val Leu Asp
            500                 505                 510

Ser Asp Gly Ser Tyr Phe Met Tyr Ser Lys Leu Arg Val Glu Lys Lys
        515                 520                 525

Asn Trp Val Glu Arg Asn Ser Tyr Ser Cys Ser Val Val His Glu Gly
    530                 535                 540

Leu His Asn His His Thr Thr Lys Ser Phe Ser Arg Thr Pro Gly Lys
545                 550                 555                 560

<210> SEQ ID NO 13
<211> LENGTH: 1692
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgaagtggg tgacctttat ctccctgctg ttcctgtttt cctccgccta cagcatcgtg      60
atgacccagt cccctagctc cctgagcgct agcgtgggag accgggtgac catcacctgt     120
cgggcctccc agagcatttc cagctacctg aactggtacc agcagaagcc cggcaaggcc     180
cctaagctgc tgatttacgc tgccagcagc ctgcagtccg gagtgcctcc caggtttagc     240
ggctccggat ccggcaccga gttcaccctg accatctcct ccctgcagcc cgaggacttc     300
gccacctact actgtcagca ggccaacagc tttccccccca cctttggcca aggaaccaag     360
gtggacatca gaggaccgt ggccggaggc ggaggctccg gcggcggcgg ctccggcggc     420
ggcggctccc tggtgcagtc cggcgctgaa gtgaagaagc tggcgcctc cgtgaaggtg     480 tcctgcgagg cctccggcta caccttcacc aactactaca tccactggct gaggcaggct     540
cctggacagg gcctggagtg gatgggcatc atcaacccct ccggaggctc caccacctac     600
gcccagaagt tccagggcag gatcaccatg acaagggaca cctccaccaa caccctgtac     660
atggaactgt cctccctccg gtccgaggac accgccatct actactgcgc caggagggat     720
tgcaggggcc ctagctgcta cttcgcttac tggggccagg gaaccaccgt gaccgtgtcc     780
tccgcctcca ccaagggcat cacgtgcccT ccccccatgt ccgtggaaca cgcagacatc     840
tgggtcaaga gctacagctt gtactccagg gagcggtaca tttgtaactc tggtttcaag     900
cgtaaagccg gcacgtccag cctgacggag tgcgtgttga caaggccac gaatgtcgcc     960 cactggacaa cccccagtct caaatgcatt agagagccga atcttgtga caaaactcac    1020 acatgcccac cgtgcccagc acctgaactc ctggggggac cgtcagtctt cctcttcccc    1080
ccaaaaccca aggacaccct catgatctcc cggacccctg aggtcacatg cgtggtggtg    1140
gacgtgagcc acgaagaccc tgaggtcaag ttcaactggt acgtggacgg cgtggaggtg    1200
```

```
cataatgcca agacaaagcc gcgggaggag cagtacaaca gcacgtaccg tgtggtcagc   1260
gtcctcaccg tcctgcacca ggactggctg aatggcaagg agtacaagtg caaggtctcc   1320
aacaaagccc tcccagcccc catcgagaaa accatctcca aagccaaagg gcagccccga   1380
gaaccacagg tgtacaccct gcccccatcc cgggatgagc tgaccaagaa ccaggtcagc   1440
ctgacctgcc tggtcaaagg cttctatccc agcgacatcg ccgtggagtg ggagagcaat   1500
gggcagccgg agaacaacta caagaccacg cctcccgtgc tggactccga cggctccttc   1560
ttcctctaca gcaagctcac cgtggacaag agcaggtggc agcaggggaa cgtcttctca   1620
tgctccgtga tgcatgaggc tctgcacaac cactacacgc agaagagcct ctccctgtct   1680
cctggtaaat aa                                                       1692
```

<210> SEQ ID NO 14
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Lys Trp Val Thr Phe Ile Ser Leu Leu Phe Leu Phe Ser Ala
1               5                   10                  15

Tyr Ser Ile Val Met Thr Gln Ser Pro Ser Ser Leu Ser Ala Ser Val
            20                  25                  30

Gly Asp Arg Val Thr Ile Thr Cys Arg Ala Ser Gln Ser Ile Ser Ser
        35                  40                  45

Tyr Leu Asn Trp Tyr Gln Gln Lys Pro Gly Lys Ala Pro Lys Leu Leu
    50                  55                  60

Ile Tyr Ala Ala Ser Ser Leu Gln Ser Gly Val Pro Pro Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Asn Ser Phe Pro
            100                 105                 110

Pro Thr Phe Gly Gln Gly Thr Lys Val Asp Ile Lys Arg Thr Val Ala
        115                 120                 125

Gly Gly Gly Gly Ser Gly Gly Gly Ser Gly Gly Gly Gly Ser Leu
    130                 135                 140

Val Gln Ser Gly Ala Glu Val Lys Lys Pro Gly Ala Ser Val Lys Val
145                 150                 155                 160

Ser Cys Glu Ala Ser Gly Tyr Thr Phe Thr Asn Tyr Tyr Ile His Trp
                165                 170                 175

Leu Arg Gln Ala Pro Gly Gln Gly Leu Glu Trp Met Gly Ile Ile Asn
            180                 185                 190

Pro Ser Gly Gly Ser Thr Thr Tyr Ala Gln Lys Phe Gln Gly Arg Ile
        195                 200                 205

Thr Met Thr Arg Asp Thr Ser Thr Asn Thr Leu Tyr Met Glu Leu Ser
    210                 215                 220

Ser Leu Arg Ser Glu Asp Thr Ala Ile Tyr Tyr Cys Ala Arg Arg Asp
225                 230                 235                 240

Cys Arg Gly Pro Ser Cys Tyr Phe Ala Tyr Trp Gly Gln Gly Thr Thr
                245                 250                 255

Val Thr Val Ser Ser Ala Ser Thr Lys Gly Ile Thr Cys Pro Pro Pro
```

```
                260                 265                 270
Met Ser Val Glu His Ala Asp Ile Trp Val Lys Ser Tyr Ser Leu Tyr
                275                 280                 285
Ser Arg Glu Arg Tyr Ile Cys Asn Ser Gly Phe Lys Arg Lys Ala Gly
                290                 295                 300
Thr Ser Ser Leu Thr Glu Cys Val Leu Asn Lys Ala Thr Asn Val Ala
305                 310                 315                 320
His Trp Thr Thr Pro Ser Leu Lys Cys Ile Arg Glu Pro Lys Ser Cys
                    325                 330                 335
Asp Lys Thr His Thr Cys Pro Pro Cys Pro Ala Pro Glu Leu Leu Gly
                340                 345                 350
Gly Pro Ser Val Phe Leu Phe Pro Pro Lys Pro Lys Asp Thr Leu Met
                355                 360                 365
Ile Ser Arg Thr Pro Glu Val Thr Cys Val Val Val Asp Val Ser His
                370                 375                 380
Glu Asp Pro Glu Val Lys Phe Asn Trp Tyr Val Asp Gly Val Glu Val
385                 390                 395                 400
His Asn Ala Lys Thr Lys Pro Arg Glu Glu Gln Tyr Asn Ser Thr Tyr
                    405                 410                 415
Arg Val Val Ser Val Leu Thr Val Leu His Gln Asp Trp Leu Asn Gly
                420                 425                 430
Lys Glu Tyr Lys Cys Lys Val Ser Asn Lys Ala Leu Pro Ala Pro Ile
                435                 440                 445
Glu Lys Thr Ile Ser Lys Ala Lys Gly Gln Pro Arg Glu Pro Gln Val
                450                 455                 460
Tyr Thr Leu Pro Pro Ser Arg Asp Glu Leu Thr Lys Asn Gln Val Ser
465                 470                 475                 480
Leu Thr Cys Leu Val Lys Gly Phe Tyr Pro Ser Asp Ile Ala Val Glu
                    485                 490                 495
Trp Glu Ser Asn Gly Gln Pro Glu Asn Asn Tyr Lys Thr Thr Pro Pro
                500                 505                 510
Val Leu Asp Ser Asp Gly Ser Phe Phe Leu Tyr Ser Lys Leu Thr Val
                515                 520                 525
Asp Lys Ser Arg Trp Gln Gln Gly Asn Val Phe Ser Cys Ser Val Met
                530                 535                 540
His Glu Ala Leu His Asn His Tyr Thr Gln Lys Ser Leu Ser Leu Ser
545                 550                 555                 560
Pro Gly Lys
```

<210> SEQ ID NO 15
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgaagtggg taacctttat ttcccttctt tttctcttta gctcggctta ttccgacatc    60
atgatgaccc agtccccttc ctccctgtcc gtgagcgctg gcgagaaggc taccatcagc    120
tgcaagtcct cccagtccct gttcaacagc aacgccaaga ccaactacct gaactggtac    180
ctgcagaagc ccggccagtc ccccaagctg ctgatctatt acgctagcac caggcatacc    240
ggcgtgcccg acaggtttag gggatccggc agcggcaccg acttcaccct gaccatctcc    300

-continued

```
agcgtgcagg acgaggacct cgctttctac tactgccagc aatggtacga ttacccttac    360
accttcggcg ctggcaccaa ggtggagatt aagaggggcg gaggcggatc cggcggcggc    420
ggctccggcg gcggaggctc ccagattcag ctgcaggagt ccggccctgg actggtcaac    480
cctagccagt ccctgagcct gtcctgttcc gtgacaggct atagcatcac cagcggctac    540
ggctggaact ggatcaggca gtttcccggc agaaagtgg agtggatggg cttcatctac    600
tacgagggct ccacctacta taaccccctcc atcaagtccc ggatcagcat caccagggat    660
acctccaaga accagttctt cctgcaagtc aactccgtga ccaccgaaga caccgccacc    720
tactactgcg ccaggcagac aggctacttc gactactggg gccagggcac aatggtgacc    780
gtcagcagcg ccatcacgtg ccctccccccc atgtccgtgg aacacgcaga catctgggtc    840
aagagctaca gcttgtactc cagggagcgg tacatttgta actctggttt caagcgtaaa    900
gccggcacgt ccagcctgac ggagtgcgtg ttgaacaagg ccacgaatgt cgcccactgg    960
acaaccccca gtctcaaatg cattagagaa ccaagagggc ccacaatcaa gccctgtcct   1020
ccatgcaaat gcccagcacc taacctcttg ggtggaccat ccgtcttcat cttccctcca   1080
aagatcaagg atgtactcat gatctccctg agccccatag tcacatgtgt ggtggtggat   1140
gtgagcgagg atgacccaga tgtccagatc agctggtttg tgaacaacgt ggaagtacac   1200
acagctcaga cacaaaccca tagagaggat tacaacagta ctctccgggt ggtcagtgcc   1260
ctccccatcc agcaccagga ctggatgagt ggcaaggagt tcaaatgcaa ggtcaacaac   1320
aaagacctcc cagcgcccat cgagagaacc atctcaaaac ccaaagggtc agtaagagct   1380
ccacaggtat atgtcttgcc tccaccagaa gaagagatga ctaagaaaca ggtcactctg   1440
acctgcatgg tcacagactt catgcctgaa gacatttacg tggagtggac caacaacggg   1500
aaaacagagc taaactacaa gaacactgaa ccagtcctgg actctgatgg ttcttacttc   1560
atgtacagca agctgagagt ggaaaagaag aactgggtgg aaagaaatag ctactcctgt   1620
tcagtggtcc acgagggtct gcacaatcac cacacgacta gagcttctc ccggactcca   1680
ggtaaataa                                                            1689
```

<210> SEQ ID NO 16
<211> LENGTH: 562
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Lys Trp Val Thr Phe Ile Ser Leu Leu Phe Leu Phe Ser Ala
1               5                   10                  15

Tyr Ser Asp Ile Met Met Thr Gln Ser Pro Ser Ser Leu Ser Val Ser
            20                  25                  30

Ala Gly Glu Lys Ala Thr Ile Ser Cys Lys Ser Gln Ser Leu Phe
        35                  40                  45

Asn Ser Asn Ala Lys Thr Asn Tyr Leu Asn Trp Tyr Leu Gln Lys Pro
    50                  55                  60

Gly Gln Ser Pro Lys Leu Leu Ile Tyr Tyr Ala Ser Thr Arg His Thr
65                  70                  75                  80

Gly Val Pro Asp Arg Phe Arg Gly Ser Gly Ser Gly Thr Asp Phe Thr
                85                  90                  95

Leu Thr Ile Ser Ser Val Gln Asp Glu Asp Leu Ala Phe Tyr Tyr Cys
            100                 105                 110
```

-continued

```
Gln Gln Trp Tyr Asp Tyr Pro Tyr Thr Phe Gly Ala Gly Thr Lys Val
        115                 120                 125
Glu Ile Lys Arg Gly Gly Gly Ser Gly Gly Gly Gly Ser Gly Gly
130                 135                 140
Gly Gly Ser Gln Ile Gln Leu Gln Glu Ser Gly Pro Gly Leu Val Asn
145                 150                 155                 160
Pro Ser Gln Ser Leu Ser Leu Ser Cys Ser Val Thr Gly Tyr Ser Ile
                165                 170                 175
Thr Ser Gly Tyr Gly Trp Asn Trp Ile Arg Gln Phe Pro Gly Gln Lys
                180                 185                 190
Val Glu Trp Met Gly Phe Ile Tyr Tyr Glu Gly Ser Thr Tyr Tyr Asn
                195                 200                 205
Pro Ser Ile Lys Ser Arg Ile Ser Ile Thr Arg Asp Thr Ser Lys Asn
                210                 215                 220
Gln Phe Phe Leu Gln Val Asn Ser Val Thr Thr Glu Asp Thr Ala Thr
225                 230                 235                 240
Tyr Tyr Cys Ala Arg Gln Thr Gly Tyr Phe Asp Tyr Trp Gly Gln Gly
                    245                 250                 255
Thr Met Val Thr Val Ser Ser Ala Ile Thr Cys Pro Pro Pro Met Ser
                260                 265                 270
Val Glu His Ala Asp Ile Trp Val Lys Ser Tyr Ser Leu Tyr Ser Arg
                275                 280                 285
Glu Arg Tyr Ile Cys Asn Ser Gly Phe Lys Arg Lys Ala Gly Thr Ser
                290                 295                 300
Ser Leu Thr Glu Cys Val Leu Asn Lys Ala Thr Asn Val Ala His Trp
305                 310                 315                 320
Thr Thr Pro Ser Leu Lys Cys Ile Arg Glu Pro Arg Gly Pro Thr Ile
                    325                 330                 335
Lys Pro Cys Pro Pro Cys Lys Cys Pro Ala Pro Asn Leu Leu Gly Gly
                340                 345                 350
Pro Ser Val Phe Ile Phe Pro Pro Lys Ile Lys Asp Val Leu Met Ile
                355                 360                 365
Ser Leu Ser Pro Ile Val Thr Cys Val Val Val Asp Val Ser Glu Asp
                370                 375                 380
Asp Pro Asp Val Gln Ile Ser Trp Phe Val Asn Asn Val Glu Val His
385                 390                 395                 400
Thr Ala Gln Thr Gln Thr His Arg Glu Asp Tyr Asn Ser Thr Leu Arg
                    405                 410                 415
Val Val Ser Ala Leu Pro Ile Gln His Gln Asp Trp Met Ser Gly Lys
                420                 425                 430
Glu Phe Lys Cys Lys Val Asn Asn Lys Asp Leu Pro Ala Pro Ile Glu
                435                 440                 445
Arg Thr Ile Ser Lys Pro Lys Gly Ser Val Arg Ala Pro Gln Val Tyr
                450                 455                 460
Val Leu Pro Pro Pro Glu Glu Glu Met Thr Lys Lys Gln Val Thr Leu
465                 470                 475                 480
Thr Cys Met Val Thr Asp Phe Met Pro Glu Asp Ile Tyr Val Glu Trp
                    485                 490                 495
Thr Asn Asn Gly Lys Thr Glu Leu Asn Tyr Lys Asn Thr Glu Pro Val
                500                 505                 510
Leu Asp Ser Asp Gly Ser Tyr Phe Met Tyr Ser Lys Leu Arg Val Glu
                515                 520                 525
```

```
Lys Lys Asn Trp Val Glu Arg Asn Ser Tyr Ser Cys Ser Val Val His
        530                 535                 540

Glu Gly Leu His Asn His His Thr Thr Lys Ser Phe Ser Arg Thr Pro
545                 550                 555                 560

Gly Lys

<210> SEQ ID NO 17
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggaatgga gctgggtgtt cctgttcttt ctgtccgtga ccaccggtgt ccactccctg      60
cctgtgctga ctcaaccacc ctcggtgtct gaagtccccg ggcagagggt caccatttcc    120
tgttctggag gcatctccaa catcggaagc aatgctgtaa actggtacca gcacttccca    180
ggaaaggctc ccaaactcct catctattat aatgatctgc tgccctcagg ggtctctgac    240
cgattctctg cctccaagtc tggcacctca gcctccctgg ccatcagtgg gctccggtcc    300
gaggatgagg ctgattatta ctgtgcagca tgggatgaca tctgagtgc ttatgtcttc    360 gcaactggga ccaaggtcac cgtcctgagt ggaggtggcg gatccggagg tggaggttct    420
ggtggaggtg ggagtcaggt tcagctggtg cagtctgggg ctgaggtgaa gaagcctggg    480
gcctcagtga aggtctcctg caaggcttct ggttacacct ttaccagcta tggtatcagc    540
tgggtgcgac aggcccctgg acaagggctt gagtggatgg gatggatcag cgcttacaat    600
ggtaacacaa actatgcaca gaagctccag ggcagagtca ccatgaccac agacacatcc    660
acgagcacag cctacatgga gctgaggagc ctgagatctg acgacacggc cgtgtattac    720
tgtgcgagag ggttatacgg tgacgaggac tactggggcc agggaaccct ggtcaccgtg    780 agctcaaaact gggttaacgt aataagtgat ttgaaaaaaa ttgaagatct tattcaatct    840
atgcatattg atgctacttt atatacggaa agtgatgttc accccagttg caaagtaaca    900
gcaatgaagt gctttctctt ggagttacaa gttatttcac ttgagtccgg agatgcaagt    960
attcatgata cagtagaaaa tctgatcatc ctagcaaacg acagtttgtc ttctaatggg   1020
aatgtaacag aatctggatg caaagaatgt gaggaactgg aggaaaaaaa tattaaagaa   1080
tttttgcaga gttttgtaca tattgtccaa atgttcatca acacttctta a             1131

<210> SEQ ID NO 18
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Glu Trp Ser Trp Val Phe Leu Phe Phe Leu Ser Val Thr Thr Gly
1               5                   10                  15

Val His Ser Leu Pro Val Leu Thr Gln Pro Pro Ser Val Ser Glu Val
            20                  25                  30

Pro Gly Gln Arg Val Thr Ile Ser Cys Ser Gly Gly Ile Ser Asn Ile
        35                  40                  45

Gly Ser Asn Ala Val Asn Trp Tyr Gln His Phe Pro Gly Lys Ala Pro
    50                  55                  60
```

-continued

```
Lys Leu Leu Ile Tyr Tyr Asn Asp Leu Leu Pro Ser Gly Val Ser Asp
 65                  70                  75                  80

Arg Phe Ser Ala Ser Lys Ser Gly Thr Ser Ala Ser Leu Ala Ile Ser
                 85                  90                  95

Gly Leu Arg Ser Glu Asp Glu Ala Asp Tyr Tyr Cys Ala Ala Trp Asp
            100                 105                 110

Asp Asn Leu Ser Ala Tyr Val Phe Ala Thr Gly Thr Lys Val Thr Val
        115                 120                 125

Leu Ser Gly Gly Gly Ser Gly Gly Gly Ser Gly Gly Gly Gly
    130                 135                 140

Ser Gln Val Gln Leu Val Gln Ser Gly Ala Glu Val Lys Lys Pro Gly
145                 150                 155                 160

Ala Ser Val Lys Val Ser Cys Lys Ala Ser Gly Tyr Thr Phe Thr Ser
                165                 170                 175

Tyr Gly Ile Ser Trp Val Arg Gln Ala Pro Gly Gln Gly Leu Glu Trp
            180                 185                 190

Met Gly Trp Ile Ser Ala Tyr Asn Gly Asn Thr Asn Tyr Ala Gln Lys
        195                 200                 205

Leu Gln Gly Arg Val Thr Met Thr Thr Asp Thr Ser Thr Ser Thr Ala
    210                 215                 220

Tyr Met Glu Leu Arg Ser Leu Arg Ser Asp Asp Thr Ala Val Tyr Tyr
225                 230                 235                 240

Cys Ala Arg Gly Leu Tyr Gly Asp Glu Asp Tyr Trp Gly Gln Gly Thr
                245                 250                 255

Leu Val Thr Val Ser Ser Asn Trp Val Asn Val Ile Ser Asp Leu Lys
            260                 265                 270

Lys Ile Glu Asp Leu Ile Gln Ser Met His Ile Asp Ala Thr Leu Tyr
        275                 280                 285

Thr Glu Ser Asp Val His Pro Ser Cys Lys Val Thr Ala Met Lys Cys
    290                 295                 300

Phe Leu Leu Glu Leu Gln Val Ile Ser Leu Glu Ser Gly Asp Ala Ser
305                 310                 315                 320

Ile His Asp Thr Val Glu Asn Leu Ile Ile Leu Ala Asn Asp Ser Leu
                325                 330                 335

Ser Ser Asn Gly Asn Val Thr Glu Ser Gly Cys Lys Glu Cys Glu Glu
            340                 345                 350

Leu Glu Glu Lys Asn Ile Lys Glu Phe Leu Gln Ser Phe Val His Ile
        355                 360                 365

Val Gln Met Phe Ile Asn Thr Ser
    370                 375

<210> SEQ ID NO 19
<211> LENGTH: 768
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgaagtggg tgaccttcat cagcctgctg ttcctgttct ccagcgccta ctcccaggtg      60
cagctggtgg agtccggagg aggcctggtg gagcctggag gatccctgag gctgtcctgt     120
gccgccagcg gcatcatctt caagatcaac gacatgggct ggtatcggca ggcccctggc     180
aaaaggaggg agtgggtggc cgcttccaca ggaggcgatg aggccatcta cagggactcc     240
```

```
gtgaaggaca ggttcaccat ctccagggac gccaagaact ccgtgttcct gcagatgaac    300
tccctgaagc cgaggatac cgccgtgtac tactgcaccg ccgtgatctc caccgatagg    360
gacggcaccg agtggaggag gtactggggc cagggcacac aggtgactgt gtcctccggc    420
ggcaactggg ttaacgtaat aagtgatttg aaaaaaattg aagatcttat tcaatctatg    480
catattgatg ctactttata tacggaaagt gatgttcacc ccagttgcaa agtaacagca    540
atgaagtgct ttctcttgga gttacaagtt atttcacttg agtccggaga tgcaagtatt    600
catgatacag tagaaaatct gatcatccta gcaaacgaca gtttgtcttc taatgggaat    660
gtaacagaat ctggatgcaa agaatgtgag gaactggagg aaaaaaatat taaagaattt    720
ttgcagagtt ttgtacatat tgtccaaatg ttcatcaaca cttcttaa                768
```

<210> SEQ ID NO 20
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Lys Trp Val Thr Phe Ile Ser Leu Leu Phe Leu Phe Ser Ala
1               5                   10                  15

Tyr Ser Gln Val Gln Leu Val Glu Ser Gly Gly Gly Leu Val Glu Pro
            20                  25                  30

Gly Gly Ser Leu Arg Leu Ser Cys Ala Ala Ser Gly Ile Ile Phe Lys
        35                  40                  45

Ile Asn Asp Met Gly Trp Tyr Arg Gln Ala Pro Gly Lys Arg Arg Glu
    50                  55                  60

Trp Val Ala Ala Ser Thr Gly Gly Asp Glu Ala Ile Tyr Arg Asp Ser
65                  70                  75                  80

Val Lys Asp Arg Phe Thr Ile Ser Arg Asp Ala Lys Asn Ser Val Phe
                85                  90                  95

Leu Gln Met Asn Ser Leu Lys Pro Glu Asp Thr Ala Val Tyr Tyr Cys
            100                 105                 110

Thr Ala Val Ile Ser Thr Asp Arg Asp Gly Thr Glu Trp Arg Arg Tyr
        115                 120                 125

Trp Gly Gln Gly Thr Gln Val Thr Val Ser Ser Gly Gly Asn Trp Val
    130                 135                 140

Asn Val Ile Ser Asp Leu Lys Lys Ile Glu Asp Leu Ile Gln Ser Met
145                 150                 155                 160

His Ile Asp Ala Thr Leu Tyr Thr Glu Ser Asp Val His Pro Ser Cys
                165                 170                 175

Lys Val Thr Ala Met Lys Cys Phe Leu Leu Glu Leu Gln Val Ile Ser
            180                 185                 190

Leu Glu Ser Gly Asp Ala Ser Ile His Asp Thr Val Glu Asn Leu Ile
        195                 200                 205

Ile Leu Ala Asn Asp Ser Leu Ser Ser Asn Gly Asn Val Thr Glu Ser
    210                 215                 220

Gly Cys Lys Glu Cys Glu Glu Leu Glu Glu Lys Asn Ile Lys Glu Phe
225                 230                 235                 240

Leu Gln Ser Phe Val His Ile Val Gln Met Phe Ile Asn Thr Ser
                245                 250                 255
```

<210> SEQ ID NO 21
<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atgaagtggg tgaccttcat cagcctgctg ttcctgttct ccagcgccta ctcccaggtg      60
cagctggtgg agtccggagg aggcctggtg agcctggag  gatccctgag gctgtcctgt     120
gccgccagcg gcatcatctt caagatcaac gacatgggct ggtatcggca ggcccctggc     180
aaaaggaggg agtgggtggc cgcttccaca ggaggcgatg aggccatcta caggactcc     240
gtgaaggaca ggttcaccat ctccagggac gccaagaact ccgtgttcct gcagatgaac     300
tccctgaagc ccgaggatac cgccgtgtac tactgcaccg ccgtgatctc caccgatagg     360
gacggcaccg agtggaggag gtactggggc cagggcacac aggtgactgt gtcctccggc     420
ggcatcacgt gtcctcctcc tatgtccgtg aacacgcag acatctgggt caagagctac     480
agcttgtact ccagggagcg gtacatttgt aactctggtt caagcgtaa agccggcacg     540
tccagcctga cggagtgcgt gttgaacaag gccacgaatg tcgcccactg gacaaccccc     600
agtctcaaat gcattagaga accaagaggg cccacaatca gccctgtcc  tccatgcaaa     660
tgcccagcac ctaacctctt gggtggacca tccgtcttca tcttccctcc aaagatcaag     720
gatgtactca tgatctccct gagccccata gtcacatgtg tggtggtgga tgtgagcgag     780
gatgacccag atgtccagat cagctggttt gtgaacaacg tggaagtaca cacagctcag     840
acacaaaccc atagagagga ttacaacagt actctccggg tggtcagtgc cctccccatc     900
cagcaccagg actggatgag tggcaaggag ttcaaatgca aggtcaacaa caaagacctc     960
ccagcgccca tcgagagaac catctcaaaa cccaaaggt  cagtaagagc tccacaggta    1020
tatgtcttgc ctccaccaga agaagagatg actaagaaac aggtcactct gacctgcatg    1080
gtcacagact tcatgcctga agacatttac gtggagtgga ccaacaacgg gaaaacagag    1140
ctaaactaca gaacactga ccagtcctg  gactctgatg gttcttactt catgtacagc    1200
aagctgagag tggaaaagaa gaactgggtg gaaagaaata gctactcctg ttcagtggtc    1260
cacgagggtc tgcacaatca ccacacgact aagagcttct cccggactcc aggtaaa      1317
```

<210> SEQ ID NO 22
<211> LENGTH: 439
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Lys Trp Val Thr Phe Ile Ser Leu Leu Phe Leu Phe Ser Ser Ala
1               5                   10                  15

Tyr Ser Gln Val Gln Leu Val Glu Ser Gly Gly Gly Leu Val Glu Pro
            20                  25                  30

Gly Gly Ser Leu Arg Leu Ser Cys Ala Ala Ser Gly Ile Ile Phe Lys
        35                  40                  45

Ile Asn Asp Met Gly Trp Tyr Arg Gln Ala Pro Gly Lys Arg Arg Glu
    50                  55                  60

Trp Val Ala Ala Ser Thr Gly Gly Asp Glu Ala Ile Tyr Arg Asp Ser
65                  70                  75                  80
```

Val Lys Asp Arg Phe Thr Ile Ser Arg Asp Ala Lys Asn Ser Val Phe
            85                  90                  95

Leu Gln Met Asn Ser Leu Lys Pro Glu Asp Thr Ala Val Tyr Tyr Cys
            100                 105                 110

Thr Ala Val Ile Ser Thr Asp Arg Asp Gly Thr Glu Trp Arg Arg Tyr
            115                 120                 125

Trp Gly Gln Gly Thr Gln Val Thr Val Ser Ser Gly Gly Ile Thr Cys
        130                 135                 140

Pro Pro Pro Met Ser Val Glu His Ala Asp Ile Trp Val Lys Ser Tyr
145                 150                 155                 160

Ser Leu Tyr Ser Arg Glu Arg Tyr Ile Cys Asn Ser Gly Phe Lys Arg
                165                 170                 175

Lys Ala Gly Thr Ser Ser Leu Thr Glu Cys Val Leu Asn Lys Ala Thr
                180                 185                 190

Asn Val Ala His Trp Thr Thr Pro Ser Leu Lys Cys Ile Arg Glu Pro
                195                 200                 205

Arg Gly Pro Thr Ile Lys Pro Cys Pro Pro Cys Lys Cys Pro Ala Pro
        210                 215                 220

Asn Leu Leu Gly Gly Pro Ser Val Phe Ile Phe Pro Pro Lys Ile Lys
225                 230                 235                 240

Asp Val Leu Met Ile Ser Leu Ser Pro Ile Val Thr Cys Val Val Val
                245                 250                 255

Asp Val Ser Glu Asp Asp Pro Asp Val Gln Ile Ser Trp Phe Val Asn
                260                 265                 270

Asn Val Glu Val His Thr Ala Gln Thr Gln Thr His Arg Glu Asp Tyr
            275                 280                 285

Asn Ser Thr Leu Arg Val Val Ser Ala Leu Pro Ile Gln His Gln Asp
290                 295                 300

Trp Met Ser Gly Lys Glu Phe Lys Cys Lys Val Asn Asn Lys Asp Leu
305                 310                 315                 320

Pro Ala Pro Ile Glu Arg Thr Ile Ser Lys Pro Lys Gly Ser Val Arg
                325                 330                 335

Ala Pro Gln Val Tyr Val Leu Pro Pro Glu Glu Glu Met Thr Lys
            340                 345                 350

Lys Gln Val Thr Leu Thr Cys Met Val Thr Asp Phe Met Pro Glu Asp
            355                 360                 365

Ile Tyr Val Glu Trp Thr Asn Asn Gly Lys Thr Glu Leu Asn Tyr Lys
        370                 375                 380

Asn Thr Glu Pro Val Leu Asp Ser Asp Gly Ser Tyr Phe Met Tyr Ser
385                 390                 395                 400

Lys Leu Arg Val Glu Lys Lys Asn Trp Val Glu Arg Asn Ser Tyr Ser
                405                 410                 415

Cys Ser Val Val His Glu Gly Leu His Asn His His Thr Thr Lys Ser
                420                 425                 430

Phe Ser Arg Thr Pro Gly Lys
            435

<210> SEQ ID NO 23
<211> LENGTH: 1119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgaagtggg tgaccttcat cagcctgctg ttcctgttct ccagcgccta ctccaacatc      60
cagatgaccc agtccccttc cgccatgagc gcttccgtgg gcgacagggt gaccatcacc     120
tgcaaggcct cccaggacat ccacaggtac ctgtcctggt tccagcagaa gcccggcaag     180
gtgcccaagc acctgatcta cagggctaac aggctggtgt ccggcgtgcc ttccaggttt     240
tccggctccg gctccggcac cgagttcacc ctgaccatct ccagcctgca gcccgaggac     300
ttcgccacct actactgcct gcagtacgac gagttcccct acaccttcgg cggcggcacc     360
aaggtggaga tcaagggagg tggcggatcc ggaggtggag gttctggtgg aggtgggagt     420
cagatgcagc tggtacagtc cggcgccgag gtgaagaaga ccggctccag cgtgaaggtg     480
tcctgcaagg cctccggctt caacatcaag gactactacc tgcactgggt gaggcaggcc     540
cctggacaag ccctggagtg gatgggctgg atcgaccccg acaacggcga caccgagtac     600
gcccagaagt tccaggacag ggtgaccatc accaggggaca ggtccatgag caccgcctac     660
atggagctgt cctccctgag gtccgaggac accgccatgt actactgcaa cgccgcctac     720
ggctcctcct cctaccccat ggactactgg ggccagggca ccaccgtgac cgtgaactgg     780
gttaacgtaa taagtgattt gaaaaaaatt gaagatctta ttcaatctat gcatattgat     840
gctactttat atacggaaag tgatgttcac cccagttgca aagtaacagc aatgaagtgc     900
tttctcttgg agttacaagt tatttcactt gagtccggag atgcaagtat tcatgataca     960
gtagaaaatc tgatcatcct agcaaacgac agtttgtctt ctaatgggaa tgtaacagaa    1020
tctggatgca agaatgtgga ggaactggag gaaaaaaata ttaaagaatt tttgcagagt    1080
tttgtacata ttgtccaaat gttcatcaac acttcttaa                           1119
```

<210> SEQ ID NO 24
<211> LENGTH: 372
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ala Met Ser Ala Ser
            20                  25                  30

Val Gly Asp Arg Val Thr Ile Thr Cys Lys Ala Ser Gln Asp Ile His
        35                  40                  45

Arg Tyr Leu Ser Trp Phe Gln Gln Lys Pro Gly Lys Val Pro Lys His
    50                  55                  60

Leu Ile Tyr Arg Ala Asn Arg Leu Val Ser Gly Val Pro Ser Arg Phe
65                  70                  75                  80

Ser Gly Ser Gly Ser Gly Thr Glu Phe Thr Leu Thr Ile Ser Ser Leu
                85                  90                  95

Gln Pro Glu Asp Phe Ala Thr Tyr Tyr Cys Leu Gln Tyr Asp Glu Phe
            100                 105                 110

Pro Tyr Thr Phe Gly Gly Gly Thr Lys Val Glu Ile Lys Gly Gly Gly
        115                 120                 125

Gly Ser Gly Gly Gly Gly Ser Gly Gly Gly Ser Gln Met Gln Leu
    130                 135                 140

Val Gln Ser Gly Ala Glu Val Lys Lys Thr Gly Ser Ser Val Lys Val
```

```
                145                 150                 155                 160
Ser Cys Lys Ala Ser Gly Phe Asn Ile Lys Asp Tyr Tyr Leu His Trp
                    165                 170                 175
Val Arg Gln Ala Pro Gly Gln Ala Leu Glu Trp Met Gly Trp Ile Asp
                180                 185                 190
Pro Asp Asn Gly Asp Thr Glu Tyr Ala Gln Lys Phe Gln Asp Arg Val
            195                 200                 205
Thr Ile Thr Arg Asp Arg Ser Met Ser Thr Ala Tyr Met Glu Leu Ser
        210                 215                 220
Ser Leu Arg Ser Glu Asp Thr Ala Met Tyr Tyr Cys Asn Ala Ala Tyr
225                 230                 235                 240
Gly Ser Ser Tyr Pro Met Asp Tyr Trp Gly Gln Gly Thr Thr Val
                245                 250                 255
Thr Val Asn Trp Val Asn Val Ile Ser Asp Leu Lys Lys Ile Glu Asp
                260                 265                 270
Leu Ile Gln Ser Met His Ile Asp Ala Thr Leu Tyr Thr Glu Ser Asp
            275                 280                 285
Val His Pro Ser Cys Lys Val Thr Ala Met Lys Cys Phe Leu Leu Glu
        290                 295                 300
Leu Gln Val Ile Ser Leu Glu Ser Gly Asp Ala Ser Ile His Asp Thr
305                 310                 315                 320
Val Glu Asn Leu Ile Ile Leu Ala Asn Asp Ser Leu Ser Ser Asn Gly
                325                 330                 335
Asn Val Thr Glu Ser Gly Cys Lys Glu Cys Glu Glu Leu Glu Glu Lys
                340                 345                 350
Asn Ile Lys Glu Phe Leu Gln Ser Phe Val His Ile Val Gln Met Phe
            355                 360                 365
Ile Asn Thr Ser
    370

<210> SEQ ID NO 25
<211> LENGTH: 1668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgaagtggg tgaccttcat cagcctgctg ttcctgttct ccagcgccta ctccaacatc      60
cagatgaccc agtccccttc cgccatgagc gcttccgtgg gcgacagggt gaccatcacc     120
tgcaaggcct cccaggacat ccacaggtac ctgtcctggt tccagcagaa gcccggcaag     180
gtgcccaagc acctgatcta cagggctaac aggctggtgt ccggcgtgcc ttccaggttt     240
tccggctccg gctccggcac cgagttcacc ctgaccatct ccagcctgca gcccgaggac     300
ttcgccacct actactgcct gcagtacgac gagttcccct acaccttcgg cggcggcacc     360
aaggtggaga tcaagggagg tggcggatcc ggaggtggag gttctggtgg aggtgggagt     420
cagatgcagc tggtacagtc cggcgccgag gtgaagaaga ccggctccag cgtgaaggtg     480
tcctgcaagg cctccggctt caacatcaag gactactacc tgcactgggt gaggcaggcc     540
cctggacaag ccctggagtg gatgggctgg atcgaccccg acaacggcga caccgagtac     600
gcccagaagt tccaggacag ggtgaccatc accagggaca ggtccatgag caccgcctac     660
atggagctgt cctccctgag gtccgaggac accgccatgt actactgcaa cgccgcctac     720
```

```
ggctcctcct cctaccccat ggactactgg ggccagggca ccaccgtgac cgtgatcacg    780
tgtcctcctc ctatgtccgt ggaacacgca gacatctggg tcaagagcta cagcttgtac    840
tccagggagc ggtacatttg taactctggt ttcaagcgta aagccggcac gtccagcctg    900
acggagtgcg tgttgaacaa ggccacgaat gtcgcccact ggacaacccc cagtctcaaa    960
tgcattagag agccgaaatc ttgtgacaaa actcacacat gcccaccgtg cccagcacct   1020
gaactcctgg ggggaccgtc agtcttcctc ttccccccaa aacccaagga cacccccatg   1080
atctcccgga cccctgaggt cacatgcgtg gtggtggacg tgagccacga agaccctgag   1140
gtcaagttca actggtacgt ggacggcgtg gaggtgcata atgccaagac aaagccgcgg   1200
gaggagcagt acaacagcac gtaccgtgtg gtcagcgtcc tcaccgtcct gcaccaggac   1260
tggctgaatg gcaaggagta caagtgcaag gtctccaaca aagccctccc agcccccatc   1320
gagaaaacca tctccaaagc caaagggcag ccccgagaac cacaggtgta caccctgccc   1380
ccatcccggg atgagctgac caagaaccag gtcagcctga cctgcctggt caaaggcttc   1440
tatcccagcg acatcgccgt ggagtgggag agcaatgggc agccggagaa caactacaag   1500
accacgcctc ccgtgctgga ctccgacggc tccttcttcc tctacagcaa gctcaccgtg   1560
gacaagagca ggtggcagca ggggaacgtc ttctcatgct ccgtgatgca tgaggctctg   1620
cacaaccact acacgcagaa gagcctctcc ctgtctcctg gtaaataa               1668
```

<210> SEQ ID NO 26  
<211> LENGTH: 555  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 26

```
Met Lys Trp Val Thr Phe Ile Ser Leu Leu Phe Leu Phe Ser Ser Ala
1               5                   10                  15

Tyr Ser Asn Ile Gln Met Thr Gln Ser Pro Ser Ala Met Ser Ala Ser
            20                  25                  30

Val Gly Asp Arg Val Thr Ile Thr Cys Lys Ala Ser Gln Asp Ile His
        35                  40                  45

Arg Tyr Leu Ser Trp Phe Gln Gln Lys Pro Gly Lys Val Pro Lys His
    50                  55                  60

Leu Ile Tyr Arg Ala Asn Arg Leu Val Ser Gly Val Pro Ser Arg Phe
65                  70                  75                  80

Ser Gly Ser Gly Ser Gly Thr Glu Phe Thr Leu Thr Ile Ser Ser Leu
                85                  90                  95

Gln Pro Glu Asp Phe Ala Thr Tyr Tyr Cys Leu Gln Tyr Asp Glu Phe
            100                 105                 110

Pro Tyr Thr Phe Gly Gly Gly Thr Lys Val Glu Ile Lys Gly Gly Gly
        115                 120                 125

Gly Ser Gly Gly Gly Gly Ser Gly Gly Gly Gly Ser Gln Met Gln Leu
    130                 135                 140

Val Gln Ser Gly Ala Glu Val Lys Lys Thr Gly Ser Ser Val Lys Val
145                 150                 155                 160

Ser Cys Lys Ala Ser Gly Phe Asn Ile Lys Asp Tyr Tyr Leu His Trp
                165                 170                 175

Val Arg Gln Ala Pro Gly Gln Ala Leu Glu Trp Met Gly Trp Ile Asp
            180                 185                 190
```

Pro Asn Gly Asp Thr Glu Tyr Ala Gln Lys Phe Gln Asp Arg Val
              195                 200                 205

Thr Ile Thr Arg Asp Arg Ser Met Ser Thr Ala Tyr Met Glu Leu Ser
    210                 215                 220

Ser Leu Arg Ser Glu Asp Thr Ala Met Tyr Tyr Cys Asn Ala Ala Tyr
225                 230                 235                 240

Gly Ser Ser Ser Tyr Pro Met Asp Tyr Trp Gly Gln Gly Thr Thr Val
                245                 250                 255

Thr Val Ile Thr Cys Pro Pro Met Ser Val Glu His Ala Asp Ile
            260                 265                 270

Trp Val Lys Ser Tyr Ser Leu Tyr Ser Arg Glu Arg Tyr Ile Cys Asn
        275                 280                 285

Ser Gly Phe Lys Arg Lys Ala Gly Thr Ser Ser Leu Thr Glu Cys Val
290                 295                 300

Leu Asn Lys Ala Thr Asn Val Ala His Trp Thr Thr Pro Ser Leu Lys
305                 310                 315                 320

Cys Ile Arg Glu Pro Lys Ser Cys Asp Lys Thr His Thr Cys Pro Pro
                325                 330                 335

Cys Pro Ala Pro Glu Leu Leu Gly Gly Pro Ser Val Phe Leu Phe Pro
            340                 345                 350

Pro Lys Pro Lys Asp Thr Leu Met Ile Ser Arg Thr Pro Glu Val Thr
        355                 360                 365

Cys Val Val Val Asp Val Ser His Glu Asp Pro Glu Val Lys Phe Asn
370                 375                 380

Trp Tyr Val Asp Gly Val Glu Val His Asn Ala Lys Thr Lys Pro Arg
385                 390                 395                 400

Glu Glu Gln Tyr Asn Ser Thr Tyr Arg Val Val Ser Val Leu Thr Val
                405                 410                 415

Leu His Gln Asp Trp Leu Asn Gly Lys Glu Tyr Lys Cys Lys Val Ser
            420                 425                 430

Asn Lys Ala Leu Pro Ala Pro Ile Glu Lys Thr Ile Ser Lys Ala Lys
        435                 440                 445

Gly Gln Pro Arg Glu Pro Gln Val Tyr Thr Leu Pro Pro Ser Arg Asp
450                 455                 460

Glu Leu Thr Lys Asn Gln Val Ser Leu Thr Cys Leu Val Lys Gly Phe
465                 470                 475                 480

Tyr Pro Ser Asp Ile Ala Val Glu Trp Glu Ser Asn Gly Gln Pro Glu
                485                 490                 495

Asn Asn Tyr Lys Thr Thr Pro Pro Val Leu Asp Ser Asp Gly Ser Phe
            500                 505                 510

Phe Leu Tyr Ser Lys Leu Thr Val Asp Lys Ser Arg Trp Gln Gln Gly
        515                 520                 525

Asn Val Phe Ser Cys Ser Val Met His Glu Ala Leu His Asn His Tyr
530                 535                 540

Thr Gln Lys Ser Leu Ser Leu Ser Pro Gly Lys
545                 550                 555

<210> SEQ ID NO 27
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

-continued

```
atgaagtggg tgaccttcat cagcctgctg ttcctgttct ccagcgccta ctccaccgcc    60
aaggagccct gcatggccaa gttcggccct ctgccctcca gtggcagatg gcctcctcc   120
gagcctccct gtgtgaacaa ggtgtccgac tggaagctgg agatcctgca gaacggcctg   180
tacctgatct acggccaggt ggcccccaac gccaactaca cgacgtggc ccccttcgag    240
gtgcggctgt acaagaacaa ggacatgatc cagaccctga ccaacaagtc caagatccag   300
aacgtgggcg gcacctatga gctgcacgtg gcgacacca tcgacctgat cttcaactcc    360
gagcaccagg tgctgaagaa caacacctac tggggcatca actgggttaa cgtaataagt   420
gatttgaaaa aaattgaaga tcttattcaa tctatgcata ttgatgctac tttatatacg   480
gaaagtgatg ttcacccag ttgcaaagta acagcaatga agtgctttct cttggagtta    540
caagttattt cacttgagtc cggagatgca agtattcatg atacagtaga aaatctgatc   600
atcctagcaa acgacagttt gtcttctaat gggaatgtaa cagaatctgg atgcaaagaa   660
tgtgaggaac tggaggaaaa aaatattaaa gaattttttgc agagttttgt acatattgtc   720
caaatgttca tcaacacttc ttaa                                          744
```

<210> SEQ ID NO 28
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Lys Trp Val Thr Phe Ile Ser Leu Leu Phe Leu Phe Ser Ser Ala
1               5                   10                  15

Tyr Ser Thr Ala Lys Glu Pro Cys Met Ala Lys Phe Gly Pro Leu Pro
            20                  25                  30

Ser Lys Trp Gln Met Ala Ser Ser Glu Pro Pro Cys Val Asn Lys Val
        35                  40                  45

Ser Asp Trp Lys Leu Glu Ile Leu Gln Asn Gly Leu Tyr Leu Ile Tyr
    50                  55                  60

Gly Gln Val Ala Pro Asn Ala Asn Tyr Asn Asp Val Ala Pro Phe Glu
65                  70                  75                  80

Val Arg Leu Tyr Lys Asn Lys Asp Met Ile Gln Thr Leu Thr Asn Lys
                85                  90                  95

Ser Lys Ile Gln Asn Val Gly Gly Thr Tyr Glu Leu His Val Gly Asp
            100                 105                 110

Thr Ile Asp Leu Ile Phe Asn Ser Glu His Gln Val Leu Lys Asn Asn
        115                 120                 125

Thr Tyr Trp Gly Ile Asn Trp Val Asn Val Ile Ser Asp Leu Lys Lys
    130                 135                 140

Ile Glu Asp Leu Ile Gln Ser Met His Ile Asp Ala Thr Leu Tyr Thr
145                 150                 155                 160

Glu Ser Asp Val His Pro Ser Cys Lys Val Thr Ala Met Lys Cys Phe
                165                 170                 175

Leu Leu Glu Leu Gln Val Ile Ser Leu Glu Ser Gly Asp Ala Ser Ile
            180                 185                 190

His Asp Thr Val Glu Asn Leu Ile Ile Leu Ala Asn Asp Ser Leu Ser
        195                 200                 205

Ser Asn Gly Asn Val Thr Glu Ser Gly Cys Lys Glu Cys Glu Glu Leu
    210                 215                 220
```

Glu Lys Asn Ile Lys Glu Phe Leu Gln Ser Phe Val His Ile Val
225                 230                 235                 240

Gln Met Phe Ile Asn Thr Ser
            245

<210> SEQ ID NO 29
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atgaagtggg tgaccttcat cagcctgctg ttcctgttct ccagcgccta ctccaccgcc      60
aaggagccct gcatggccaa gttcggccct ctgccctcca gtggcagat ggcctcctcc      120 gagcctccct gtgtgaacaa ggtgtccgac tggaagctgg agatcctgca gaacggcctg     180
tacctgatct acggccaggt ggcccccaac gccaactaca cgacgtggc ccccttcgag      240 gtgcggctgt acaagaacaa ggacatgatc cagaccctga ccaacaagtc caagatccag     300
aacgtgggcg gcacctatga gctgcacgtg ggcgacacca tcgacctgat cttcaactcc     360
gagcaccagg tgctgaagaa caacacctac tggggcatca tcacgtgtcc tcctcctatg     420
tccgtggaac acgcagacat ctgggtcaag agctacagct tgtactccag ggagcggtac     480
atttgtaact ctggtttcaa gcgtaaagcc ggcacgtcca gcctgacgga gtgcgtgttg     540
aacaaggcca cgaatgtcgc ccactggaca accccagtc tcaaatgcat agagagccg      600 aaatcttgtg acaaaactca cacatgccca ccgtgcccag cacctgaact cctgggggga     660
ccgtcagtct tcctcttccc cccaaaaccc aaggacaccc tcatgatctc ccggacccct     720
gaggtcacat gcgtggtggt ggacgtgagc cacgaagacc ctgaggtcaa gttcaactgg     780
tacgtggacg gcgtggaggt gcataatgcc aagacaaagc cgcgggagga gcagtacaac     840
agcacgtacc gtgtggtcag cgtcctcacc gtcctgcacc aggactggct gaatggcaag     900
gagtacaagt gcaaggtctc caacaaagcc ctcccagccc ccatcgagaa aaccatctcc     960
aaagccaaag ggcagccccg agaaccacag gtgtacaccc tgcccccatc ccgggatgag    1020
ctgaccaaga accaggtcag cctgacctgc ctggtcaaag gcttctatcc agcgacatc    1080 gccgtggagt gggagagcaa tgggcagccg gagaacaact acaagaccac gcctcccgtg    1140
ctggactccg acggctcctt cttcctctac agcaagctca ccgtggacaa gagcaggtgg    1200
cagcagggga acgtcttctc atgctccgtg atgcatgagg ctctgcacaa ccactacacg    1260
cagaagagcc tctccctgtc tctgggtaaa taa                                 1293

<210> SEQ ID NO 30
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Lys Trp Val Thr Phe Ile Ser Leu Leu Phe Leu Phe Ser Ser Ala
1               5                   10                  15

Tyr Ser Thr Ala Lys Glu Pro Cys Met Ala Lys Phe Gly Pro Leu Pro
            20                  25                  30

Ser Lys Trp Gln Met Ala Ser Ser Glu Pro Pro Cys Val Asn Lys Val
    35                  40                  45

Ser Asp Trp Lys Leu Glu Ile Leu Gln Asn Gly Leu Tyr Leu Ile Tyr
50                  55                  60

Gly Gln Val Ala Pro Asn Ala Asn Tyr Asn Asp Val Ala Pro Phe Glu
65                  70                  75                  80

Val Arg Leu Tyr Lys Asn Lys Asp Met Ile Gln Thr Leu Thr Asn Lys
                85                  90                  95

Ser Lys Ile Gln Asn Val Gly Gly Thr Tyr Glu Leu His Val Gly Asp
            100                 105                 110

Thr Ile Asp Leu Ile Phe Asn Ser Glu His Gln Val Leu Lys Asn Asn
            115                 120                 125

Thr Tyr Trp Gly Ile Ile Thr Cys Pro Pro Met Ser Val Glu His
            130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Glu Pro Lys Ser Cys Asp Lys Thr His Thr
            195                 200                 205

Cys Pro Pro Cys Pro Ala Pro Glu Leu Leu Gly Gly Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Lys Phe Asn Trp Tyr Val Asp Gly Val Glu Val His Asn Ala Lys Thr
            260                 265                 270

Lys Pro Arg Glu Glu Gln Tyr Asn Ser Thr Tyr Arg Val Val Ser Val
            275                 280                 285

Leu Thr Val Leu His Gln Asp Trp Leu Asn Gly Lys Glu Tyr Lys Cys
    290                 295                 300

Lys Val Ser Asn Lys Ala Leu Pro Ala Pro Ile Glu Lys Thr Ile Ser
305                 310                 315                 320

Lys Ala Lys Gly Gln Pro Arg Glu Pro Gln Val Tyr Thr Leu Pro Pro
                325                 330                 335

Ser Arg Asp Glu Leu Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
            355                 360                 365

Gln Pro Glu Asn Asn Tyr Lys Thr Thr Pro Pro Val Leu Asp Ser Asp
    370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
                405                 410                 415

Asn His Tyr Thr Gln Lys Ser Leu Ser Leu Ser Pro Gly Lys
            420                 425                 430

<210> SEQ ID NO 31
<211> LENGTH: 1131
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 31

```
atgaagtggg tgaccttcat cagcctgctg ttcctgttct ccagcgccta ctccgagatc    60
gtgctgaccc agtccctgc  taccctgtcc ctgtccctg   gcgagagggc taccctgtcc   120
tgcagggcca ggcaatccat ctccaactac ctgcactggt accagcagaa acctggccag   180
gcccccaggc tgctgatcta ctacgcctcc cagtccatct ccggcatccc tgacaggttc   240
agcggatccg gctccggcac cgacttcacc ctgaccatct ccaggctgga gcctgaggac   300
ttcgccgtgt actactgcca gcagtccaac tcctggcctc tgaccttcgg ccagggcacc   360
aaggtggaga tcaagcgggg aggtggcgga tccggaggtg gaggttctgg tggaggtggg   420
agtgaggtgc agctggtgca gtccggcgcc gaagtgaaga gcccggagc  ctccgtgaag   480
gtgtcctgca aggcctccgg ctacaccttc accaggtact ggatgcactg ggtgaggcag   540
gcccctggac agggactgga gtggatcggc gccatctacc ccggcaactc cgacacctcc   600
tacaaccaga agttcaaggg caaggccacc atcaccgccg acacctccac caacaccgcc   660
tacatggagc tgtcctccct gaggtccgag gacaccgccg tgtactactg cgctagggc    720
gaggagatcg gcgtgaggag gtggttcgcc tactggggac agggcaccct ggtgaccgtg   780
tccagcaact gggttaacgt aataagtgat tgaaaaaaa  ttgaagatct tattcaatct   840
atgcatattg atgctacttt atatacggaa agtgatgttc accccagttg caaagtaaca   900
gcaatgaagt gctttctctt ggagttacaa gttatttcac ttgagtccgg agatgcaagt   960
attcatgata cagtagaaaa tctgatcatc ctagcaaacg acagtttgtc ttctaatggg   1020
aatgtaacag aatctggatg caaagaatgt gaggaactgg aggaaaaaaa tattaaagaa   1080
tttttgcaga gttttgtaca tattgtccaa atgttcatca acacttctta a            1131
```

<210> SEQ ID NO 32
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Lys Trp Val Thr Phe Ile Ser Leu Leu Phe Leu Phe Ser Ser Ala
1               5                   10                  15

Tyr Ser Glu Ile Val Leu Thr Gln Ser Pro Ala Thr Leu Ser Leu Ser
            20                  25                  30

Pro Gly Glu Arg Ala Thr Leu Ser Cys Arg Ala Arg Gln Ser Ile Ser
        35                  40                  45

Asn Tyr Leu His Trp Tyr Gln Gln Lys Pro Gly Gln Ala Pro Arg Leu
    50                  55                  60

Leu Ile Tyr Tyr Ala Ser Gln Ser Ile Ser Gly Ile Pro Asp Arg Phe
65                  70                  75                  80

Ser Gly Ser Gly Ser Gly Thr Asp Phe Thr Leu Thr Ile Ser Arg Leu
                85                  90                  95

Glu Pro Glu Asp Phe Ala Val Tyr Tyr Cys Gln Gln Ser Asn Ser Trp
            100                 105                 110

Pro Leu Thr Phe Gly Gln Gly Thr Lys Val Glu Ile Lys Arg Gly Gly
        115                 120                 125
```

```
Gly Gly Ser Gly Gly Gly Ser Gly Gly Gly Ser Glu Val Gln
    130                 135                 140
Leu Val Gln Ser Gly Ala Glu Val Lys Lys Pro Gly Ala Ser Val Lys
145                 150                 155                 160
Val Ser Cys Lys Ala Ser Gly Tyr Thr Phe Thr Arg Tyr Trp Met His
                165                 170                 175
Trp Val Arg Gln Ala Pro Gly Gln Gly Leu Glu Trp Ile Gly Ala Ile
            180                 185                 190
Tyr Pro Gly Asn Ser Asp Thr Ser Tyr Asn Gln Lys Phe Lys Gly Lys
        195                 200                 205
Ala Thr Ile Thr Ala Asp Thr Ser Thr Asn Thr Ala Tyr Met Glu Leu
    210                 215                 220
Ser Ser Leu Arg Ser Glu Asp Thr Ala Val Tyr Tyr Cys Ala Arg Gly
225                 230                 235                 240
Glu Glu Ile Gly Val Arg Arg Trp Phe Ala Tyr Trp Gly Gln Gly Thr
                245                 250                 255
Leu Val Thr Val Ser Ser Asn Trp Val Asn Val Ile Ser Asp Leu Lys
            260                 265                 270
Lys Ile Glu Asp Leu Ile Gln Ser Met His Ile Asp Ala Thr Leu Tyr
        275                 280                 285
Thr Glu Ser Asp Val His Pro Ser Cys Lys Val Thr Ala Met Lys Cys
    290                 295                 300
Phe Leu Leu Glu Leu Gln Val Ile Ser Leu Glu Ser Gly Asp Ala Ser
305                 310                 315                 320
Ile His Asp Thr Val Glu Asn Leu Ile Ile Leu Ala Asn Asp Ser Leu
                325                 330                 335
Ser Ser Asn Gly Asn Val Thr Glu Ser Gly Cys Lys Glu Cys Glu Glu
            340                 345                 350
Leu Glu Glu Lys Asn Ile Lys Glu Phe Leu Gln Ser Phe Val His Ile
        355                 360                 365
Val Gln Met Phe Ile Asn Thr Ser
    370                 375

<210> SEQ ID NO 33
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atgaagtggg tgaccttcat cagcctgctg ttcctgttct ccagcgccta ctccgagatc      60
gtgctgaccc agtcccctgc taccctgtcc ctgtcccctg gcgagagggc taccctgtcc     120
tgcagggcca gcaatccat  tccaactac ctgcactggt accagcagaa acctggccag     180
gcccccaggc tgctgatcta ctacgcctcc agtccatct  ccggcatccc tgacaggttc     240
agcggatccg gctccggcac cgacttcacc ctgaccatct ccaggctgga gcctgaggac     300
ttcgccgtgt actactgcca gcagtccaac tcctggcctc tgaccttcgg ccagggcacc     360
aaggtggaga tcaagcgggg aggtggcgga tccggaggtg gaggttctgg tggaggtggg     420
agtgaggtgc agctggtgca gtccggcgcc gaagtgaaga gcccggagc  ctccgtgaag     480 gtgtcctgca aggcctccgg ctacaccttc accaggtact ggatgcactg ggtgaggcag     540
gcccctggac agggactgga gtggatcggc gccatctacc ccggcaactc cgacacctcc     600
```

```
tacaaccaga agttcaaggg caaggccacc atcaccgccg acacctccac caacaccgcc    660
tacatggagc tgtcctccct gaggtccgag acaccgccg tgtactactg cgctaggggc     720
gaggagatcg gcgtgaggag gtggttcgcc tactggggac agggcaccct ggtgaccgtg   780
tccagcatca cgtgtcctcc tcctatgtcc gtggaacacg cagacatctg ggtcaagagc   840
tacagcttgt actccaggga gcggtacatt tgtaactctg gtttcaagcg taaagccggc   900
acgtccagcc tgacggagtg cgtgttgaac aaggccacga atgtcgccca ctggacaacc   960
cccagtctca aatgcattag agagccgaaa tcttgtgaca aaactcacac atgcccaccg  1020
tgcccagcac ctgaactcct gggggaccg tcagtcttcc tcttccccc aaaacccaag    1080 gacaccctca tgatctcccg gacccctgag gtcacatgcg tggtggtgga cgtgagccac   1140
gaagaccctg aggtcaagtt caactggtac gtggacggcg tggaggtgca taatgccaag   1200
acaaagccgc gggaggagca gtacaacagc acgtaccgtg tggtcagcgt cctcaccgtc   1260
ctgcaccagg actggctgaa tgcaaggag tacaagtgca aggtctccaa caaagccctc    1320
ccagccccca tcgagaaaac catctccaaa gccaagggc agccccgaga accacaggtg    1380
tacaccctgc ccccatcccg ggatgagctg accaagaacc aggtcagcct gacctgcctg   1440
gtcaaaggct tctatcccag cgacatcgcc gtggagtggg agagcaatgg gcagccggag   1500
aacaactaca agaccacgcc tcccgtgctg gactccgacg gctccttctt cctctacagc   1560
aagctcaccg tggacaagag caggtggcag caggggaacg tcttctcatg ctccgtgatg   1620
catgaggctc tgcacaacca ctacacgcag aagagcctct ccctgtctcc tggtaaataa   1680
```

<210> SEQ ID NO 34
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Lys Trp Val Thr Phe Ile Ser Leu Leu Phe Leu Phe Ser Ser Ala
1               5                   10                  15

Tyr Ser Glu Ile Val Leu Thr Gln Ser Pro Ala Thr Leu Ser Leu Ser
            20                  25                  30

Pro Gly Glu Arg Ala Thr Leu Ser Cys Arg Ala Arg Gln Ser Ile Ser
        35                  40                  45

Asn Tyr Leu His Trp Tyr Gln Gln Lys Pro Gly Gln Ala Pro Arg Leu
    50                  55                  60

Leu Ile Tyr Tyr Ala Ser Gln Ser Ile Ser Gly Ile Pro Asp Arg Phe
65                  70                  75                  80

Ser Gly Ser Gly Ser Gly Thr Asp Phe Thr Leu Thr Ile Ser Arg Leu
                85                  90                  95

Glu Pro Glu Asp Phe Ala Val Tyr Tyr Cys Gln Gln Ser Asn Ser Trp
            100                 105                 110

Pro Leu Thr Phe Gly Gln Gly Thr Lys Val Glu Ile Lys Arg Gly Gly
        115                 120                 125

Gly Gly Ser Gly Gly Gly Gly Ser Gly Gly Gly Gly Ser Glu Val Gln
    130                 135                 140

Leu Val Gln Ser Gly Ala Glu Val Lys Lys Pro Gly Ala Ser Val Lys
145                 150                 155                 160

Val Ser Cys Lys Ala Ser Gly Tyr Thr Phe Thr Arg Tyr Trp Met His

```
                165                 170                 175
Trp Val Arg Gln Ala Pro Gly Gln Gly Leu Glu Trp Ile Gly Ala Ile
            180                 185                 190

Tyr Pro Gly Asn Ser Asp Thr Ser Tyr Asn Gln Lys Phe Lys Gly Lys
        195                 200                 205

Ala Thr Ile Thr Ala Asp Thr Ser Thr Asn Thr Ala Tyr Met Glu Leu
210                 215                 220

Ser Ser Leu Arg Ser Glu Asp Thr Ala Val Tyr Tyr Cys Ala Arg Gly
225                 230                 235                 240

Glu Glu Ile Gly Val Arg Arg Trp Phe Ala Tyr Trp Gly Gln Gly Thr
                245                 250                 255

Leu Val Thr Val Ser Ser Ile Thr Cys Pro Pro Met Ser Val Glu
            260                 265                 270

His Ala Asp Ile Trp Val Lys Ser Tyr Ser Leu Tyr Ser Arg Glu Arg
            275                 280                 285

Tyr Ile Cys Asn Ser Gly Phe Lys Arg Lys Ala Gly Thr Ser Ser Leu
        290                 295                 300

Thr Glu Cys Val Leu Asn Lys Ala Thr Asn Val Ala His Trp Thr Thr
305                 310                 315                 320

Pro Ser Leu Lys Cys Ile Arg Glu Pro Lys Ser Cys Asp Lys Thr His
                325                 330                 335

Thr Cys Pro Pro Cys Pro Ala Pro Glu Leu Leu Gly Gly Pro Ser Val
            340                 345                 350

Phe Leu Phe Pro Pro Lys Pro Lys Asp Thr Leu Met Ile Ser Arg Thr
        355                 360                 365

Pro Glu Val Thr Cys Val Val Val Asp Val Ser His Glu Asp Pro Glu
370                 375                 380

Val Lys Phe Asn Trp Tyr Val Asp Gly Val Glu Val His Asn Ala Lys
385                 390                 395                 400

Thr Lys Pro Arg Glu Glu Gln Tyr Asn Ser Thr Tyr Arg Val Val Ser
                405                 410                 415

Val Leu Thr Val Leu His Gln Asp Trp Leu Asn Gly Lys Glu Tyr Lys
            420                 425                 430

Cys Lys Val Ser Asn Lys Ala Leu Pro Ala Pro Ile Glu Lys Thr Ile
        435                 440                 445

Ser Lys Ala Lys Gly Gln Pro Arg Glu Pro Gln Val Tyr Thr Leu Pro
450                 455                 460

Pro Ser Arg Asp Glu Leu Thr Lys Asn Gln Val Ser Leu Thr Cys Leu
465                 470                 475                 480

Val Lys Gly Phe Tyr Pro Ser Asp Ile Ala Val Glu Trp Glu Ser Asn
                485                 490                 495

Gly Gln Pro Glu Asn Asn Tyr Lys Thr Thr Pro Pro Val Leu Asp Ser
            500                 505                 510

Asp Gly Ser Phe Phe Leu Tyr Ser Lys Leu Thr Val Asp Lys Ser Arg
        515                 520                 525

Trp Gln Gln Gly Asn Val Phe Ser Cys Ser Val Met His Glu Ala Leu
530                 535                 540

His Asn His Tyr Thr Gln Lys Ser Leu Ser Leu Ser Pro Gly Lys
545                 550                 555

<210> SEQ ID NO 35
<211> LENGTH: 1662
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 35

```
atgaagtggg tgaccttcat cagcctgctg ttcctgttct ccagcgccta ctccgacatc      60
cagatgaccc agtcccctgc ttccctgtcc gcttccgtgg gcgacagggt gaccatcacc     120
tgcctggcct cccagaccat cgacacctgg ctggcctggt acctgcagaa gcccggcaag     180
tccccccagc tgctgatcta cgccgctacc aacctggccg acggcgtgcc tagcaggttt     240
tccggctccg gctccggcac cgacttctcc ttcaccatct cctccctgca gcccgaggac     300
ttcgccacct actactgcca gcaggtgtac tcctccccct cccttcgg ccagggcacc       360
aagctggaga tcaagggagg tggcggatcc ggaggtggag gttctggtgg aggtgggagt     420
cagatccagc tggtgcagtc cggcggcgaa gtgaaaaagc ccggcgccag cgtgagggtg     480
tcctgtaagg cctccggcta ctccttcacc gactacaacg tgtactgggt gaggcagtcc     540
cccggcaagg gactggagtg gatcggctac atcgacccct acaacggcat caccatctac     600
gaccagaact tcaagggcaa ggccaccctg accgtggaca gtccacctc cacagcctac      660
atggagctgt cctccctgag gtccgaggac accgccgtgt acttctgcgc cagggacgtg     720
accaccgctc tggacttctg gggacagggc accaccgtga ccgtgagctc catcacgtgt     780
cctcctccta tgtccgtgga acacgcagac atctgggtca gagctacag cttgtactcc      840
agggagcggt acatttgtaa ctctggtttc aagcgtaaag ccggcacgtc cagcctgacg     900
gagtgcgtgt gaacaaggc cacgaatgtc gcccactgga caaccccag tctcaaatgc       960
attagagagc gaaatcttg tgacaaaact cacacatgcc caccgtgccc agcacctgaa      1020
ctcctggggg gaccgtcagt cttcctcttc cccccaaaac ccaaggacac cctcatgatc     1080
tcccggaccc ctgaggtcac atgcgtggtg gtggacgtga gccacgaaga ccctgaggtc     1140
aagttcaact ggtacgtgga cggcgtggag gtgcataatg ccaagacaaa gccgcgggag     1200
gagcagtaca acagcacgta ccgtgtggtc agcgtcctca ccgtcctgca ccaggactgg     1260
ctgaatggca aggagtacaa gtgcaaggtc tccaacaaag ccctcccagc ccccatcgag     1320
aaaaccatct ccaaagccaa agggcagccc cgagaaccac aggtgtacac cctgccccca     1380
tcccgggatg agctgaccaa gaaccaggtc agcctgacct gcctggtcaa aggcttctat     1440
cccagcgaca tcgccgtgga gtgggagagc aatgggcagc cggagaacaa ctacaagacc     1500
acgcctcccg tgctggactc cgacggctcc ttcttcctct acagcaagct caccgtggac     1560
aagagcaggt ggcagcaggg gaacgtcttc tcatgctccg tgatgcatga ggctctgcac     1620
aaccactaca cgcagaagag cctctccctg tctcctggta aa                        1662
```

<210> SEQ ID NO 36
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Lys Trp Val Thr Phe Ile Ser Leu Leu Phe Leu Phe Ser Ser Ala
1               5                   10                  15

Tyr Ser Asp Ile Gln Met Thr Gln Ser Pro Ala Ser Leu Ser Ala Ser
            20                  25                  30
```

-continued

Val Gly Asp Arg Val Thr Ile Thr Cys Leu Ala Ser Gln Thr Ile Asp
         35                  40                  45

Thr Trp Leu Ala Trp Tyr Leu Gln Lys Pro Gly Lys Ser Pro Gln Leu
 50                  55                  60

Leu Ile Tyr Ala Ala Thr Asn Leu Ala Asp Gly Val Pro Ser Arg Phe
 65                  70                  75                  80

Ser Gly Ser Gly Ser Gly Thr Asp Phe Ser Phe Thr Ile Ser Ser Leu
                 85                  90                  95

Gln Pro Glu Asp Phe Ala Thr Tyr Tyr Cys Gln Gln Val Tyr Ser Ser
             100                 105                 110

Pro Phe Thr Phe Gly Gln Gly Thr Lys Leu Glu Ile Lys Gly Gly Gly
         115                 120                 125

Gly Ser Gly Gly Gly Gly Ser Gly Gly Gly Gly Ser Gln Ile Gln Leu
 130                 135                 140

Val Gln Ser Gly Gly Glu Val Lys Lys Pro Gly Ala Ser Val Arg Val
145                 150                 155                 160

Ser Cys Lys Ala Ser Gly Tyr Ser Phe Thr Asp Tyr Asn Val Tyr Trp
                 165                 170                 175

Val Arg Gln Ser Pro Gly Lys Gly Leu Glu Trp Ile Gly Tyr Ile Asp
             180                 185                 190

Pro Tyr Asn Gly Ile Thr Ile Tyr Asp Gln Asn Phe Lys Gly Lys Ala
         195                 200                 205

Thr Leu Thr Val Asp Lys Ser Thr Ser Thr Ala Tyr Met Glu Leu Ser
 210                 215                 220

Ser Leu Arg Ser Glu Asp Thr Ala Val Tyr Phe Cys Ala Arg Asp Val
225                 230                 235                 240

Thr Thr Ala Leu Asp Phe Trp Gly Gln Gly Thr Thr Val Thr Val Ser
                 245                 250                 255

Ser Ile Thr Cys Pro Pro Pro Met Ser Val Glu His Ala Asp Ile Trp
             260                 265                 270

Val Lys Ser Tyr Ser Leu Tyr Ser Arg Glu Arg Tyr Ile Cys Asn Ser
         275                 280                 285

Gly Phe Lys Arg Lys Ala Gly Thr Ser Ser Leu Thr Glu Cys Val Leu
 290                 295                 300

Asn Lys Ala Thr Asn Val Ala His Trp Thr Thr Pro Ser Leu Lys Cys
305                 310                 315                 320

Ile Arg Glu Pro Lys Ser Cys Asp Lys Thr His Thr Cys Pro Pro Cys
                 325                 330                 335

Pro Ala Pro Glu Leu Leu Gly Gly Pro Ser Val Phe Leu Phe Pro Pro
             340                 345                 350

Lys Pro Lys Asp Thr Leu Met Ile Ser Arg Thr Pro Glu Val Thr Cys
         355                 360                 365

Val Val Val Asp Val Ser His Glu Asp Pro Glu Val Lys Phe Asn Trp
 370                 375                 380

Tyr Val Asp Gly Val Glu Val His Asn Ala Lys Thr Lys Pro Arg Glu
385                 390                 395                 400

Glu Gln Tyr Asn Ser Thr Tyr Arg Val Val Ser Val Leu Thr Val Leu
                 405                 410                 415

His Gln Asp Trp Leu Asn Gly Lys Glu Tyr Lys Cys Lys Val Ser Asn
             420                 425                 430

Lys Ala Leu Pro Ala Pro Ile Glu Lys Thr Ile Ser Lys Ala Lys Gly
         435                 440                 445

Gln Pro Arg Glu Pro Gln Val Tyr Thr Leu Pro Pro Ser Arg Asp Glu

Leu Thr Lys Asn Gln Val Ser Leu Thr Cys Leu Val Lys Gly Phe Tyr
465                 470                 475                 480

Pro Ser Asp Ile Ala Val Glu Trp Glu Ser Asn Gly Gln Pro Glu Asn
            485                 490                 495

Asn Tyr Lys Thr Thr Pro Pro Val Leu Asp Ser Asp Gly Ser Phe Phe
        500                 505                 510

Leu Tyr Ser Lys Leu Thr Val Asp Lys Ser Arg Trp Gln Gln Gly Asn
        515                 520                 525

Val Phe Ser Cys Ser Val Met His Glu Ala Leu His Asn His Tyr Thr
    530                 535                 540

Gln Lys Ser Leu Ser Leu Ser Pro Gly Lys
545             550

<210> SEQ ID NO 37
<211> LENGTH: 1137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atggattttc aggtgcagat tatcagcttc ctgctaatca gtgcttcagt cataatgtca      60
agaggacagg tgcagctggt tcagagcggt gcggaagtta aaaagccggg ctcttccgtg     120
aaagttagct gcaaagcgtc tggttatacc ttcaccgact acaacatgca ctgggtccgc     180
caggccccag ccagggtct ggaatggatc ggttatattt acccgtacaa cggtggcacg     240
ggatataacc agaaattcaa atccaaagct accatcactg cggacgaaag caccaacacc     300
gcatatatgg aattgtcttc tctgcgtagc gaagataccg cggtttacta ttgcgctcgt     360
ggtcgtccag cgatggatta ctggggtcag ggcaccctgg tgaccgtgag ctctggcgga     420
ggcggatctg gtggtggcgg atccggtgga ggcggaagcg atatccagat gacccagtcc     480
ccgagctccc tgtctgccag cgtgggcgac cgcgtgacta tcacctgccg tgcgtccgaa     540
agcgtggata actacggcat ttcctttatg aactggttcc agcagaaacc gggtaaagcc     600
ccgaaactgc tgatttatgc ggcctctaac cagggcagcg tgtgtgccga ccgcttttcc     660
ggcagcggtt cggggaccga tttcactctg accatttcta gcctgcagcc agatgacttc     720
gcgacctact actgccaaca gtctaaagaa gttccgtgga ccttcggtca gggtaccaaa     780
gttgaaatta aaaactgggt taacgtaata agtgatttga aaaaaattga agatcttatt     840
caatctatgc atattgatgc tactttatat acggaaagtg atgttcaccc cagttgcaaa     900
gtaacagcaa tgaagtgctt tctcttggag ttacaagtta tttcacttga gtccggagat     960
gcaagtattc atgatacagt agaaaatctg atcatcctag caaacgacag tttgtcttct    1020
aatgggaatg taacagaatc tggatgcaaa gaatgtgagg aactggagga aaaaaatatt    1080
aaagaatttt tgcagagttt tgtacatatt gtccaaatgt tcatcaacac ttcttaa      1137

<210> SEQ ID NO 38
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Asp Phe Gln Val Gln Ile Ile Ser Phe Leu Leu Ile Ser Ala Ser
1               5                   10                  15

Val Ile Met Ser Arg Gly Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Tyr Thr Phe Thr Asp Tyr Asn Met His Trp Val Arg Gln Ala Pro Gly
    50                  55                  60

Gln Gly Leu Glu Trp Ile Gly Tyr Ile Tyr Pro Tyr Asn Gly Gly Thr
65                  70                  75                  80

Gly Tyr Asn Gln Lys Phe Lys Ser Lys Ala Thr Ile Thr Ala Asp Glu
                85                  90                  95

Ser Thr Asn Thr Ala Tyr Met Glu Leu Ser Ser Leu Arg Ser Glu Asp
            100                 105                 110

Thr Ala Val Tyr Tyr Cys Ala Arg Gly Arg Pro Ala Met Asp Tyr Trp
        115                 120                 125

Gly Gln Gly Thr Leu Val Thr Val Ser Ser Gly Gly Gly Gly Ser Gly
130                 135                 140

Gly Gly Gly Ser Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Glu Ser Val Asp Asn Tyr Gly Ile Ser Phe Met Asn Trp
            180                 185                 190

Phe Gln Gln Lys Pro Gly Lys Ala Pro Lys Leu Leu Ile Tyr Ala Ala
        195                 200                 205

Ser Asn Gln Gly Ser Gly Val Pro Ser Arg Phe Ser Gly Ser Gly Ser
210                 215                 220

Gly Thr Asp Phe Thr Leu Thr Ile Ser Ser Leu Gln Pro Asp Asp Phe
225                 230                 235                 240

Ala Thr Tyr Tyr Cys Gln Gln Ser Lys Glu Val Pro Trp Thr Phe Gly
                245                 250                 255

Gln Gly Thr Lys Val Glu Ile Lys Asn Trp Val Asn Val Ile Ser Asp
            260                 265                 270

Leu Lys Lys Ile Glu Asp Leu Ile Gln Ser Met His Ile Asp Ala Thr
        275                 280                 285

Leu Tyr Thr Glu Ser Asp Val His Pro Ser Cys Lys Val Thr Ala Met
290                 295                 300

Lys Cys Phe Leu Leu Glu Leu Gln Val Ile Ser Leu Glu Ser Gly Asp
305                 310                 315                 320

Ala Ser Ile His Asp Thr Val Glu Asn Leu Ile Ile Leu Ala Asn Asp
                325                 330                 335

Ser Leu Ser Ser Asn Gly Asn Val Thr Glu Ser Gly Cys Lys Glu Cys
            340                 345                 350

Glu Glu Leu Glu Glu Lys Asn Ile Lys Glu Phe Leu Gln Ser Phe Val
        355                 360                 365

His Ile Val Gln Met Phe Ile Asn Thr Ser
    370                 375
```

<210> SEQ ID NO 39
<211> LENGTH: 1686
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 39

```
atggattttc aggtgcagat tatcagcttc ctgctaatca gtgcttcagt cataatgtca      60
agaggacagg tgcagctggt tcagagcggt gcggaagtta aaaagccggg ctcttccgtg     120
aaagttagct gcaaagcgtc tggttatacc ttcaccgact acaacatgca ctgggtccgc     180
caggccccag ccagggtct ggaatggatc ggttatattt acccgtacaa cggtggcacg      240
ggatataacc agaaattcaa atccaaagct accatcactg cggacgaaag caccaacacc     300
gcatatatgg aattgtcttc tctgcgtagc gaagataccg cggtttacta ttgcgctcgt     360
ggtcgtccag cgatggatta ctggggtcag gcaccctgg tgaccgtgag ctctggcgga      420
ggcggatctg gtggtggcgg atccggtgga ggcggaagcg atatccagat gacccagtcc     480
ccgagctccc tgtctgccag cgtgggcgac cgcgtgacta tcacctgccg tgcgtccgaa     540
agcgtggata actacggcat tccttatatg aactggttcc agcagaaacc gggtaaagcc     600
ccgaaactgc tgatttatgc ggcctctaac cagggcagcg gtgtgccgag ccgcttttcc     660
ggcagcggtt cggggaccga tttcactctg accatttcta cctgcagcc agatgacttc      720
gcgacctact actgccaaca gtctaaagaa gttccgtgga ccttcggtca gggtaccaaa     780
gttgaaatta aaatcacgtg tcctcctcct atgtccgtgg aacacgcaga catctgggtc     840
aagagctaca gcttgtactc cagggagcgg tacatttgta actctggttt caagcgtaaa     900
gccggcacgt ccagcctgac ggagtgcgtg ttgaacaagg ccacgaatgt cgcccactgg     960
acaaccccca gtctcaaatg cattagagag ccgaaatctt gtgacaaaac tcacacatgc    1020
ccaccgtgcc cagcacctga actcctgggg ggaccgtcag tcttcctctt ccccccaaaa    1080
cccaaggaca ccctcatgat ctcccggacc cctgaggtca catgcgtggt ggtggacgtg    1140
agccacgaag accctgaggt caagttcaac tggtacgtgg acggcgtgga ggtgcataat    1200
gccaagacaa agccgcggga ggagcagtac aacagcacgt accgtgtggt cagcgtcctc    1260
accgtcctgc accaggactg gctgaatggc aaggagtaca agtgcaaggt ctccaacaaa    1320
gccctcccag ccccatcga gaaaaccatc tccaaagcca agggcagcc ccgagaacca     1380
caggtgtaca ccctgccccc atcccgggat gagctgacca agaaccaggt cagcctgacc    1440
tgcctggtca aaggcttcta tcccagcgac atcgccgtgg agtgggagag caatgggcag    1500
ccggagaaca actacaagac cacgcctccc gtgctggact ccgacggctc cttcttcctc    1560
tacagcaagc tcaccgtgga caagagcagg tggcagcagg gaacgtctt ctcatgctcc     1620
gtgatgcatg aggctctgca caaccactac acgcagaaga gcctctccct gtctcctggt    1680
aaataa                                                                1686
```

<210> SEQ ID NO 40
<211> LENGTH: 561
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Met Asp Phe Gln Val Gln Ile Ile Ser Phe Leu Leu Ile Ser Ala Ser
1               5                   10                  15

Val Ile Met Ser Arg Gly Gln Val Gln Leu Val Gln Ser Gly Ala Glu
            20                  25                  30

Val Lys Lys Pro Gly Ser Ser Val Lys Val Ser Cys Lys Ala Ser Gly
            35                  40                  45

Tyr Thr Phe Thr Asp Tyr Asn Met His Trp Val Arg Gln Ala Pro Gly
            50                  55                  60

Gln Gly Leu Glu Trp Ile Gly Tyr Ile Tyr Pro Tyr Asn Gly Gly Thr
65                  70                  75                  80

Gly Tyr Asn Gln Lys Phe Lys Ser Lys Ala Thr Ile Thr Ala Asp Glu
                85                  90                  95

Ser Thr Asn Thr Ala Tyr Met Glu Leu Ser Ser Leu Arg Ser Glu Asp
            100                 105                 110

Thr Ala Val Tyr Tyr Cys Ala Arg Gly Arg Pro Ala Met Asp Tyr Trp
            115                 120                 125

Gly Gln Gly Thr Leu Val Thr Val Ser Ser Gly Gly Gly Gly Ser Gly
130                 135                 140

Gly Gly Gly Ser Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Glu Ser Val Asp Asn Tyr Gly Ile Ser Phe Met Asn Trp
            180                 185                 190

Phe Gln Gln Lys Pro Gly Lys Ala Pro Lys Leu Leu Ile Tyr Ala Ala
            195                 200                 205

Ser Asn Gln Gly Ser Gly Val Pro Ser Arg Phe Ser Gly Ser Gly Ser
            210                 215                 220

Gly Thr Asp Phe Thr Leu Thr Ile Ser Ser Leu Gln Pro Asp Asp Phe
225                 230                 235                 240

Ala Thr Tyr Tyr Cys Gln Gln Ser Lys Glu Val Pro Trp Thr Phe Gly
                245                 250                 255

Gln Gly Thr Lys Val Glu Ile Lys Ile Thr Cys Pro Pro Pro Met Ser
            260                 265                 270

Val Glu His Ala Asp Ile Trp Val Lys Ser Tyr Ser Leu Tyr Ser Arg
            275                 280                 285

Glu Arg Tyr Ile Cys Asn Ser Gly Phe Lys Arg Lys Ala Gly Thr Ser
            290                 295                 300

Ser Leu Thr Glu Cys Val Leu Asn Lys Ala Thr Asn Val Ala His Trp
305                 310                 315                 320

Thr Thr Pro Ser Leu Lys Cys Ile Arg Glu Pro Lys Ser Cys Asp Lys
                325                 330                 335

Thr His Thr Cys Pro Pro Cys Pro Ala Pro Glu Leu Leu Gly Gly Pro
            340                 345                 350

Ser Val Phe Leu Phe Pro Pro Lys Pro Lys Asp Thr Leu Met Ile Ser
            355                 360                 365

Arg Thr Pro Glu Val Thr Cys Val Val Val Asp Val Ser His Glu Asp
            370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
                405                 410                 415

Val Ser Val Leu Thr Val Leu His Gln Asp Trp Leu Asn Gly Lys Glu
            420                 425                 430

Tyr Lys Cys Lys Val Ser Asn Lys Ala Leu Pro Ala Pro Ile Glu Lys
            435                 440                 445

```
Thr Ile Ser Lys Ala Lys Gly Gln Pro Arg Glu Pro Gln Val Tyr Thr
450                 455                 460
Leu Pro Pro Ser Arg Asp Glu Leu Thr Lys Asn Gln Val Ser Leu Thr
465                 470                 475                 480
Cys Leu Val Lys Gly Phe Tyr Pro Ser Asp Ile Ala Val Glu Trp Glu
                485                 490                 495
Ser Asn Gly Gln Pro Glu Asn Asn Tyr Lys Thr Thr Pro Pro Val Leu
                500                 505                 510
Asp Ser Asp Gly Ser Phe Phe Leu Tyr Ser Lys Leu Thr Val Asp Lys
                515                 520                 525
Ser Arg Trp Gln Gln Gly Asn Val Phe Ser Cys Ser Val Met His Glu
530                 535                 540
Ala Leu His Asn His Tyr Thr Gln Lys Ser Leu Ser Leu Ser Pro Gly
545                 550                 555                 560
Lys
```

<210> SEQ ID NO 41
<211> LENGTH: 1626
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 41

```
atgaagtggg tgaccttcat cagcctgctg ttcctgttct ccagcgccta ctccatgaag      60
tgggtgacct tcatcagcct gctgttcctg ttctccagcg cctactccga tttagtgttt     120
ctgttcgacg gctccatgtc tttacagccc gatgagttcc agaagatttt agacttcatg     180
aaggacgtga tgaagaaact gtccaacacc agctaccagt tcgctgccgt gcagttctcc     240
acctcctaca agaccgagtt cgacttctcc gactacgtga gcggaaggac ccccgatgct     300
ttactgaagc acgtcaagca catgctgctg ctcaccaaca cctttggcgc catcaactac     360
gtggccaccg aggtgtttcg tgaggaactg ggagctcggc ccgatgccac caaggtgctg     420
attatcatca ccgacggcga agccaccgat agcggaaaca tcgatgccgc caaggacatc     480
atccggtaca ttatcggcat cggcaagcac ttccagacca aggagagcca agagacttta     540
cacaagttcg cctccaagcc cgcttccgag ttcgtgtgca ttttagacac cttcgagtgt     600
ttaaaggatt tatttaccga gctgcagaag aagatctacg tgattgaggg caccagcaag     660
caagatctga cctccttcaa catggagctg tccagcagcg gcatttccgc tgatttatct     720
cgtggccacg ccatcacgtg tcctcctcct atgtccgtgg aacacgcaga catctgggtc     780
aagagctaca gcttgtactc cagggagcgg tacatttgta actctggttt caagcgtaaa     840
gccggcacgt ccagcctgac ggagtgcgtg ttgaacaagg ccacgaatgt cgcccactgg     900
acaaccccca gtctcaaatg cattagagag ccgaaatctt gtgacaaaac tcacacatgc     960
ccaccgtgcc cagcacctga actcctgggg ggaccgtcag tcttcctctt ccccccaaaa    1020
cccaaggaca ccctcatgat ctcccggacc cctgaggtca catgcgtggt ggtggacgtg    1080
agccacgaag accctgaggt caagttcaac tggtacgtgg acggcgtgga ggtgcataat    1140
gccaagacaa agccgcggga ggagcagtac aacagcacgt accgtgtggt cagcgtcctc    1200
accgtcctgc accaggactg gctgaatggc aaggagtaca agtgcaaggt ctccaacaaa    1260
gccctcccag cccccatcga gaaaaccatc tccaaagcca agggcagccc cgagaaccca    1320
caggtgtaca ccctgccccc atcccgggat gagctgacca agaaccaggt cagcctgacc    1380
```

```
tgcctggtca aaggcttcta tcccagcgac atcgccgtgg agtgggagag caatgggcag   1440
ccggagaaca actacaagac cacgcctccc gtgctggact ccgacggctc cttcttcctc   1500
tacagcaagc tcaccgtgga caagagcagg tggcagcagg ggaacgtctt ctcatgctcc   1560
gtgatgcatg aggctctgca caaccactac acgcagaaga gcctctccct gtctcctggt   1620
aaataa                                                              1626
```

<210> SEQ ID NO 42
<211> LENGTH: 523
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Met Lys Trp Val Thr Phe Ile Ser Leu Leu Phe Leu Phe Ser Ser Ala
1               5                   10                  15

Tyr Ser Asp Leu Val Phe Leu Phe Asp Gly Ser Met Ser Leu Gln Pro
            20                  25                  30

Asp Glu Phe Gln Lys Ile Leu Asp Phe Met Lys Asp Val Met Lys Lys
        35                  40                  45

Leu Ser Asn Thr Ser Tyr Gln Phe Ala Ala Val Gln Phe Ser Thr Ser
    50                  55                  60

Tyr Lys Thr Glu Phe Asp Phe Ser Asp Tyr Val Lys Arg Lys Asp Pro
65                  70                  75                  80

Asp Ala Leu Leu Lys His Val Lys His Met Leu Leu Leu Thr Asn Thr
                85                  90                  95

Phe Gly Ala Ile Asn Tyr Val Ala Thr Glu Val Phe Arg Glu Glu Leu
            100                 105                 110

Gly Ala Arg Pro Asp Ala Thr Lys Val Leu Ile Ile Ile Thr Asp Gly
        115                 120                 125

Glu Ala Thr Asp Ser Gly Asn Ile Asp Ala Ala Lys Asp Ile Ile Arg
    130                 135                 140

Tyr Ile Ile Gly Ile Gly Lys His Phe Gln Thr Lys Glu Ser Gln Glu
145                 150                 155                 160

Thr Leu His Lys Phe Ala Ser Lys Pro Ala Ser Glu Phe Val Cys Ile
                165                 170                 175

Leu Asp Thr Phe Glu Cys Leu Lys Asp Leu Phe Thr Glu Leu Gln Lys
            180                 185                 190

Lys Ile Tyr Val Ile Glu Gly Thr Ser Lys Gln Asp Leu Thr Ser Phe
        195                 200                 205

Asn Met Glu Leu Ser Ser Ser Gly Ile Ser Ala Asp Leu Ser Arg Gly
    210                 215                 220

His Ala Ile Thr Cys Pro Pro Met Ser Val Glu His Ala Asp Ile
225                 230                 235                 240

Trp Val Lys Ser Tyr Ser Leu Tyr Ser Arg Glu Arg Tyr Ile Cys Asn
                245                 250                 255

Ser Gly Phe Lys Arg Lys Ala Gly Thr Ser Ser Leu Thr Glu Cys Val
            260                 265                 270

Leu Asn Lys Ala Thr Asn Val Ala His Trp Thr Thr Pro Ser Leu Lys
        275                 280                 285

Cys Ile Arg Glu Pro Lys Ser Cys Asp Lys Thr His Thr Cys Pro Pro
    290                 295                 300
```

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
            325                 330                 335

Cys Val Val Asp Val Ser His Glu Asp Pro Glu Val Lys Phe Asn
        340                 345                 350

Trp Tyr Val Asp Gly Val Glu Val His Asn Ala Lys Thr Lys Pro Arg
            355                 360                 365

Glu Glu Gln Tyr Asn Ser Thr Tyr Arg Val Val Ser Val Leu Thr Val
370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
                405                 410                 415

Gly Gln Pro Arg Glu Pro Gln Val Tyr Thr Leu Pro Pro Ser Arg Asp
            420                 425                 430

Glu Leu Thr Lys Asn Gln Val Ser Leu Thr Cys Leu Val Lys Gly Phe
        435                 440                 445

Tyr Pro Ser Asp Ile Ala Val Glu Trp Glu Ser Asn Gly Gln Pro Glu
450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
        515                 520

<210> SEQ ID NO 43
<211> LENGTH: 2457
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atgaagtggg tgaccttcat cagcctgctg ttcctgttct ccagcgccta ctccagcggc      60
gtgttccagc tgcagctgca agagtttatc aacgagaggg gcgtgctggc ttccggtcgt     120
ccttgtgagc ccggttgtag dacctttttc cgggtgtgtt taaagcattt tcaagctgtg     180
gtgtcccccg gaccttgtac cttcggcacc gtgtccaccc ccgttctggg caccaactcc     240
ttcgccgttc gtgacgacag ctccggagga ggtcgtaatc ctttacagct gcctttcaac     300
tttacttggc ccggcacctt ctccctcatc atcgaagctt ggcatgcccc cggtgacgat     360
ctgcggcccg aagctctgcc ccccgatgct taatcagca agattgccat tcaaggttct     420
ttagccgtgg gccagaactg gctgctggac gagcagacca gcacactcac tcgtctgagg     480
tactcctatc gtgtgatctg cagcgacaac tactacggcg acaattgcag ccggctgtgc     540
aagaagagga cgaccacttt cggccattac gtctgccagc ccgacggcaa tttatcttgt     600
ctgcccggtt ggaccggcga gtactgtcag cagcccatct gtttaagcgg ctgccacgag     660
cagaacggct actgcagcaa gcccgctgag tgtctgtgta ggcccggctg gcaaggtagg     720
ctgtgcaacg agtgcatccc ccacaatggc tgtcggcacg gcacttgttc cacccccttg     780

```
cagtgcactt gtgacgaggg ctggggaggt ttattctgcg accaagatct gaactactgc    840
acccaccaca gcccttgtaa gaacggagct acttgttcca acagcggcca gaggtcctac    900
acttgtactt gtaggcccgg ttacaccggc gtcgactgcg aactggaact gagcgaatgc    960
gatagcaacc cttgtcgtaa cggcggcagc tgcaaggacc aagaagacgg ctaccactgt   1020
ttatgccctc ccggatacta cggtttacac tgcgagcact ccacactgtc ttgtgccgac   1080
tccccttgtt tcaacggcgg aagctgtcgt gagaggaacc aaggtgccaa ctacgcttgt   1140
gagtgccctc ccaacttcac cggctccaac tgcgagaaga aggtggatcg ttgcacctcc   1200
aacccttgcg ccaacggcgg ccagtgttta ataggggcc cttcccggat gtgtcgttgt   1260
cgtcccggtt ttaccggcac ctactgcgag ctgcacgtca gcgattgcgc ccggaatcct   1320
tgcgctcacg gcggaacttg tcacgattta gagaacggtt taatgtgcac ttgtcccgct   1380
ggattcagcg gtcgtaggtg tgaggtgagg acctccatcg acgcttgtgc cagcagccct   1440
tgcttcaatc gtgccacttg ttacaccgat ttatccaccg acaccttcgt gtgcaactgc   1500
ccctacggct tcgtgggatc tcgttgcgag ttccccgttg gcctgcctcc tagctttccc   1560
tggatcacgt gtcctcctcc tatgtccgtg gaacacgcag acatctgggt caagagctac   1620
agcttgtact ccagggagcg gtacatttgt aactctggtt tcaagcgtaa agccggcacg   1680
tccagcctga cggagtgcgt gttgaacaag gccacgaatg tcgcccactg dacaaccccc   1740
agtctcaaat gcattagaga gccgaaatct tgtgacaaaa ctcacacatg cccaccgtgc   1800
ccagcacctg aactcctggg gggaccgtca gtcttcctct tccccccaaa acccaaggac   1860
accctcatga tctcccggac ccctgaggtc acatgcgtgg tggtggacgt gagccacgaa   1920
gaccctgagg tcaagttcaa ctggtacgtg gacggcgtgg aggtgcataa tgccaagaca   1980
aagccgcggg aggagcagta caacagcacg taccgtgtgg tcagcgtcct caccgtcctg   2040
caccaggact ggctgaatgg caaggagtac aagtgcaagg tctccaacaa agccctccca   2100
gccccatcg agaaaaccat ctccaaagcc aaagggcagc cccgagaacc acaggtgtac   2160
accctgcccc catcccggga tgagctgacc aagaaccagg tcagcctgac ctgcctggtc   2220
aaaggcttct atcccagcga catcgccgtg gagtgggaga gcaatgggca gccggagaac   2280
aactacaaga ccacgcctcc cgtgctggac tccgacggct ccttcttcct ctacagcaag   2340
ctcaccgtgg acaagagcag gtggcagcag gggaacgtct tctcatgctc cgtgatgcat   2400
gaggctctgc acaaccacta cacgcagaag agcctctccc tgtctcctgg taaatáa       2457
```

<210> SEQ ID NO 44
<211> LENGTH: 818
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Lys Trp Val Thr Phe Ile Ser Leu Leu Phe Leu Phe Ser Ser Ala
1               5                   10                  15

Tyr Ser Ser Gly Val Phe Gln Leu Gln Leu Gln Glu Phe Ile Asn Glu
            20                  25                  30

Arg Gly Val Leu Ala Ser Gly Arg Pro Cys Glu Pro Gly Cys Arg Thr
        35                  40                  45

Phe Phe Arg Val Cys Leu Lys His Phe Gln Ala Val Val Ser Pro Gly
    50                  55                  60

-continued

```
Pro Cys Thr Phe Gly Thr Val Ser Thr Pro Val Leu Gly Thr Asn Ser
 65                  70                  75                  80

Phe Ala Val Arg Asp Asp Ser Ser Gly Gly Arg Asn Pro Leu Gln
                 85                  90                  95

Leu Pro Phe Asn Phe Thr Trp Pro Gly Thr Phe Ser Leu Ile Ile Glu
                100                 105                 110

Ala Trp His Ala Pro Gly Asp Asp Leu Arg Pro Glu Ala Leu Pro Pro
                115                 120                 125

Asp Ala Leu Ile Ser Lys Ile Ala Ile Gln Gly Ser Leu Ala Val Gly
                130                 135                 140

Gln Asn Trp Leu Leu Asp Glu Gln Thr Ser Thr Leu Thr Arg Leu Arg
145                 150                 155                 160

Tyr Ser Tyr Arg Val Ile Cys Ser Asp Asn Tyr Tyr Gly Asp Asn Cys
                165                 170                 175

Ser Arg Leu Cys Lys Lys Arg Asn Asp His Phe Gly His Tyr Val Cys
                180                 185                 190

Gln Pro Asp Gly Asn Leu Ser Cys Leu Pro Gly Trp Thr Gly Glu Tyr
                195                 200                 205

Cys Gln Gln Pro Ile Cys Leu Ser Gly Cys His Glu Gln Asn Gly Tyr
                210                 215                 220

Cys Ser Lys Pro Ala Glu Cys Leu Cys Arg Pro Gly Trp Gln Gly Arg
225                 230                 235                 240

Leu Cys Asn Glu Cys Ile Pro His Asn Gly Cys Arg His Gly Thr Cys
                245                 250                 255

Ser Thr Pro Trp Gln Cys Thr Cys Asp Glu Gly Trp Gly Gly Leu Phe
                260                 265                 270

Cys Asp Gln Asp Leu Asn Tyr Cys Thr His His Ser Pro Cys Lys Asn
                275                 280                 285

Gly Ala Thr Cys Ser Asn Ser Gly Gln Arg Ser Tyr Thr Cys Thr Cys
                290                 295                 300

Arg Pro Gly Tyr Thr Gly Val Asp Cys Glu Leu Glu Leu Ser Glu Cys
305                 310                 315                 320

Asp Ser Asn Pro Cys Arg Asn Gly Gly Ser Cys Lys Asp Gln Glu Asp
                325                 330                 335

Gly Tyr His Cys Leu Cys Pro Pro Gly Tyr Tyr Gly Leu His Cys Glu
                340                 345                 350

His Ser Thr Leu Ser Cys Ala Asp Ser Pro Cys Phe Asn Gly Gly Ser
                355                 360                 365

Cys Arg Glu Arg Asn Gln Gly Ala Asn Tyr Ala Cys Glu Cys Pro Pro
                370                 375                 380

Asn Phe Thr Gly Ser Asn Cys Glu Lys Lys Val Asp Arg Cys Thr Ser
385                 390                 395                 400

Asn Pro Cys Ala Asn Gly Gly Gln Cys Leu Asn Arg Gly Pro Ser Arg
                405                 410                 415

Met Cys Arg Cys Arg Pro Gly Phe Thr Gly Thr Tyr Cys Glu Leu His
                420                 425                 430

Val Ser Asp Cys Ala Arg Asn Pro Cys Ala His Gly Gly Thr Cys His
                435                 440                 445

Asp Leu Glu Asn Gly Leu Met Cys Thr Cys Pro Ala Gly Phe Ser Gly
                450                 455                 460

Arg Arg Cys Glu Val Arg Thr Ser Ile Asp Ala Cys Ala Ser Ser Pro
465                 470                 475                 480

Cys Phe Asn Arg Ala Thr Cys Tyr Thr Asp Leu Ser Thr Asp Thr Phe
```

| | | | | 485 | | | | 490 | | | | 495 | | |
|---|---|---|---|---|---|---|---|---|---|---|---|---|---|---|
| Val | Cys | Asn | Cys | Pro | Tyr | Gly | Phe | Val | Gly | Ser | Arg | Cys | Glu | Phe | Pro |
| | | | 500 | | | | | 505 | | | | 510 | | |
| Val | Gly | Leu | Pro | Pro | Ser | Phe | Pro | Trp | Ile | Thr | Cys | Pro | Pro | Met |
| | | | 515 | | | | | 520 | | | | 525 | | |
| Ser | Val | Glu | His | Ala | Asp | Ile | Trp | Val | Lys | Ser | Tyr | Ser | Leu | Tyr | Ser |
| | | 530 | | | | | 535 | | | | | 540 | | |
| Arg | Glu | Arg | Tyr | Ile | Cys | Asn | Ser | Gly | Phe | Lys | Arg | Lys | Ala | Gly | Thr |
| 545 | | | | | 550 | | | | | 555 | | | | | 560 |
| Ser | Ser | Leu | Thr | Glu | Cys | Val | Leu | Asn | Lys | Ala | Thr | Asn | Val | Ala | His |
| | | | | 565 | | | | | 570 | | | | | 575 | |
| Trp | Thr | Thr | Pro | Ser | Leu | Lys | Cys | Ile | Arg | Glu | Pro | Lys | Ser | Cys | Asp |
| | | | 580 | | | | | 585 | | | | 590 | | |
| Lys | Thr | His | Thr | Cys | Pro | Pro | Cys | Pro | Ala | Pro | Glu | Leu | Leu | Gly | Gly |
| | | | 595 | | | | | 600 | | | | 605 | | |
| Pro | Ser | Val | Phe | Leu | Phe | Pro | Pro | Lys | Pro | Lys | Asp | Thr | Leu | Met | Ile |
| | | 610 | | | | | 615 | | | | | 620 | | |
| Ser | Arg | Thr | Pro | Glu | Val | Thr | Cys | Val | Val | Val | Asp | Val | Ser | His | Glu |
| 625 | | | | | 630 | | | | | 635 | | | | | 640 |
| Asp | Pro | Glu | Val | Lys | Phe | Asn | Trp | Tyr | Val | Asp | Gly | Val | Glu | Val | His |
| | | | | 645 | | | | | 650 | | | | | 655 | |
| Asn | Ala | Lys | Thr | Lys | Pro | Arg | Glu | Glu | Gln | Tyr | Asn | Ser | Thr | Tyr | Arg |
| | | | 660 | | | | | 665 | | | | 670 | | |
| Val | Val | Ser | Val | Leu | Thr | Val | Leu | His | Gln | Asp | Trp | Leu | Asn | Gly | Lys |
| | | 675 | | | | | 680 | | | | | 685 | | |
| Glu | Tyr | Lys | Cys | Lys | Val | Ser | Asn | Lys | Ala | Leu | Pro | Ala | Pro | Ile | Glu |
| | 690 | | | | | 695 | | | | | 700 | | | |
| Lys | Thr | Ile | Ser | Lys | Ala | Lys | Gly | Gln | Pro | Arg | Glu | Pro | Gln | Val | Tyr |
| 705 | | | | | 710 | | | | | 715 | | | | | 720 |
| Thr | Leu | Pro | Pro | Ser | Arg | Asp | Glu | Leu | Thr | Lys | Asn | Gln | Val | Ser | Leu |
| | | | 725 | | | | | 730 | | | | | 735 | |
| Thr | Cys | Leu | Val | Lys | Gly | Phe | Tyr | Pro | Ser | Asp | Ile | Ala | Val | Glu | Trp |
| | | | 740 | | | | | 745 | | | | 750 | | |
| Glu | Ser | Asn | Gly | Gln | Pro | Glu | Asn | Asn | Tyr | Lys | Thr | Thr | Pro | Pro | Val |
| | 755 | | | | | 760 | | | | | 765 | | | |
| Leu | Asp | Ser | Asp | Gly | Ser | Phe | Phe | Leu | Tyr | Ser | Lys | Leu | Thr | Val | Asp |
| | 770 | | | | | 775 | | | | | 780 | | | |
| Lys | Ser | Arg | Trp | Gln | Gln | Gly | Asn | Val | Phe | Ser | Cys | Ser | Val | Met | His |
| 785 | | | | | 790 | | | | | 795 | | | | | 800 |
| Glu | Ala | Leu | His | Asn | His | Tyr | Thr | Gln | Lys | Ser | Leu | Ser | Leu | Ser | Pro |
| | | | 805 | | | | | 810 | | | | | 815 | |
| Gly | Lys | | | | | | | | | | | | | | |

<210> SEQ ID NO 45
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
atggaatgga gctgggtctt tctcttcttc ctgtcagtaa ccaccggtgt ccactcctcc     60
tatgtgctga ctcagcctcc ctccgcgtcc gggtctcctg gacagtcagt caccatctcc    120

```
tgcactggaa ccagcagtga cgttggtaat aataactatg tctcctggta ccaacagcac    180
ccaggcaaag cccccaaact catgatttat gatgtcagta atcggccctc aggggtttct    240
actcgcttct ctggctccaa gtctggcaac acggcctccc tgaccatctc tgggctccag    300
gctgaggacg aggctgatta ttactgcagc tcatatacaa ccagcagtac ttatgtcttc    360
ggaactggga ccaagctgac cgtcctgggg cagccaaagg cgggaggtgg cggatccgga    420
ggtggaggtt ctggtggagg tgggagtctg gtgcaatctg gggctgaggt gaagaagcct    480
ggggcctcag tgaaggtctc ctgcaaggct tctggataca ccttcaccgg ctactatatg    540
cactgggtgc gacaggcccc tggacaaggg cttgagtgga tgggatggat caaccctaac    600
agtggtggca caaactatgc acagaagttc caggcagag tcaccatgac caggaacacc    660
tccataagca cagcctacat ggagttgagc agcctgagat ctgacgacac ggccgtgtat    720
tactgtgcga gagagatgta ttactatggt tcggggtaca actggttcga cccctggggc    780
cagggaaccc tggtcaccgt gagctcaatc acgtgtcctc ctcctatgtc cgtggaacac    840
gcagacatct gggtcaagag ctacagcttg tactccaggg agcggtacat ttgtaactct    900
ggtttcaagc gtaaagccgg cacgtccagc ctgacggagt gcgtgttgaa caaggccacg    960
aatgtcgccc actggacaac ccccagtctc aaatgcatta gagagccgaa atcttgtgac   1020
aaaactcaca catgcccacc gtgcccagca cctgaactcc tggggggacc gtcagtcttc   1080
ctcttccccc caaaacccaa ggacaccctc atgatctccc ggacccctga ggtcacatgc   1140
gtggtggtgg acgtgagcca cgaagaccct gaggtcaagt tcaactggta cgtggacggc   1200
gtggaggtgc ataatgccaa gacaaagccg cgggaggagc agtacaacag cacgtaccgt   1260
gtggtcagcg tcctcaccgt cctgcaccag gactggctga atggcaagga gtacaagtgc   1320
aaggtctcca acaaagccct cccagccccc atcgagaaaa ccatctccaa agccaaaggg   1380
cagccccgag aaccacaggt gtacaccctg cccccatccc gggatgagct gaccaagaac   1440
caggtcagcc tgacctgcct ggtcaaaggc ttctatccca gcgacatcgc cgtggagtgg   1500
gagagcaatg ggcagccgga gaacaactac aagaccacgc ctcccgtgct ggactccgac   1560
ggctccttct cctctacag caagctcacc gtggacaaga gcaggtggca gcaggggaac   1620
gtcttctcat gctccgtgat gcatgaggct ctgcacaacc actacacgca gaagagcctc   1680
tccctgtctc ctggtaaata a                                             1701
```

<210> SEQ ID NO 46
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Glu Trp Ser Trp Val Phe Leu Phe Phe Leu Ser Val Thr Thr Gly
1               5                   10                  15

Val His Ser Ser Tyr Val Leu Thr Gln Pro Pro Ser Ala Ser Gly Ser
                20                  25                  30

Pro Gly Gln Ser Val Thr Ile Ser Cys Thr Gly Thr Ser Ser Asp Val
            35                  40                  45

Gly Asn Asn Asn Tyr Val Ser Trp Tyr Gln Gln His Pro Gly Lys Ala
        50                  55                  60

Pro Lys Leu Met Ile Tyr Asp Val Ser Asn Arg Pro Ser Gly Val Ser
65                  70                  75                  80

```
Thr Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Ser Ser Tyr
            100                 105                 110

Thr Thr Ser Ser Thr Tyr Val Phe Gly Thr Gly Thr Lys Leu Thr Val
        115                 120                 125

Leu Gly Gln Pro Lys Ala Gly Gly Gly Ser Gly Gly Gly Gly Ser
    130                 135                 140

Gly Gly Gly Gly Ser Leu Val Gln Ser Gly Ala Glu Val Lys Lys Pro
145                 150                 155                 160

Gly Ala Ser Val Lys Val Ser Cys Lys Ala Ser Gly Tyr Thr Phe Thr
                165                 170                 175

Gly Tyr Tyr Met His Trp Val Arg Gln Ala Pro Gly Gln Gly Leu Glu
            180                 185                 190

Trp Met Gly Trp Ile Asn Pro Asn Ser Gly Gly Thr Asn Tyr Ala Gln
        195                 200                 205

Lys Phe Gln Gly Arg Val Thr Met Thr Arg Asn Thr Ser Ile Ser Thr
    210                 215                 220

Ala Tyr Met Glu Leu Ser Ser Leu Arg Ser Asp Asp Thr Ala Val Tyr
225                 230                 235                 240

Tyr Cys Ala Arg Glu Met Tyr Tyr Gly Ser Gly Tyr Asn Trp Phe
                245                 250                 255

Asp Pro Trp Gly Gln Gly Thr Leu Val Thr Val Ser Ser Ile Thr Cys
            260                 265                 270

Pro Pro Pro Met Ser Val Glu His Ala Asp Ile Trp Val Lys Ser Tyr
        275                 280                 285

Ser Leu Tyr Ser Arg Glu Arg Tyr Ile Cys Asn Ser Gly Phe Lys Arg
    290                 295                 300

Lys Ala Gly Thr Ser Ser Leu Thr Glu Cys Val Leu Asn Lys Ala Thr
305                 310                 315                 320

Asn Val Ala His Trp Thr Thr Pro Ser Leu Lys Cys Ile Arg Glu Pro
                325                 330                 335

Lys Ser Cys Asp Lys Thr His Thr Cys Pro Pro Cys Pro Ala Pro Glu
            340                 345                 350

Leu Leu Gly Gly Pro Ser Val Phe Leu Phe Pro Pro Lys Pro Lys Asp
        355                 360                 365

Thr Leu Met Ile Ser Arg Thr Pro Glu Val Thr Cys Val Val Val Asp
    370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
            420                 425                 430

Leu Asn Gly Lys Glu Tyr Lys Cys Lys Val Ser Asn Lys Ala Leu Pro
        435                 440                 445

Ala Pro Ile Glu Lys Thr Ile Ser Lys Ala Lys Gly Gln Pro Arg Glu
    450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495
```

```
Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
        515                 520                 525

Leu Thr Val Asp Lys Ser Arg Trp Gln Gln Gly Asn Val Phe Ser Cys
    530                 535                 540

Ser Val Met His Glu Ala Leu His Asn His Tyr Thr Gln Lys Ser Leu
545                 550                 555                 560

Ser Leu Ser Pro Gly Lys
            565

<210> SEQ ID NO 47
<211> LENGTH: 1665
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atgaagtggg tgaccttcat cagcctgctg ttcctgttct ccagcgccta ctcctacatc     60
cacgtgaccc agtcccccctc ctctttaagc gtgagcatcg agatcgtgt gaccatcaac    120 tgccagacct cccaaggtgt gggctccgat ttacactggt accagcacaa gcccggtcgg    180 gccccccaagc tgctgatcca ccacaccagc tccgtgagg atggcgtgcc ctctcgtttc    240
tccggctccg gcttccatac ctccttcaat ttaaccatca gcgatttaca agctgacgac    300
atcgccacct actactgcca agttctccag ttcttcggcc ggggctctcg tctgcatatc    360
aagggaggcg gcggatccgg cggcgaggc agcggcggag gcggatctcg tgctcatctg    420
gtgcagagcg gaaccgccat gaagaagccc ggtgctagcg tgcgggtgtc ttgtcagacc    480
agcggataca ccttcaccgc ccacatttta ttctggtttc gtcaagctcc cggtcgtgga    540
ctggaatggg tgggctggat caagccccag tatggcgccg tgaactttgg cggcggcttt    600
cgtgatcggg tgactttaac tcgtgacgtg tatcgggaga tcgcctacat ggacattagg    660
ggtttaaagc ccgacgatac cgccgtgtac tactgcgctc gtgatcgttc ctacggcgat    720
agcagctggg ctttagatgc ttggggccaa ggtaccacag tgtggtccgc catcacgtgt    780
cctcctccta tgtccgtgga acacgcagac atctgggtca agagctacag cttgtactcc    840
agggagcggt acatttgtaa ctctggtttc aagcgtaaag ccggcacgtc cagcctgacg    900
gagtgcgtgt tgaacaaggc cacgaatgtc gcccactgga caacccccag tctcaaatgc    960
attagagagc cgaaatcttg tgacaaaact cacacatgcc caccgtgccc agcacctgaa   1020 ctcctgggggg accgtcagt cttcctcttc ccccccaaaac ccaaggacac cctcatgatc   1080
tcccggaccc ctgaggtcac atgcgtggtg gtggacgtga gccacgaaga ccctgaggtc   1140
aagttcaact ggtacgtgga cggcgtggag gtgcataatg ccaagacaaa gccgcgggag   1200
gagcagtaca acagcacgta ccgtgtggtc agcgtcctca ccgtcctgca ccaggactgg   1260
ctgaatggca aggagtacaa gtgcaaggtc tccaacaaag ccctcccagc ccccatcgag   1320
aaaaccatct ccaaagccaa agggcagccc cgagaaccac aggtgtacac cctgcccccca   1380 tcccgggatg agctgaccaa gaaccaggtc agcctgacct gcctggtcaa aggcttctat   1440
cccagcgaca tcgccgtgga gtgggagagc aatgggcagc cggagaacaa ctacaagacc   1500
acgcctcccg tgctggactc cgacggctcc ttcttcctct acagcaagct caccgtggac   1560
aagagcaggt ggcagcaggg gaacgtcttc tcatgctccg tgatgcatga ggctctgcac   1620
```

```
aaccactaca cgcagaagag cctctccctg tctcctggta aataa           1665
```

<210> SEQ ID NO 48
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
atgaagtggg tgaccttcat cagcctgctg ttcctgttct ccagcgccta ctccgtggtg    60
atgacccagt ccccttccac cctgtccgct tccgtgggcg acaccatcac catcacctgc   120
agggcctccc agtccatcga cctggctg gcctggtacc agcagaagcc cggcaaggcc     180
cccaagctgc tgatctacaa ggcctccacc ctgaagaccg gcgtgccctc caggttttcc   240
ggatccggct ccggcaccga gttcaccctg accatcagcg gcctgcagtt cgacgacttc   300
gccacctacc actgccagca ctacgccggc tactccgcca cctttggaca gggcaccagg   360
gtggagatca agggaggtgg cggatccgga ggtggaggtt ctggtggagg tgggagtgag   420
gtgcagctgg tggaatccgg aggcggcctg gtgaaagctg gcggaagcct gatcctgagc   480
tgcggcgtgt ccaacttcag gatctccgcc cacaccatga actgggtgag gagggtgcct   540
ggaggaggac tggagtgggt ggccagcatc tccacctcct ccacctacag ggactacgcc   600
gacgccgtga agggcaggtt caccgtgagc agggacgacc tggaggactt cgtgtacctg   660
cagatgcaca gatgcgggt ggaggacacc gccatctact actgcgccag aaagggctcc   720
gacaggctgt ccgacaacga ccccttgac gcctggggcc ctggaaccgt ggtgacagtg   780
tcccccatca cgtgtcctcc tcctatgtcc gtggaacacg cagacatctg ggtcaagagc   840
tacagcttgt actccaggga gcggtacatt tgtaactctg gtttcaagcg taaagccggc   900
acgtccagcc tgacggagtg cgtgttgaac aaggccacga atgtcgccca ctggacaacc   960
cccagtctca aatgcattag agagccgaaa tcttgtgaca aaactcacac atgcccaccg  1020
tgcccagcac ctgaactcct ggggggaccg tcagtcttcc tcttccccc aaaacccaag   1080
gacaccctca tgatctcccg gacccctgag gtcacatgcg tggtggtgga cgtgagccac  1140
gaagaccctg aggtcaagtt caactggtac gtggacggcg tggaggtgca taatgccaag  1200
acaaagccgc gggaggagca gtacaacagc acgtaccgtg tggtcagcgt cctcaccgtc  1260
ctgcaccagg actggctgaa tggcaaggag tacaagtgca aggtctccaa caaagccctc  1320
ccagccccca tcgagaaaac catctccaaa gccaagggc agccccgaga accacaggtg   1380
tacaccctgc cccatcccg ggatgagctg accaagaacc aggtcagcct gacctgcctg  1440
gtcaaaggct tctatcccag cgacatcgcc gtggagtggg agagcaatgg gcagccggag  1500
aacaactaca agaccacgcc tcccgtgctg gactccgacg gctccttctt cctctacagc  1560
aagctcaccg tggacaagag caggtggcag caggggaacg tcttctcatg ctccgtgatg  1620
catgaggctc tgcacaacca ctacacgcag aagagcctct ccctgtctcc tggtaaataa  1680
```

<210> SEQ ID NO 49
<211> LENGTH: 1674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atgaagtggg tgaccttcat cagcctgctg ttcctgttct ccagcgccta ctcctcctcc    60
ctgacccaga gccccggaac actctccctc tcccccggtg agaccgctat catctcttgt   120
aggaccagcc agtacggctc tttagcttgg tatcaacaga ggcccggcca agctcctagg   180
ctggtcattt acagcggcag cacaagggcc gccggcatcc ccgataggtt ctccggctcc   240
cggtggggcc ccgattacaa tttaacaatc tccaatttag agtccggaga cttcggcgtc   300
tactactgcc agcagtacga gttcttcggc caaggtacca aagtgcaagt tgatatcaag   360
ggcggcggag gctccggcgg cggcggatcc ggcggaggag gatcccaagt taggctgtcc   420
cagagcggag gccagatgaa gaagcccggt gactccatgc ggatcagctg tcgtgccagc   480
ggctacgagt tcatcaactg ccccatcaac tggattcgtc tggcccccgg taagcggccc   540
gaatggatgg gctggatgaa acctcgtcac ggcgctgtgt cctacgctcg tcagctgcaa   600
ggtcgtgtga ccatgactcg tgacatgtac agcgagaccg cctttttaga gctgaggtct   660
ttaacctccg acgacaccgc tgtgtacttc tgcacccggg gcaagtactg caccgctcgg   720
gactactaca actgggactt cgagcactgg ggccaaggta cacccgtgac agtgtcctcc   780
atcacgtgtc ctcctcctat gtccgtggaa cacgcagaca tctgggtcaa gagctacagc   840
ttgtactcca gggagcggta catttgtaac tctggtttca agcgtaaagc cggcacgtcc   900
agcctgacgg agtgcgtgtt gaacaaggcc acgaatgtcg cccactggac aaccccagt   960
ctcaaatgca ttagagagcc gaaatcttgt gacaaaactc acacatgccc accgtgccca  1020
gcacctgaac tcctgggggg accgtcagtc ttcctcttcc ccccaaaacc caaggacacc  1080
ctcatgatct cccggacccc tgaggtcaca tgcgtggtgg tggacgtgag ccacgaagac  1140
cctgaggtca agttcaactg gtacgtggac ggcgtggagg tgcataatgc caagacaaag  1200
ccgcgggagg agcagtacaa cagcacgtac cgtgtggtca gcgtcctcac cgtcctgcac  1260
caggactggc tgaatggcaa ggagtacaag tgcaaggtct ccaacaaagc cctcccagcc  1320
cccatcgaga aaaccatctc caaagccaaa gggcagcccc gagaaccaca ggtgtacacc  1380
ctgcccccat cccgggatga gctgaccaag aaccaggtca gcctgacctg cctggtcaaa  1440
ggcttctatc ccagcgacat cgccgtggag tgggagagca atgggcagcc ggagaacaac  1500
tacaagacca cgcctcccgt gctggactcc gacggctcct tcttcctcta cagcaagctc  1560
accgtggaca agagcaggtg gcagcagggg aacgtcttct catgctccgt gatgcatgag  1620
gctctgcaca accactacac gcagaagagc ctctccctgt cctctggtaa ataa         1674
```

<210> SEQ ID NO 50
<211> LENGTH: 1716
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

```
atgaagtggg tgaccttcat cagcctgctg ttcctgttct ccagcgccta ctcctccagc    60
tacgtgaggc ctctctccgt ggctctgggc gaaacagctc gtatcagctg cggtcgtcaa   120
gctctgggat ctcgtgctgt gcagtggtac cagcaccggc ccggtcaagc tcccatttta   180
ctgatctaca acaaccaaga tcggccctcc ggcatcccg aaaggtttag cggcacccc   240
gatatcaact tcggcacaag ggccacttta accattagcg gagtggaggc cggcgacgag   300
```

```
gccgactact actgccacat gtgggactcc cggtccggct tttcttggag ctttggcggc      360
gctactcgtc tgacagtgct gggcggaggc ggctccggag gcggcggcag cggaggaggc      420
ggatcccaag ttcagctgca agaatccgga cccggtttag tgaagcccag cgagacttta      480
agcgtgactt gtagcgtgag cggcgacagc atgaacaact actactgac ttggattcgt       540
cagagccccg gtaagggttt agagtggatc ggctacatct ccgaccggga gtccgccacc      600
tacaacccct ctttaaactc ccgggtggtg atctctcgtg acacctccaa gaaccagctg      660
tctttaaagc tgaactccgt gaccccgct gacaccgccg tgtactactg cgctaccgct        720
aggcggggcc agaggatcta cggcgtggtg agcttcggcg agttcttcta ctactacagc      780
atggacgtgt ggggcaaagg caccaccgtg accgtgtcct ccatcacgtg tcctcctcct      840
atgtccgtgg aacacgcaga catctgggtc aagagctaca gcttgtactc cagggagcgg      900
tacatttgta actctggttt caagcgtaaa gccggcacgt ccagcctgac ggagtgcgtg      960
ttgaacaagg ccacgaatgt cgcccactgg acaaccccca gtctcaaatg cattagagag     1020
ccgaaatctt gtgacaaaac tcacacatgc ccaccgtgcc cagcacctga actcctgggg     1080
ggaccgtcag tcttcctctt ccccccaaaa cccaaggaca ccctcatgat ctcccggacc     1140
cctgaggtca catgcgtggt ggtggacgtg agccacgaag accctgaggt caagttcaac     1200
tggtacgtgg acggcgtgga ggtgcataat gccaagacaa agccgcggga ggagcagtac     1260
aacagcacgt accgtgtggt cagcgtcctc accgtcctgc accaggactg gctgaatggc     1320
aaggagtaca gtgcaaggt ctccaacaaa gccctcccag ccccatcga gaaaaccatc       1380
tccaaagcca agggcagcc ccgagaacca caggtgtaca cctgccccc atcccgggat       1440
gagctgacca gaaccaggt cagcctgacc tgcctggtca aaggcttcta tcccagcgac     1500
atcgccgtgg agtgggagag caatgggcag ccggagaaca actacaagac cacgcctccc     1560
gtgctggact ccgacggctc cttcttcctc tacagcaagc tcaccgtgga caagagcagg     1620
tggcagcagg ggaacgtctt ctcatgctcc gtgatgcatg aggctctgca caaccactac     1680
acgcagaaga gcctctccct gtctcctggt aaataa                                1716
```

<210> SEQ ID NO 51
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Met Lys Trp Val Thr Phe Ile Ser Leu Leu Phe Leu Phe Ser Ser Ala
1               5                   10                  15

Tyr Ser Tyr Ile His Val Thr Gln Ser Pro Ser Ser Leu Ser Val Ser
            20                  25                  30

Ile Gly Asp Arg Val Thr Ile Asn Cys Gln Thr Ser Gln Gly Val Gly
        35                  40                  45

Ser Asp Leu His Trp Tyr Gln His Lys Pro Gly Arg Ala Pro Lys Leu
    50                  55                  60

Leu Ile His His Thr Ser Ser Val Glu Asp Gly Val Pro Ser Arg Phe
65                  70                  75                  80

Ser Gly Ser Gly Phe His Thr Ser Phe Asn Leu Thr Ile Ser Asp Leu
                85                  90                  95

Gln Ala Asp Asp Ile Ala Thr Tyr Tyr Cys Gln Val Leu Gln Phe Phe
            100                 105                 110
```

```
Gly Arg Gly Ser Arg Leu His Ile Lys Gly Gly Gly Ser Gly Gly
            115                 120                 125

Gly Gly Ser Gly Gly Gly Ser Arg Ala His Leu Val Gln Ser Gly
        130                 135                 140

Thr Ala Met Lys Lys Pro Gly Ala Ser Val Arg Val Ser Cys Gln Thr
145                 150                 155                 160

Ser Gly Tyr Thr Phe Thr Ala His Ile Leu Phe Trp Phe Arg Gln Ala
                165                 170                 175

Pro Gly Arg Gly Leu Glu Trp Val Gly Trp Ile Lys Pro Gln Tyr Gly
                180                 185                 190

Ala Val Asn Phe Gly Gly Phe Arg Asp Arg Val Thr Leu Thr Arg
            195                 200                 205

Asp Val Tyr Arg Glu Ile Ala Tyr Met Asp Ile Arg Gly Leu Lys Pro
        210                 215                 220

Asp Asp Thr Ala Val Tyr Tyr Cys Ala Arg Asp Arg Ser Tyr Gly Asp
225                 230                 235                 240

Ser Ser Trp Ala Leu Asp Ala Trp Gly Gln Gly Thr Thr Val Trp Ser
                245                 250                 255

Ala Ile Thr Cys Pro Pro Met Ser Val Glu His Ala Asp Ile Trp
            260                 265                 270

Val Lys Ser Tyr Ser Leu Tyr Ser Arg Glu Arg Tyr Ile Cys Asn Ser
        275                 280                 285

Gly Phe Lys Arg Lys Ala Gly Thr Ser Ser Leu Thr Glu Cys Val Leu
        290                 295                 300

Asn Lys Ala Thr Asn Val Ala His Trp Thr Thr Pro Ser Leu Lys Cys
305                 310                 315                 320

Ile Arg Glu Pro Lys Ser Cys Asp Lys Thr His Thr Cys Pro Pro Cys
                325                 330                 335

Pro Ala Pro Glu Leu Leu Gly Gly Pro Ser Val Phe Leu Phe Pro Pro
                340                 345                 350

Lys Pro Lys Asp Thr Leu Met Ile Ser Arg Thr Pro Glu Val Thr Cys
            355                 360                 365

Val Val Val Asp Val Ser His Glu Asp Pro Glu Val Lys Phe Asn Trp
        370                 375                 380

Tyr Val Asp Gly Val Glu Val His Asn Ala Lys Thr Lys Pro Arg Glu
385                 390                 395                 400

Glu Gln Tyr Asn Ser Thr Tyr Arg Val Val Ser Val Leu Thr Val Leu
                405                 410                 415

His Gln Asp Trp Leu Asn Gly Lys Glu Tyr Lys Cys Lys Val Ser Asn
                420                 425                 430

Lys Ala Leu Pro Ala Pro Ile Glu Lys Thr Ile Ser Lys Ala Lys Gly
            435                 440                 445

Gln Pro Arg Glu Pro Gln Val Tyr Thr Leu Pro Pro Ser Arg Asp Glu
        450                 455                 460

Leu Thr Lys Asn Gln Val Ser Leu Thr Cys Leu Val Lys Gly Phe Tyr
465                 470                 475                 480

Pro Ser Asp Ile Ala Val Glu Trp Glu Ser Asn Gly Gln Pro Glu Asn
                485                 490                 495

Asn Tyr Lys Thr Thr Pro Pro Val Leu Asp Ser Asp Gly Ser Phe Phe
                500                 505                 510

Leu Tyr Ser Lys Leu Thr Val Asp Lys Ser Arg Trp Gln Gln Gly Asn
            515                 520                 525
```

```
Val Phe Ser Cys Ser Val Met His Glu Ala Leu His Asn His Tyr Thr
    530                 535                 540
Gln Lys Ser Leu Ser Leu Ser Pro Gly Lys
545                 550

<210> SEQ ID NO 52
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Lys Trp Val Thr Phe Ile Ser Leu Leu Phe Leu Phe Ser Ser Ala
1               5                   10                  15
Tyr Ser Val Val Met Thr Gln Ser Pro Ser Thr Leu Ser Ala Ser Val
                20                  25                  30
Gly Asp Thr Ile Thr Ile Thr Cys Arg Ala Ser Gln Ser Ile Glu Thr
            35                  40                  45
Trp Leu Ala Trp Tyr Gln Gln Lys Pro Gly Lys Ala Pro Lys Leu Leu
    50                  55                  60
Ile Tyr Lys Ala Ser Thr Leu Lys Thr Gly Val Pro Ser Arg Phe Ser
65                  70                  75                  80
Gly Ser Gly Ser Gly Thr Glu Phe Thr Leu Thr Ile Ser Gly Leu Gln
                85                  90                  95
Phe Asp Asp Phe Ala Thr Tyr His Cys Gln His Tyr Ala Gly Tyr Ser
            100                 105                 110
Ala Thr Phe Gly Gln Gly Thr Arg Val Glu Ile Lys Gly Gly Gly Gly
        115                 120                 125
Ser Gly Gly Gly Gly Ser Gly Gly Gly Ser Glu Val Gln Leu Val
    130                 135                 140
Glu Ser Gly Gly Gly Leu Val Lys Ala Gly Gly Ser Leu Ile Leu Ser
145                 150                 155                 160
Cys Gly Val Ser Asn Phe Arg Ile Ser Ala His Thr Met Asn Trp Val
                165                 170                 175
Arg Arg Val Pro Gly Gly Gly Leu Glu Trp Val Ala Ser Ile Ser Thr
            180                 185                 190
Ser Ser Thr Tyr Arg Asp Tyr Ala Asp Ala Val Lys Gly Arg Phe Thr
        195                 200                 205
Val Ser Arg Asp Asp Leu Glu Asp Phe Val Tyr Leu Gln Met His Lys
    210                 215                 220
Met Arg Val Glu Asp Thr Ala Ile Tyr Tyr Cys Ala Arg Lys Gly Ser
225                 230                 235                 240
Asp Arg Leu Ser Asp Asn Asp Pro Phe Asp Ala Trp Gly Pro Gly Thr
                245                 250                 255
Val Val Thr Val Ser Pro Ile Thr Cys Pro Pro Met Ser Val Glu
            260                 265                 270
His Ala Asp Ile Trp Val Lys Ser Tyr Ser Leu Tyr Ser Arg Glu Arg
        275                 280                 285
Tyr Ile Cys Asn Ser Gly Phe Lys Arg Lys Ala Gly Thr Ser Ser Leu
    290                 295                 300
Thr Glu Cys Val Leu Asn Lys Ala Thr Asn Val Ala His Trp Thr Thr
305                 310                 315                 320
Pro Ser Leu Lys Cys Ile Arg Glu Pro Lys Ser Cys Asp Lys Thr His
                325                 330                 335
```

Thr Cys Pro Pro Cys Pro Ala Pro Glu Leu Leu Gly Gly Pro Ser Val
            340                 345                 350

Phe Leu Phe Pro Pro Lys Pro Lys Asp Thr Leu Met Ile Ser Arg Thr
            355                 360                 365

Pro Glu Val Thr Cys Val Val Val Asp Val Ser His Glu Asp Pro Glu
370                 375                 380

Val Lys Phe Asn Trp Tyr Val Asp Gly Val Glu Val His Asn Ala Lys
385                 390                 395                 400

Thr Lys Pro Arg Glu Glu Gln Tyr Asn Ser Thr Tyr Arg Val Val Ser
            405                 410                 415

Val Leu Thr Val Leu His Gln Asp Trp Leu Asn Gly Lys Glu Tyr Lys
            420                 425                 430

Cys Lys Val Ser Asn Lys Ala Leu Pro Ala Pro Ile Glu Lys Thr Ile
            435                 440                 445

Ser Lys Ala Lys Gly Gln Pro Arg Glu Pro Gln Val Tyr Thr Leu Pro
450                 455                 460

Pro Ser Arg Asp Glu Leu Thr Lys Asn Gln Val Ser Leu Thr Cys Leu
465                 470                 475                 480

Val Lys Gly Phe Tyr Pro Ser Asp Ile Ala Val Glu Trp Glu Ser Asn
            485                 490                 495

Gly Gln Pro Glu Asn Asn Tyr Lys Thr Thr Pro Pro Val Leu Asp Ser
            500                 505                 510

Asp Gly Ser Phe Phe Leu Tyr Ser Lys Leu Thr Val Asp Lys Ser Arg
            515                 520                 525

Trp Gln Gln Gly Asn Val Phe Ser Cys Ser Val Met His Glu Ala Leu
            530                 535                 540

His Asn His Tyr Thr Gln Lys Ser Leu Ser Leu Ser Pro Gly Lys
545                 550                 555

<210> SEQ ID NO 53
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Lys Trp Val Thr Phe Ile Ser Leu Leu Phe Leu Phe Ser Ser Ala
1               5                   10                  15

Tyr Ser Ser Ser Leu Thr Gln Ser Pro Gly Thr Leu Ser Leu Ser Pro
            20                  25                  30

Gly Glu Thr Ala Ile Ile Ser Cys Arg Thr Ser Gln Tyr Gly Ser Leu
            35                  40                  45

Ala Trp Tyr Gln Gln Arg Pro Gly Gln Ala Pro Arg Leu Val Ile Tyr
        50                  55                  60

Ser Gly Ser Thr Arg Ala Ala Gly Ile Pro Asp Arg Phe Ser Gly Ser
65                  70                  75                  80

Arg Trp Gly Pro Asp Tyr Asn Leu Thr Ile Ser Asn Leu Glu Ser Gly
            85                  90                  95

Asp Phe Gly Val Tyr Tyr Cys Gln Gln Tyr Glu Phe Phe Gly Gln Gly
            100                 105                 110

Thr Lys Val Gln Val Asp Ile Lys Gly Gly Gly Ser Gly Gly Gly
            115                 120                 125

Gly Ser Gly Gly Gly Gly Ser Gln Val Arg Leu Ser Gln Ser Gly Gly

```
            130                 135                 140
Gln Met Lys Lys Pro Gly Asp Ser Met Arg Ile Ser Cys Arg Ala Ser
145                 150                 155                 160

Gly Tyr Glu Phe Ile Asn Cys Pro Ile Asn Trp Ile Arg Leu Ala Pro
                165                 170                 175

Gly Lys Arg Pro Glu Trp Met Gly Trp Met Lys Pro Arg His Gly Ala
            180                 185                 190

Val Ser Tyr Ala Arg Gln Leu Gln Gly Arg Val Thr Met Thr Arg Asp
        195                 200                 205

Met Tyr Ser Glu Thr Ala Phe Leu Glu Leu Arg Ser Leu Thr Ser Asp
    210                 215                 220

Asp Thr Ala Val Tyr Phe Cys Thr Arg Gly Lys Tyr Cys Thr Ala Arg
225                 230                 235                 240

Asp Tyr Tyr Asn Trp Asp Phe Glu His Trp Gly Gln Gly Thr Pro Val
                245                 250                 255

Thr Val Ser Ser Ile Thr Cys Pro Pro Pro Met Ser Val Glu His Ala
            260                 265                 270

Asp Ile Trp Val Lys Ser Tyr Ser Leu Tyr Ser Arg Glu Arg Tyr Ile
        275                 280                 285

Cys Asn Ser Gly Phe Lys Arg Lys Ala Gly Thr Ser Ser Leu Thr Glu
    290                 295                 300

Cys Val Leu Asn Lys Ala Thr Asn Val Ala His Trp Thr Thr Pro Ser
305                 310                 315                 320

Leu Lys Cys Ile Arg Glu Pro Lys Ser Cys Asp Lys Thr His Thr Cys
                325                 330                 335

Pro Pro Cys Pro Ala Pro Glu Leu Leu Gly Gly Pro Ser Val Phe Leu
            340                 345                 350

Phe Pro Pro Lys Pro Lys Asp Thr Leu Met Ile Ser Arg Thr Pro Glu
        355                 360                 365

Val Thr Cys Val Val Val Asp Val Ser His Glu Asp Pro Glu Val Lys
    370                 375                 380

Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
                405                 410                 415

Thr Val Leu His Gln Asp Trp Leu Asn Gly Lys Glu Tyr Lys Cys Lys
            420                 425                 430

Val Ser Asn Lys Ala Leu Pro Ala Pro Ile Glu Lys Thr Ile Ser Lys
        435                 440                 445

Ala Lys Gly Gln Pro Arg Glu Pro Gln Val Tyr Thr Leu Pro Pro Ser
    450                 455                 460

Arg Asp Glu Leu Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
    530                 535                 540

His Tyr Thr Gln Lys Ser Leu Ser Leu Ser Pro Gly Lys
545                 550                 555
```

<210> SEQ ID NO 54
<211> LENGTH: 571
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Met Lys Trp Val Thr Phe Ile Ser Leu Leu Phe Leu Phe Ser Ser Ala
1               5                   10                  15

Tyr Ser Ser Tyr Val Arg Pro Leu Ser Val Ala Leu Gly Glu Thr
            20                  25                  30

Ala Arg Ile Ser Cys Gly Arg Gln Ala Leu Gly Ser Arg Ala Val Gln
            35                  40                  45

Trp Tyr Gln His Arg Pro Gly Gln Ala Pro Ile Leu Leu Ile Tyr Asn
        50                  55                  60

Asn Gln Asp Arg Pro Ser Gly Ile Pro Glu Arg Phe Ser Gly Thr Pro
65                  70                  75                  80

Asp Ile Asn Phe Gly Thr Arg Ala Thr Leu Thr Ile Ser Gly Val Glu
                85                  90                  95

Ala Gly Asp Glu Ala Asp Tyr Tyr Cys His Met Trp Asp Ser Arg Ser
            100                 105                 110

Gly Phe Ser Trp Ser Phe Gly Ala Thr Arg Leu Thr Val Leu Gly
            115                 120                 125

Gly Gly Gly Ser Gly Gly Gly Gly Ser Gly Gly Gly Gly Ser Gln Val
130                 135                 140

Gln Leu Gln Glu Ser Gly Pro Gly Leu Val Lys Pro Ser Glu Thr Leu
145                 150                 155                 160

Ser Val Thr Cys Ser Val Ser Gly Asp Ser Met Asn Asn Tyr Tyr Trp
                165                 170                 175

Thr Trp Ile Arg Gln Ser Pro Gly Lys Gly Leu Glu Trp Ile Gly Tyr
            180                 185                 190

Ile Ser Asp Arg Glu Ser Ala Thr Tyr Asn Pro Ser Leu Asn Ser Arg
        195                 200                 205

Val Val Ile Ser Arg Asp Thr Ser Lys Asn Gln Leu Ser Leu Lys Leu
210                 215                 220

Asn Ser Val Thr Pro Ala Asp Thr Ala Val Tyr Tyr Cys Ala Thr Ala
225                 230                 235                 240

Arg Arg Gly Gln Arg Ile Tyr Gly Val Val Ser Phe Gly Glu Phe Phe
                245                 250                 255

Tyr Tyr Tyr Ser Met Asp Val Trp Gly Lys Gly Thr Thr Val Thr Val
            260                 265                 270

Ser Ser Ile Thr Cys Pro Pro Met Ser Val Glu His Ala Asp Ile
        275                 280                 285

Trp Val Lys Ser Tyr Ser Leu Tyr Ser Arg Glu Arg Tyr Ile Cys Asn
        290                 295                 300

Ser Gly Phe Lys Arg Lys Ala Gly Thr Ser Ser Leu Thr Glu Cys Val
305                 310                 315                 320

Leu Asn Lys Ala Thr Asn Val Ala His Trp Thr Thr Pro Ser Leu Lys
                325                 330                 335

Cys Ile Arg Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
```

```
                    355                 360                 365
Pro Lys Pro Lys Asp Thr Leu Met Ile Ser Arg Thr Pro Glu Val Thr
            370                 375                 380

Cys Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                        405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
            435                 440                 445

Asn Lys Ala Leu Pro Ala Pro Ile Glu Lys Thr Ile Ser Lys Ala Lys
450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Glu Leu Leu Gly Gly
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Glu Ala Ala Gly Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57
```

```
Lys Cys Lys Ser Leu
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Cys Ala Ser Leu
1               5
```

MULTIMERIC IL-15-BASED MOLECULES

CROSS REFERENCE TO RELATED APPLICATIONS

This application is a Continuation of application Ser. No. 15/789,985 filed on Oct. 21, 2017, which claims the benefit of U.S. Provisional Application 62/513,964 filed on Jun. 1, 2017 and U.S. Provisional Application 62/411,216 filed on Oct. 21, 2016. The entire contents of these applications are incorporated herein by reference in their entirety.

INCORPORATION BY REFERENCE OF SEQUENCE LISTING

The instant application contains a Sequence Listing which has been filed electronically in ASCII format and is hereby incorporated by reference in its entirety. Said ASCII copy, created on Jan. 26, 2018, is named 48277_529001US_SL.txt and is 173,524 bytes in size.

FIELD OF THE INVENTION

This invention relates generally to the field of multimeric fusion molecules.

BACKGROUND OF THE INVENTION

Prior to the invention described herein, there was a pressing need to develop new strategies to target various effector molecules to a disease site to provide therapeutic benefit without the side effects associated with non-specific immune activity.

SUMMARY OF THE INVENTION

The invention is based, at least in part, on the surprising discovery that multi-specific IL-15-based protein complexes enhance the stimulation of immune cells and promote their activity against disease cells, thereby resulting in reduction or prevention of disease. These IL-15-based protein complexes also show increased binding to disease and target antigens. Provided herein are multi-specific protein complexes with one domain comprising IL-15 or a functional variant and a binding domain specific to a disease antigen, immune checkpoint or signaling molecule. Specifically, described herein are protein complexes comprising an IL-15N72D:IL-15RαSu-Ig Fc scaffold fused to binding domains that recognize programmed death ligand 1 (PD-L1), programmed death 1 (PD-1), cytotoxic T-lymphocyte associated protein 4 (CTLA-4), cluster of differentiation 47 (CD47), T-cell immunoglobulin and mucin-domain containing-3 (TIM-3, TIM3) or glucocorticoid-induced tumor necrosis factor receptor (TNFR) family related gene (GITR). These complexes induce NK and T cell responses via IL-15 activity and further augment immune responses through immune checkpoint blockade via the anti-PD-L1, PD-1, CTLA-4, CD47, TIM3 or GITR binding domains (FIG. 1). In some cases, these complexes also recognize antigens, such as PD-L1, single stranded deoxyribonucleic acid (ssDNA), CD20, human epidermal growth factor receptor 2 (HER2), epidermal growth factor receptor (EGFR), CD19, CD38, CD52, disialoganglioside (GD2), CD33, Notch1, intercellular adhesion molecule 1 (ICAM-1), tissue factor or HIV envelope, expressed on disease cells and stimulate antibody-dependent cell-mediated cytotoxicity (ADCC) and complement-dependent cytotoxicity (CDC) against the disease cell via the Fc binding domain.

Provided is an isolated soluble fusion protein complex comprising at least two soluble proteins. For example, the first protein comprises an interleukin-15 (IL-15) polypeptide, e.g., a variant IL-15 polypeptide comprising an N72D mutation (IL-15N72D). The second protein comprises a soluble IL-15 receptor alpha sushi-binding domain (IL-15RαSu) fused to an immunoglobulin Fc domain (IL-15RαSu/Fc). A third component of the isolated soluble fusion protein complex comprises a binding domain that recognizes a disease antigen, immune checkpoint molecule or a signaling molecule, e.g., PD-L1, PD-1, CTLA-4, CD47, TIM3 or GITR, wherein the binding domain is fused to the either the IL-15N72D or the IL-15RαSu/Fc protein. In some cases, these binding domains are fused to both the IL-15N72D and IL-15RαSu/Fc proteins. In other cases, one of these binding domains is fused to the IL-15N72D or the IL-15RαSu/Fc proteins and a second binding domain, i.e. specific to an immune checkpoint or signaling molecule or a disease antigen, is fused to the other protein. In one aspect, the disease antigen is associated with neoplasia, infectious disease, or autoimmune disease. In some cases, the first or second soluble protein further comprises a binding domain that recognizes a disease antigen, e.g., PD-L1, ssDNA, CD20, HER2, EGFR, CD19, CD38, CD52, GD2, CD33, Notch1, intercellular adhesion molecule 1 (ICAM-1), tissue factor or HIV envelope or other known antigens, expressed on disease cells. Alternatively, either the IL-15N72D or the IL-15RαSu/Fc protein comprise the binding domain specific to a disease antigen, immune checkpoint or signaling molecule and the other protein (IL-15RαSu/Fc or IL-15N72D protein, respectively) do not comprise an additional fused binding domain. The IL-15N72D domain of the first protein binds to the soluble IL-15RαSu domain of the second protein to form a soluble fusion protein complex. An exemplary fusion protein complex comprises an anti-PD-L1 antibody covalently linked to an IL-15N72D and/or an IL-15RαSu/Fc fusion protein (FIG. 1 and FIG. 2). Alternatively, the first protein comprises an anti-PD-L1 antibody covalently linked to a soluble IL-15 receptor alpha sushi-binding domain (IL-15RαSu) fused to an immunoglobulin Fc domain whereas the second protein comprises a binding domain that recognizes disease antigens covalently linked and a variant interleukin-15 (IL-15) polypeptide comprising an N72D mutation (IL-15N72D).

In some cases, the binding domain comprises a single chain antibody (scAb or scFv) wherein an immunoglobulin light chain variable domain is covalently linked to an immunoglobulin heavy chain variable domain by a polypeptide linker sequence. Alternatively, the binding domain comprises a soluble or extracellular ligand or receptor domain capable of acting as an immune checkpoint inhibitor or immune agonist.

Exemplary first proteins comprise the amino acid sequences set forth in SEQ ID NOs: 2, 6, 10, 18, 20, 24, 28, 32, or 38. Exemplary second proteins comprise the amino acid sequences set forth in SEQ ID NOs: 4, 8, 12, 14, 16, 22, 26, 30, 34, 36, 40, 42, 44, 46, 51, 52, 53, or 54. Exemplary nucleic acid sequences encoding the first protein comprise the sequences set forth in SEQ ID NOs: 1, 5, 9, 17, 19, 23, 27, 31 or 37. Exemplary nucleic acid sequences encoding the second protein comprise the sequences set forth in SEQ ID NOs: 3, 7, 11, 13, 15, 21, 25, 29, 33, 35, 39, 41, 43, 45, 47, 48, 49, or 50. In one aspect, the nucleic acid sequence(s) further comprises a promoter, translation initiation signal, and leader sequence operably linked to the sequence encoding the fusion protein. Also provided are DNA vector(s) comprising the nucleic acid sequences described herein. For example, the nucleic acid sequence is in a vector for replication, expression, or both.

Also provided is a soluble fusion protein complex comprising a first soluble fusion protein complex covalently linked to a second soluble fusion protein complex. For example, the soluble fusion protein complexes of the invention are multimerized, e.g., dimerized, trimerized, or otherwise multimerized (e.g., 4 complexes, 5 complexes, etc.). For example, the multimers are homomultimers or heteromultimers. The soluble fusion protein complexes are joined by covalent bonds, e.g., disulfide bonds, chemical cross-linking agents. In some cases, one soluble fusion protein is covalently linked to another soluble fusion protein by a disulfide bond linking the Fc domain of the first soluble protein to the Fc domain of the second soluble protein.

The Fc domain or functional fragment thereof includes an Fc domain selected from the group consisting of IgG Fc domain, human IgG1 Fc domain, human IgG2 Fc domain, human IgG3 Fc domain, human IgG4 Fc domain, IgA Fc domain, IgD Fc domain, IgE Fc domain, and IgM Fc domain; mouse IgG2A domain, or any combination thereof. Optionally, the Fc domain includes an amino acid change that results in an Fc domain with altered complement or Fc receptor binding properties or altered dimerization or glycosylation profiles. Amino acid changes to produce an Fc domain with altered complement or Fc receptor binding properties or altered dimerization or glycosylation profiles are known in the art. For example, a substitution of leucine residues at positions 234 and 235 of the IgG1 CH2 (numbering based on antibody consensus sequence) (i.e., . . . P E L L G G . . . (SEQ_ID_NO: 55)) with alanine residues (i.e., . . . P E A A G G . . . (SEQ_ID_NO: 56)) results in a loss of Fc gamma receptor binding, whereas the substitution of the lysine residue at position 322 of the IgG1 CH2 (numbering based on antibody consensus sequence) (i.e., . . . K C K S L . . . (SEQ_ID_NO: 57)) with an alanine residue (i.e., . . . K C A S L . . . (SEQ_ID_NO: 58)) results in a loss of complement activation. In some examples, such mutations are combined.

In some aspects, the binding domain is covalently linked to an IL-15 polypeptide (or functional fragment thereof) by a polypeptide linker sequence. Similarly, the binding domain is covalently linked to an IL-15Rα polypeptide (or functional fragment thereof) by polypeptide linker sequence. Optionally, the IL-15Rα polypeptide (or functional fragment thereof) is covalently linked to the Fc domain (or functional fragment thereof) by polypeptide linker sequence. Each polypeptide linker sequence can be selected independently. Optionally, the polypeptide linker sequences are the same. Alternatively, they are different.

Optionally, the soluble fusion protein complexes of the invention are provided wherein at least one of the soluble fusion proteins comprise a detectable label. Detectable labels include, but are not limited to, biotin, streptavidin, an enzyme, or catalytically active fragment thereof, a radionuclide, a nanoparticle, a paramagnetic metal ion, or a fluorescent, phosphorescent, or chemiluminescent molecule, or any combination thereof.

In some embodiments, a nucleic acid sequence encoding a first soluble protein comprises the sequence set forth in one of SEQ ID NOS: 1, 5, 9, 17, 19, 23, 27, 31 or 37. In some embodiments, a nucleic acid sequence encoding the second soluble protein comprises the sequence set forth in one of SEQ ID NOS: 3, 7, 11, 13, 15, 21, 25, 29, 33, 35, 39, 41, 43, 45, 47, 48, 49 or 50.

In some embodiments, a nucleic acid sequence comprises SEQ ID NOS. 1, 3, 5, 7, 9, 11, 13, 15, 17, 19, 21, 23, 25, 27, 29, 31, 33, 35, 37, 35, 39, 41, 43, 45, 47, 48, 49 or 50.

The nucleic acid sequences further comprise a promoter, translation initiation signal, and leader sequence operably linked to the sequence encoding the soluble protein.

In other embodiments, a peptide comprises SEQ ID NOS: 2, 4, 6, 8, 10, 12, 14, 16, 18, 20, 22, 24, 26, 28, 30, 32, 34, 36, 38, 40, 42, 44, 46, 51, 52, 53 or 54.

The invention provides method for making the soluble fusion protein complexes of the invention. The method includes the steps of: a) introducing into a first host cell a DNA vector with appropriate control sequences encoding the first protein, b) culturing the first host cell in media under conditions sufficient to express the first protein in the cell or the media; c) purifying the first protein from the host cells or media, d) introducing into a second host cell a DNA vector with appropriate control sequences encoding the second protein, e) culturing the second host cell in media under conditions sufficient to express the second protein in the cell or the media; and f) purifying the second protein from the host cells or media, and g) mixing the first and second proteins under conditions sufficient to allow binding between IL-15 domain of a first protein and the soluble IL-15Rα domain of a second protein to form the soluble fusion protein complex.

In some cases, the method further includes mixing the first and second protein under conditions sufficient to allow formation of a disulfide bond between the polypeptides expressed from the expression vectors.

Alternatively, methods for making soluble fusion protein complexes of the invention are carried out by a) introducing into a host cell a DNA vector with appropriate control sequences encoding the first protein and a DNA vector with appropriate control sequences encoding the second protein, b) culturing the host cell in media under conditions sufficient to express the proteins in the cell or the media and allow association between IL-15 domain of a first protein and the soluble IL-15Rα domain of a second protein to form the soluble fusion protein complex; and c) purifying the soluble fusion protein complex from the host cells or media.

In one aspect, the method further includes mixing the first and second protein under conditions sufficient to allow formation of a disulfide bond between the polypeptides expressed from the expression vectors.

Also provided are methods for making soluble fusion protein complexes comprising a) introducing into a host cell a DNA vector with appropriate control sequences encoding the first and second proteins, b) culturing the host cell in media under conditions sufficient to express the proteins in the cell or the media and allow association between IL-15 domain of a first protein and the soluble IL-15Rα domain of a second protein to form the soluble fusion protein complex, and to allow formation of a disulfide bond between the polypeptides; and c) purifying the soluble fusion protein complex from the host cells or media.

Optionally, the method further includes mixing the first and second protein under conditions sufficient to allow formation of a disulfide bond between the polypeptides expressed from the expression vectors.

Methods for treating a neoplasia, infectious disease, or autoimmune disease in a subject in need thereof are carried out by administering to a subject an effective amount of a pharmaceutical composition comprising a soluble fusion protein complex described herein, e.g., a soluble anti-PD-L1 scAb/IL-15N72D:anti-PD-L1 scAb/IL-15RαSu/Fc fusion protein complex, thereby treating the neoplasia, infectious disease, or autoimmune disease. For example, methods for treating solid or hematological malignancies in a subject in need thereof are carried out by administering to a subject an effective amount of a pharmaceutical composition comprising a soluble anti-human PD-L1 scAb/huIL-15N72D:anti-human PD-L1 scAb/huIL-15RαSu/huIgG1 Fc fusion protein complex, thereby treating the malignancy. Exemplary anti-human PD-L1 scAb/huIL-15N72D proteins comprise the amino acid sequences set forth in SEQ ID NOs: 2 and 6. Exemplary anti-human PD-L1 scAb/huIL-15RαSu/huIgG1 Fc proteins comprise the amino acid sequences set forth in SEQ ID NOs: 4 and 8.

Suitable neoplasias for treatment with the methods described herein include a glioblastoma, prostate cancer, acute myeloid leukemia, B-cell neoplasm, multiple myeloma, B-cell lymphoma, B cell non-Hodgkin's lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, prostate cancer, pancreatic cancer, colorectal cancer, ovarian cancer, non-small cell lung carcinoma, and squamous cell head and neck carcinoma.

An exemplary infection for treatment using the methods described herein is infection with human immunodeficiency virus (HIV). Exemplary nucleic acid sequences include: SEQ ID NOS: 47, 48, 49 or 50. Exemplary amino acid sequences include: SEQ ID NOS: 51, 52, 53 or 54. The methods described herein are also useful to treat bacterial infections (e.g., gram positive or gram negative bacteria) (Oleksiewicz et al. 2012. Arch Biochem Biophys. 526:124-31). An exemplary autoimmune disease for treatment using the methods described herein is an autoimmune disease mediated by B cells. Such autoimmune diseases include rheumatoid arthritis, multiple sclerosis, idiopathic thrombocytopaenia, IgM-mediated polyneuropathy, Factor VIII deficiency, systemic lupus erythematosus, Sjögren's syndrome, inflammatory myositis, pemphigus vulgaris, neuromyelitis optica, ANCA-associated vasculitis, chronic inflammatory demyelinating polyneuropathy, autoimmune anemias, pure red cell aplasia, thrombotic thrombocytopenic purpura (TTP), idiopathic thrombocytopenic purpura (ITP), Evans syndrome, vasculitis (for example granulomatosis with polyangiitis, formerly Wegener's), bullous skin disorders (for example pemphigus, pemphigoid), type 1 diabetes mellitus, anti-NMDA receptor encephalitis and Devic's disease, Graves' ophthalmopathy, autoimmune pancreatitis, Opsoclonus myoclonus syndrome (OMS), and IgG4-related disease.

The pharmaceutical composition comprising a fusion protein complex is administered in an effective amount. For example, an effective amount of the pharmaceutical composition is between about 1 µg/kg and 100 µg/kg, e.g., 1, 5, 10, 15, 20, 25, 30, 35, 40, 45, 50, 55, 60, 65, 70, 75, 80, 85, 90, 95, or 100 µg/kg. Alternatively, T×M complex is administered as a fixed dose or based on body surface area (i.e., per $m^2$).

The pharmaceutical composition comprising the fusion protein complex is administered at least one time per month, e.g., twice per month, once per week, twice per week, once per day, twice per day, every 8 hours, every 4 hours, every 2 hours, or every hour. Suitable modes of administration for the pharmaceutical composition include systemic administration, intravenous administration, local administration, subcutaneous administration, intramuscular administration, intratumoral administration, inhalation, and intraperitoneal administration.

Preferably, the fusion protein complex increases serum levels of interferon gamma (IFN-γ), and/or stimulates $CD4^+$ and $CD8^+$ T cells and NK cells to kill diseased cells or tumor cells in a subject.

In certain aspects of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt), and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15/IL-2 $\beta\gamma_C$ receptors (IL-15R) compared to the native IL-15 polypeptide. Alternatively, the IL-15 variant functions as an IL-15 antagonist as demonstrated by e.g., decreased binding activity for the IL-15R compared to the native IL-15 polypeptide.

Methods for killing a target cell are carried out by a) contacting a plurality of cells with a soluble fusion protein complex of the invention, wherein the plurality of cells further include immune cells bearing the IL-15R chains recognized by the IL-15 domain, or immune cells bearing checkpoint or signaling molecules modulated by the checkpoint inhibitor or immune agonist binding domains, and the target disease cells; b) activating the immune cells via the IL-15R or signaling molecules or via blockade of the checkpoint molecules; and c) killing the target disease cells by the activated immune cells. For example, the target disease cells are tumor cells, autoimmune cells, or virally infected cells. In some cases, the binding domain comprises an anti-PD-L1 antibody.

Methods for killing a target cell further comprise a) contacting a plurality of cells with a soluble fusion protein complex of the invention, wherein the plurality of cells further include immune cells bearing Fc receptor chains recognized by the Fc domain, and the target disease cells bearing an antigen recognized by binding domain such as an antigen-specific scAb; b) forming a specific binding complex (bridge) between the antigen on the target disease cells and Fc receptor chains on the immune cells sufficient to bind and activate the immune cells; and c) killing the target disease cells by the bound activated immune cells. For example, the target disease cells are tumor cells, autoimmune cells, or virally infected cells. In some cases, the binding domain comprises an anti-PD-L1 antibody.

Also provided are methods for preventing or treating disease in a patient, the method including the steps of: a) administering to the patient a soluble fusion protein complex of the invention; b) activating the immune cells in the patient; and c) damaging or killing the disease cells via the activated immune cells sufficient to prevent or treat the disease in the patient.

The invention also provides methods for preventing or treating disease in a patient in which the diseased cells, the method including the steps of: a) mixing immune cells bearing IL-15R chains or checkpoint or signaling molecules with a soluble fusion protein complex of the invention; b) activating the immune cells; c) administering to the patient the activated immune cells; and d) damaging or killing the disease cells via the activated immune cells sufficient to prevent or treat the disease in the patient.

Administration of the fusion protein complexes of the invention induces an immune response in a subject. For example, administration of the fusion protein complexes of the invention induces an immune response against cells associated with neoplasia, infectious disease, or autoimmune disease. In one aspect, the fusion protein complex of the invention increases immune cell proliferation.

The invention provides methods of stimulating immune responses in a mammal by administering to the mammal an effective amount of the soluble fusion protein complex of the invention. The invention also provides methods of suppressing immune responses in a mammal by administering to the mammal an effective amount of the soluble fusion protein complex of any one of the invention.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, or small compound.

By "T×M" is meant a complex comprising an IL-15N72D:IL-15RαSu/Fc scaffold linked to a binding domain (FIG. 2). An exemplary T×M is an IL-15N72D:IL-15RαSu complex comprising a fusion to a binding domain that specifically recognizes PD-L1 (PD-L1 T×M).

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The term "binding domain" is intended to encompass an antibody, single chain antibody, Fab, Fv, T-cell receptor binding domain, ligand binding domain, receptor binding domain, or other antigen-specific polypeptides known in the art.

The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. F(ab')$_2$, Fab', Fab, Fv) capable of binding the epitope, antigen, or antigenic fragment of interest.

By "binding to" a molecule is meant having a physicochemical affinity for that molecule.

"Detect" refers to identifying the presence, absence, or amount of the analyte to be detected.

By "disease" is meant any condition or disorder that damages or interferes with the normal function of a cell, tissue, or organ. Examples of diseases include neoplasias, autoimmune diseases and viral infections.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full-length polypeptides and nucleic acid, respectively. A nucleic acid fragment of almost any length is employed. For example, illustrative polynucleotide segments with total lengths of about 10,000, about 5,000, about 3,000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The terms "isolated", "purified", or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In particular embodiments, the neoplasia is multiple myeloma, beta-cell lymphoma, urothelial/bladder carcinoma, or melanoma. As used herein, "obtaining" as in "obtaining an agent" includes synthesizing, purchasing, or otherwise acquiring the agent.

By "reduces" is meant a negative alteration of at least 5%, 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100.mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 95% identity to a reference amino acid sequence (for example, any one of the amino acid sequences described herein) or nucleic acid sequence (for example, any one of the nucleic acid sequences described herein). Preferably, such a sequence is at least 99% identical at the amino acid level or nucleotide level to the sequence used for comparison.

Sequence identity is typically measured using sequence analysis software (for example, Sequencher, Gene Codes Corporation, 775 Technology Drive, Ann Arbor, Mich.; Vector NTI, Life Technologies, 3175 Staley Rd. Grand Island, N.Y.). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline. The subject is preferably a mammal in need of such treatment, e.g., a subject that has been diagnosed with B cell lymphoma or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to affect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition, or symptoms associated therewith be completely eliminated.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference.

Genbank and NCBI submissions indicated by accession number cited herein are incorporated herein by reference. All other published references, documents, manuscripts, and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 9A is a schematic diagram illustrating "4 headed" and "2 headed" PD-L1 TxM complexes.

15C show bar charts illustrating the percentage of different immune cell subsets in the spleens and lymph nodes, respectively, of mice treated with PBS, ALT-803, four-headed mouse-specific PD-L1 TxM (T4M-mPD-L1), and two-headed mouse-specific PD-L1 TxM (T2M-mPD-L1).

Figure 16:
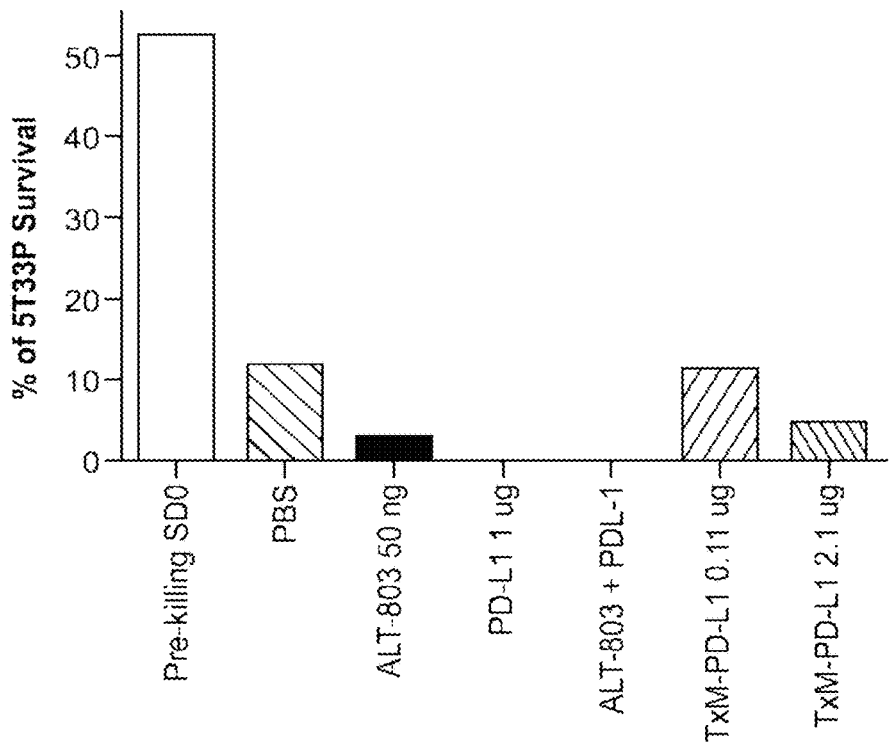

FIG. 16 is a bar chart illustrating the cytotoxicity of immune cells against 5T33 myeloma cells induced by PD-L1 TxM, anti-PD-L1 Ab or ALT-803.

Figure 17:
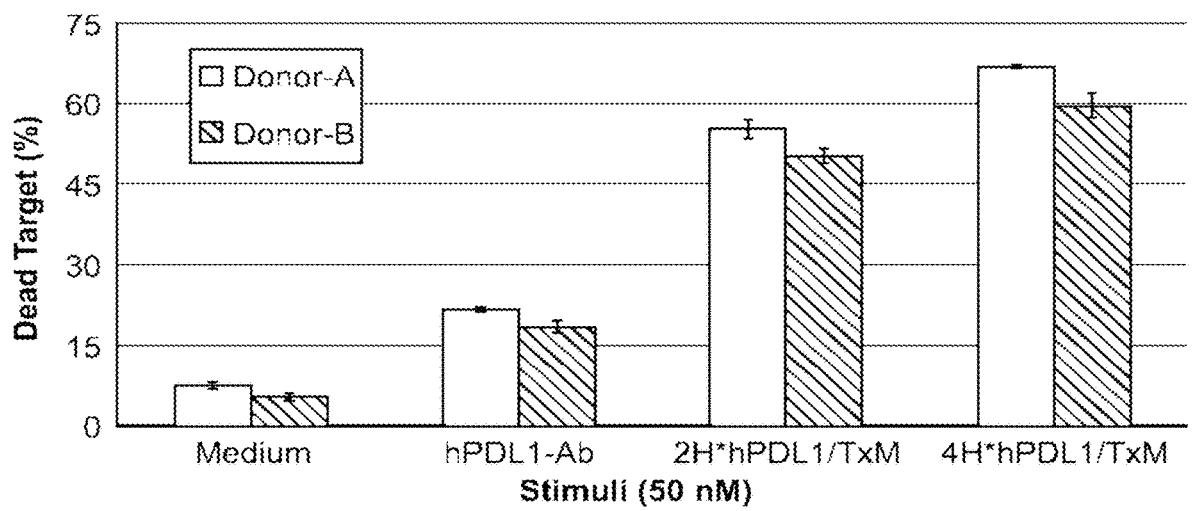

FIG. 17 is a bar chart illustrating the cytotoxicity of human immune cells against PD-L1-positive SW1990 human pancreatic cancer cells induced by anti-human PD-L1 Ab, two-headed human-specific PD-L1 TxM (T4M-mPD-L1), or four-headed human-specific PD-L1 TxM (T2M-mPD-L1) compared to medium alone.

Figure 18:
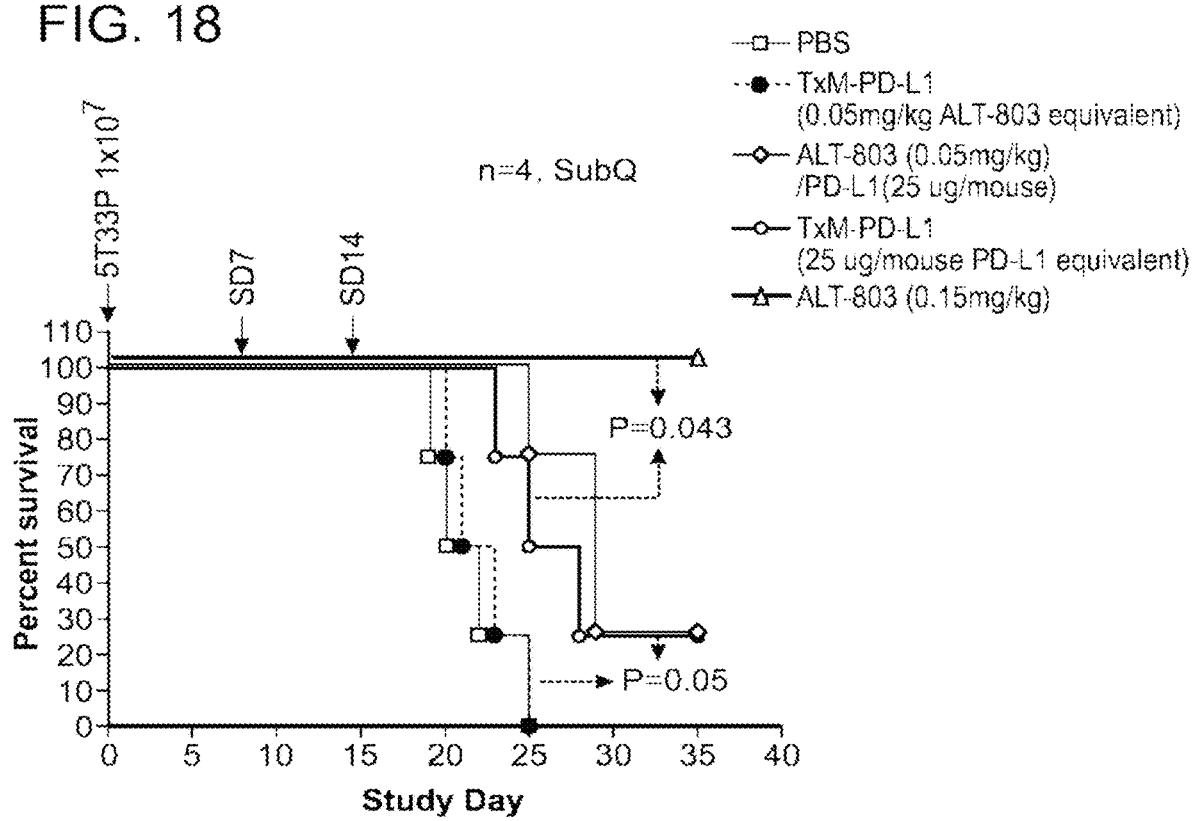

FIG. 18 is a line graph illustrating the survival of mice bearing 5T33 myeloma tumors following treatment with PD-L1 TxM complex, ALT-803, ALT-803+anti-PD-L1 Ab or PBS.

Figure 19:
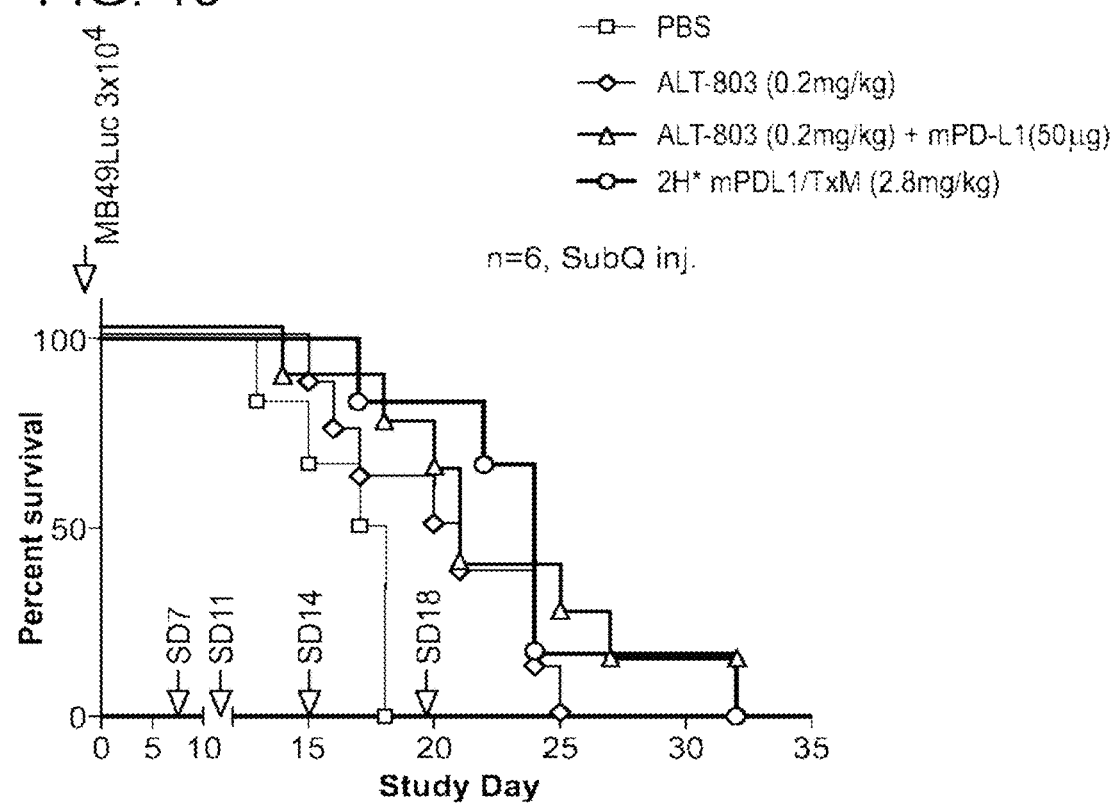

FIG. 19 is a line graph illustrating the survival of mice bearing orthotopic MB491uc bladder tumors following treatment with 2H PD-L1 TxM complex, ALT-803, ALT-803+anti-PD-L1 Ab or PBS.

Figure 20A:
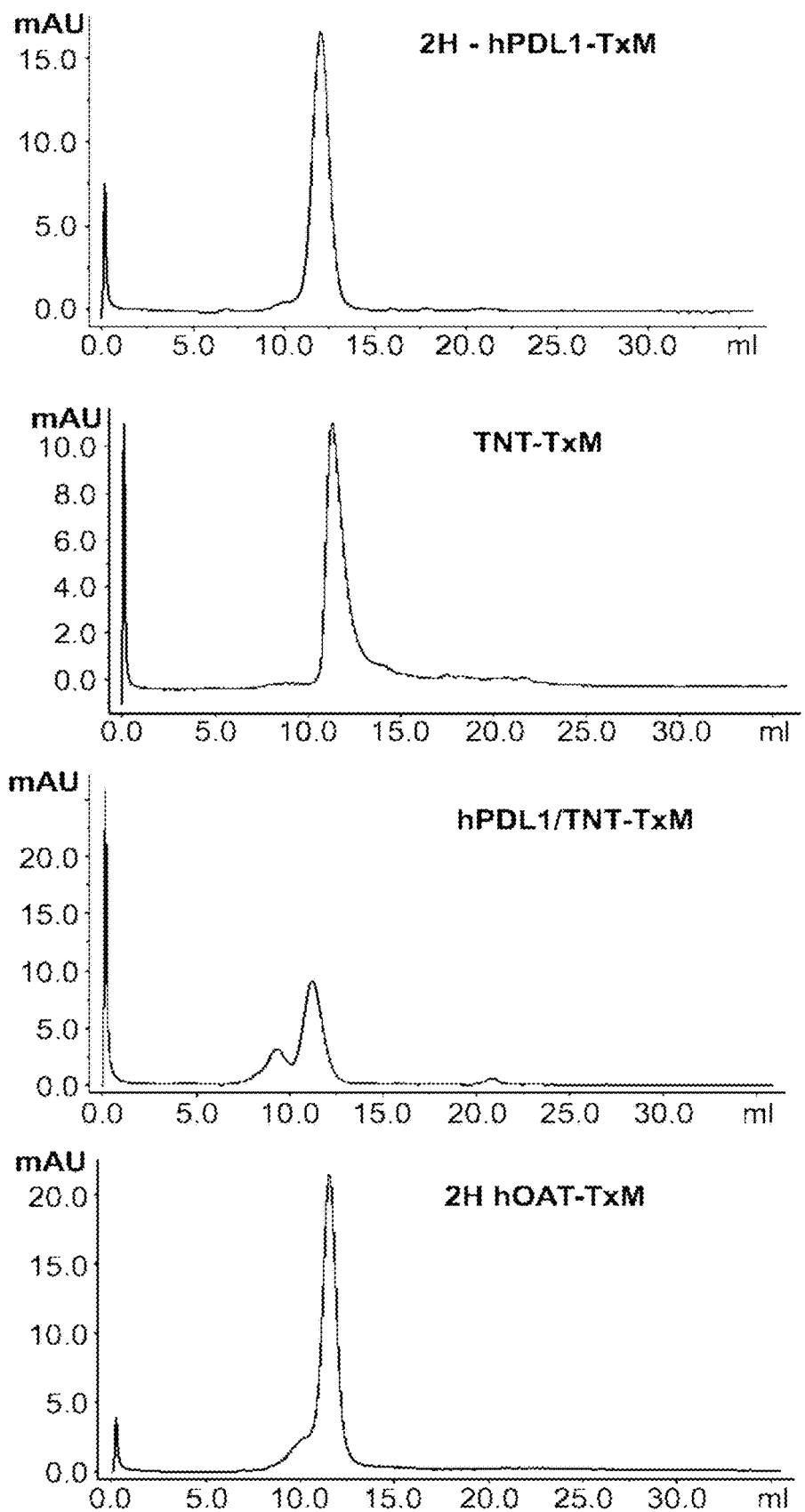
Figure 20B:
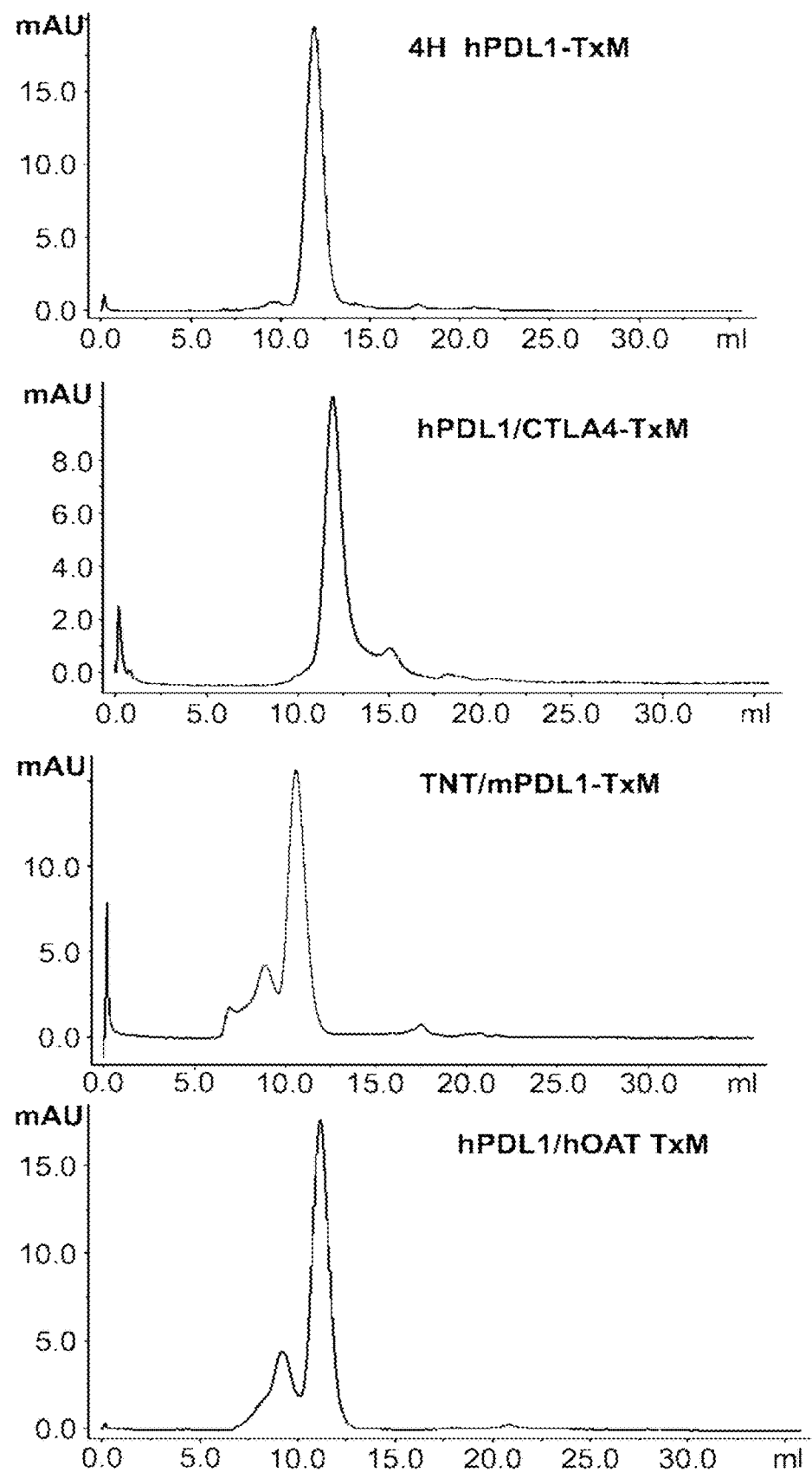

FIGS. 20A and 20B show line graphs representing the chromatographic profiles of different purified TxM proteins following elution on an analytical size exclusion column, demonstrating separation of TxM complexes from protein aggregates.

Figure 21A:
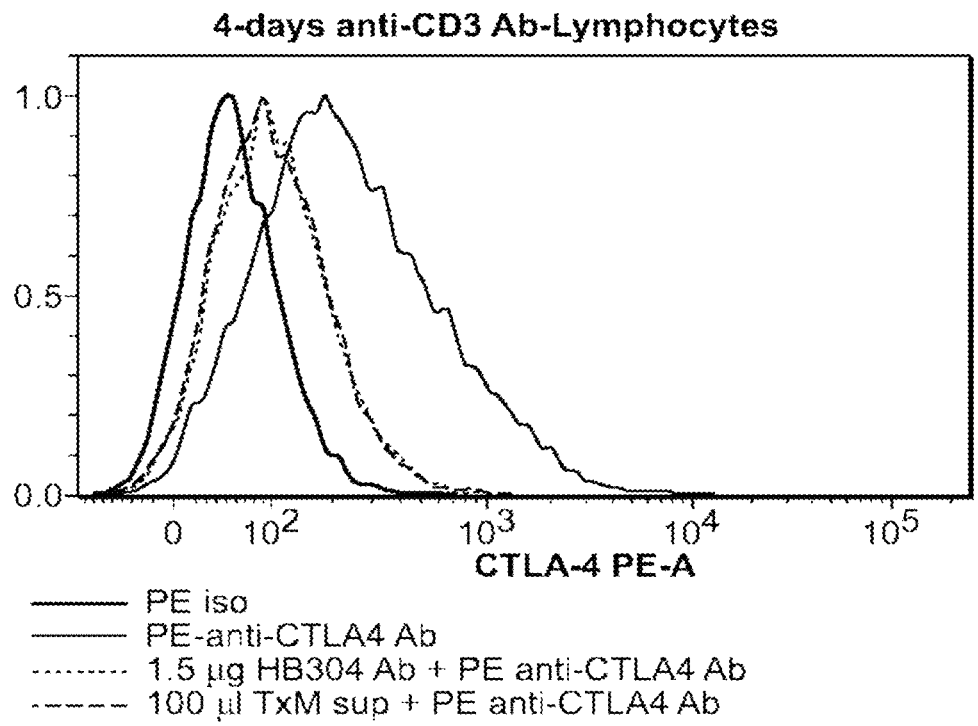
Figure 21B:
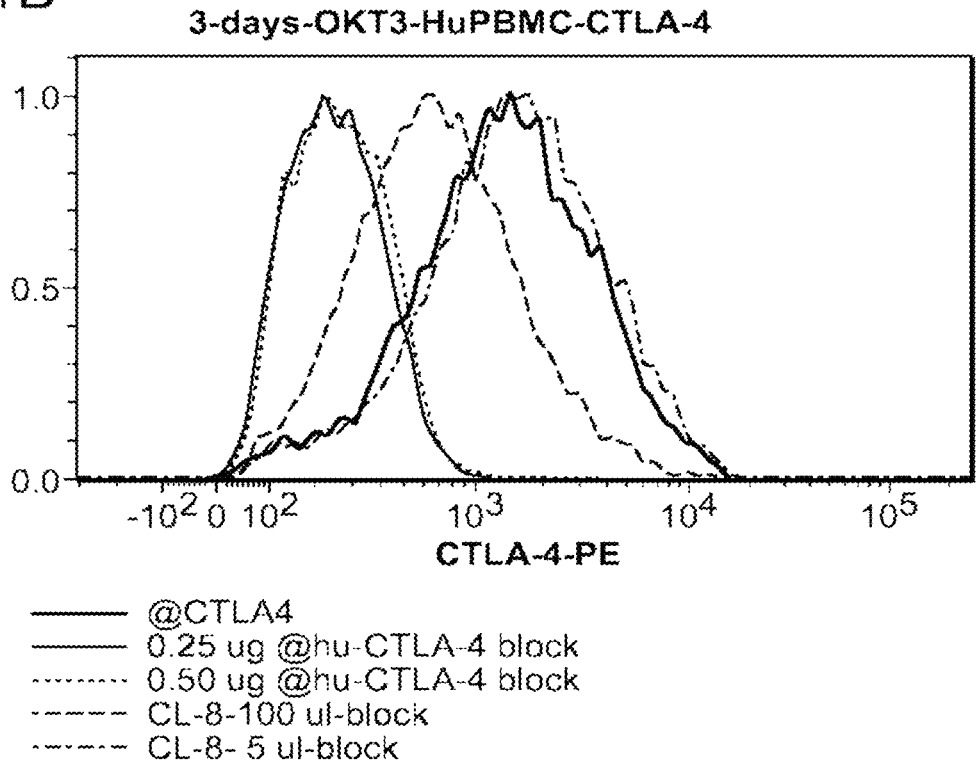

FIG. 21A is a line graph showing the blocking activity of a CTLA-4 TxM complex of CTLA-4 expressed on mouse lymphocytes. FIG. 21B is a line graph showing the blocking activity of a CTLA-4 TxM complex of CTLA-4 expressed on human lymphocytes.

Figure 22A:
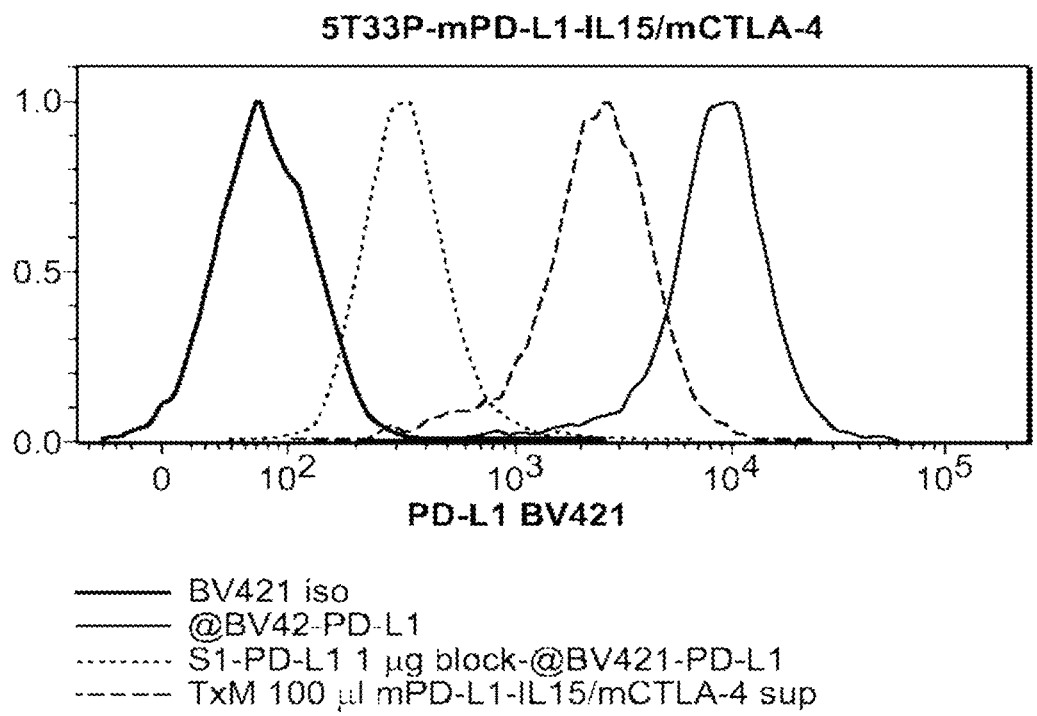
Figure 22B:
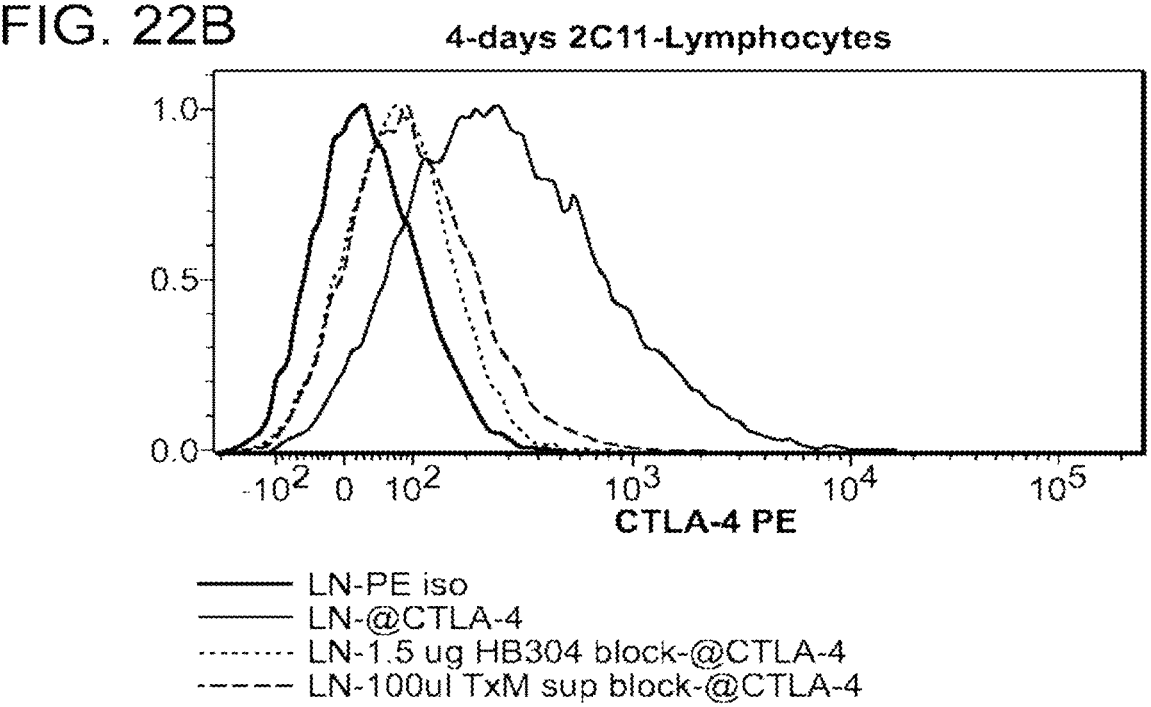

FIG. 22A is a line graph showing the blocking activity of a PD-L1/CTLA-4 TxM complex of PD-L1 expressed on mouse 5T33P tumor cells. FIG. 22B is a line graph showing the blocking activity of a PD-L1/CTLA-4 TxM complex of CTLA-4 expressed on mouse lymphocytes.

Figure 23A:
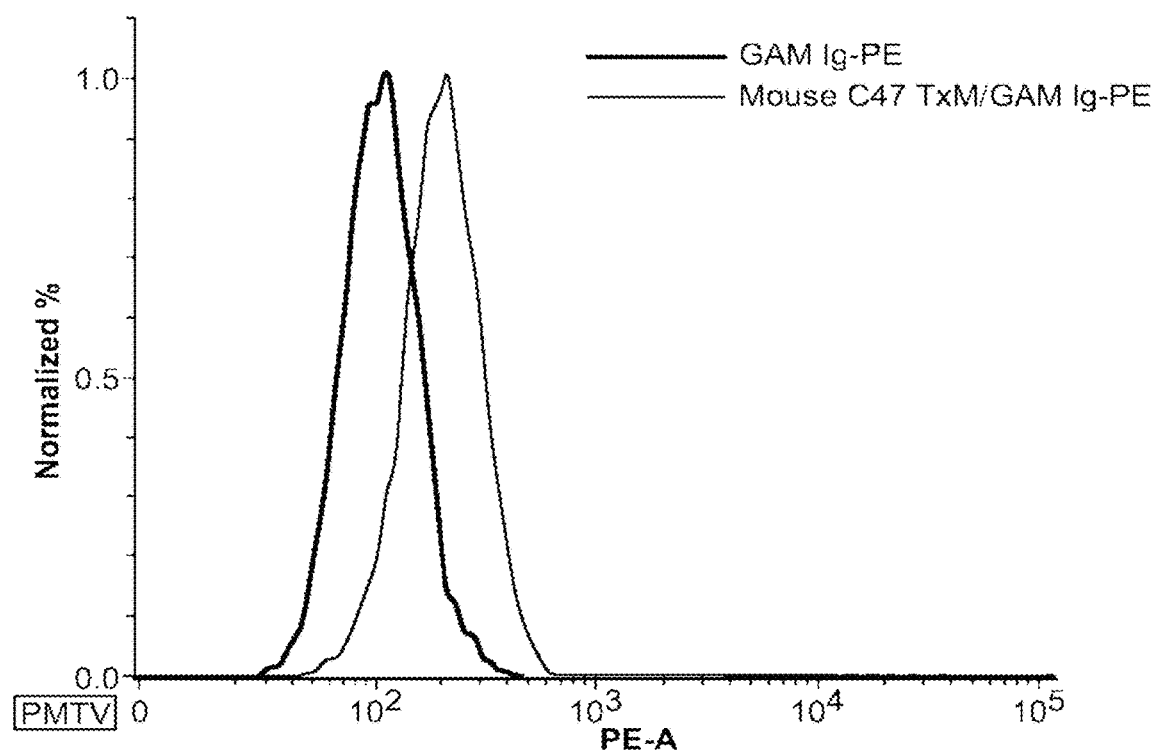
Figure 23B:
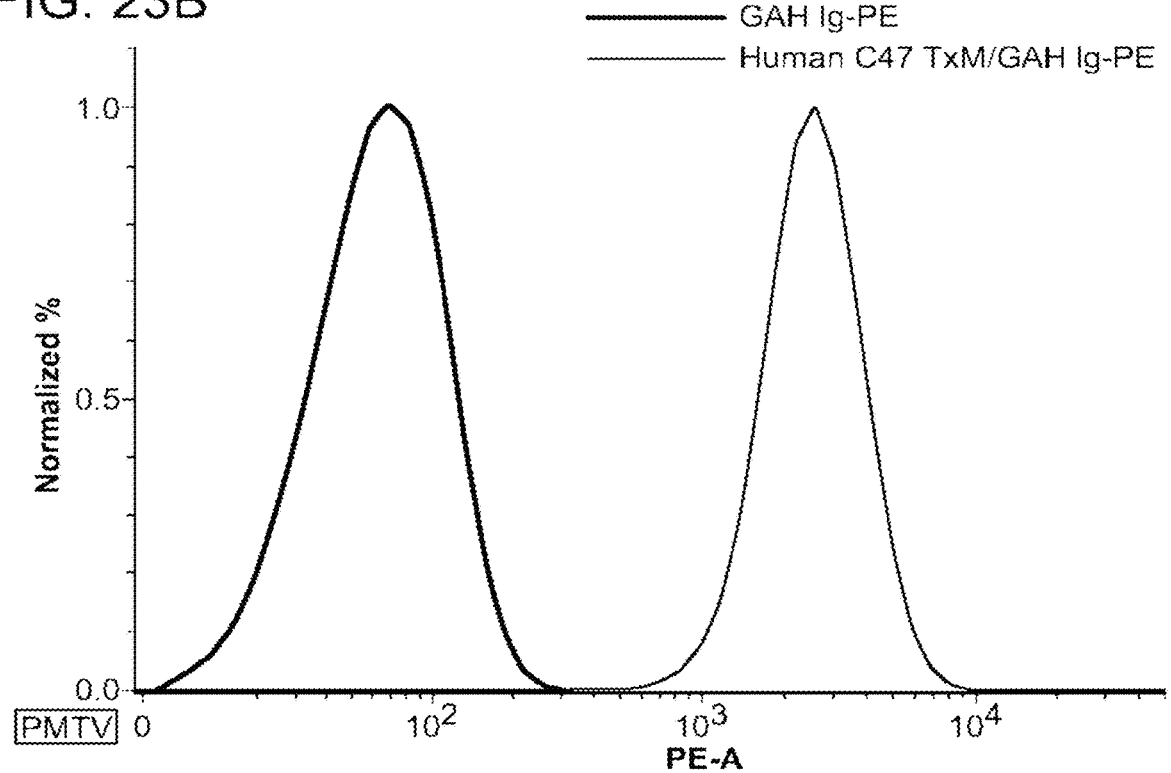

FIG. 23A is a line graph showing the binding activity of a CD47 TxM complex to CD47-bearing mouse B16F10 melanoma tumor cells. FIG. 23B is a line graph showing the binding activity of a CD47 TxM complex to CD47-bearing human Jurkat T cells.

Figure 24A:
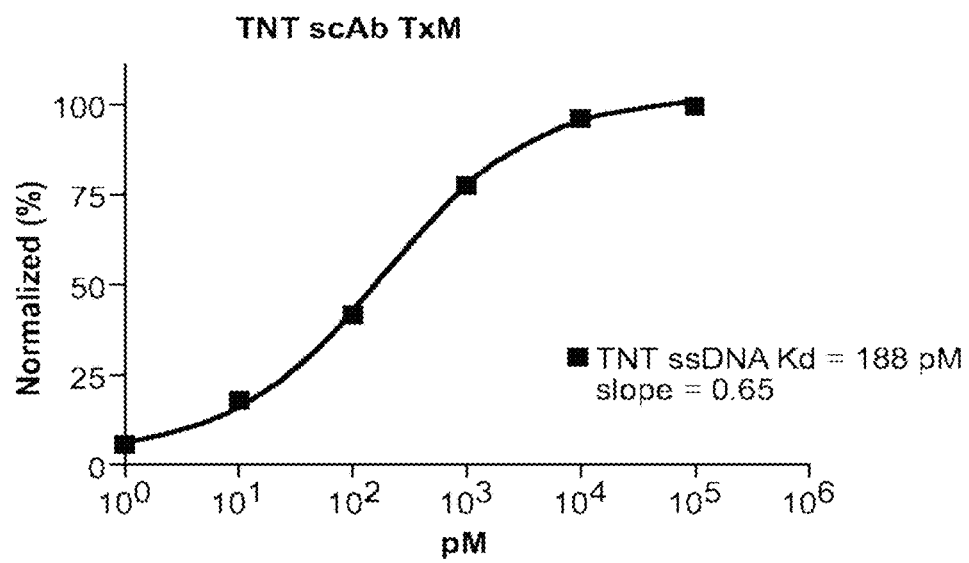
Figure 24B:
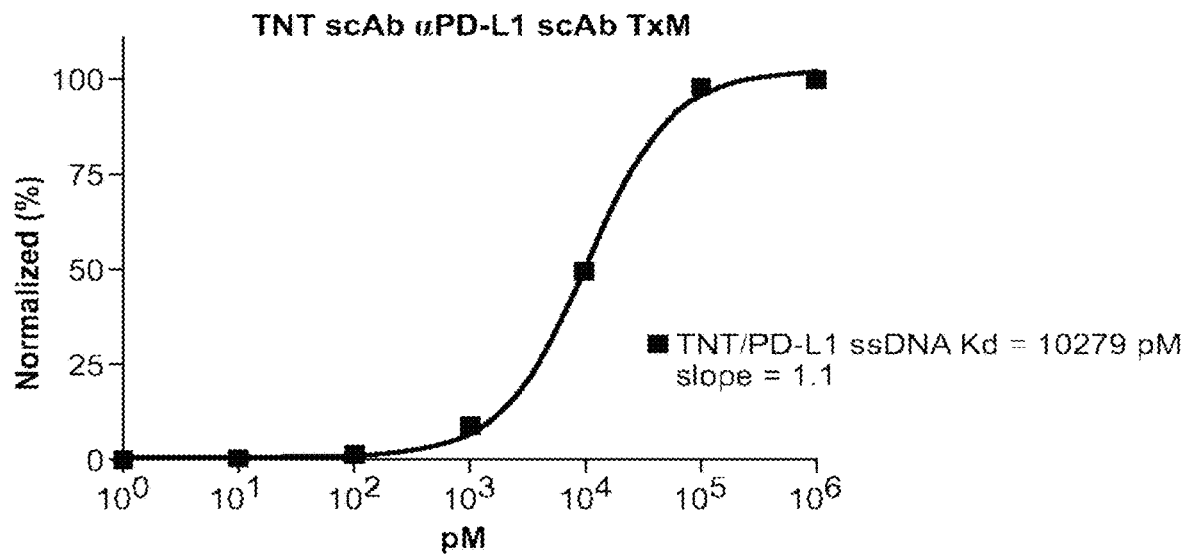

FIG. 24A is a line graph demonstrating the binding activity of an TNT scAb TxM complex to single stranded DNA. FIG. 24B is a line graph demonstrating the binding activity of an TNT scAb/anti-PD-L1 scAb TxM complex to single stranded DNA.

Figure 25A:
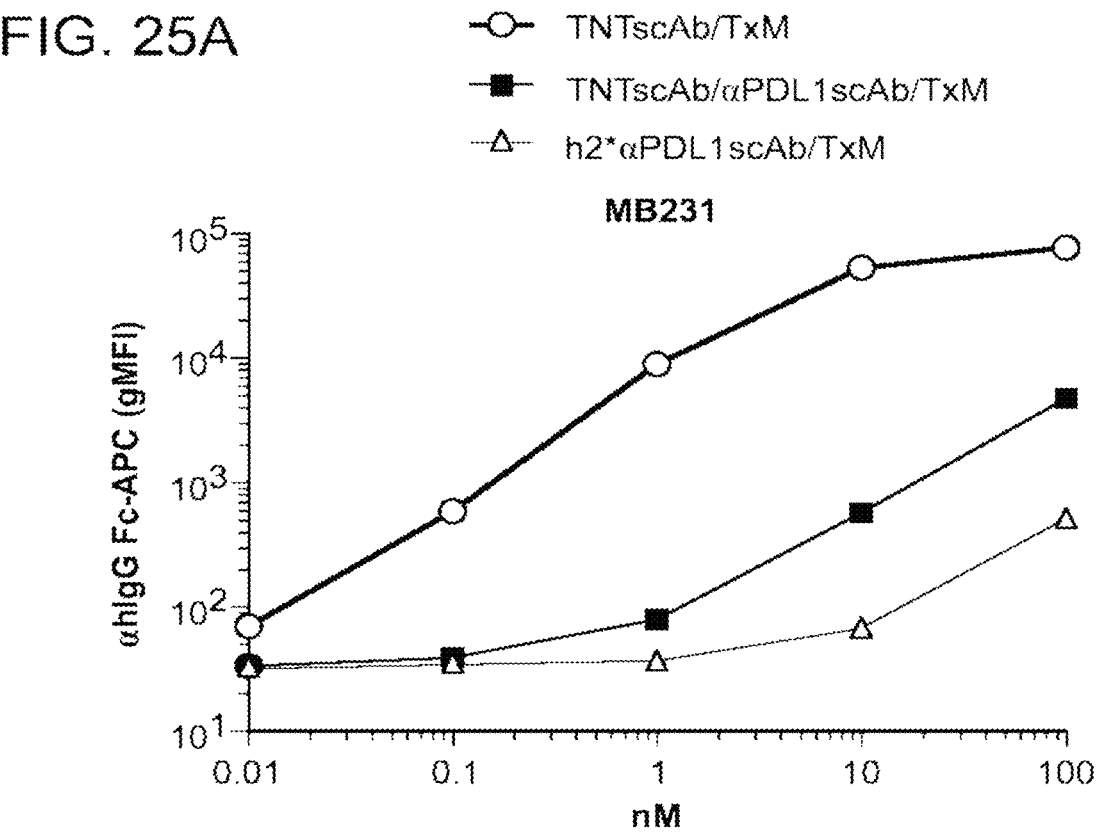
Figure 25B:
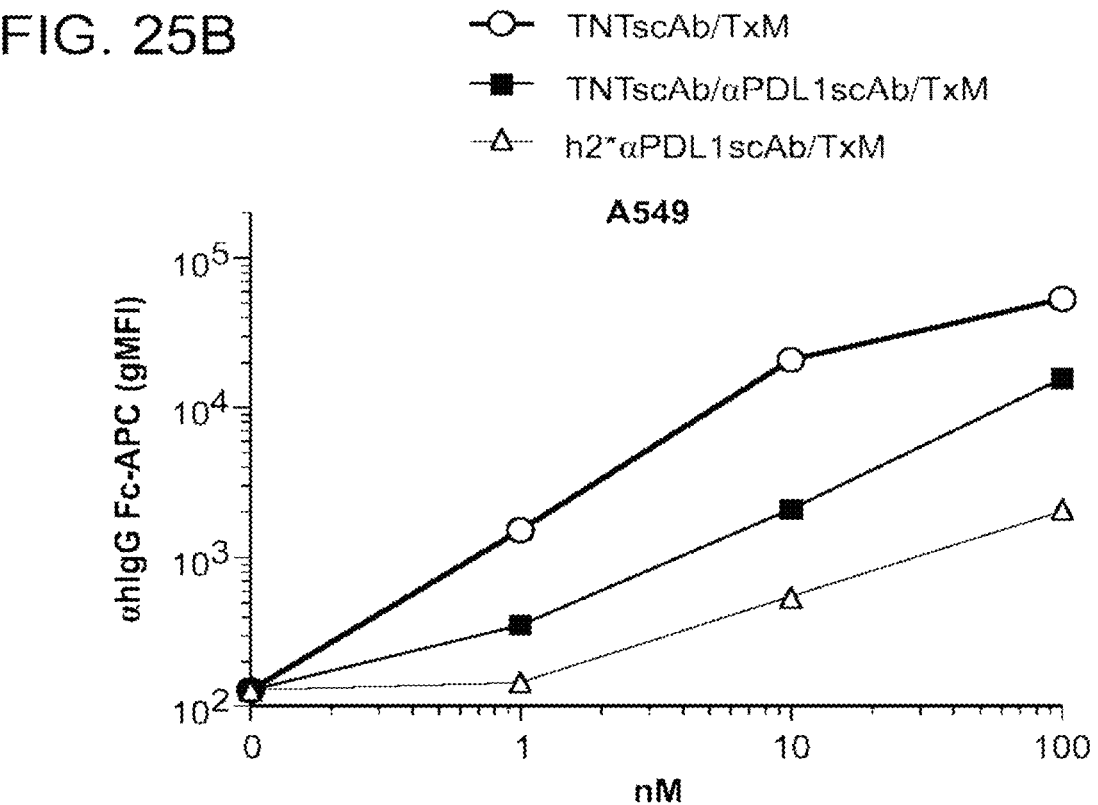

FIG. 25A is a line graph showing the binding activity of TNT scAb TxM, TNT scAb/anti-PD-L1 scAb TxM and 2-headed anti-PD-L1 scAb TxM complexes to permeabilized human MB231 breast cancer cells. FIG. 25B is a line graph showing the binding activity of TNT scAb TxM, TNT scAb/anti-PD-L1 scAb TxM and 2-headed anti-PD-L1 scAb TxM complexes to permeabilized human A549 lung cancer cells.

FIG. 26 is a line graph showing the binding activity of 2-headed hOAT scAb TxM, anti-human PD-L1 scAb/hOAT scAb TxM, 2-headed anti-human PD-L1 scAb TxM complexes and hOAT and anti-human PD-L1 control Abs to human TF-positive PD-L1-positive SW1990 human pancreatic cancer cells.

Figure 27A:
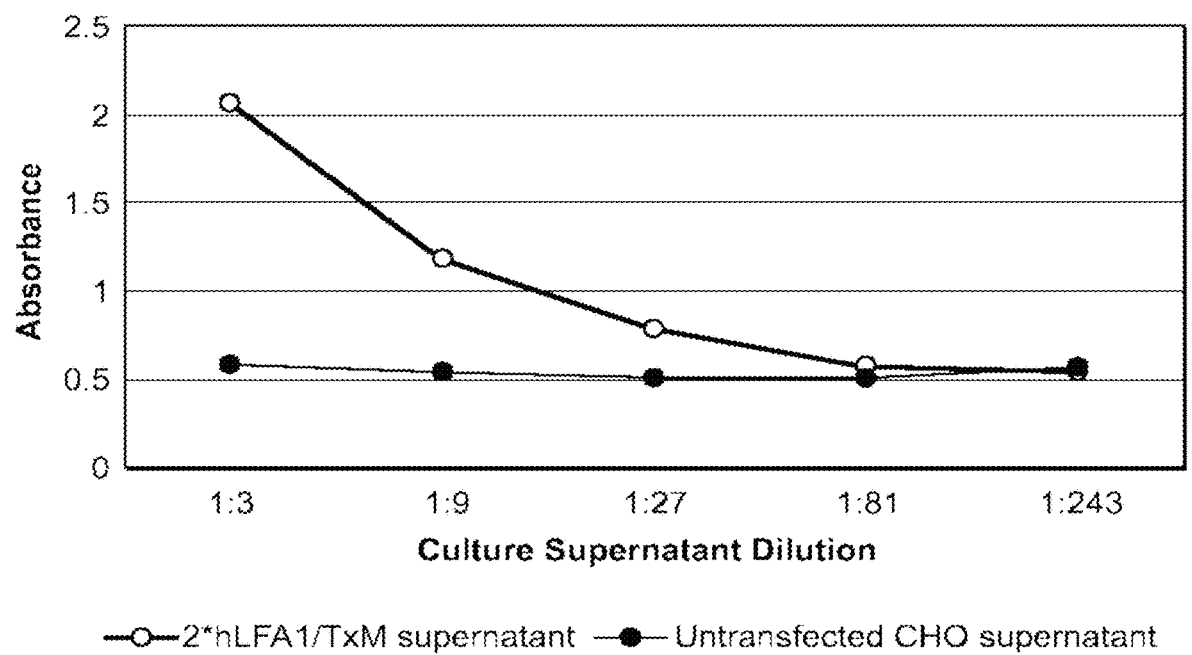
Figure 27B:
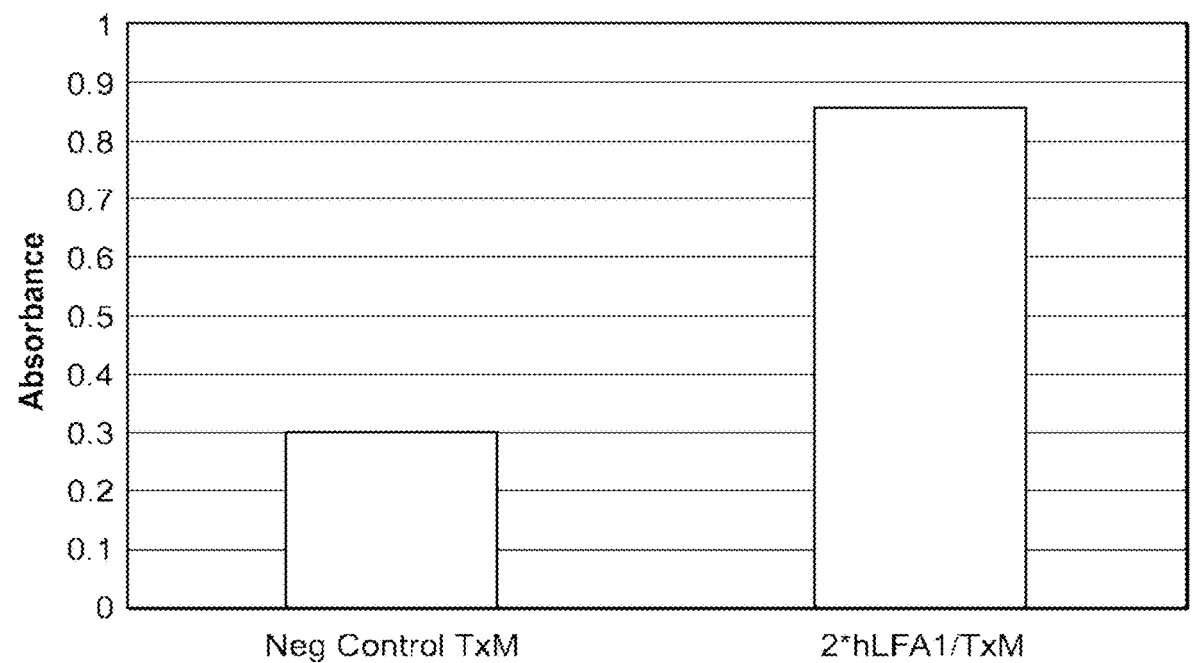

FIG. 27A is a line graph demonstrating the binding activity of an LFA-1 TxM complex to antibodies specific to human IL-15 and human IgG. FIG. 27B is a bar graph showing the binding activity of an LFA-1 TxM complex to ICAM-1.

Figure 28:
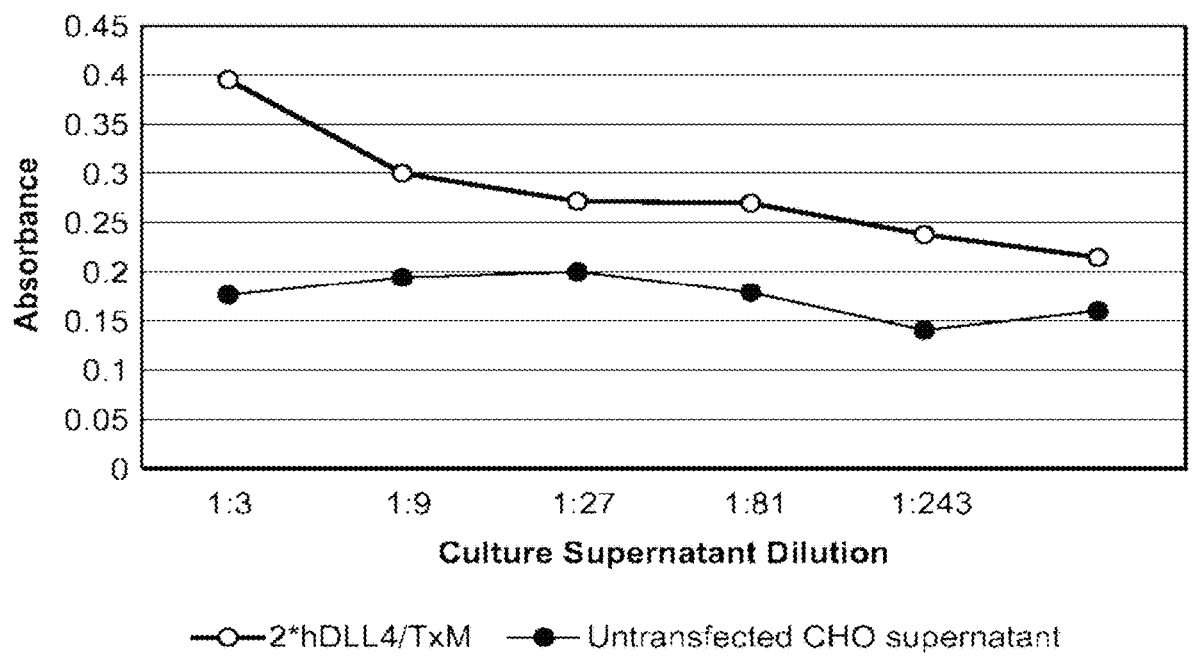

FIG. 28 is a line graph demonstrating the binding activity of a Notch1-specific TxM complex to antibodies specific to human IL-15 and human IgG.

Figure 29:
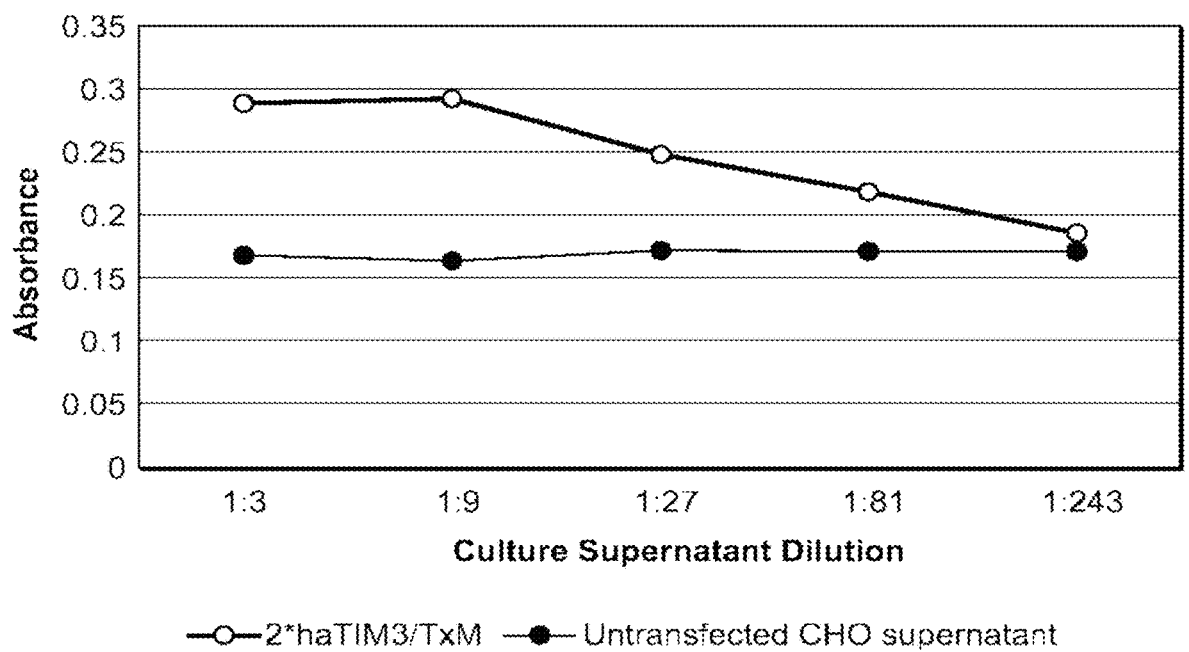

FIG. 29 is a line graph demonstrating the binding activity of an anti-human TIM3 scAb TxM complex to antibodies specific to human IL-15 and human IgG.

Figure 30A:
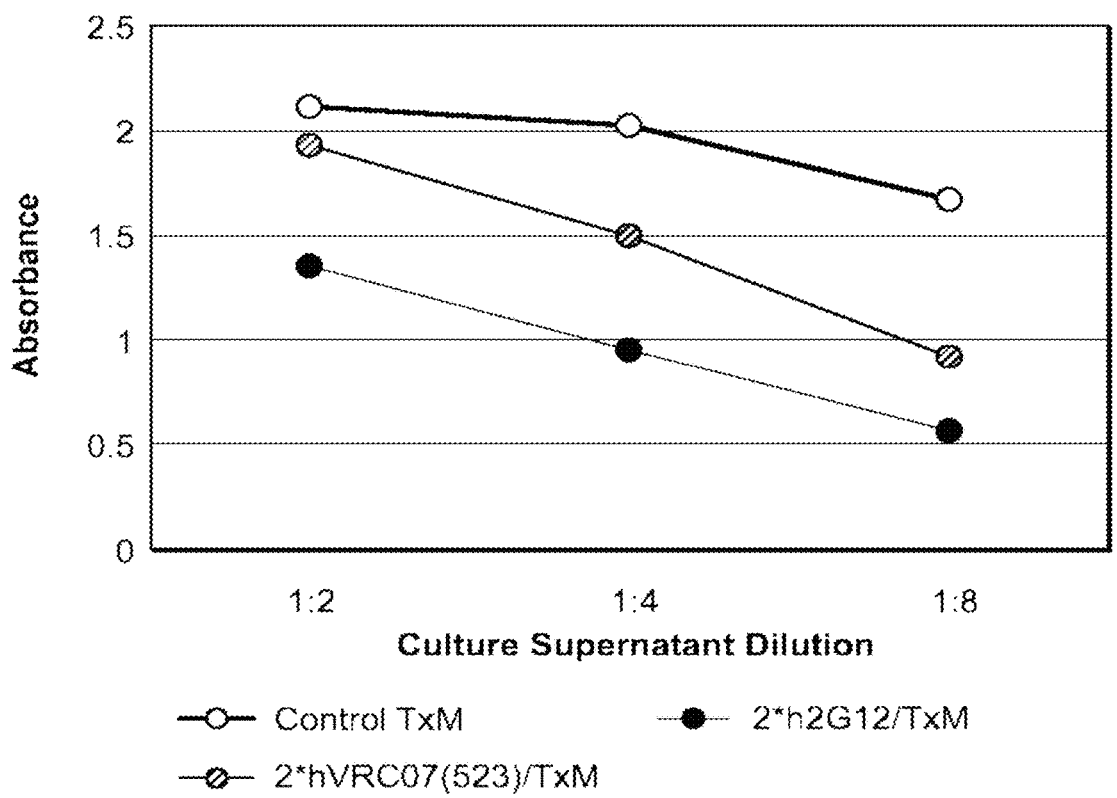
Figure 30B:
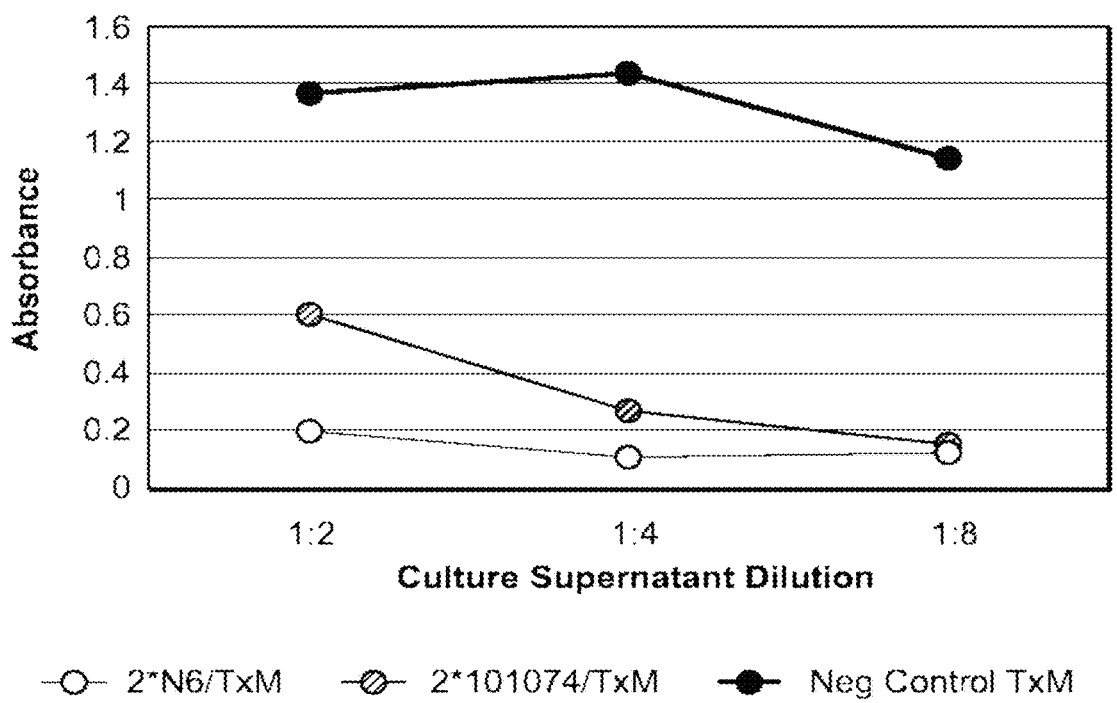
Figure 30C:
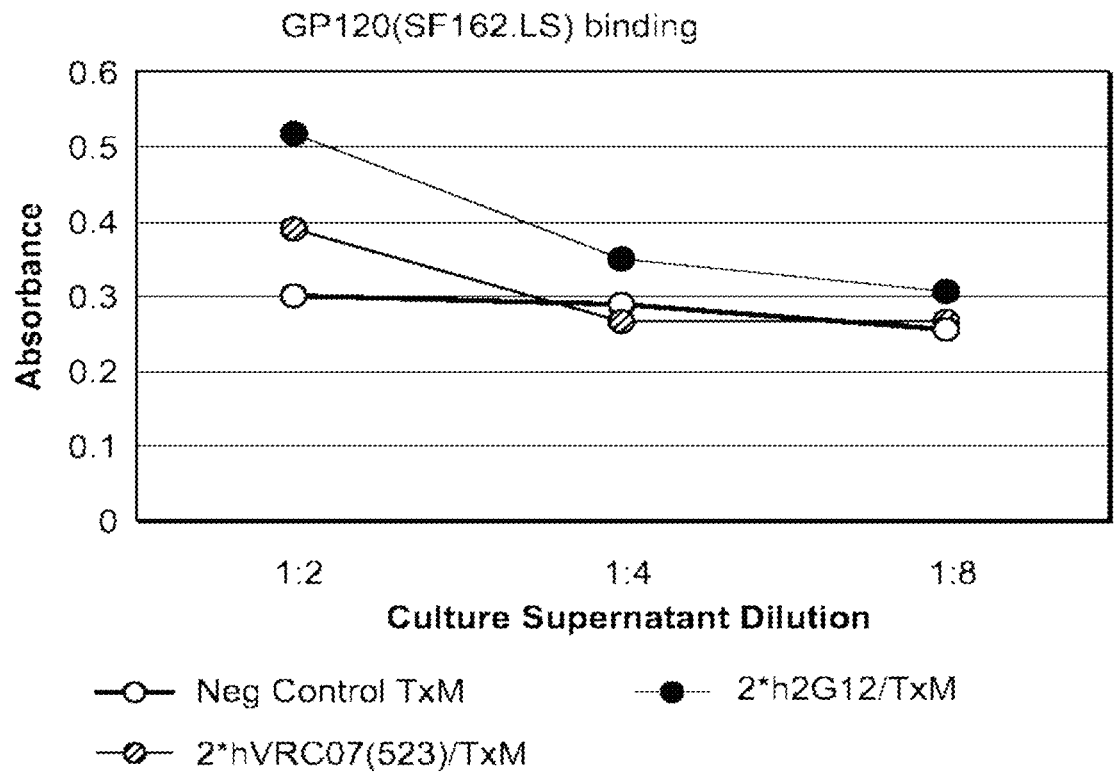
Figure 30D:
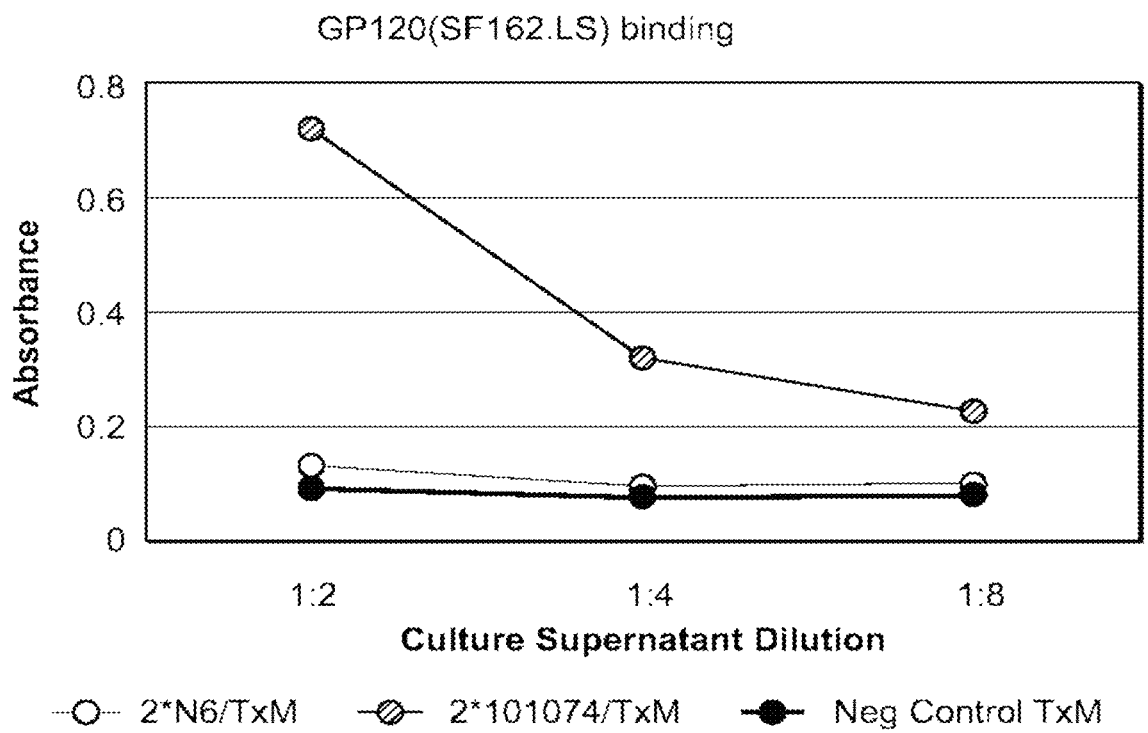
Figure 30E:
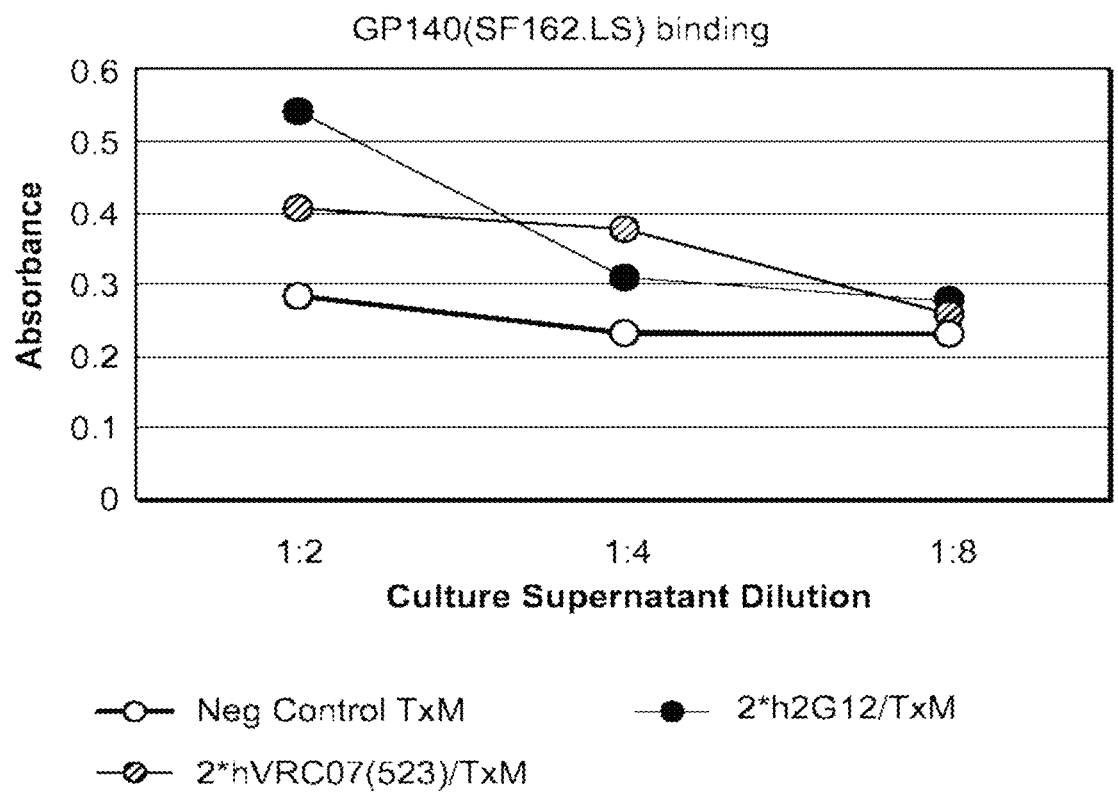
Figure 30F:
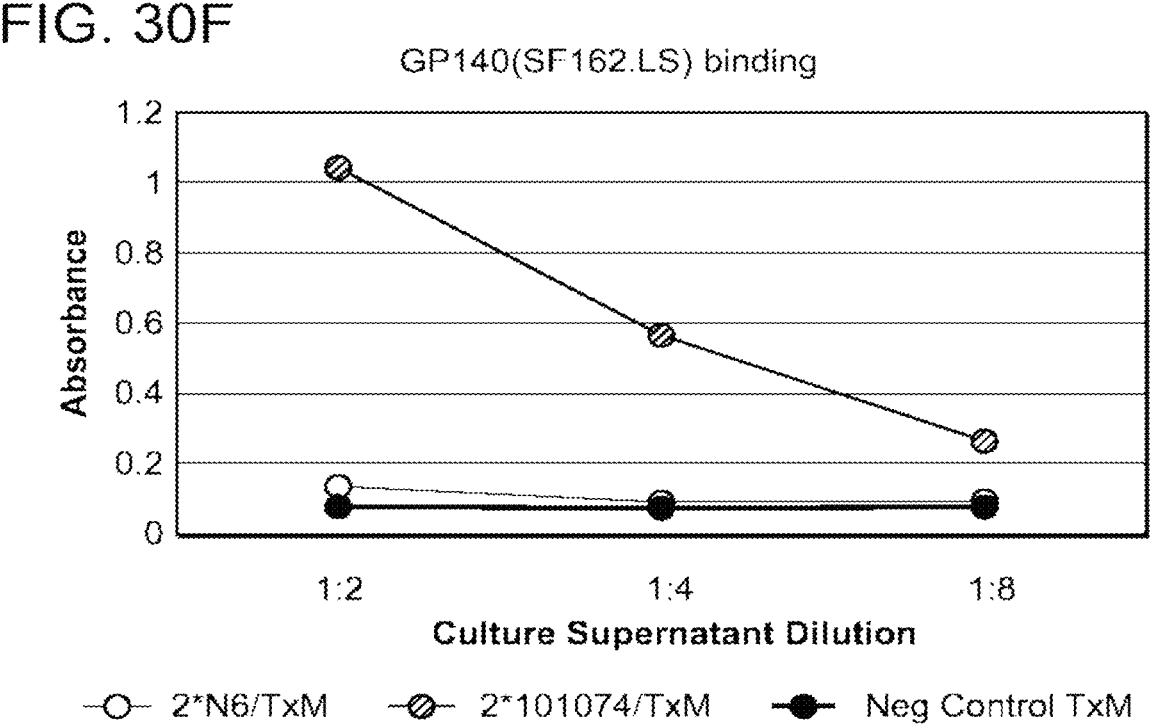

FIG. 30A and FIG. 30B are line graphs demonstrating the binding activity of HIV-specific bNAb scFv TxM complexes to antibodies specific to human IL-15 and human IgG.

FIG. 30C through FIG. 30F show line graphs demonstrating the binding activity of HIV-specific bNAb TxM complexes to HIV envelope proteins.

Figure 31:
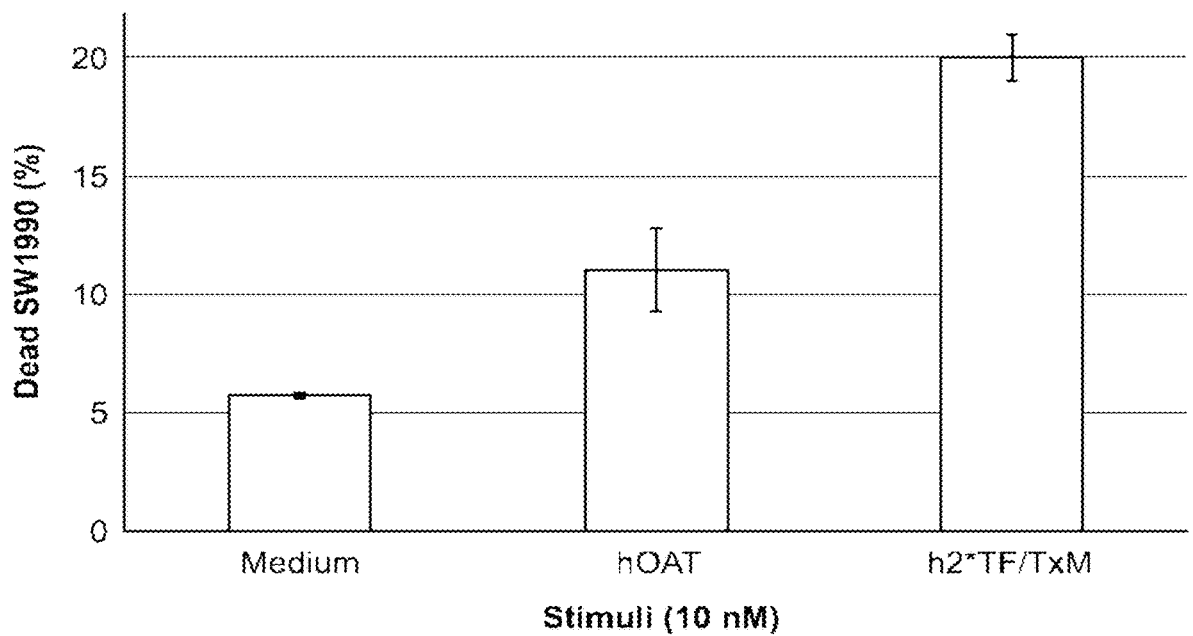

FIG. 31 is a bar chart illustrating the cytotoxicity of human immune cells against human TF-positive SW1990 human pancreatic cancer cells induced by 2-headed hOAT scAb TxM or hOAT control Ab compared to medium alone.

DETAILED DESCRIPTION

Figure 1:
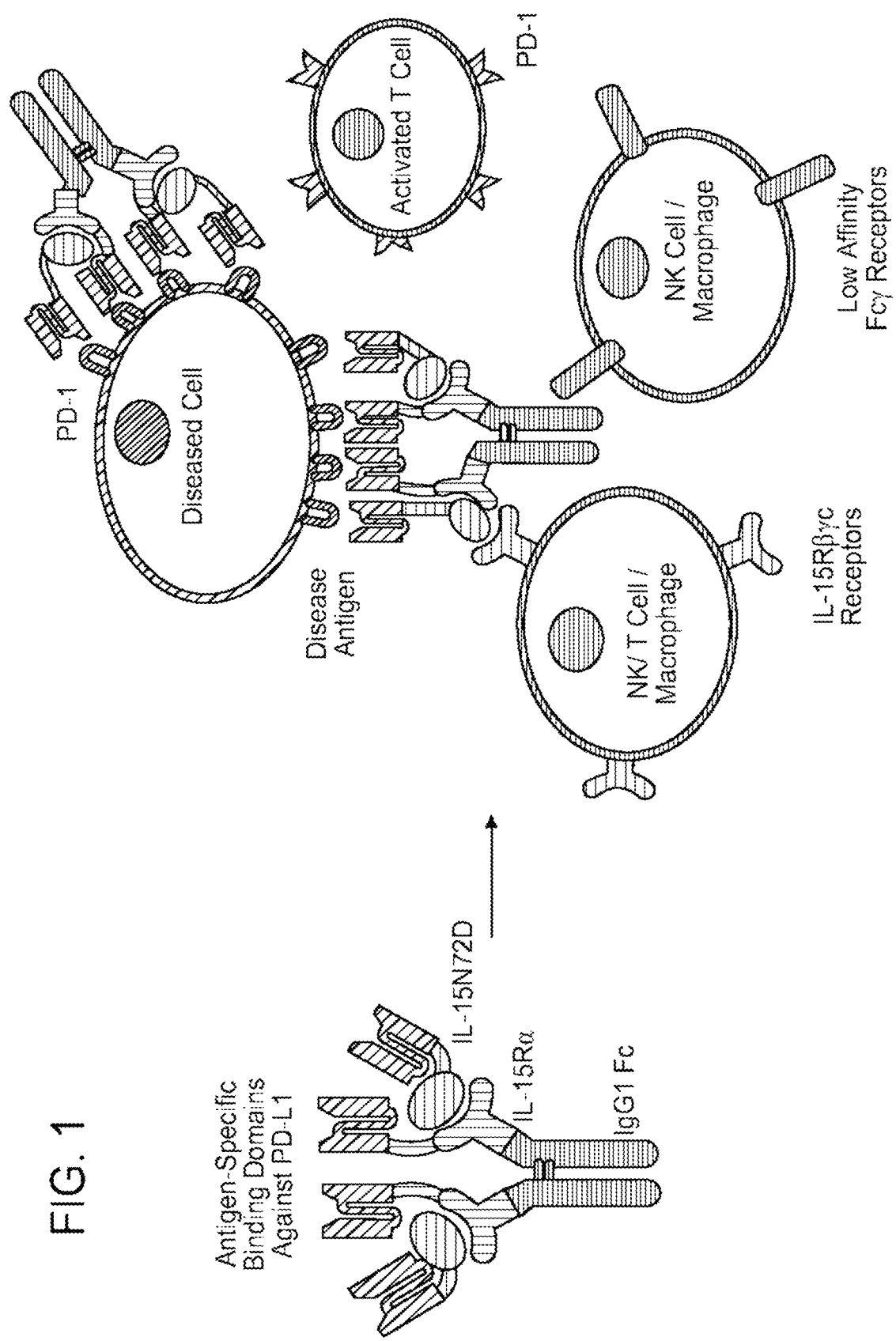
FIG. 1 is a schematic diagram illustrating the activity of the PD-L1 TxM complex comprising anti-PD-L1 scAb/huIL-15N72D and anti-PD-L1 scAb/huIL-15RαSu/Fc fusion proteins, and its immune-mediated effects against disease cells expressing PD-L1 antigen.

The invention is based, at least in part, on the surprising discovery that multi-specific IL-15-based protein complexes enhance the activity of immune cells and promote their activity against disease cells, thereby resulting in reduction or prevention of disease. These protein complexes also show increased binding to disease and target antigens. Provided herein are multi-specific protein complexes with one domain comprising IL-15 or a functional variant and a binding domain comprising a disease-specific binding domain, immune checkpoint inhibitor or immune agonist. Such protein complexes have utility in methods for treating a neoplasia, infectious disease, or autoimmune disease in a subject. Specifically, as described in detail below, a soluble anti-PD-L1 scAb/huIL-15N72D:anti-PD-L1 scAb/huIL-15RαSu/huIgG1 Fc complex ("PD-L1 TxM") stimulated immune cells to kill tumor target cells (FIG. 1). Thus, provided herein are compositions featuring PD-L1 TxM and methods of using such compositions to enhance an immune response against a neoplasia (e.g., solid and hematologic tumors).

As described herein, the use of proteins with the capability of targeting diseased cells for host immune recognition and response is an effective strategy for treating cancer, infectious diseases, and autoimmune diseases. As described in U.S. Pat. No. 8,507,222 (incorporated herein by reference), a protein scaffold comprising IL-15 and IL-15 receptor α domains has been used to generate multi-specific proteins capable of recognizing antigens on disease cells and receptors on immune cells. See, U.S. Pat. No. 8,507,222 at Example 15. Described herein is the generation of soluble multi-specific protein complexes comprising IL-15 and IL-15 receptor α linked to one or more binding domains recognizing immune checkpoint or signaling molecules. In some cases, these complexes also comprise binding domains that recognize antigens, such as PD-L1, ssDNA, CD20, HER2, EGFR, CD19, CD38, CD52, GD2, CD33, Notch1, intercellular adhesion molecule 1 (ICAM-1), tissue factor, HIV envelope or other tumor antigens, expressed on disease cells.

In some cases, the binding domain comprises a single chain antibody wherein an immunoglobulin light chain variable domain covalently linked to an immunoglobulin heavy chain variable domain by a polypeptide linker sequence. The single chain antibody domain can be arranged in either the VH-linker-VL or VL-linker-VH format. Alternatively, the binding domain comprises a soluble or extracellular ligand or receptor domain capable of acting as an immune checkpoint inhibitor or immune agonist. The binding domains recognizing an immune checkpoint or signaling molecule are linked to either the N- or C-termini of the IL-15 or IL-15 receptor α proteins with or without an additional linker sequence so long as binding activity is maintained. Preferably, the binding domain is linked to the N-terminus of the human IL-15N72D superagonist protein (huIL-15N72D). Alternatively, the binding domain is linked to the C-terminus of the human IL-15N72D protein. Preferably, the binding domain is linked to the N-terminus of the human IL-15 receptor α sushi domain (huIL-15RαSu). Alternatively, the binding domain is linked to the C-terminus of the huIL-15RαSuFc protein. In some cases, the multi-specific protein complexes of the invention further comprise an IgG Fc domain for protein dimerization and recognition of CD16 receptors on immune cells. Such a domain mediates stimulation of antibody-dependent cellular cytotoxicity (ADCC), antibody-dependent cellular phagocytosis (ADCP) and complement-dependent cytotoxicity (CDC) against target cells. In some examples, it is useful to employ Fc domains with enhanced or decreased CD16 binding activity. In one aspect, the Fc domain contains amino acid substitutions L234A and L235A (LALA) (number based on Fc consensus sequence) that reduce ADCC activity, but retain the ability to form disulfide-bound dimers.

Interleukin-15

Interleukin-15 (IL-15) is an important cytokine for the development, proliferation, and activation of effector NK cells and $CD8^+$ memory T cells. IL-15 binds to the IL-15 receptor α (IL-15Rα) and is presented in trans to the IL-2/IL-15 receptor β-common γ chain (IL-15Rβ$γ_c$) complex on effector cells. IL-15 and IL-2 share binding to the IL-15Rβ$γ_c$, and signal through STAT3 and STAT5 pathways. However, unlike IL-2, IL-15 does not support maintenance of $CD4^+CD25^+ToxP3^+$ regulatory T (Treg) cells or induce cell death of activated $CD8^+$ T cells, effects that may have limited the therapeutic activity of IL-2 against multiple myeloma. Additionally, IL-15 is the only cytokine known to provide anti-apoptotic signaling to effector $CD8^+$ T cells. IL-15, either administered alone or as a complex with the IL-15Rα, exhibits potent anti-tumor activities against well-established solid tumors in experimental animal models and, thus, has been identified as one of the most promising immunotherapeutic drugs that could potentially cure cancer.

To facilitate clinical development of an IL-15-based cancer therapeutic, an IL-15 mutant (IL-15N72D) with increased biological activity compared to IL-15 was identified (Zhu et al., J Immunol, 183: 3598-3607, 2009). The pharmacokinetics and biological activity of this IL-15 super-agonist (IL-15N72D) was further improved by the creation of IL-15N72D:IL-15Rα/Fc fusion complex (ALT-803), such that the super agonist complex has at least 25-times the activity of the native cytokine in vivo (Han et al., Cytokine, 56: 804-810, 2011).

Immune Checkpoint Inhibitor and Immune Agonist Domains

In other embodiments, the binding domain is specific to an immune checkpoint or signaling molecule or its ligand and acts as an inhibitor of immune checkpoint suppressive activity or as an agonist of immune stimulatory activity. Such immune checkpoint and signaling molecules and ligands include PD-1, PD-L1, PD-L2, CTLA-4, CD28, CD80, CD86, B7-H3, B7-H4, B7-H5, ICOS-L, ICOS, BTLA, CD137L, CD137, HVEM, KIR, 4-1BB, OX40L, CD70, CD27, CD47, CIS, OX40, GITR, IDO, TIM3, GAL9, VISTA, CD155, TIGIT, LIGHT, LAIR-1, Siglecs and A2aR (Pardoll D M. 2012. Nature Rev Cancer 12:252-264, Thaventhiran T, et al. 2012. J Clin Cell Immunol S12:004).

Additionally, preferred antibody domains of the invention may include ipilimumab and/or tremelimumab (anti-CTLA4), nivolumab, pembrolizumab, pidilizumab, TSR-042, ANB011, AMP-514 and AMP-224 (a ligand-Fc fusion) (anti-PD1), atezolizumab (MPDL3280A), avelumab (MSB0010718C), durvalumab (MEDI4736), MEDI0680, and BMS-9365569 (anti-PDL1), MEDI6469 (anti-OX40 agonist), BMS-986016, IMP701, IMP731, IMP321 (anti-LAG3) and GITR ligand.

Antigen-Specific Binding Domains

Antigen-specific binding domains consist of polypeptides that specifically bind to targets on diseased cells. Alternatively, these domains may bind to targets on other cells that support the diseased state, such as targets on stromal cells that support tumor growth or targets on immune cells that support disease-mediated immunosuppression. Antigen-specific binding domains include antibodies, single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins (Weidle, U H, et al. 2013. Cancer Genomics & Proteomics 10: 155-168)) known in the art.

In certain embodiments, the antigen for the antigen-specific binding domain comprises a cell surface receptor or ligand. In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

Preferably, the antigen-specific binding domain is capable of binding to an antigen on a tumor cell. Tumor-specific binding domain may be derived from antibodies approved for treatment of patients with cancer include rituximab, ofatumumab, and obinutuzumab (anti-CD20 Abs); trastuzumab and pertuzumab (anti-HER2 Abs); cetuximab and panitumumab (anti-EGFR Abs); and alemtuzumab (anti-CD52 Ab). Similarly, binding domains from approved antibody-effector molecule conjugates specific to CD20 ($^{90}$Y-labeled ibritumomab tiuxetan, $^{131}$I-labeled tositumomab), HER2 (ado-trastuzumab emtansine), CD30 (brentuximab vedotin) and CD33 (gemtuzumab ozogamicin) (Sliwkowski M X, Mellman I. 2013 Science 341:1192) could be used.

Additionally, preferred binding domains of the invention may include various other tumor-specific antibody domains known in the art. The antibodies and their respective targets for treatment of cancer include but are not limited to nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti-CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxorubicin immunoconjugate (anti-Lewis-Y antigen), CC49 (anti-TAG-72), cedelizumab (anti-CD4), Ch.14.18 (anti-GD2), ch-TNT (anti-DNA associated antigens), citatuzumab bogatox (anti-EpCAM), cixutumumab (anti-IGF-1 receptor), clivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HER3), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-5AC), epitumomab cituxetan (anti-episialin), epratuzumab (anti-CD22), ertumaxomab (anti-HER2/neu, CD3), etaracizumab (anti-integrin αvβ3), faralimomab (anti-Interferon receptor), farletuzumab (anti-folate receptor 1), FBTA05 (anti-CD20), ficlatuzumab (anti-HGF), figitumumab (anti-IGF-1 receptor), flanvotumab (anti-TYRP1(glycoprotein 75)), fresolimumab (anti-TGF β), futuximab (anti-EGFR), galiximab (anti-CD80), ganitumab (anti-IGF-I), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), IMAB362 (anti-CLDN18.2), IMC-CS4 (anti-CSF1R), IMC-TR1 (TGFβRII), imgatuzumab (anti-EGFR), inclacumab (anti-selectin P), indatuximab ravtansine (anti-SDC1), inotuzumab ozogamicin (anti-CD22), intetumumab (anti-CD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (anti-PDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor α-chain), milatuzumab (anti-CD74), minretumomab (anti-TAG-72), mitumomab (anti-GD3 ganglioside), mogamulizumab (anti-CCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-Rα), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MUC1), parsatuzumab (anti-EGFL7), pascolizumab (anti-IL-4), patritumab (anti-HER3), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-FAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vantictumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (anti-integrin α5β1), vorsetuzumab mafodotin (anti-CD70), votumumab (anti-tumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAP1), and GDC-0199 (anti-Bcl-2).

Other antibody domains or tumor target binding proteins useful in the invention (e.g. TCR domains) include, but are not limited to, those that bind the following antigens (note, the cancer indications indicated represent non-limiting examples): aminopeptidase N (CD13), annexin A1, B7-H3 (CD276, various cancers), CA125 (ovarian cancers), CA15-3 (carcinomas), CA19-9 (carcinomas), L6 (carcinomas), Lewis Y (carcinomas), Lewis X (carcinomas), alpha fetoprotein (carcinomas), CA242 (colorectal cancers), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma, B-cell neoplasmas, autoimmune diseases), CD21 (B-cell lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (metastatic melanoma, sarcoma), CD52 (leukemia), CD56 (small cell lung cancers, ovarian cancer, Merkel cell carcinoma, and the liquid tumor, multiple myeloma), CD66e (carcinomas), CD70 (metastatic renal cell carcinoma and non-Hodgkin lymphoma), CD74 (multiple myeloma), CD80 (lymphoma), CD98 (carcinomas), CD123 (leukemia), mucin (carcinomas), CD221 (solid tumors), CD22? (breast, ovarian cancers), CD262 (NSCLC and other cancers), CD309 (ovarian cancers), CD326 (solid tumors), CEACAM3 (colorectal, gastric cancers), CEACAM5 (CEA, CD66e) (breast, colorectal and lung cancers), DLL4 (A-like-4), EGFR (various cancers), CTLA4 (melanoma), CXCR4 (CD 184, heme-oncology, solid tumors), Endoglin (CD 105, solid tumors), EPCAM (epithelial cell adhesion molecule, bladder, head, neck, colon, NHL prostate, and ovarian cancers), ERBB2 (lung, breast, prostate cancers), FCGR1 (autoimmune diseases), FOLR (folate receptor, ovarian cancers), FGFR (carcinomas), GD2 ganglioside (carcinomas), G-28 (a cell surface antigen glycolipid, melanoma), GD3 idiotype (carcinomas), heat shock proteins (carcinomas), HER1 (lung, stomach cancers), HER2 (breast, lung and ovarian cancers), HLA-DR10 (NHL), HLA-DRB (NHL, B cell leukemia), human chorionic gonadotropin (carcinomas), IGF1R (solid tumors, blood cancers), IL-2 receptor (T-cell leukemia and lymphomas), IL-6R (multiple myeloma, RA, Castleman's disease, IL6 dependent tumors), integrins ($\alpha v \beta 3$, $\alpha 5 \beta 1$, $\alpha 6 \beta 4$, $\alpha 11 \beta 3$, $\alpha 5 \beta 5$, $\alpha v \beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 (breast, ovarian, cervix, bronchus and gastrointestinal cancer), MUC16 (CA125) (ovarian cancers), CEA (colorectal cancer), gp100 (melanoma), MARTI (melanoma), MPG (melanoma), MS4A1 (membrane-spanning 4-domains subfamily A, small cell lung cancers, NHL), nucleolin, Neu oncogene product (carcinomas), P21 (carcinomas), nectin-4 (carcinomas), paratope of anti-(N-glycolylneuraminic acid, breast, melanoma cancers), PLAP-like testicular alkaline phosphatase (ovarian, testicular cancers), PSMA (prostate tumors), PSA (prostate), ROB04, TAG 72 (tumour associated glycoprotein 72, AML, gastric, colorectal, ovarian cancers), T cell transmembrane protein (cancers), Tie (CD202b), tissue factor, TNFRSF10B (tumor necrosis factor receptor superfamily member 10B, carcinomas), TNFRSF13B (tumor necrosis factor receptor superfamily member 13B, multiple myeloma, NHL, other cancers, RA and SLE), TPBG (trophoblast glycoprotein, renal cell carcinoma), TRAIL-R1 (tumor necrosis apoptosis inducing ligand receptor 1, lymphoma, NHL, colorectal, lung cancers), VCAM-1 (CD106, Melanoma), VEGF, VEGF-A, VEGF-2 (CD309) (various cancers). Some other tumor associated antigen targets have been reviewed (Gerber, et al, mAbs 2009 1:247-253; Novellino et al, Cancer Immunol Immunother. 2005 54:187-207, Franke, et al, Cancer Biother Radiopharm. 2000, 15:459-76, Guo, et al., Adv Cancer Res. 2013; 119: 421-475, Parmiani et al. J Immunol. 2007 178: 1975-9). Examples of these antigens include Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), annexin A1, nucleolin, endoglin (CD105), ROB04, amino-peptidase N, -like-4 (DLL4), VEGFR-2 (CD309), CXCR4 (CD184), Tie2, B7-H3, WT1, MUC1, LMP2, HPV E6 E7, EGFRvIII, HER-2/neu, idiotype, MAGE A3, p53 nonmutant, NY-ESO-1, GD2, CEA, MelanA/MARTI, Ras mutant, gp100, p53 mutant, proteinase3 (PR1), bcr-abl, tyrosinase, survivin, hTERT, sarcoma translocation breakpoints, EphA2, PAP, ML-IAP, AFP, EpCAM, ERG (TMPRSS2 ETS fusion gene), NA17, PAX3, ALK, androgen receptor, cyclin B 1, polysialic acid, MYCN, RhoC, TRP-2, GD3, fucosyl GM1, mesothelin, PSCA, MAGE A1, sLe(a), CYPIB I, PLAC1, GM3, BORIS, Tn, GloboH, ETV6-AML, NY-BR-1, RGS5, SART3, STn, carbonic anhydrase IX, PAX5, OY-TES1, sperm protein 17, LCK, HMWMAA, AKAP-4, SSX2, XAGE 1, B7H3, legumain, Tie 2, Page4, VEGFR2, MAD-CT-1, FAP, PDGFR-β, MAD-CT-2, Notch1, ICAM1 and Fos-related antigen 1.

Additionally, preferred binding domains of the invention include those specific to antigens and epitope targets associated with infected cells that are known in the art. Such targets include but are not limited those derived from the following infectious agents are of interest: HIV virus (particularly antigens derived from the HIV envelope spike and/or gp120 and gp41 epitopes), Human papilloma virus (HPV), *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum*, -influenzae B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M arginini, Acholeplasma laidlawii, M. salivarium* and *M. pneumoniae*.

T-Cell Receptors (TCRs)

T-cells are a subgroup of cells which together with other immune cell types (polymorphonuclear cells, eosinophils, basophils, mast cells, B-cells, NK cells), constitute the cellular component of the immune system. Under physiological conditions, T-cells function in immune surveillance and in the elimination of foreign antigen. However, under pathological conditions, there is compelling evidence that T-cells play a major role in the causation and propagation of disease. In these disorders, breakdown of T-cell immunological tolerance, either central or peripheral is a fundamental process in the causation of autoimmune disease.

The TCR complex is composed of at least seven transmembrane proteins. The disulfide-linked ($\alpha\beta$ or $\gamma\delta$) heterodimer forms the monotypic antigen recognition unit, while the invariant chains of CD3, consisting of $\epsilon$, $\gamma$, $\delta$, $\zeta$, and $\eta$ chains, are responsible for coupling the ligand binding to signaling pathways that result in T-cell activation and the elaboration of the cellular immune responses. Despite the gene diversity of the TCR chains, two structural features are common to all known subunits. First, they are transmembrane proteins with a single transmembrane spanning domain—presumably alpha-helical. Second, all TCR chains have the unusual feature of possessing a charged amino acid within the predicted transmembrane domain. The invariant chains have a single negative charge, conserved between the mouse and human, and the variant chains possess one (TCR-β) or two (TCR-α) positive charges. The transmembrane sequence of TCR-α is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an α and β chain resembling an immunoglobulin variable (V) and constant (C) region. The TCR α chain includes a covalently linked V-α and C-α chain, whereas the β chain includes a V-β chain covalently linked to a C-β chain. The V-α and V-β chains form a pocket or cleft that can bind a superantigen or antigen in the context of a major histocompatibility complex (MHC) (known in humans as an HLA complex). See, Davis *Ann. Rev. of Immunology* 3: 537 (1985); *Fundamental Immunology* 3rd Ed., W. Paul Ed. Rsen Press LTD. New York (1993).

The extracellular domains of the TCR chains (αβ or γδ) can also engineered as fusions to heterologous transmembrane domains for expression on the cell surface. Such TCRs may include fusions to CD3, CD28, CD8, 4-1BB and/or chimeric activation receptor (CAR) transmembrane or activation domains. TCRs can also be the soluble proteins comprising one or more of the antigen binding domains of αβ or γδ chains. Such TCRs may include the TCR variable domains or function fragments thereof with or without the TCR constant domains. Soluble TCRs may be heterodimeric or single-chain molecules.

Fc Domain

Protein complexes of the invention may contain an Fc domain. For example, PD-L1 T×M comprises an anti-PD-L1 scAb/huIL-15N72D:anti-PD-L1 scAb/huIL-15RαSu/hu-IgG1 Fc fusion complex. Fusion proteins that combine the Fc regions of IgG with the domains of another protein, such as various cytokines and soluble receptors have been reported (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_H1$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15Rα covalently linked to the Fc portion of the human heavy chain IgG protein are described herein.

The term "Fc" refers to the fragment crystallizable region which is the constant region of an antibody that interacts with cell surface receptors called Fc receptors and some proteins of the complement system. Such an "Fc" is in dimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins. In some embodiments, Fc domain of the complex is capable of interacting with Fc receptors to mediate antibody-dependent cell-mediated cytotoxicity (ADCC) and/or antibody dependent cellular phagocytosis (ADCP). In other applications, the complex comprises an Fc domain (e.g., IgG4 Fc) that is incapable of effectively mediating ADCC or ADCP.

In some embodiments, the term "Fc variant" refers to a molecule or sequence that is modified from a native Fc, but still comprises a binding site for the salvage receptor, FcRn. International applications WO 97/34631 and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that alters one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) antibody-dependent cellular cytotoxicity (ADCC) or (8) antibody-dependent cellular phagocytosis (ADCP). Such alterations can increase or decrease any one or more of these Fc properties. Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Fusions Protein Complexes

Figure 2:
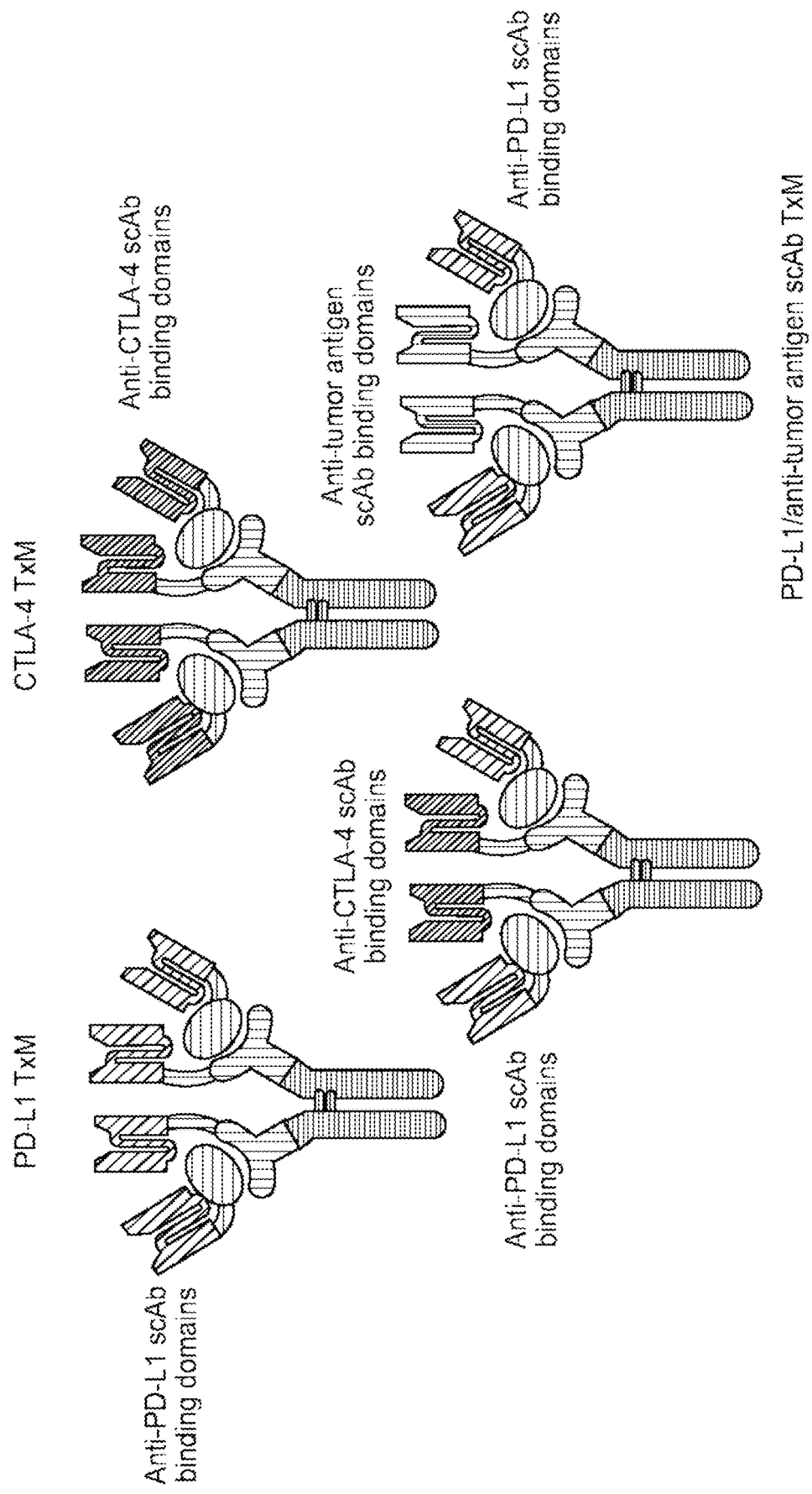
FIG. 2 is a schematic diagram illustrating different TxM complexes comprising the IL-15/IL-15RαSu/Fc scaffold fused to binding domains that recognize immune checkpoint molecules, immune signaling molecule and/or disease antigens.

The invention provides for fusion protein complexes (FIG. 1 and FIG. 2). In some cases, the first protein comprises a first biologically active polypeptide covalently linked to interleukin-15 (IL-15) or functional fragment thereof; and the second protein comprises a second biologically active polypeptide covalently linked to soluble interleukin-15 receptor alpha (IL-15Rα) polypeptide or functional fragment thereof, where the IL-15 domain of a first protein binds to the soluble IL-15Rα domain of the second protein to form a soluble fusion protein complex. Fusion protein complexes of the invention also comprise immunoglobulin Fc domain or a functional fragment thereof linked to one or both of the first and second proteins. Preferably, the Fc domains linked to the fusion proteins interact to form a fusion protein complex. Such a complex may be stabilized by disulfide bond formation between the immunoglobulin Fc domains. In one aspect, the soluble fusion protein complexes of the invention include an IL-15 polypeptide, IL-15 variant or a functional fragment thereof and a soluble IL-15Rα polypeptide or a functional fragment thereof, wherein one or both of the IL-15 and IL-15Rα polypeptides further include an immunoglobulin Fc domain or a functional fragment thereof.

In certain examples, one or both of the first and second proteins comprises an antibody or functional fragment thereof. For example, one of the binding domain comprises a soluble anti-PD-L1 single chain antibody or functional fragment thereof. In another example, the other or second binding domain comprises an anti-CTLA4 single chain antibody or a disease antigen-specific antibody or functional fragment thereof. In one embodiment, the invention provides PD-L1 T×M, comprising a soluble anti-PD-L1 scAb/huIL-15N72D:anti-PD-L1 scAb/huIL-15RαSu/huIgG1 Fc fusion protein complex. In this complex, the huIL-15N72D and huIL-15RαSu domains interact and the huIgG1 Fc domains on two anti-PD-L1 scAb/huIL-15RαSu/huIgG1 Fc fusion protein to form a multichain fusion protein complex.

As used herein, the term "biologically active polypeptide" or "effector molecule" is meant an amino acid sequence such as a protein, polypeptide, or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptide or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a fusion complex of the invention and then evaluating whether the fusion complex inhibits further development of the cells.

Covalently linking the effector molecule to the fusion protein complexes of the invention in accordance with the invention provides a number of significant advantages. Fusion protein complexes of the invention can be produced that contain a single effector molecule, including a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of a fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.

Linkers

The fusion complexes of the invention preferably also include a flexible linker sequence interposed between the IL-15 or IL-15Rα domains and the biologically active polypeptide. The linker sequence should allow effective positioning of the biologically active polypeptide with respect to the IL-15 or IL-15Rα domains to allow functional activity of both domains.

In certain cases, the soluble fusion protein complex has a linker wherein the first biologically active polypeptide is covalently linked to IL-15 (or functional fragment thereof) by polypeptide linker sequence. In other aspects, the soluble fusion protein complex as described herein has a linker wherein the second biologically active polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. For example, the IL-15 or IL-15Rα domains are effectively positioned to allow interactions with immune cells to initiate or inhibit an immune reaction, or to inhibit or stimulate cell development.

The fusion complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. For example, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generate a single-chain molecule with the desired functional activity.

Preferably, the linker sequence comprises from about 7 to 20 amino acids, more preferably from about 10 to 20 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine, and serine, to provide for flexibility. Preferably, about 80 or 90 percent or greater of the linker sequence comprises glycine, alanine, or serine residues, particularly glycine and serine residues.

Different linker sequences could be used including any of a number of flexible linker designs that have been used successfully to join antibody variable regions together (see, Whitlow, M. et al., (1991) Methods: A Companion to Methods in Enzymology, 2:97-105).

Pharmaceutical Therapeutics

The invention provides pharmaceutical compositions comprising fusion protein complexes for use as a therapeutic. In one aspect, fusion protein complex of the invention is administered systemically, for example, formulated in a pharmaceutically-acceptable buffer such as physiological saline. Preferable routes of administration include, for example, instillation into the bladder, subcutaneous, intravenous, intraperitoneal, intramuscular, intratumoral or intradermal injections that provide continuous, sustained, or effective levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, autoimmune or infectious diseases, although in certain instances lower amounts will be needed because of the increased specificity of the compound. A compound is administered at a dosage that enhances an immune response of a subject, or that reduces the proliferation, survival, or invasiveness of a neoplastic, infected, or autoimmune cell as determined by a method known to one skilled in the art.

Formulation of Pharmaceutical Compositions

The administration of the fusion protein complex of the invention for the treatment of a neoplasia, infectious or autoimmune disease is by any suitable means that results in a concentration of the therapeutic that, combined with other components, is effective in ameliorating, reducing, or stabilizing said neoplasia, infectious or autoimmune disease. The fusion protein complex of the invention may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intravesicular, intratumoral or intraperitoneal) administration route. For example, the pharmaceutical compositions are formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 µg compound/kg body weight to about 5000 mg compound/kg body weight; or from about 5 mg/kg body weight to about 4,000 mg/kg body weight or from about 10 mg/kg body weight to about 3,000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. For example, the dose is about 1, 5, 10, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,600, 1,700, 1,800, 1,900, 2,000, 2,500, 3,000, 3,500, 4,000, 4,500, or 5,000 mg/kg body weight. Alternatively, doses are in the range of about 5 mg compound/Kg body weight to about 20 mg compound/kg body weight. In another example, the doses are about 8, 10, 12, 14, 16 or 18 mg/kg body weight. Preferably, the fusion protein complex is administered at 0.5 mg/kg-about 10 mg/kg (e.g., 0.5, 1, 3, 5, 10 mg/kg). Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes. Preferably, the fusion protein complex is formulated in an excipient suitable for parenteral administration.

Parenteral Compositions

The pharmaceutical composition comprising a fusion protein complex of the invention are administered parenterally by injection, infusion, or implantation (subcutaneous, intravenous, intramuscular, intratumoral, intravesicular, intraperitoneal) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising a fusion protein complex of the invention for parenteral use are provided in unit dosage forms (e.g., in single-dose ampoules). Alternatively, the composition is provided in vials containing several doses and in which a suitable preservative may be added (see below). The composition is in the form of a solution, a suspension, an emulsion, an infusion device, or a delivery device for implantation, or it is presented as a dry powder to be reconstituted with water or another suitable vehicle before use. Apart from the active agent that reduces or ameliorates a neoplasia, infectious or autoimmune disease, the composition includes suitable parenterally acceptable carriers and/or excipients. The active therapeutic agent(s) may be incorporated into microspheres, microcapsules, nanoparticles, liposomes for controlled release. Furthermore, the composition may include suspending, solubilizing, stabilizing, pH-adjusting agents, tonicity adjusting agents, and/or dispersing, agents.

As indicated above, the pharmaceutical compositions comprising a fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol.

The present invention provides methods of treating neoplasia, infectious or autoimmune diseases or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplasia, infectious or autoimmune disease or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplasia, infectious disease, autoimmune disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The fusion protein complexes of the invention may be used in the treatment of any other disorders in which an increase in an immune response is desired.

The invention also provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some cases, a second level of Marker in the subject is determined at a time point later than the determination of the first level, and the two levels are compared to monitor the course of disease or the efficacy of the therapy. In certain aspects, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Optionally, the fusion protein complex of the invention is administered in combination with any other standard therapy; such methods are known to the skilled artisan and described in Remington's Pharmaceutical Sciences by E. W. Martin. If desired, fusion protein complexes of the invention is administered in combination with any conventional antineoplastic therapy, including but not limited to, immunotherapy, therapeutic antibodies, targeted therapy, surgery, radiation therapy, or chemotherapy.

Kits or Pharmaceutical Systems

Pharmaceutical compositions comprising the fusion protein complex of the invention may be assembled into kits or pharmaceutical systems for use in ameliorating a neoplasia, infectious or autoimmune disease. Kits or pharmaceutical systems according to this aspect of the invention comprise a carrier means, such as a box, carton, tube, having in close confinement therein one or more container means, such as vials, tubes, ampoules, bottles, and the like. The kits or pharmaceutical systems of the invention may also comprise associated instructions for using the fusion protein complex of the invention.

Recombinant Protein Expression

In general, preparation of the fusion protein complexes of the invention (e.g., components of a T×M complex) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transfection and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein) raised against the polypeptide may be attached to a column and used to isolate the recombinant polypeptide. Lysis and fractionation of polypeptide-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory Techniques in Biochemistry and Molecular Biology, eds., Work and Burdon, Elsevier, 1980).

As used herein, biologically active polypeptides or effector molecules of the invention may include factors such as cytokines, chemokines, growth factors, protein toxins, immunoglobulin domains or other bioactive proteins such as enzymes. Also, biologically active polypeptides may include conjugates to other compounds such as non-protein toxins, cytotoxic agents, chemotherapeutic agents, detectable labels, radioactive materials, and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-1, IL-17, TGF and TNF cytokine families, and to IL-1 through IL-35, IFN-α, IFN-β, IFNγ, TGF-β, TNF-α, and TNFβ.

In an aspect of the invention, the first protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL-2, although fundamental differences have been well characterized (Waldmann, T A, 2006, Nature Rev. Immunol. 6:595-601).

In another aspect of the invention, the first protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rα polypeptide and functions as an IL-15 agonist or antagonist. Preferably, IL-15 variants with agonist activity have super agonist activity. The IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some cases, the sequence of the IL-15 variant has at least one amino acid change, e.g. substitution or deletion, compared to the native IL-2 sequence, such changes resulting in IL-15 agonist or antagonist activity. Preferably, the amino acid substitutions/deletions are in the domains of IL-15 that interact with IL-15Rβ and/or γC. More preferably, the amino acid substitutions/deletions do not affect binding to the IL-15Rα polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally, suitable amino acid substitutions can be conservative or non-conservative changes and insertions of additional amino acids. Preferably, IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, DBA, D61A, N65A, N72R, V104P or Q108A substitutions result in IL-15 variants with antagonist activity and N72D substitutions result in IL-15 variants with agonist activity.

Chemokines, similar to cytokines, are defined as any chemical factor or molecule which when exposed to other cells are responsible for any of a number of multiple effects of cellular immunity. Suitable chemokines may include but are not limited to the CXC, CC, C, and CX$_3$C chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), Shiga toxin, abrin, cholera toxin, ricin, saporin, *pseudomonas* exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; phosphorescent or chemiluminescent molecules or a label detectable by PET, ultrasound, or MRI such as Gd—or paramagnetic metal ion-based contrast agents. See e.g., Moskaug, et al. *J. Biol. Chem.* 264, 15709 (1989); Pastan, I. et al. *Cell* 47, 641, 1986; Pastan et al., Recombinant Toxins as Novel Therapeutic Agents, *Ann. Rev. Biochem.* 61, 331, (1992); "Chimeric Toxins" Olsnes and Phil, *Pharmac. Ther.*, 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

A protein fusion or conjugate complex that includes a covalently linked IL-15 and IL-15Rα domains has several important uses. For example, the protein fusion or conjugate complex comprising an anti-PD-L1 scAb can be employed to deliver the IL-15:IL-15Rα complex to certain cells, e.g., tumor cells that express PD-L1. Accordingly, the protein fusion or conjugate complex provides means of selectively damaging or killing cells comprising the ligand. Examples of cells or tissue capable of being damaged or killed by the protein fusion or conjugate complexes include tumors and virally or bacterially infected cells expressing one or more ligands. Cells or tissue susceptible to being damaged or killed can be readily assayed by the methods disclosed herein.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammals. Sequences of these polypeptides and encoding nucleic acids are known in the literature, including human interleukin 15 (IL15) mRNA—GenBank: U14407.1 (incorporated herein by reference), *Mus musculus* interleukin 15 (IL15) mRNA—GenBank: U14332.1 (incorporated herein by reference), human interleukin-15 receptor alpha chain precursor (IL15RA) mRNA—GenBank: U31628.1 (incorporated herein by reference), *Mus musculus* interleukin 15 receptor, alpha chain—GenBank: BC095982.1 (incorporated herein by reference).

In some settings, it can be useful to make the protein fusion or conjugate complexes of the present invention polyvalent, e.g., to increase the valency of the sc-antibody. In particular, interactions between the IL-15 and IL-15Rα domains of the fusion protein complex provide a means of generating polyvalent complexes. In addition, the polyvalent fusion protein can be made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, Aldrichimica Acta, 26:91:101 (1993)). Exemplary dendrimers for use in accordance with the present invention include e.g. E9 starburst polyamine dendrimer and E9 combust polyamine dendrimer, which can link cystine residues. Exemplary nanoparticles include liposomes, core-shell particles, or PLGA-based particles.

In another aspect, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 CH2-CH3, are capable of stably interacting to create the Fc region. Preferred immunoglobulin domains including Fc domains also comprise regions with effector functions, including Fc receptor or complement protein binding activity, and/or with glycosylation sites. In some aspects, the immunoglobulin domains of the fusion protein complex contain mutations that reduce or augment Fc receptor or complement binding activity or glycosylation or dimerization, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present fusion proteins (e.g., components of T×M). Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See, Sambrook et al., supra and Ausubel et al. supra.

Included in the invention are methods for making a soluble fusion protein complex, the method comprising introducing into a host cell a DNA vector as described herein encoding the first and second proteins, culturing the host cell in media under conditions sufficient to express the fusion proteins in the cell or the media and allow association between IL-15 domain of a first protein and the soluble IL-15Rα domain of a second protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity, and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization, and wash conditions of 40-50 C, 6×SSC (sodium chloride/sodium citrate buffer) and 0.1% SDS (sodium dodecyl sulfate) indicate about 60-70% homology, hybridization, and wash conditions of 50-65 C, 1×SSC and 0.1% SDS indicate about 82-97% homology, and hybridization, and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See, e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However, it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express the components of fusion protein complex of the invention (e.g., TxM). For example, a construct encoding one or more components of fusion protein complex of the invention can be incorporated into a suitable vector using restriction enzymes to make cuts in the vector for insertion of the construct followed by ligation. The vector containing the gene construct is then introduced into a suitable host for expression of the fusion protein. See, generally, Sambrook et al., supra. Selection of suitable vectors can be made empirically based on factors relating to the cloning protocol. For example, the vector should be compatible with, and have the proper replicon for the host that is being employed. The vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically, preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See, Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immunoblotting. Other methods for detecting expression of fusion proteins comprising biologically active polypeptides linked to IL-15 or IL-15Rα domains are disclosed in the Examples.

As mentioned generally above, a host cell can be used for preparative purposes to propagate nucleic acid encoding a desired fusion protein. Thus, a host cell can include a prokaryotic or eukaryotic cell in which production of the fusion protein is specifically intended. Thus, host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et al., *J Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired fusion protein complexes encompass non-mammalian eukaryotic cells as well, including insect (e.g., *Sp. frugiperda*), yeast (e.g., *S. cerevisiae, S. pombe, P. pastoris., K. lactis, H. polymorpha*; as generally reviewed by Fleer, R., *Current Opinion in Biotechnology*, 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1,000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10-fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His⁻ *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 µg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art λZAP and pBLUESCRIPT SK-1, Stratagene, La Jolla, Calif., pET, Novagen Inc., Madison, Wis., cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization, and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into S. cerevisiae cells by protoplast transformation or electroporation. Electroporation of S. cerevisiae is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically, the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion complex. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

The present fusion protein complexes are suitable for in vitro or in vivo use with a variety of cells that are cancerous or are infected or that may become infected by one or more diseases.

Human interleukin-15 (huIL-15) is trans-presented to immune effector cells by the human IL-15 receptor α chain (huIl-15Rα) expressed on antigen presenting cells. IL-15Rα binds huIL-15 with high affinity (38 pM) primarily through the extracellular sushi domain (huIL-15RαSu). As described herein, the huIL-15 and huIL-15RαSu domains can be used as a scaffold to construct multi-domain fusion complexes.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcomes for a number of different autoimmune indications.

In addition to its dimerization activity, the Fc fragment also provides cytotoxic effector functions through the complement activation and interaction with Fcγ receptors displayed on natural killer (NK) cells, neutrophils, phagocytes, and dendritic cells. In the context of anti-cancer therapeutic antibodies and other antibody domain-Fc fusion proteins, these activities likely play an important role in efficacy observed in animal tumor models and in cancer patients. However, these cytotoxic effector responses may not be sufficient in a number of therapeutic applications. Thus, there has been considerable interest in improving and expanding on the effector activity of the Fc domain and developing other means of recruiting cytolytic immune responses, including T cell activity, to the disease site via targeted therapeutic molecules. IgG domains have been used as a scaffold to form bispecific antibodies to improve the quality and quantity of products generated by the traditional hybridoma fusion technology. Although these methods bypass the shortcomings of other scaffolds, it has been difficult to produce bispecific antibodies in mammalian cells at levels sufficient to support clinical development and use.

In an effort to develop human-derived immunostimulatory multimeric scaffold, human IL-15 (huIL-15) and IL-15 receptor domains were used. huIL-15 is a member of the small four α-helix bundle family of cytokines that associates with the huIL-15 receptor α-chain (huIL-15Rα) with a high binding affinity (equilibrium dissociation constant (KD) ~$10^{-11}$ M). The resulting complex is then trans-presented to the human IL-2/15 receptor β/common γ chain (huIL-15RβγC) complexes displayed on the surface of T cells and NK cells. This cytokine/receptor interaction results in expansion and activation of effector T cells and NK cells, which play an important role in eradicating virally infected and malignant cells. Normally, huIL-15 and huIL-15Rα are co-produced in dendritic cells to form complexes intracellularly that are subsequently secreted and displayed as heterodimeric molecules on cell surfaces. Thus, the characteristics of huIL-15 and huIl-15Rα interactions suggest that these inter chain binding domains could serve as a human-derived immunostimulatory scaffold to make soluble dimeric molecules capable of target-specific binding.

As described in detail below, an huIL-15:huIL-15RαSu-based scaffold was used to create PD-L1 TxM. The dimeric fusion protein complexes retained immunostimulatory and target-specific biological activity of their huIL-15 domains and binding domains, indicating that the addition of huIL-15 and huIL-15Rα did not significantly alter the spatial arrangement of the fusion domains and provided an adequate degree of conformational flexibility without impacting cytokine activity. Thus, this scaffold could be used to form multivalent fusion complexes, such as the PD-L1 T×M, to increase the overall binding affinity of molecules. The soluble fusion proteins were produced at relatively high levels in recombinant CHO cell culture (mgs per liter in cell culture supernatant without extensive cell line screening or optimization) and could be readily purified from the cell culture supernatants.

The practice of the present invention employs, unless otherwise indicated, conventional techniques of molecular biology (including recombinant techniques), microbiology, cell biology, biochemistry, and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Lymphoma

Lymphoma is a type of blood cancer that occurs when B or T lymphocytes divide faster than normal cells or live longer than intended. For example, B cell lymphomas include both Hodgkin's lymphomas and most non-Hodgkin's lymphomas. B cell lymphomas express CD20.

Lymphoma may develop in the lymph nodes, spleen, bone marrow, blood, or other organs. These malignant cells often originate in the lymph nodes, presenting as an enlargement of the node, i.e., a solid tumor of lymphoid cells. Lymphoma is definitively diagnosed by a lymph node biopsy, i.e., a partial or total excision of a lymph node, which is examined under a microscope. This examination may reveal histopathological features that may indicate lymphoma. Treatment might involve chemotherapy, radiotherapy, and/or bone marrow transplantation.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Generation and Characterization of IL-15-Based Fusion Protein Complexes Comprising Anti-PD-L1 Binding Domains (PD-L1 T×M)

Cancer cells are able to turn on various immune inhibitory pathways which are regulated by immune checkpoint molecules and ligands, such as PD-L1. Antibodies that block these checkpoint molecules have been shown to enhance anti-tumor immunity. IL-15 activates and expands NK and $CD8^+$ cells while increasing their cytolytic activity. The Fc region of Ig molecules can interact with Fcγ receptors on NK cells and macrophages and mediate antibody-dependent cellular cytotoxicity (ADCC) or antibody-dependent cellular phagocytosis (ADCP) against target disease cells. As described in detail below, protein complexes comprising an IL-15N72D:IL-15RαSu/Fc scaffold fused to anti-PD-L1 binding domains were generated. These complexes recognize tumor cells via the anti-PD-L1 binding domain, induce NK and T cells responses via IL-15 activity, and stimulate ADCC and CDC via the Fc binding domain.

Specifically, constructs were made linking a single-chain anti-PD-L1 antibody to the huIL-15N72D and IL-15RαSu/Fc chains. The anti-PD-L1 single chain antibody (anti-PD-L1 scAb) sequence comprises the coding regions of the heavy and light chain V antibody domains antibody linked via a flexible linker sequence. The single chain antibody domain can be arranged in either the VH-linker-VL or VL-linker-VH format. In some cases, the anti-PD-L1 scAb is linked to the C-terminus of the IL-15N72D and/or IL-15RαSu/Fc chains. In other cases, the anti-PD-L1 is linked to the N-terminus of IL-15N72D and/or IL-15RαSu/Fc chains. Anti-PD-L1 scAbs specific to either the mouse or human PD-L1 molecules were used in these constructs.

1) The nucleic acid and protein sequences of constructs comprising an anti-human PD-L1 scAb linked to the N-terminus of the huIL-15N72D and huIL-15RαSu/huIgG1 Fc chains are shown below. The nucleic acid sequence of anti-human PD-L1 scAb/IL-15N72D construct (including signal peptide sequence and stop codon) is as follows (SEQ ID NO: 1):

```
(Signal peptide)
ATGAAGTGGGTGACCTTCATCAGCCTGCTGTTCCTGTTCTCCAGCGCCTAC

TCC (Anti-human PD-L1 scAb)
(VL)
AACATCCAGATGACCCAGTCCCCTAGCTCCGTGTCCGCCTCCGTGGGAGAT

CGGGTGACCATCACCTGTAGGGCCTCCCAGGACATCTCCAGGTGGCTGGCC

TGGTACCAGCAGAAGCCCGGCAAGGCCCCCAAGCTGCTGATCTACGCCGCC

TCCTCCCTGCAGTCCGGAGTGCCTAGCAGGTTCTCCGGCTCCGGATCCGGC

ACAGACTTCGCCCTGACCATCTCCTCCCTGCAGCCCGAGGACTTCGCCACC

TACTACTGCCAGCAGGCCGACTCCAGGTTCTCCATCACCTTCGGCCAGGGC

ACCAGGCTGGAGATCAAGAGG (Linker)
GGAGGTGGCGGATCCGGAGGTGGAGGTTCTGGTGGAGGTGGGAGT (VH)
GAGGTGCAGCTGGTGCAGTCCGGAGGAGGACTGGTGCAGCCTGGCGGATCC

CTGAGGCTGTCCTGTGCCGCTTCCGGCTTCACCTTCAGCTCCTACTCCATG

AACTGGGTGAGGCAGGCCCCTGGAAAGGGCCTGGAGTGGGTGTCCTACATC

TCCAGCTCCTCCTCCACCATCCAGTACGCCGACTCCGTGAAGGGCAGGTTC

ACCATCTCCAGGGACAACGCCAAGAACTCCCTGTACCTGCAGATGAACAGC
```

CTGAGGGACGAGGACACCGCCGTGTACTACTGCGCCAGGGGCGACTATTAC

TACGGCATGGACGTGTGGGGCCAGGGAACCACCGTGACCGTGTCCTCC (Human IL-15N72D)
AACTGGGTTAACGTAATAAGTGATTTGAAAAAAATTGAAGATCTTATTCAA

TCTATGCATATTGATGCTACTTTATATACGGAAAGTGATGTTCACCCCAGT

TGCAAAGTAACAGCAATGAAGTGCTTTCTCTTGGAGTTACAAGTTATTTCA

CTTGAGTCCGGAGATGCAAGTATTCATGATACAGTAGAAAATCTGATCATC

CTAGCAAACGACAGTTTGTCTTCTAATGGGAATGTAACAGAATCTGGATGC

AAAGAATGTGAGGAACTGGAGGAAAAAAATATTAAAGAATTTTTGCAGAGT

TTTGTACATATTGTCCAAATGTTCATCAACACTTCTTAA

The amino acid sequence of the anti-human PD-L1 scAb/IL-15N72D fusion protein (including signal peptide sequence) is as follows (SEQ ID NO: 2):

(Signal peptide)
MKWVTFISLLFLFSSAYS (Anti-human PD-L1 scAb)
(VL)
NIQMTQSPSSVSASVGDRVTITCRASQDISRWLAWYQQKPGKAPKLLIYAA

SSLQSGVPSRFSGSGSGTDFALTISSLQPEDFATYYCQQADSRFSITFGQG

TRLEIKR (Linker)
GGGGSGGGGSGGGGS (VH)
EVQLVQSGGGLVQPGGSLRLSCAASGFTFSSYSMNWVRQAPGKGLEWVSYI

SSSSSTIQYADSVKGRFTISRDNAKNSLYLQMNSLRDEDTAVYYCARGDYY

YGMDVWGQGTTVTVSS (Human IL-15N72D)
NWVNVISDLKKIEDLIQSMHIDATLYTESDVHPSCKVTAMKCFLLELQVIS

LESGDASIHDTVENLIILANDSLSSNGNVTESGCKECEELEEKNIKEFLQS

FVHIVQMFINTS

In some cases, the leader peptide is cleaved from the mature polypeptide.

The nucleic acid sequence of an anti-human PD-L1 scAb/huIL-15RαSu/huIgG1 Fc construct (including leader sequence) is as follows (SEQ ID NO: 3):

(Leader sequence)
ATGAAGTGGGTGACCTTCATCAGCCTGCTGTTCCTGTTCTCCAGCGCCTAC

TCC (Anti-human PD-L1 scAb)
(VL)
AACATCCAGATGACCCAGTCCCCTAGCTCCGTGTCCGCCTCCGTGGGAGAT

CGGGTGACCATCACCTGTAGGGCCTCCCAGGACATCTCCAGGTGGCTGGCC

TGGTACCAGCAGAAGCCCGGCAAGGCCCCCAAGCTGCTGATCTACGCCGCC

TCCTCCCTGCAGTCCGGAGTGCCTAGCAGGTTCTCCGGCTCCGGATCCGGC

ACAGACTTCGCCCTGACCATCTCCTCCCTGCAGCCCGAGGACTTCGCCACC

TACTACTGCCAGCAGGCCGACTCCAGGTTCTCCATCACCTTCGGCCAGGGC

ACCAGGCTGGAGATCAAGAGG (Linker)
GGAGGTGGCGGATCCGGAGGTGGAGGTTCTGGTGGAGGTGGGAGT (VH)
GAGGTGCAGCTGGTGCAGTCCGGAGGAGGACTGGTGCAGCCTGGCGGATCC

CTGAGGCTGTCCTGTGCCGCTTCCGGCTTCACCTTCAGCTCCTACTCCATG

AACTGGGTGAGGCAGGCCCCTGGAAAGGGCCTGGAGTGGGTGTCCTACATC

TCCAGCTCCTCCTCCACCATCCAGTACGCCGACTCCGTGAAGGGCAGGTTC

ACCATCTCCAGGGACAACGCCAAGAACTCCCTGTACCTGCAGATGAACAGC

CTGAGGGACGAGGACACCGCCGTGTACTACTGCGCCAGGGGCGACTATTAC

TACGGCATGGACGTGTGGGGCCAGGGAACCACCGTGACCGTGTCCTCC (Human IL-15R α sushi domain)
ATCACGTGCCCTCCCCCCATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Human IgG1 CH2-CH3 (Fc) domain)
GAGCCCAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG

GTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA

The amino acid sequence of the anti-human PD-L1 scAb/huIL-15RαSu/huIgG1 Fc fusion protein (including leader sequence) is as follows (SEQ ID NO: 4):

(Leader peptide)
MKWVTFISLLFLFSSAYS (Anti-human PD-L1 scAb)
(VL)
NIQMTQSPSSVSASVGDRVTITCRASQDISRWLAWYQQKPGKAPKLLIYAA

SSLQSGVPSRFSGSGSGTDFALTISSLQPEDFATYYCQQADSRFSITFGQG

TRLEIKR

-continued (Linker)
GGGGSGGGGSGGGGS (VH)
EVQLVQSGGGLVQPGGSLRLSCAASGFTFSSYSMNWVRQAPGKGLEWVSYI

SSSSSTIQYADSVKGRFTISRDNAKNSLYLQMNSLRDEDTAVYYCARGDYY

YGMDVWGQGTTVTVSS (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

In some cases, the leader peptide is cleaved from the mature polypeptide.

2) The nucleic acid and protein sequences of constructs comprising a second anti-human PD-L1 (avelumab) scAb linked to the N-terminus of the huIL-15N72D and huIL-15RαSu/huIgG1 Fc chains are shown below. The nucleic acid sequence of anti-human PD-L1 scAb/IL-15N72D construct (including signal peptide sequence and stop codon) is as follows (SEQ ID NO: 5):

(Signal peptide)
ATGAAGTGGGTGACCTTCATCAGCCTGCTGTTCCTGTTCTCCAGCGCCTAC

TCC (Anti-human PD-L1 scAb)
(VL)
CAGTCCGCTCTGACCCAGCCTGCTTCCGTGTCCGGCTCCCCTGGACAGTCC

ATCACCATCTCCTGTACCGGCACCTCCTCCGATGTGGGCGGCTACAACTAC

GTGTCCTGGTACCAGCAGCACCCCGGCAAAGCCCCCAAGCTGATGATCTAT

GACGTGTCCAACCGGCCCTCCGGCGTGTCCAACAGGTTCTCCGGCTCCAAG

TCCGGCAACACCGCCTCCCTGACAATCTCCGGCCTGCAGGCCGAGGATGAG

GCTGACTACTACTGCTCCTCCTACACCTCCTCCTCCACCAGGGTGTTCGGC

ACCGGCACCAAGGTGACCGTGCTG (Linker)
GGAGGTGGCGGATCCGGAGGTGGAGGTTCTGGTGGAGGTGGGAGT (VH)
GAGGTGCAGCTGCTGGAGTCCGGAGGCGGACTGGTGCAGCCTGGAGGATCC

CTGAGGCTGTCCTGCGCTGCCTCCGGCTTCACCTTCTCCTCCTACATCATG

ATGTGGGTGAGGCAGGCTCCTGGCAAGGGCCTGGAGTGGGTGTCCTCCATC

TACCCCTCCGGCGGCATCACCTTCTACGCCGATACCGTGAAGGGCAGGTTC

ACCATCTCCCGGGACAACTCCAAGAACACCCTGTACCTGCAGATGAACTCC

CTGAGGGCTGAGGACACCGCCGTGTACTACTGCGCCAGGATCAAGCTGGGC

ACCGTGACCACAGTGGACTACTGGGGACAGGGCACCCTGGTGACCGTGTCC

TCC

-continued (Human IL-15N72D)
AACTGGGTTAACGTAATAAGTGATTTGAAAAAAATTGAAGATCTTATTCAA

TCTATGCATATTGATGCTACTTTATATACGGAAAGTGATGTTCACCCCAGT

TGCAAAGTAACAGCAATGAAGTGCTTTCTCTTGGAGTTACAAGTTATTTCA

CTTGAGTCCGGAGATGCAAGTATTCATGATACAGTAGAAAATCTGATCATC

CTAGCAAACGACAGTTTGTCTTCTAATGGGAATGTAACAGAATCTGGATGC

AAAGAATGTGAGGAACTGGAGGAAAAAAATATTAAAGAATTTTTGCAGAGT

TTTGTACATATTGTCCAAATGTTCATCAACACTTCTTAA

The amino acid sequence of the anti-human PD-L1 scAb/IL-15N72D fusion protein (including signal peptide sequence) is as follows (SEQ ID NO: 6):

(Signal peptide)
MKWVTFISLLFLFSSAYS (Anti-human PD-L1 scAb)
(VL)
QSALTQPASVSGSPGQSITISCTGTSSDVGGYNYVSWYQQHPGKAPKLMIY

DVSNRPSGVSNRFSGSKSGNTASLTISGLQAEDEADYYCSSYTSSSTRVFG

TGTKVTVL (Linker)
GGGGSGGGGSGGGGS (VH)
EVQLLESGGGLVQPGGSLRLSCAASGFTFSSYIMMWVRQAPGKGLEWVSSI

YPSGGITFYADTVKGRFTISRDNSKNTLYLQMNSLRAEDTAVYYCARIKLG

TVTTVDYWGQGTLVTVSS (Human IL-15N72D)
NWVNVISDLKKIEDLIQSMHIDATLYTESDVHPSCKVTAMKCFLLELQVIS

LESGDASIHDTVENLIILANDSLSSNGNVTESGCKECEELEEKNIKEFLQS

FVHIVQMFINTS

In some cases, the leader peptide is cleaved from the mature polypeptide.

The nucleic acid sequence of an anti-human PD-L1 scAb/huIL-15RαSu/huIgG1 Fc construct (including leader sequence) is as follows (SEQ ID NO: 7):

(Leader sequence)
ATGAAGTGGGTGACCTTCATCAGCCTGCTGTTCCTGTTCTCCAGCGCCTAC

TCC (Anti-human PD-L1 scAb)
(VL)
CAGTCCGCTCTGACCCAGCCTGCTTCCGTGTCCGGCTCCCCTGGACAGTCC

ATCACCATCTCCTGTACCGGCACCTCCTCCGATGTGGGCGGCTACAACTAC

GTGTCCTGGTACCAGCAGCACCCCGGCAAAGCCCCCAAGCTGATGATCTAT

GACGTGTCCAACCGGCCCTCCGGCGTGTCCAACAGGTTCTCCGGCTCCAAG

TCCGGCAACACCGCCTCCCTGACAATCTCCGGCCTGCAGGCCGAGGATGAG

GCTGACTACTACTGCTCCTCCTACACCTCCTCCTCCACCAGGGTGTTCGGC

ACCGGCACCAAGGTGACCGTGCTG (Linker)
GGAGGTGGCGGATCCGGAGGTGGAGGTTCTGGTGGAGGTGGGAGT (VH)
GAGGTGCAGCTGCTGGAGTCCGGAGGCGGACTGGTGCAGCCTGGAGGATCC

CTGAGGCTGTCCTGCGCTGCCTCCGGCTTCACCTTCTCCTCCTACATCATG

ATGTGGGTGAGGCAGGCTCCTGGCAAGGGCCTGGAGTGGGTGTCCTCCATC

TACCCCTCCGGCGGCATCACCTTCTACGCCGATACCGTGAAGGGCAGGTTC

ACCATCTCCCGGGACAACTCCAAGAACACCCTGTACCTGCAGATGAACTCC

CTGAGGGCTGAGGACACCGCCGTGTACTACTGCGCCAGGATCAAGCTGGGC

ACCGTGACCACAGTGGACTACTGGGGACAGGGCACCCTGGTGACCGTGTCC

TCC (Human IL-15R αa sushi domain)
ATCACGTGCCCTCCCCCCATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Human IgG1 CH2-CH3 (Fc) domain)
GAGCCGAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG

GTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA

The amino acid sequence of the anti-human PD-L1 scAb/huIL-15RαSu/huIgG1 Fc fusion protein (including leader sequence) is as follows (SEQ ID NO: 8):

(Leader peptide)
MKWVTFISLLFLFSSAYS (Anti-human PD-L1 scAb)
(VL)
QSALTQPASVSGSPGQSITISCTGTSSDVGGYNYVSWYQQHPGKAPKLMIY

DVSNRPSGVSNRFSGSKSGNTASLTISGLQAEDEADYYCSSYTSSSTRVFG

TGTKVTVL (Linker)
GGGGSGGGGSGGGGS (VH)
EVQLLESGGGLVQPGGSLRLSCAASGFTFSSYIMMWVRQAPGKGLEWVSSI

YPSGGITFYADTVKGRFTISRDNSKNTLYLQMNSLRAEDTAVYYCARIKLG

TVTTVDYWGQGTLVTVSS (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

In some cases, the leader peptide is cleaved from the mature polypeptide.

3) The nucleic acid and protein sequences of constructs comprising am anti-mouse PD-L1 scAb linked to the N-terminus of the huIL-15N72D and huIL-15RαSu/muIgG2A Fc chains are shown below. The nucleic acid sequence of anti-mouse PD-L1 scAb/IL-15N72D construct (including signal peptide sequence and stop codon) is as follows (SEQ ID NO: 9):

(Signal peptide)
ATGACATGGACTCTACTATTCCTTGCCTTCCTTCATCACTTAACAGGGTCA

TGTGCCCAGTTTGTGCTTACTCAGCCAAACTCT (Anti-mouse PD-L1 scAb)
(VL)
GTGTCTACGAATCTCGGAAGCACAGTCAAGCTGTCTTGCAACCGCAGCACT

GGTAACATTGGAAACAATTATGTGAACTGGTACCAGCAGCATGAAGGAAGA

TCTCCCACCACTCTGATTTATTGGGATGATAGGAGACCAGATGGAGTTCCT

GACAGGTTCTCTGGCTCCATTGACAGATCTTCCAACTCAGCCCTCCTGACA

ATCAATAATGTGCAGACTGAGGATGAAACTGACTACTTCTGTCAGTCTTAC

AGTAGTGGTATGTATATTTTCGGCGGTGGAACCAAGCTCACTGTCCTA (Linker)
GGAGGTGGCGGATCCGGAGGTGGAGGTTCTGGTGGAGGTGGGAGT (VH)
GAGGTTCAGCTGCAGCAGTCTGGGGCTGAGCTGGTGAAGCCTGGGGCTTCA

GTAAAGTTGTCCTGCAAAACTTCTGGTTACACCTTCAGCAATTACTATATG

AGTTGGTTGAAGCAGATGCCTGGACAGAATATTGAGTGGATCGGAAACATT

TATGGTGGAAATGGTGGTGCTGGCTATAATCAGAAGTTCAAGGGCAAGGCC

ACACTGACAGTGGACAAATCTTCCAGCACAGCGTACATGGATCTCAGCAGC

CTGACATCTGAGGCCTCTGCAGTCTATTTTTGTGCAAGGGTCGGACTTCCC

GGCCTTTTTGATTACTGGGGCCAGGGAGTCATGGTCACAGTCTCCTCA (Human IL-15N72D)
AACTGGGTGAATGTAATAAGTGATTTGAAAAAAATTGAAGATCTTATTCAA

TCTATGCATATTGATGCTACTTTATATACGGAAAGTGATGTTCACCCCAGT

TGCAAAGTAACAGCAATGAAGTGCTTTCTCTTGGAGTTACAAGTTATTTCA

CTTGAGTCCGGAGATGCAAGTATTCATGATACAGTAGAAAATCTGATCATC

CTAGCAAACGACAGTTTGTCTTCTAATGGGAATGTAACAGAATCTGGATGC

AAAGAATGTGAGGAACTGGAGGAAAAAAATATTAAAGAATTTTTGCAGAGT

TTTGTACATATTGTCCAAATGTTCATCAACACTTCTTAA

The amino acid sequence of the anti-mouse PD-L1 scAb/IL-15N72D fusion protein (including signal peptide sequence) is as follows (SEQ ID NO: 10):

```
(Signal peptide)
MTWTLLFLAFLHHLTGSCAQFVLTQPNS (Anti-mouse PD-L1 scAb)
(VL)
VSTNLGSTVKLSCNRSTGNIGNNYVNWYQQHEGRSPTTLIYWDDRRPDGVP

DRFSGSIDRSSNSALLTINNVQTEDETDYFCQSYSSGMYIFGGGTKLTVL (Linker)
GGGGSGGGGSGGGGS (VH)
EVQLQQSGAELVKPGASVKLSCKTSGYTFSNYYMSWLKQMPGQNIEWIGNI

YGGNGGAGYNQKFKGKATLTVDKSSSTAYMDLSSLTSEASAVYFCARVGLP

GLFDYWGQGVMVTVSS (Human IL-15N72D)
NWVNVISDLKKIEDLIQSMHIDATLYTESDVHPSCKVTAMKCFLLELQVIS

LESGDASIHDTVENLIILANDSLSSNGNVTESGCKECEELEEKNIKEFLQS

FVHIVQMFINTS
```

In some cases, the leader peptide is cleaved from the mature polypeptide.

The nucleic acid sequence of an anti-mouse PD-L1 scAb/huIL-15RαSu/muIgG2A Fc construct (including leader sequence) is as follows (SEQ ID NO: 11):

```
(Signal peptide)
ATGACATGGACTCTACTATTCCTTGCCTTCCTTCATCACTTAACAGGGTCA

TGTGCCCAGTTTGTGCTTACTCAGCCAAACTCT (Anti-mouse PD-L1 scAb)
(VL)
GTGTCTACGAATCTCGGAAGCACAGTCAAGCTGTCTTGCAACCGCAGCACT

GGTAACATTGGAAACAATTATGTGAACTGGTACCAGCAGCATGAAGGAAGA

TCTCCCACCACTCTGATTTATTGGGATGATAGGAGACCAGATGGAGTTCCT

GACAGGTTCTCTGGCTCCATTGACAGATCTTCCAACTCAGCCCTCCTGACA

ATCAATAATGTGCAGACTGAGGATGAAACTGACTACTTCTGTCAGTCTTAC

AGTAGTGGTATGTATATTTTCGGCGGTGGAACCAAGCTCACTGTCCTA (Linker)
GGAGGTGGCGGATCCGGAGGTGGAGGTTCTGGTGGAGGTGGGAGT (VH)
GAGGTTCAGCTGCAGCAGTCTGGGGCTGAGCTGGTGAAGCCTGGGCTTCA

GTAAAGTTGTCCTGCAAAACTTCTGGTTACACCTTCAGCAATTACTATATG

AGTTGGTTGAAGCAGATGCCTGGACAGAATATTGAGTGGATCGGAAACATT

TATGGTGGAAATGGTGGTGCTGGCTATAATCAGAAGTTCAAGGGCAAGGCC

ACACTGACAGTGGACAAATCTTCCAGCACAGCGTACATGGATCTCAGCAGC

CTGACATCTGAGGCCTCTGCAGTCTATTTTTGTGCAAGGGTCGGACTTCCC

GGCCTTTTTGATTACTGGGGCCAGGGAGTCATGGTCACAGTCTCCTCA (Human IL-15R α sushi domain)
ATCACGTGCCCTCCCCCCATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Mouse IgG2a CH2-CH3 domain)
GAACCAAGAGGGCCCACAATCAAGCCCTGTCCTCCATGCAAATGCCCAGCA

CCTAACCTCTTGGGTGGACCATCCGTCTTCATCTTCCCTCCAAAGATCAAG

GATGTACTCATGATCTCCCTGAGCCCCATAGTCACATGTGTGGTGGTGGAT

GTGAGCGAGGATGACCCAGATGTCCAGATCAGCTGGTTTGTGAACAACGTG

GAAGTACACACAGCTCAGACACAAACCCATAGAGAGGATTACAACAGTACT

CTCCGGGTGGTCAGTGCCCTCCCCATCCAGCACCAGGACTGGATGAGTGGC

AAGGAGTTCAAATGCAAGGTCAACAACAAAGACCTCCCAGCGCCCATCGAG

AGAACCATCTCAAAACCCAAAGGGTCAGTAAGAGCTCCACAGGTATATGTC

TTGCCTCCACCAGAAGAAGAGATGACTAAGAAACAGGTCACTCTGACCTGC

ATGGTCACAGACTTCATGCCTGAAGACATTTACGTGGAGTGGACCAACAAC

GGGAAAACAGAGCTAAACTACAAGAACACTGAACCAGTCCTGGACTCTGAT

GGTTCTTACTTCATGTACAGCAAGCTGAGAGTGGAAAAGAAGAACTGGGTG

GAAAGAAATAGCTACTCCTGTTCAGTGGTCCACGAGGGTCTGCACAATCAC

CACACGACTAAGAGCTTCTCCCGGACTCCAGGTAAATAA
```

The amino acid sequence of the anti-mouse PD-L1 scAb/huIL-15RαSu/muIgG2A Fc fusion protein (including leader sequence) is as follows (SEQ ID NO: 12):

```
(Signal peptide)
MTWTLLFLAFLHHLTGSCAQFVLTQPNS (Anti-mouse PD-L1 scAb)
(VL)
VSTNLGSTVKLSCNRSTGNIGNNYVNWYQQHEGRSPTTLIYWDDRRPDGV

PDRFSGSIDRSSNSALLTINNVQTEDETDYFCQSYSSGMYIFGGGTKLTV (Linker)
GGGGSGGGGSGGGGS (VH)
EVQLQQSGAELVKPGASVKLSCKTSGYTFSNYYMSWLKQMPGQNIEWIGN

IYGGNGGAGYNQKFKGKATLTVDKSSSTAYMDLSSLTSEASAVYFCARVG

LPGLFDYWGQGVMVTVSS (Human IL-15R a sushi domain)
ITCPPPMSVEHADIWVKSYSLYSRERYICNSGFKRKAGTSSLTECVLNKA

TNVAHWTTPSLKCIR (Mouse IgG2a CH2—CH3 domain)
EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT
```

-continued

LTCMVTDFMPEDIYVEWTNNGKTELNYKNTEPVLDSDGSYFMYSKLRVEK

KNWVERNSYSCSVVHEGLHNHHTTKSFSRTPGK

In some cases, the leader peptide is cleaved from the mature polypeptide.

The anti-PD-L1 scAb/IL-15N72D and anti-PD-L1 scAb/IL-15RαSu/Fc sequences were cloned into expression vectors as described previously (U.S. Pat. No. 8,507,222, incorporated herein by reference), and the expression vectors transfected into CHO cells. Co-expression of the two constructs in CHO cells allowed formation and secretion of a soluble anti-PD-L1 scAb/IL-15N72D:anti-PD-L1 scAb/IL-15RαSu/Fc complex which was purified from the CHO cell culture supernatant using Protein A affinity chromatography.

Figure 3:
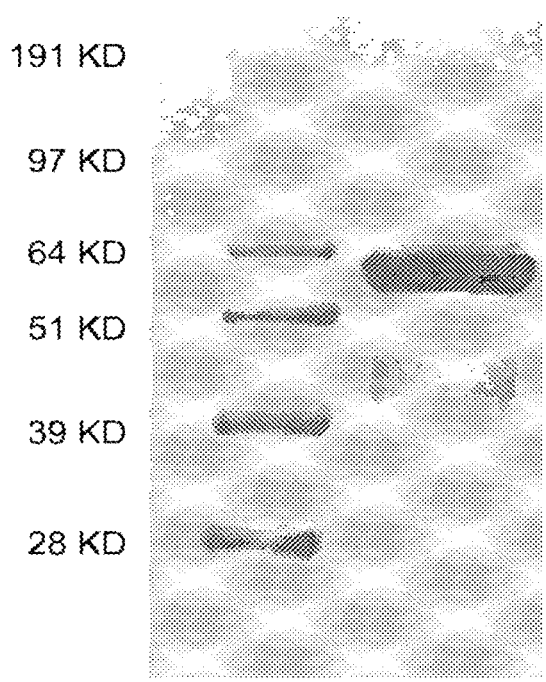
FIG. 3 is a photograph showing a sodium dodecyl sulfate polyacrylamide gel electrophoresis (SDS-PAGE) analysis of the TxM complex following disulfide bond reduction. Right lane: PD-L1 TxM; left lane: marker.

SDS-PAGE analysis of the purified anti-PD-L1 scAb/IL-15N72D:anti-PD-L1 scAb/IL-15RαSu/Fc protein complexes is shown in FIG. 3. Bands corresponding to the soluble anti-mouse PD-L1 scAb/huIL-15RαSu/muIgG2A and anti-mouse PD-L1 scAb/IL-15N72D proteins at ~60 kDa and ~40 kDa, respectively, were observed.

Example 2: In Vitro Characterization of the Activities of PD-L1 TxM

Figure 4A:
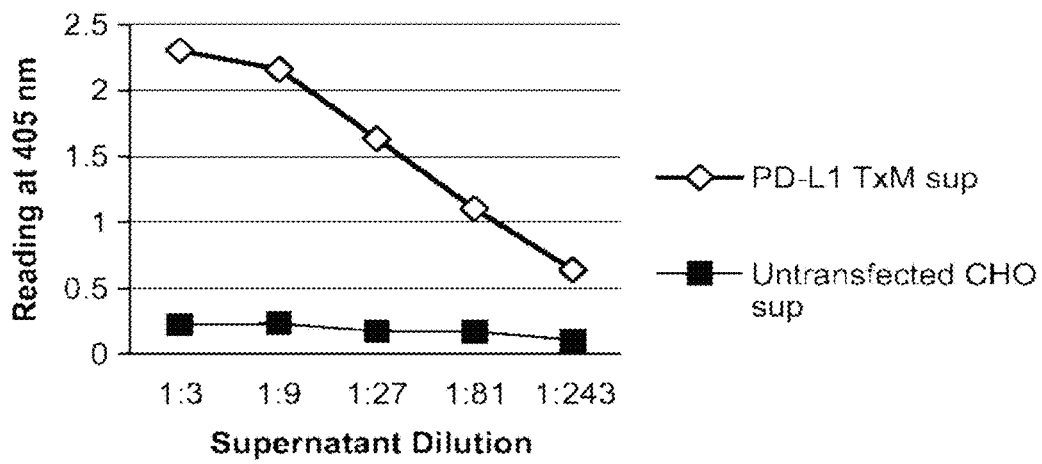
FIG. 4A is a line graph showing the binding activity of an anti-human PD-L1 TxM complex to antibodies specific to human IL-15 and human IgG.
Figure 4B:
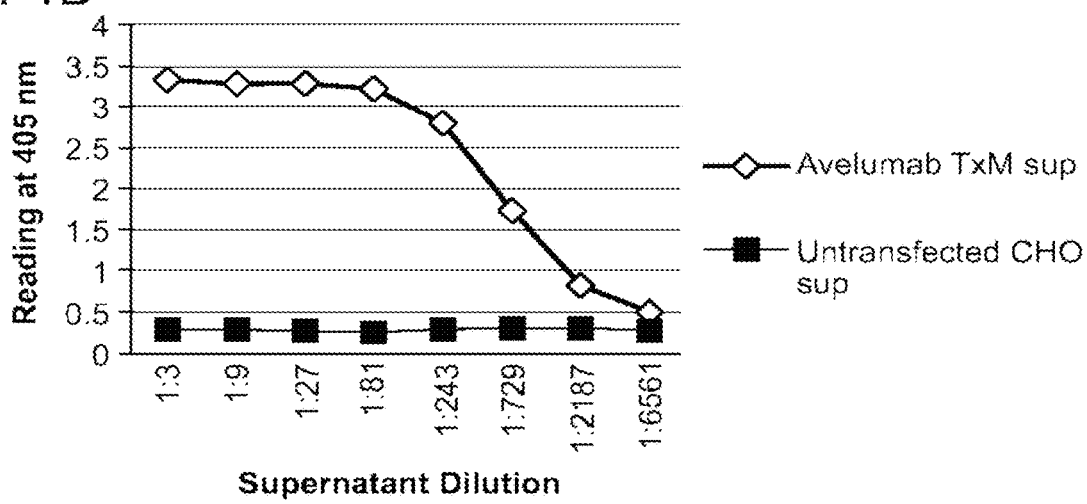
FIG. 4B is a line graph showing the binding activity of a second anti-human PD-L1 TxM complex to antibodies specific to human IL-15 and human IgG.

ELISA-based methods confirmed the formation of a PD-L1 TxM complex. In FIG. 4A, the anti-human PD-L1 scAb/IL-15N72D:anti-human PD-L1 scAb/huIL-15RαSu/huIgG1 Fc fusion protein complexes in the culture supernatant from transfected CHO cells were detected using a huIgG1/huIL15-specific ELISA with a capture antibody, anti-human IgG antibody (Jackson ImmunoResearch), and a detection antibody, biotinylated anti-human IL-15 antibody (BAM 247, R&D Systems). This is compared to a control sample using only the supernatant of media containing untransfected CHO cells. The increased signal observed in the culture supernatant from transfected CHO cells verifies formations of the PD-L1 TxM complex. Similar results were obtained from a second anti-human PD-L1 scAb/IL-15N72D:anti-human PD-L1 scAb/huIL-15RαSu/huIgG1 Fc fusion protein complex (avelumab TxM) (FIG. 4B).

Figure 4C:
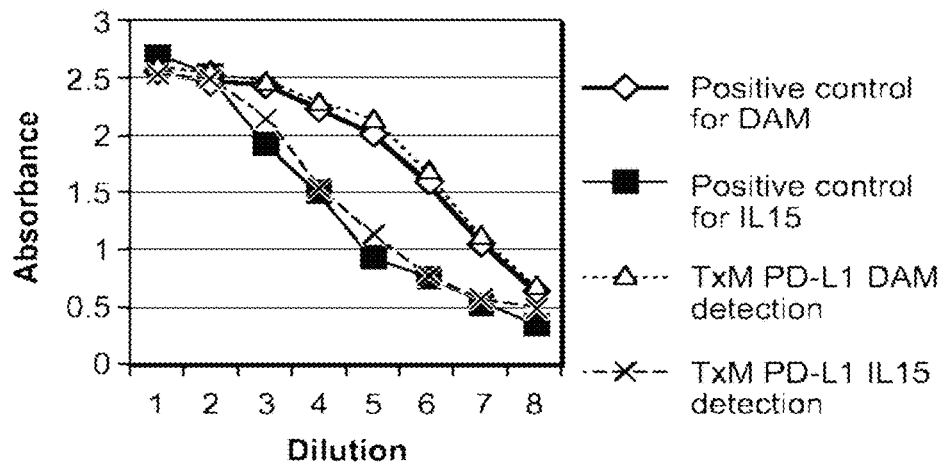
FIG. 4C is a line graph showing the binding activity of an anti-mouse PD-L1 TxM complex to antibodies specific to human IL-15 and mouse IgG.

For the mouse specific PD-L1 TxM, the fusion protein complexes were detected using a mIgG2a-specific or huIL15-specific ELISA with a capture antibody, affinipure donkey anti-mouse IgG (Jackson ImmunoResearch) or human/primate IL15 antibody (MAB647, R&D system) and a detection antibody horseradish peroxidase-affinipure donkey anti-mouse IgG (Jackson ImmunoResearch) or biotinylated anti-human IL-15 antibody (BAM 247, R&D Systems), respectively (FIG. 4C). Compared to the positive controls, antibody reactivity to the purified mouse specific PD-L1 TxM verified formation of the complex.

Figure 5A:
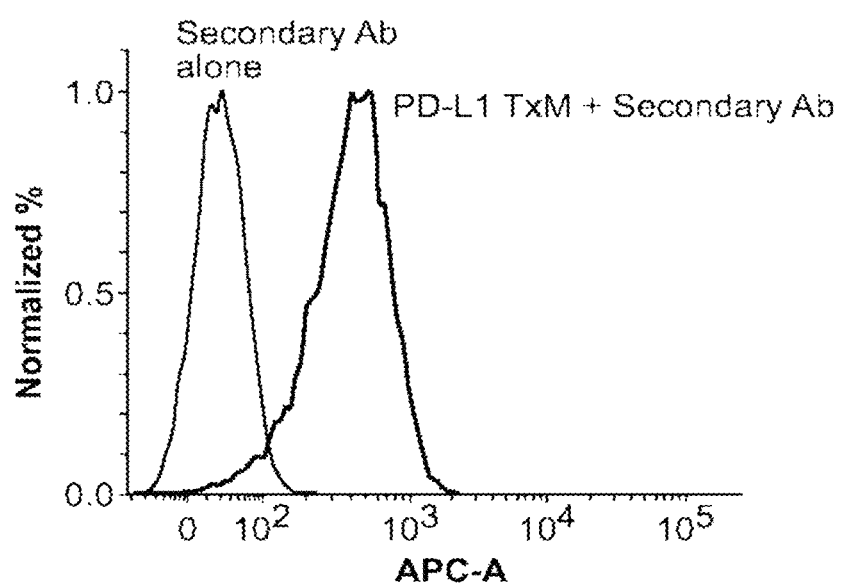
FIG. 5A is a line graph showing the binding activity of a PD-L1 TxM complex to PD-L1-bearing human MB231 tumor cells.
Figure 5B:
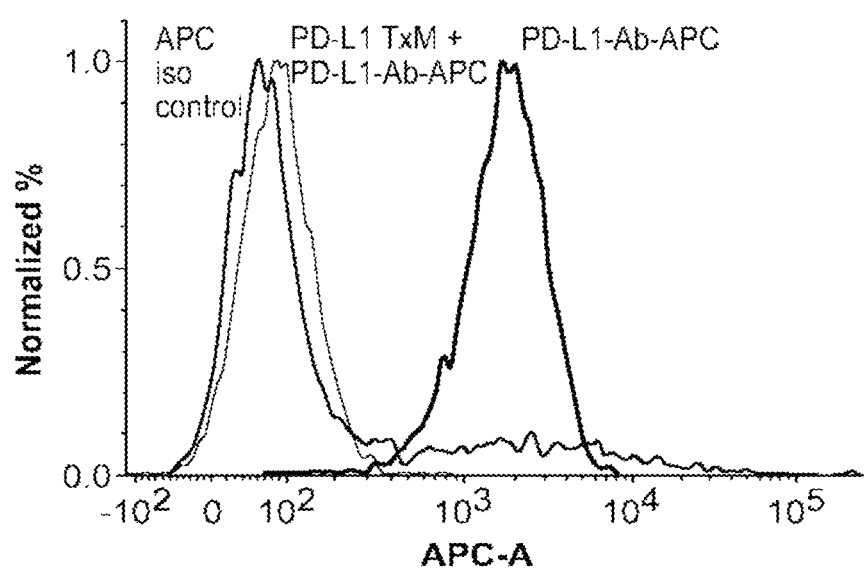
FIG. 5B is a line graph showing the blocking activity of a PD-L1 TxM complex of PD-L1 expressed on human MB231 tumor cells.
Figure 5C:
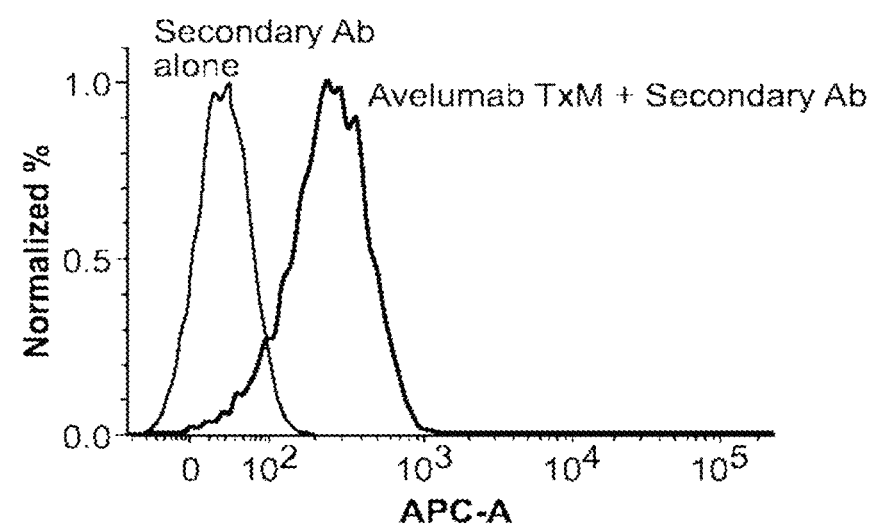
FIG. 5C is a line graph showing the binding activity of a PD-L1 TxM complex to PD-L1-bearing human MB231 tumor cells.

The ability of these fusion protein complexes to bind PD-L1 on tumor cells was also examined. The binding of human specific PD-L1 TxM was assessed by flow cytometry using receptor bearing MB231 tumor cells. In these studies, 1×10$^5$ cells were stained with PD-L1 TxM complexes. As shown in FIG. 5A, flow cytometry analysis demonstrated binding of the PD-L1 TxM complex to MB231 cells when detected using an APC conjugated mouse anti-human Fc Ab (Biolegend). In FIG. 5B, specificity of this binding was tested by using the PD-L1 TxM complex to block the staining of MB231 cells with a commercially available APC conjugated anti-human PD-L1 Ab (Biolegend). Similarly, flow cytometry analysis demonstrated binding of the avelumab-based PD-L1 TxM complex to MB231 tumor cells (FIG. 5C).

Figure 6A:
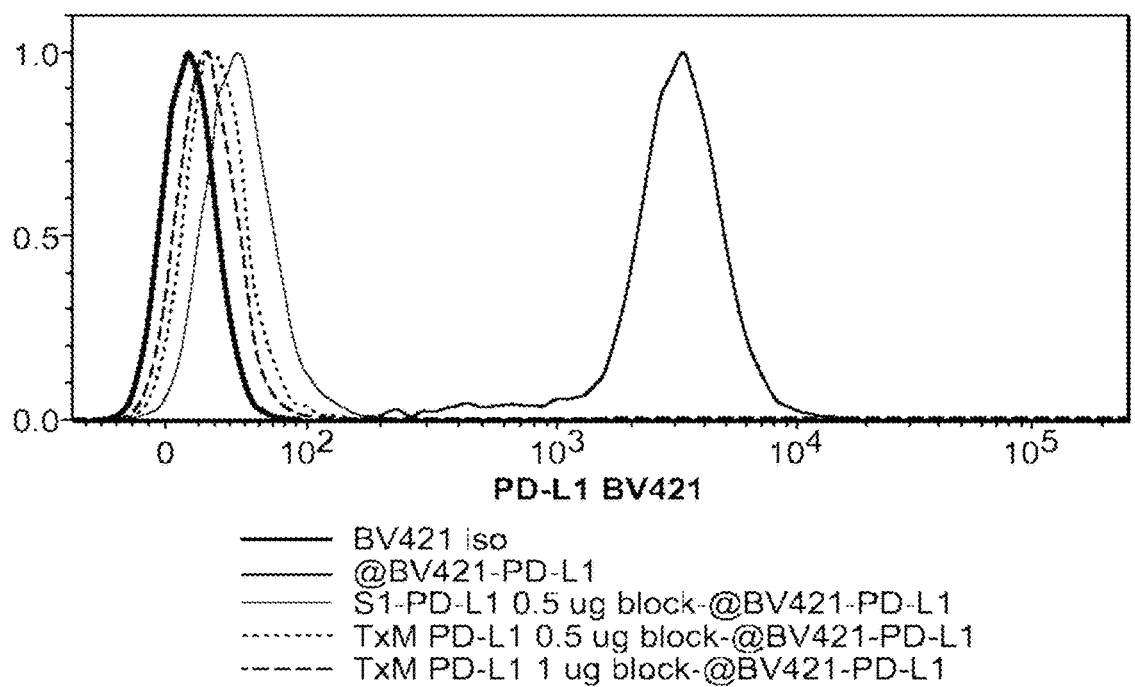
FIG. 6A is a line graph showing the blocking activity of a PD-L1 TxM complex of PD-L1 expressed on mouse 5T33P tumor cells.
Figure 6B:
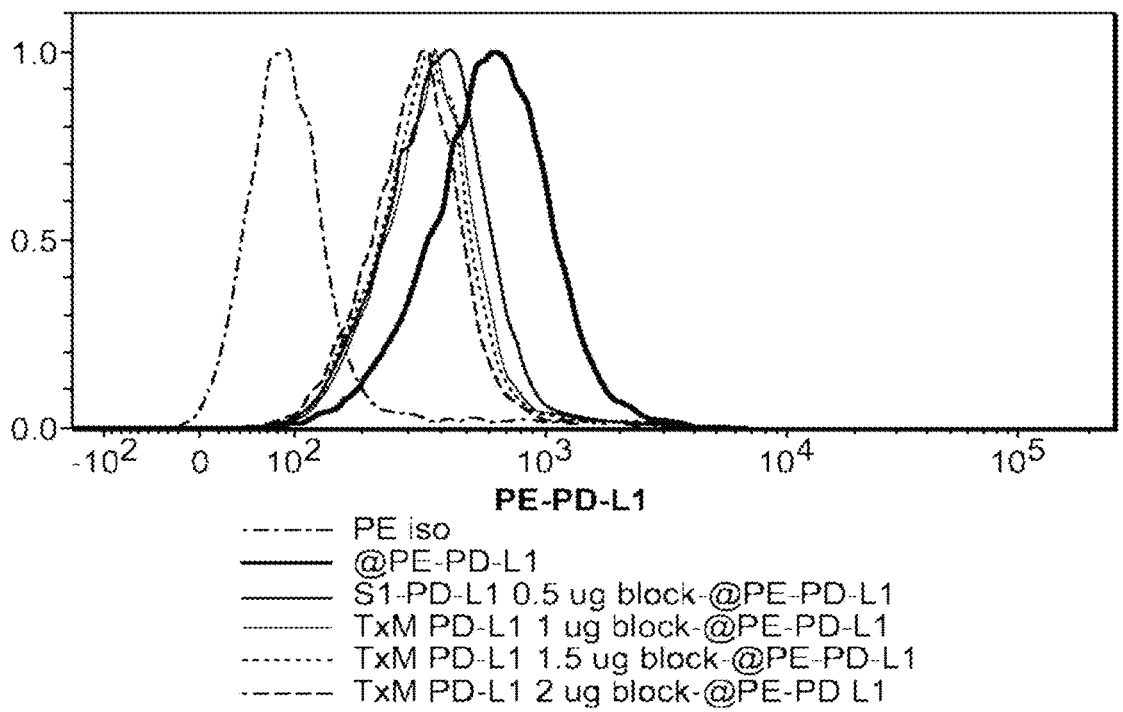
FIG. 6B is a line graph showing the blocking activity of a PD-L1 TxM complex of PD-L1 expressed on mouse MB491uc tumor cells.
Figure 7A:
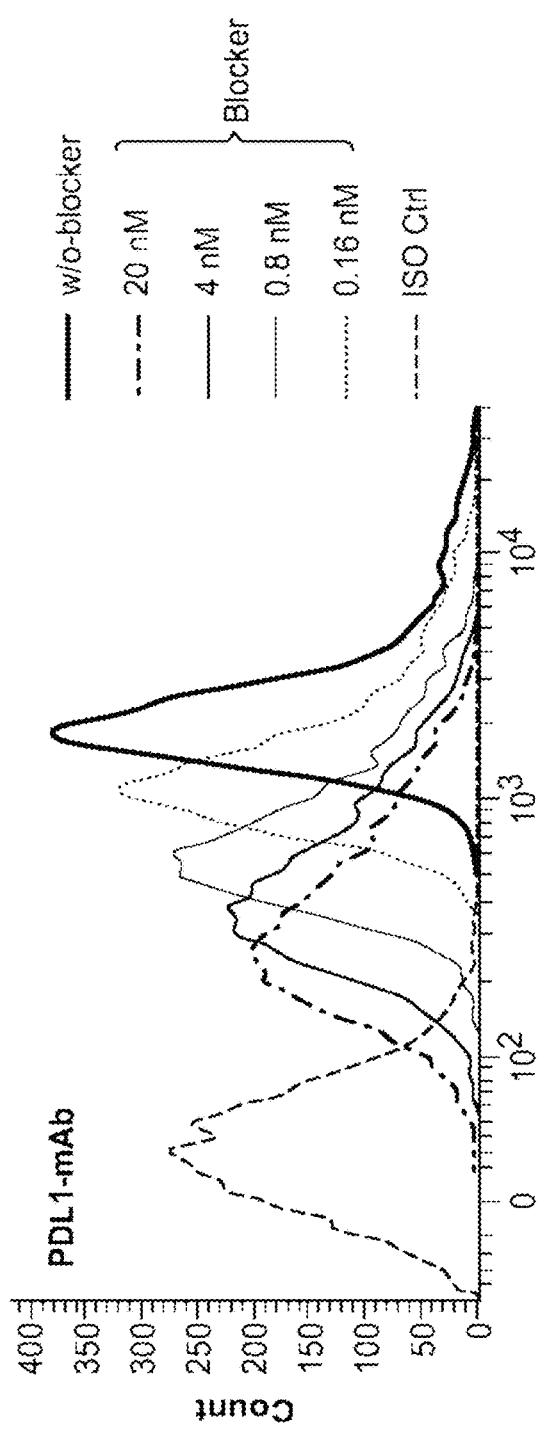
FIG. 7A and FIG. 7B are line graphs comparing the blocking activities of an anti-PD-L1 Ab and a PD-L1 TxM complex of PD-L1 expressed on mouse A20 tumor cells.
Figure 7B:
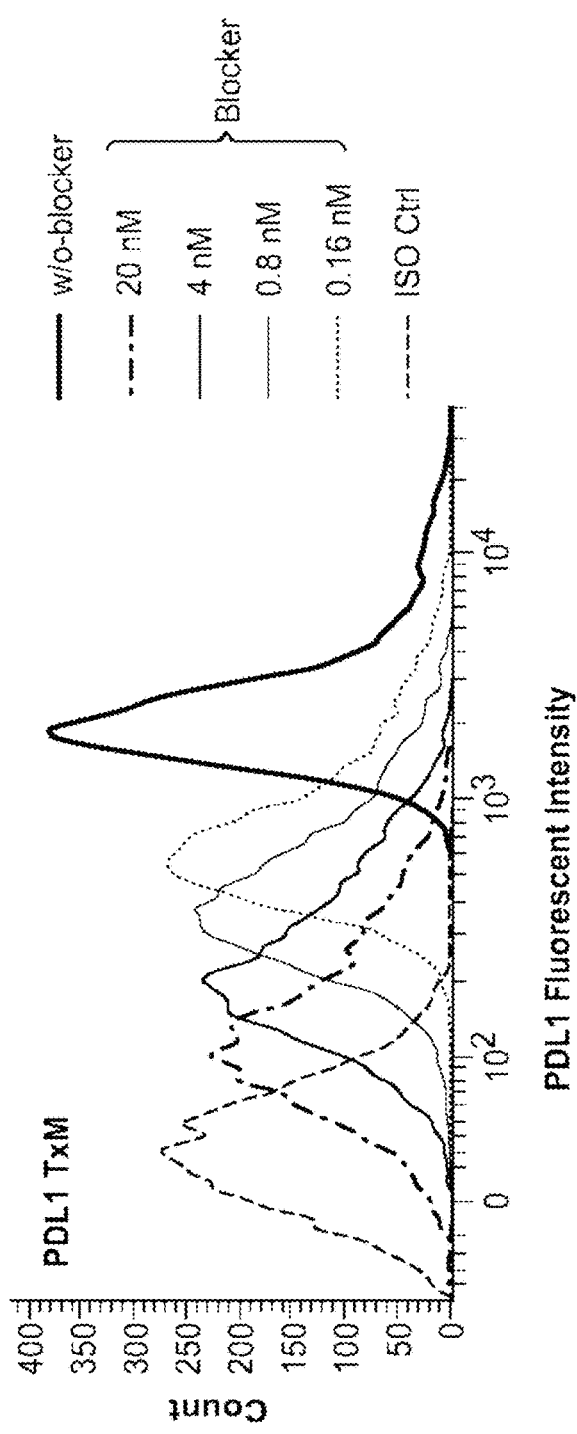

To assess binding of the mouse-specific PD-L1 TxM complexes, PD-L1-positive 5T33P myeloma and MB491uc bladder tumor cells (5×10$^5$ cells/test) initially were stained with PE or Brilliant Violet labeled anti-mouse PD-L1 Ab (2 μg/test in 100 μL) (FIG. 6A and FIG. 6B). Specificity of this binding was tested by addition of purified mouse-specific PD-L1 TxM complexes to block antibody binding to PD-L1 ligand. A purified anti-mPD-L1 Ab (S1-PD-L1) was used as a positive control. Interestingly, the PD-L1 TxM complexes were found to block PD-L1 staining on the tumor cell better than the equivalent amount of anti-PD-L1 Ab. This was further assessed in blocking studies using A20 B-cell lymphoma cells. Titration analysis indicated that PD-L1 TxM was at least 5-fold more effective than anti-PD-L1 Ab at blocking interactions with PD-L1 expressed on the tumor cell surface (FIG. 7A and FIG. 7B).

Figure 8:
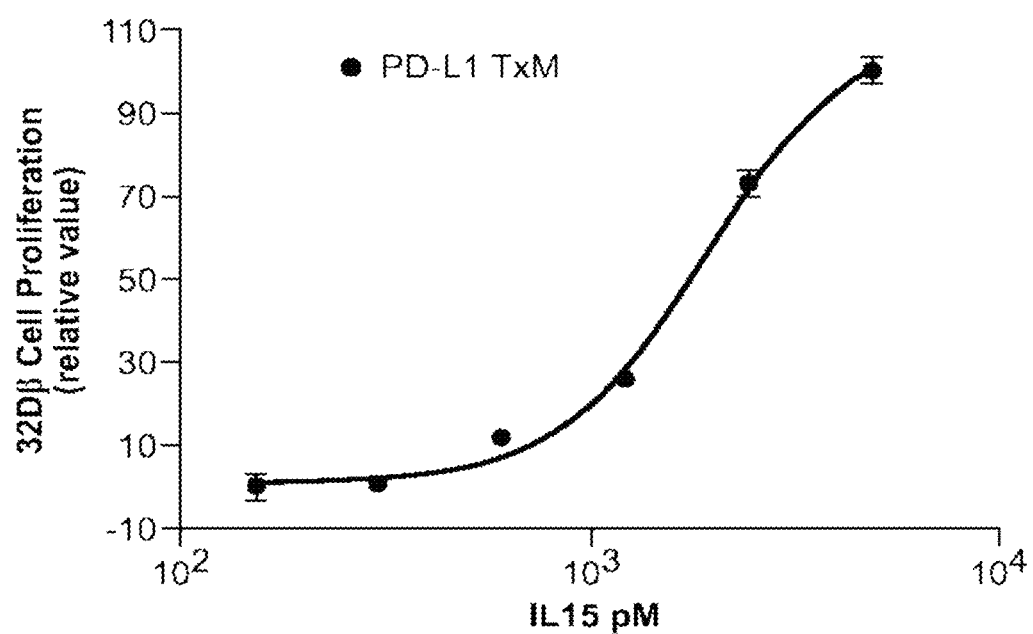
FIG. 8 is a line graph illustrating the proliferation of IL-15-dependent 32Dβ cells mediated by a PD-L1 TxM complex.

To assess the IL-15 immunostimulatory activity of PD-L1 TxM complexes, proliferation of IL-15-dependent 32Dβ cells, a mouse hematopoietic cell line, was assessed. Increasing levels of PD-L1 TxM were added to 32Dβ cells (10$^4$ cell/well) and cell proliferation was determined 2 days later using WST-1 proliferation reagent. As shown in FIG. 8, a dose dependent increase in 32Dβ cell proliferation was mediated by PD-L1 TxM verifying the immunostimulatory activity of the complex.

Further studies were conducted to assess the characteristics and activity of different forms of the PD-L1 TxM complex. Complexes comprising anti-PD-L1 scAb/IL-15N72D and anti-PD-L1 scAb/IL-15RαSu/Fc proteins are expected to have four anti-PD-L1 scAb binding domains (i.e., 4 headed (4H)) whereas complexes comprising IL-15N72D and anti-PD-L1 scAb/IL-15RαSu/Fc proteins are expected to have two anti-PD-L1 scAb binding domains (i.e., 2 headed (2H)) (FIG. 9A). These complexes are expected to have different activities based on the higher avidity binding to target cells of the 4H TxM compared to the 2H TxM. Protein fusion to the IL-15N72D has also been shown to reduce the IL-15 biological activity. Thus, the 4H TxM format is expected to have lower IL-15 activity than the 2H TxM. These differences are expected to provide advantages where high (antibody-like) targeting and lower immunostimulatory activity is preferred (i.e., 4H TxM format) or where lower targeting and higher immunostimulatory activity (immunocytokine) is preferred.

Figure 9B:
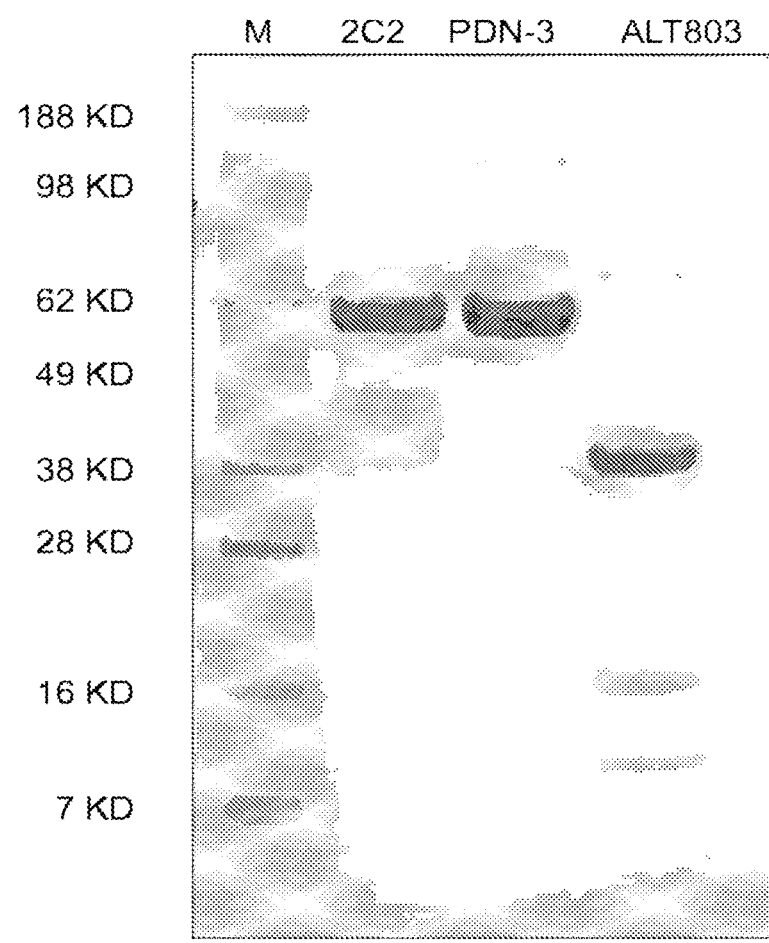
FIG. 9B is a photograph showing SDS-PAGE analysis of four- and two-headed mouse-specific PD-L1 TxM complexes following disulfide bond reduction.
Figure 9C:
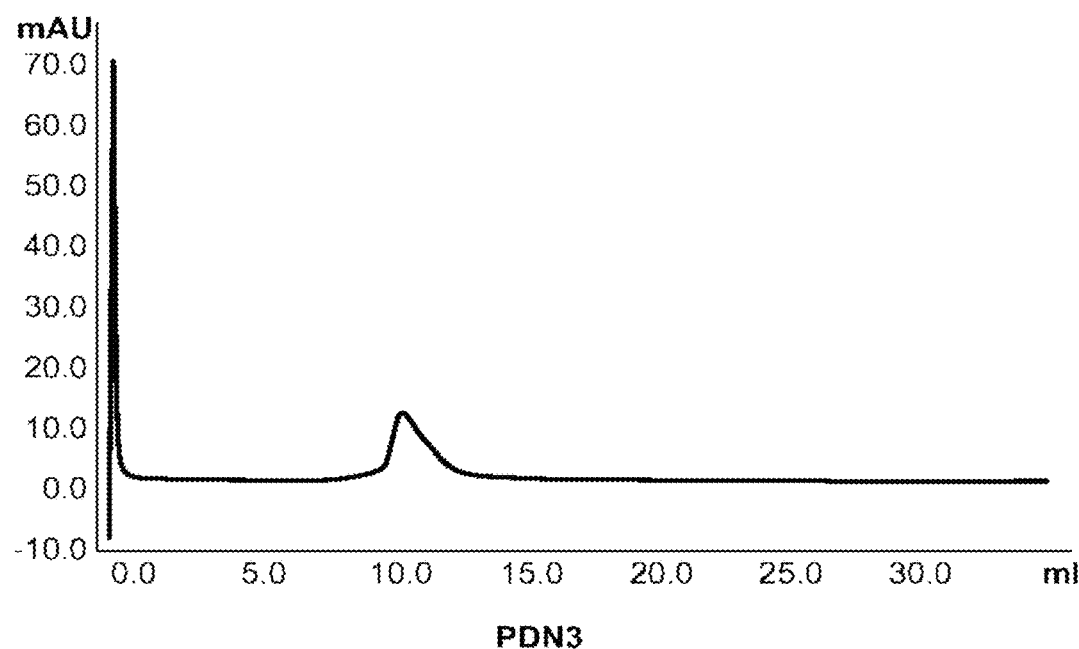
FIG. 9C and FIG. 9D show line graphs representing the chromatographic profiles of two- and four-headed mouse-specific PD-L1 TxM complexes, respectively, following elution on an analytical size exclusion column, demonstrating separation of TxM complexes from protein aggregates.
Figure 9D:
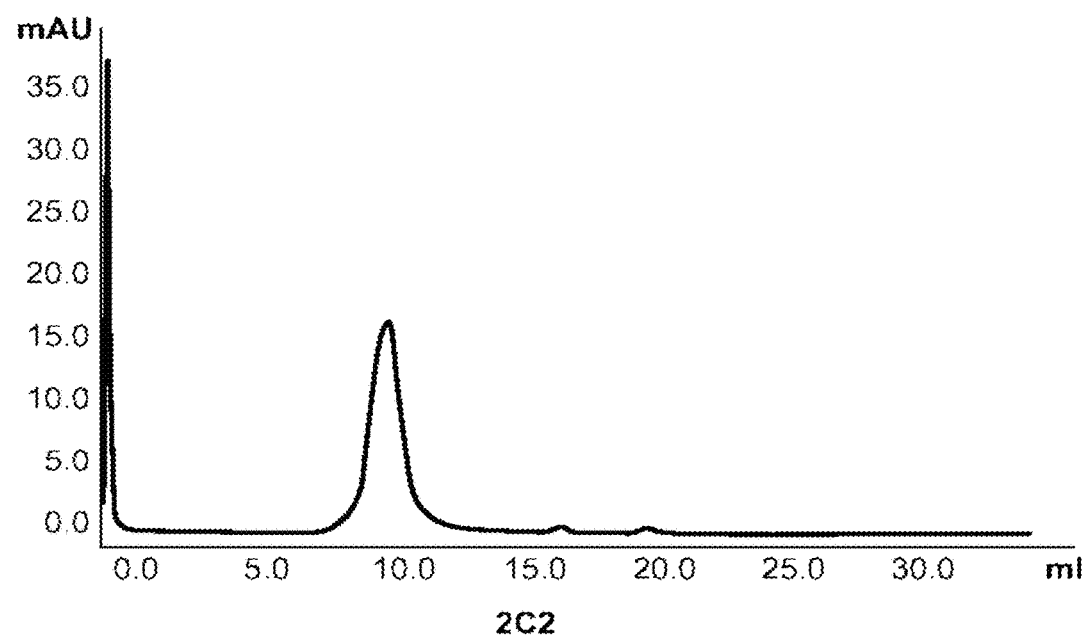

To evaluate these formats, 4H mouse-specific PD-L1 TxM (2C2) and 2H mouse-specific PD-L1 TxM (PDN3) were generated by transfecting CHO cells with anti-mouse PD-L1 scAb/IL-15N72D and anti-mouse PD-L1 scAb-/IL-15RαSu/Fc expression vectors or IL-15N72D and anti-mouse PD-L1 scAb-/IL-15RαSu/Fc expression vectors, respectively. The TxM complexes were then purified from the transfected CHO cell supernatant by Protein A chromatography and the purified proteins evaluated by reduced SDS-PAGE (FIG. 9B). Bands corresponding to the soluble anti-mouse PD-L1 scAb/huIL-15RαSu/muIgG2A, anti-mouse PD-L1 scAb/IL-15N72D and IL-15N72D proteins at ~60 kDa, ~40 kDa and ~16 kDa, respectively, were observed. Additionally, the purified 4H PD-L1 TxM (2C2) and 2H PD-L1 TxM (PDN3) complexes migrate as a single protein peak when analyzed by analytical size exclusion chromatography (SEC) (FIG. 9C and FIG. 9D). These results indicate that the two different PD-L1 TxM complexes can be produced and purified as soluble proteins with the expected structural properties.

Figure 10A:
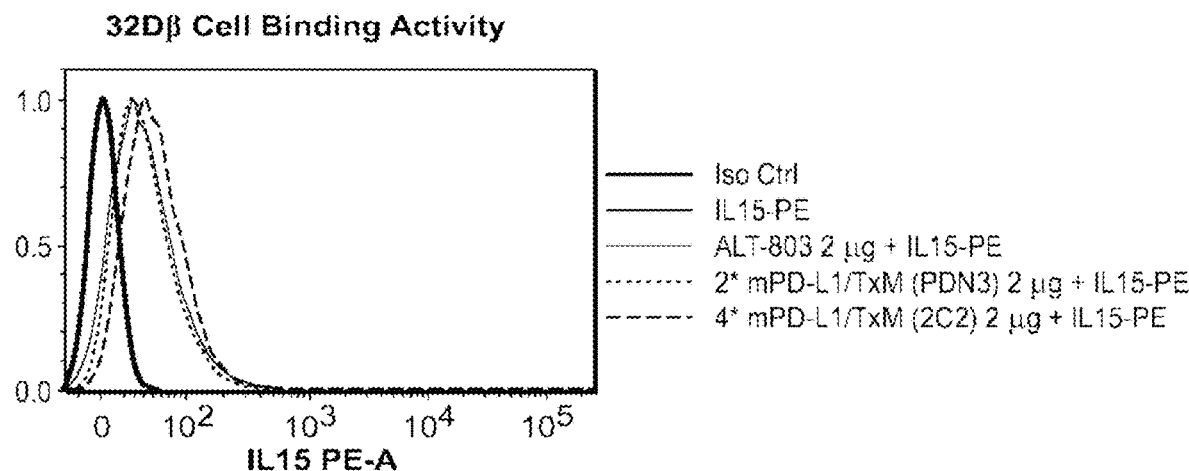
FIG. 10A is a line graph showing the binding activity of two- and four-headed mouse-specific PD-L1 TxM complexes to IL-2Rβγ-bearing 32Dβ cells.
Figure 10B:
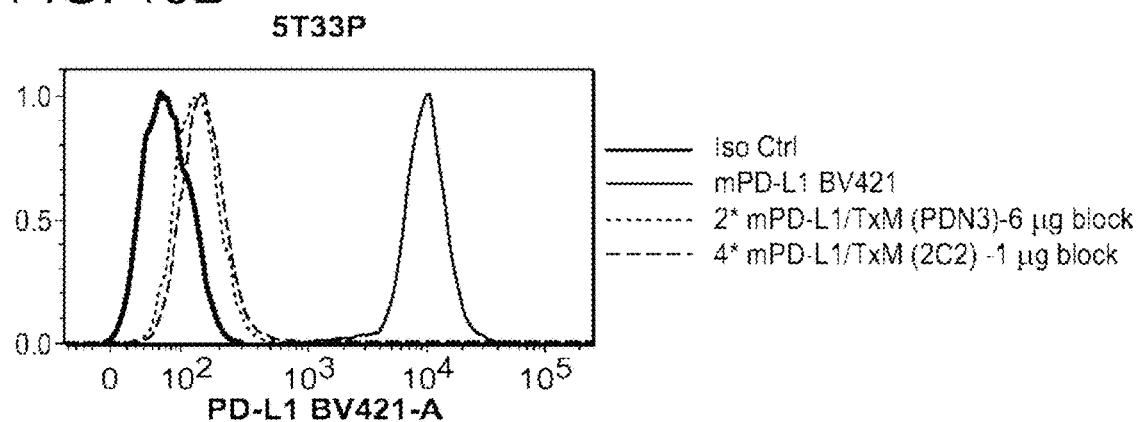
FIG. 10B and FIG. 10C show line graphs demonstrating the blocking activity of the two- and four-headed mouse-specific PD-L1 TxM complexes of PD-L1 expressed on 5T33P myeloma cells.
Figure 10C:
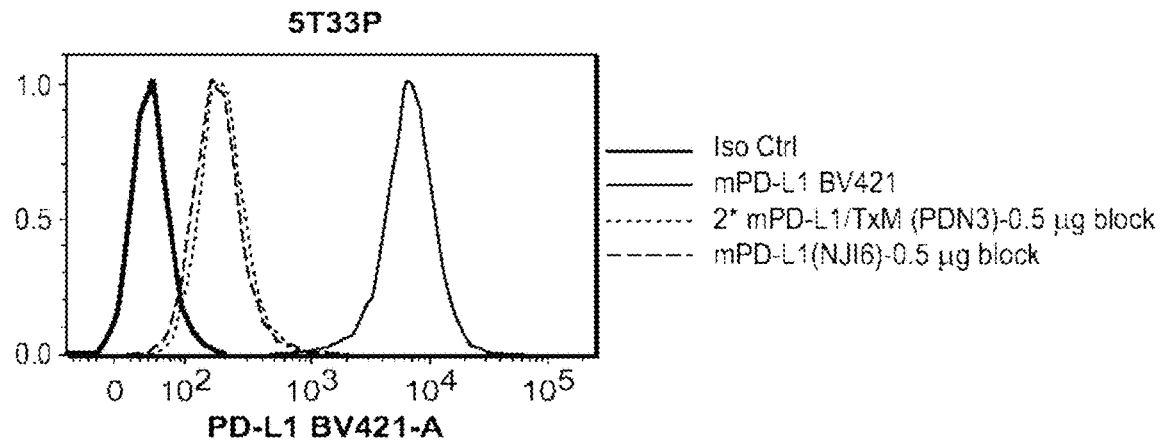

Similar to studies described above, the ability of these fusion protein complexes to bind IL-2Rβ/γ on immune cells and PD-L1 on tumor cells was examined. IL-2Rβ/γ-positive 32Dβ cells were incubated with 4H PD-L1 TxM (2C2), 2H PD-L1 TxM (PDN3) or control ALT-803 complexes. Followed by a wash step, anti-human IL-15 Ab-PE (or isotype control Ab) was added to detect bound TxM/ALT-803 complexes by flow cytometry. As shown in FIG. 10A, 4H PD-L1 TxM (2C2), 2H PD-L1 TxM (PDN3) and ALT-803 proteins were capable of 32Dβ cells compared to the controls. To assess binding to PD-L1, PD-L1-positive 5T33P myeloma cells initially were stained with Brilliant Violet 421 (BV421)-labeled anti-mouse PD-L1 Ab (10F.9G2). Specificity of this binding was tested by addition of purified 4H PD-L1 TxM (2C2) and 2H PD-L1 TxM (PDN3) complexes to block BV421 antibody binding to PD-L1 ligand (FIG. 10B and FIG. 10C). A purified anti-mPD-L1 Ab (NJI6) was used as a positive control. Consistent with its higher avidity, 1 µg of 4H PD-L1 TxM was as effective at blocking anti-PD-L1 Ab staining as 6 µg of 2H PD-L1 TxM. These results confirm that the 4H PD-L1 and 2H PD-L1 TxM complexes retain IL-2Rβ/γ and PD-L1 target binding activity.

Figure 11A:
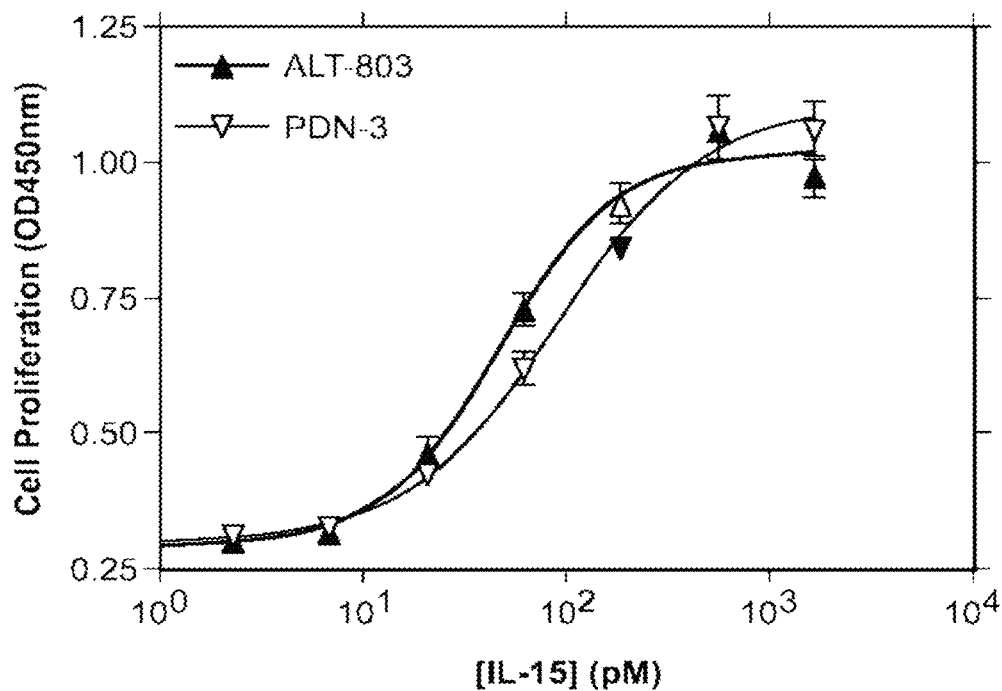
FIG. 11A is a line graph illustrating the proliferation of IL-15-dependent 32Dβ cells mediated by a two-headed mouse-specific PD-L1 TxM complex compared to ALT-803 (IL-15N72D:IL-15Rα/Fc complex).
Figure 11B:
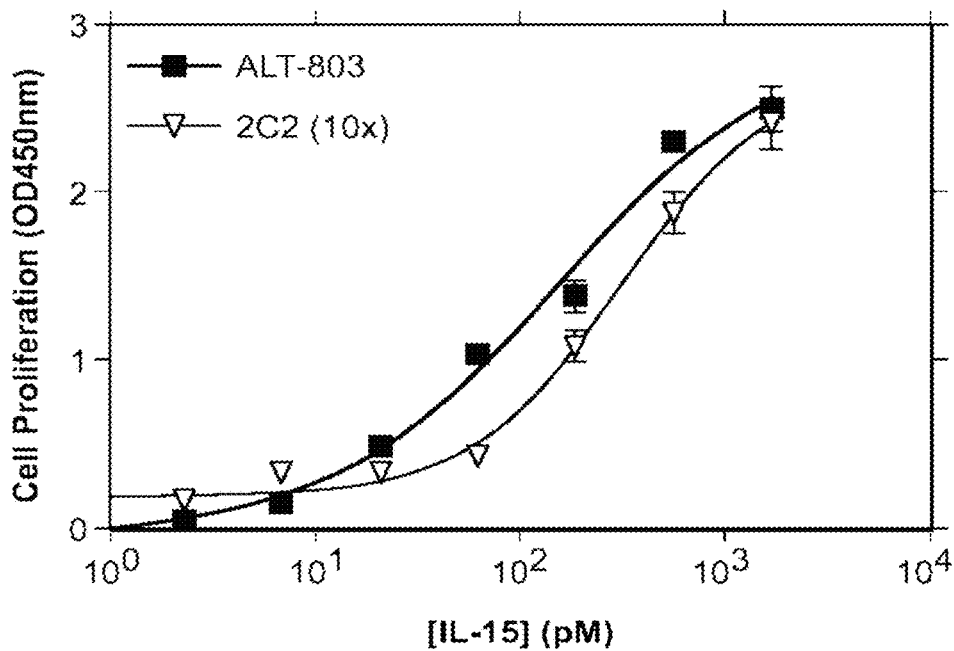
FIG. 11B is a line graph illustrating the proliferation of IL-15-dependent 32Dβ cells mediated by a four-headed mouse-specific PD-L1 TxM complex compared to ALT-803.

As described above, the IL-15 immunostimulatory activity of the mouse-specific 4H PD-L1 and 2H PD-L1 TxM complexes was determined based on proliferation of IL-15-dependent 32Dβ cells. As shown in FIG. 11A and FIG. 11B, a dose dependent increase in 32Dβ cell proliferation was mediated by either 4H PD-L1 and 2H PD-L1 TxM complexes, verifying the immunostimulatory activity of these TxM formats. The 2H PD-L1 TxM complex (PDN-3) exhibits a slight decrease in IL-15 bioactivity compared to ALT-803 whereas the 4H PD-L1 TxM complex (2C2) exhibits approximately a 30-fold decrease in IL-15 bioactivity. This is consistent with the lower IL-15 activity of previous binding domain-IL-15N72D fusion proteins.

Figure 12A:
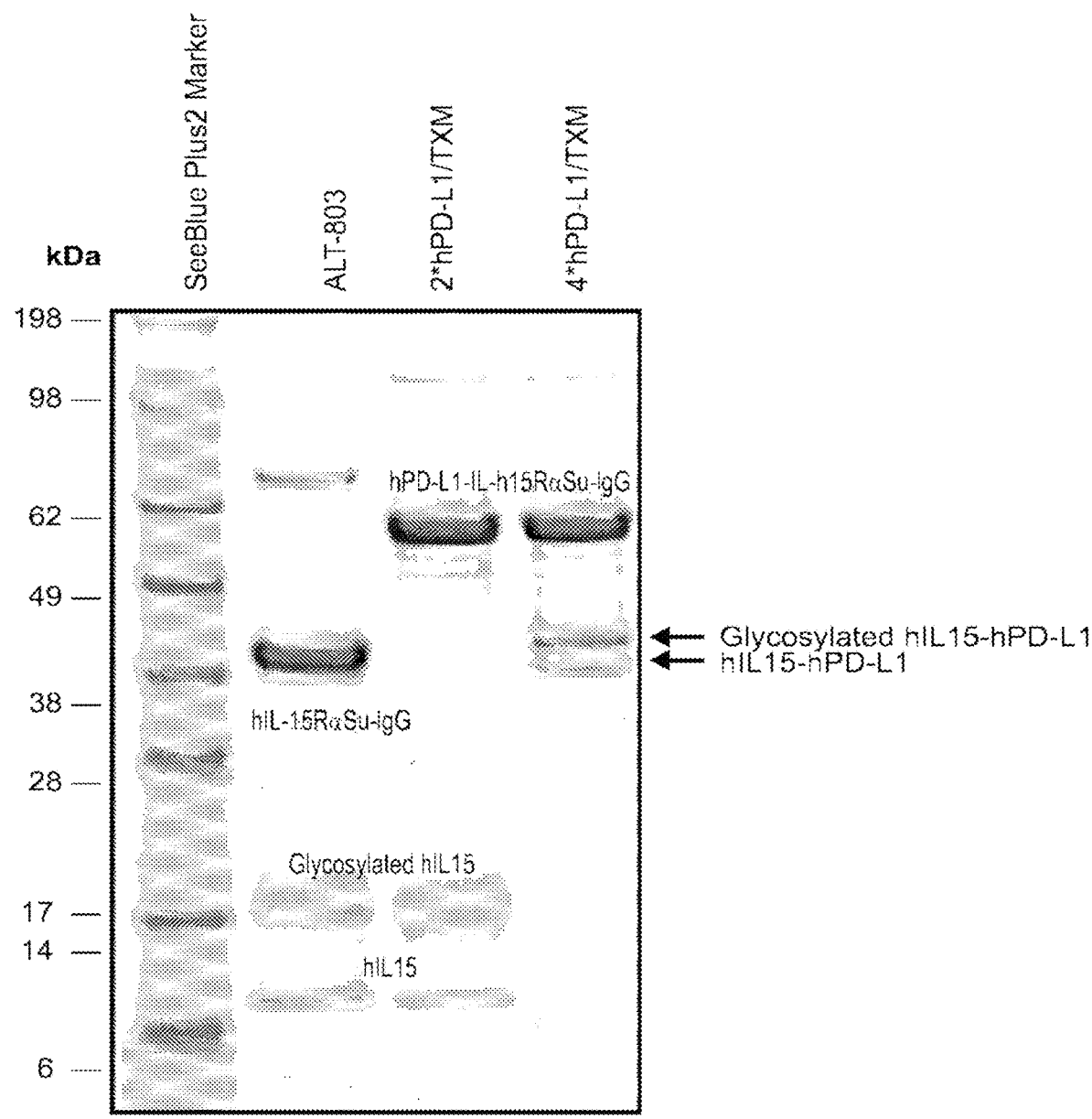
FIG. 12A is a photograph showing SDS-PAGE analysis of the two and four headed human-specific PD-L1 TxM complexes following disulfide bond reduction.
Figure 12B:
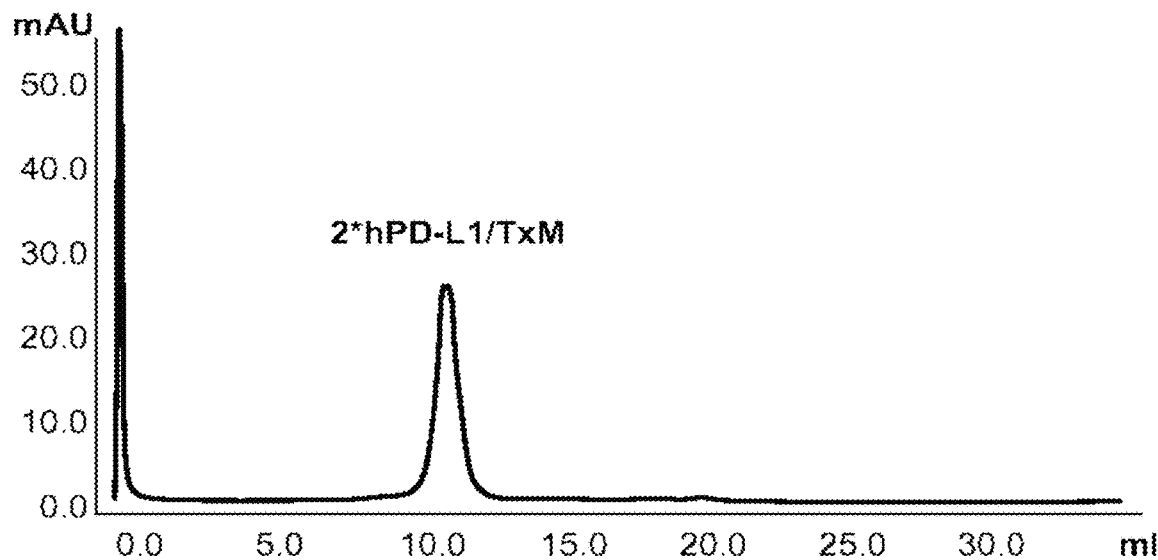
FIG. 12B and FIG. 12C show line graphs representing the chromatographic profiles of two- and four-headed human-specific PD-L1 TxM complexes, respectively, following elution on an analytical size exclusion column, demonstrating separation of TxM complexes from protein aggregates.
Figure 12C:
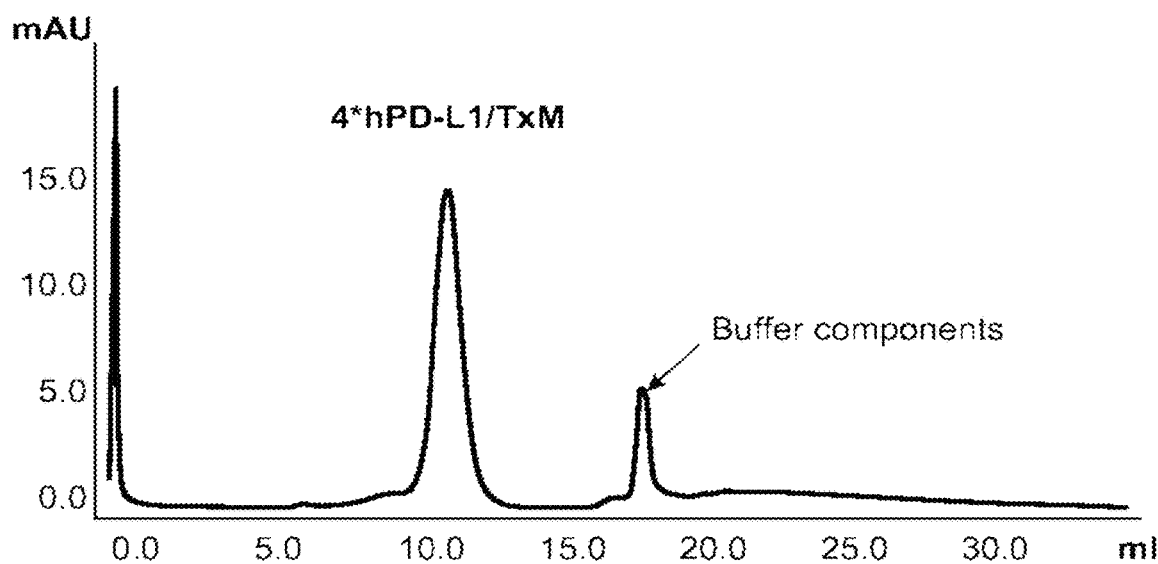

Similar studies were conducted on 4H human-specific PD-L1 TxM and 2H human-specific PD-L1 TxM complexes. These proteins were generated by transfecting CHO cells with anti-human PD-L1 scAb/IL-15N72D and anti-human PD-L1 scAb-/IL-15RαSu/Fc expression vectors or IL-15N72D and anti-human PD-L1 scAb-/IL-15RαSu/Fc expression vectors, respectively, followed by purification from cell culture supernatants via Protein A chromatography. Reduced SDS-PAGE analysis confirmed the expected protein bands in the purified 4H human-specific PD-L1 TxM and 2H human-specific PD-L1 TxM preparations (FIG. 12A). Similarly, analytical SEC indicated that the purified 4H human-specific PD-L1 TxM and 2H human-specific PD-L1 TxM complexes migrated as single protein peaks (FIG. 12B and FIG. 12C).

Figure 13:
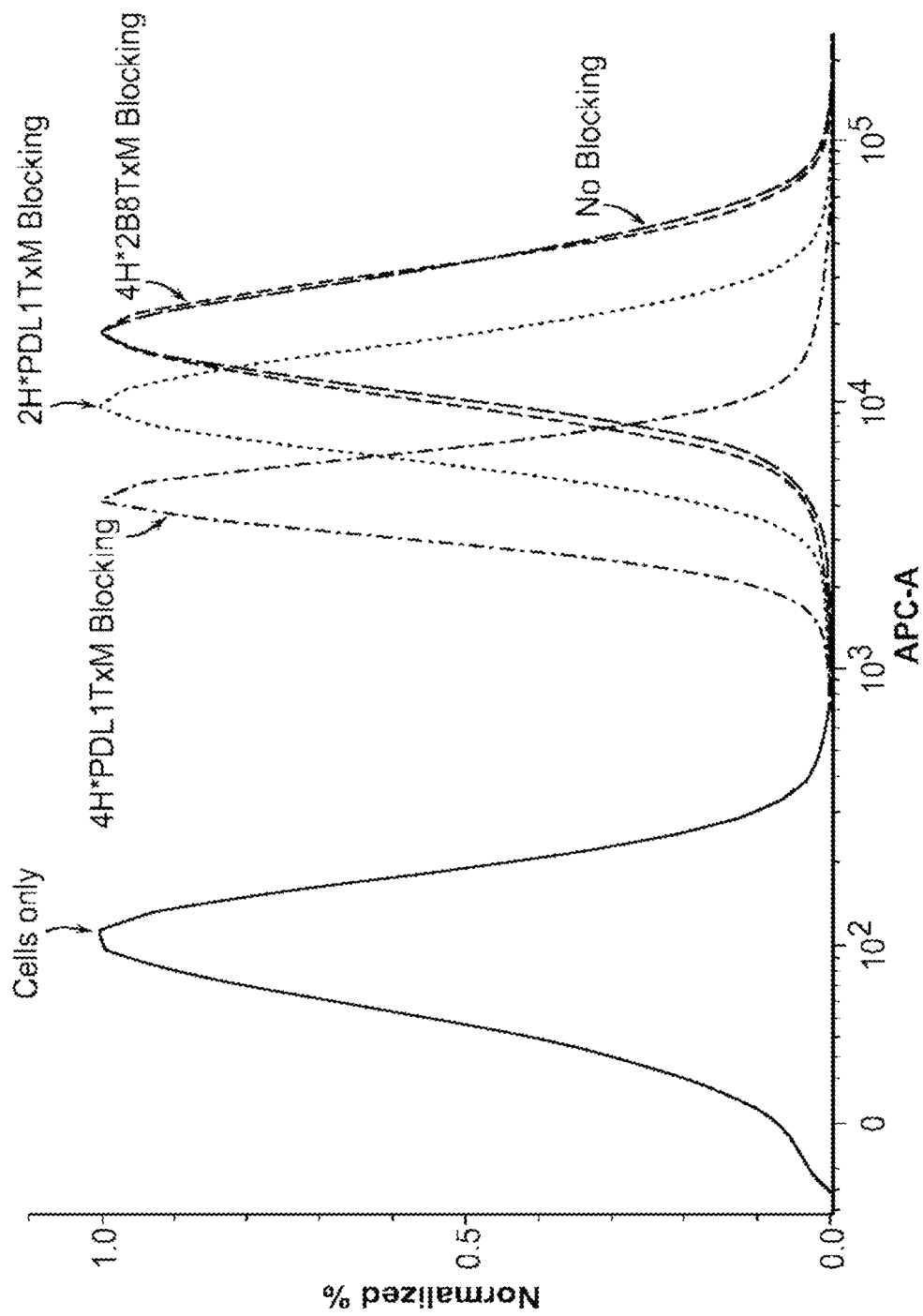
FIG. 13 is a line graph showing the blocking activity of the two- and four-headed human-specific PD-L1 TxM complexes of PD-L1 expressed on PC-3 human prostate cancer cells.

The ability of these fusion protein complexes to bind PD-L1 on tumor cells was examined. PD-L1-positive PC-3 human prostate cancer cells were stained with APC labeled anti-mouse PD-L1 Ab in the presence or absence of 10 nM of purified human-specific 4H PD-L1 TxM, 2H PD-L1 TxM or control 2H anti-CD20 scAb (2B8) TxM complexes (FIG. 13). The results show that the human-specific 4H PD-L1 and 2H PD-L1 TxM complexes were capable of blocking anti-PD-L1 Ab binding to human tumor cells, whereas the control TxM complex was not. Consistent with previous results the 4H PD-L1 TxM complex showed better binding activity than the 2H PD-L1 TxM complexes. These results confirm that the human-specific 4H PD-L1 and 2H PD-L1 TxM complexes retain PD-L1 target binding activity on human tumor cells.

Figure 14A:
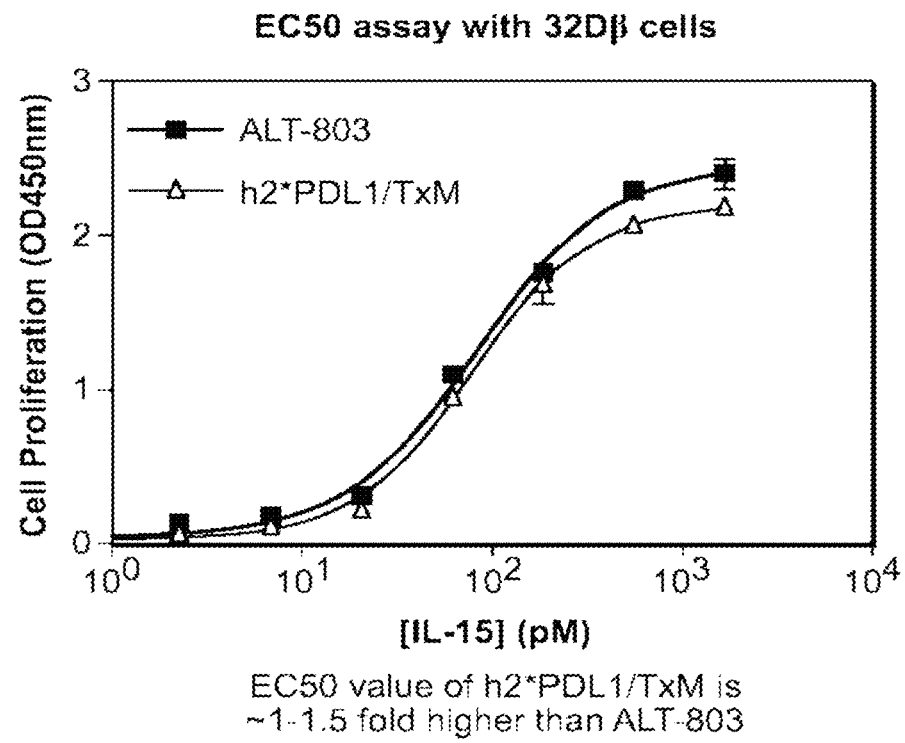
FIG. 14A is a line graph illustrating the proliferation of IL-15-dependent 32Dβ cells mediated by a two-headed human-specific PD-L1 TxM complex compared to ALT-803.
Figure 14B:
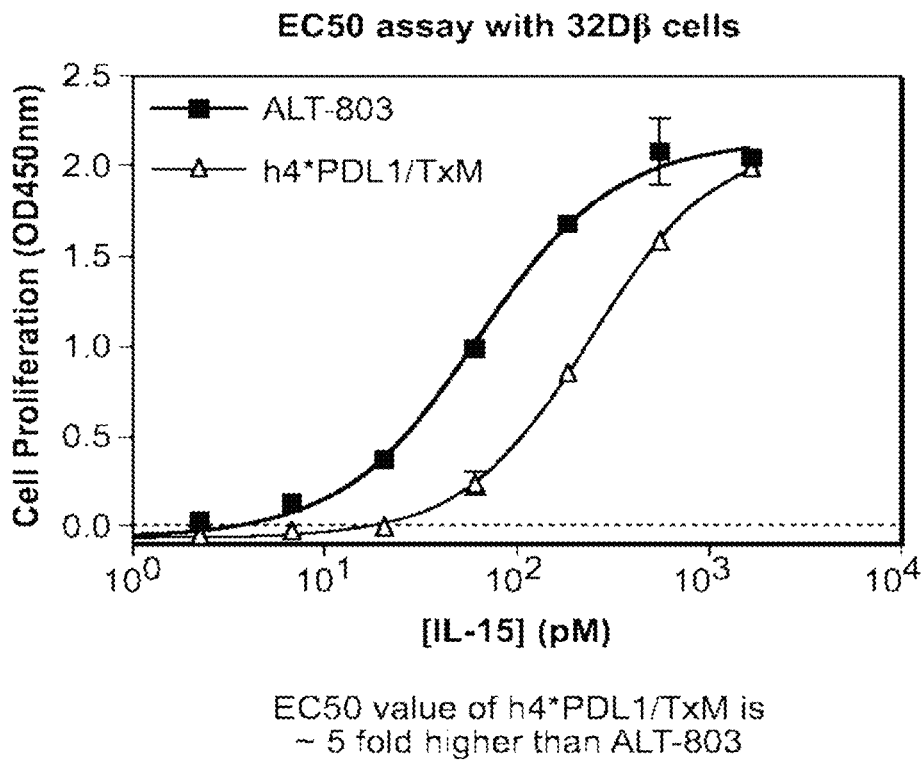
FIG. 14B is a line graph illustrating the proliferation of IL-15-dependent 32Dβ cells mediated by a four-headed human-specific PD-L1 TxM complex compared to ALT-803.

As described above, the IL-15 immunostimulatory activity of the human-specific 4H PD-L1 and 2H PD-L1 TxM complexes was determined based on proliferation of IL-15-dependent 3214 cells. As shown in FIG. 14A and FIG. 14B, a dose dependent increase in 32Dβ cell proliferation was mediated by either 4H PD-L1 and 2H PD-L1 TxM complexes, verifying the immunostimulatory activity of these TxM formats. The 2H PD-L1 TxM complex exhibits a slight decrease in IL-15 bioactivity compared to ALT-803 whereas the 4H PD-L1 TxM complex exhibits approximately a 5-fold decrease in IL-15 bioactivity compared to ALT-803. This is consistent with the lower IL-15 activity of previous binding domain-IL-15N72D fusion proteins.

Figure 15A:
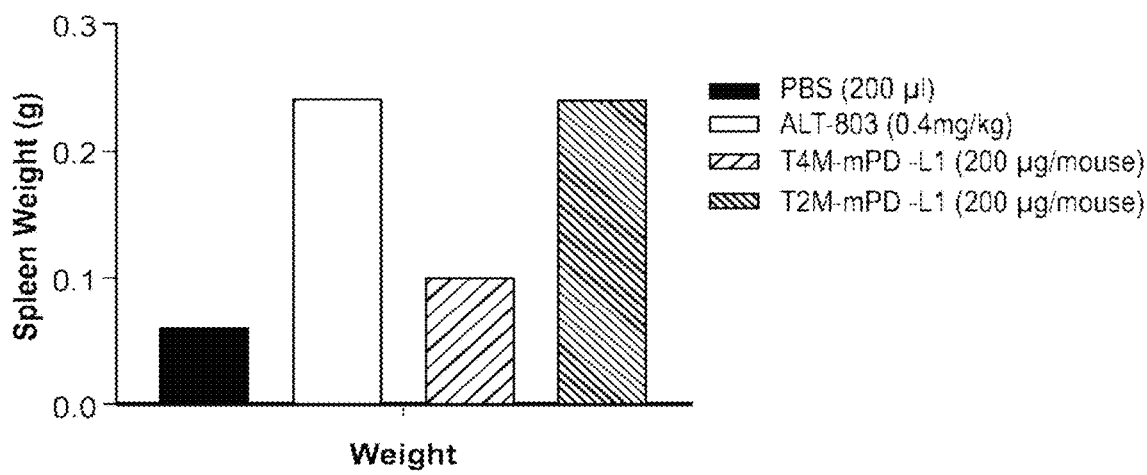
FIG. 15A is a bar chart showing the spleen weights of mice treated with PBS, ALT-803, four-headed mouse-specific PD-L1 TxM (T4M-mPD-L1), and two-headed mouse-specific PD-L1 TxM (T2M-mPD-L1).
Figure 15B:
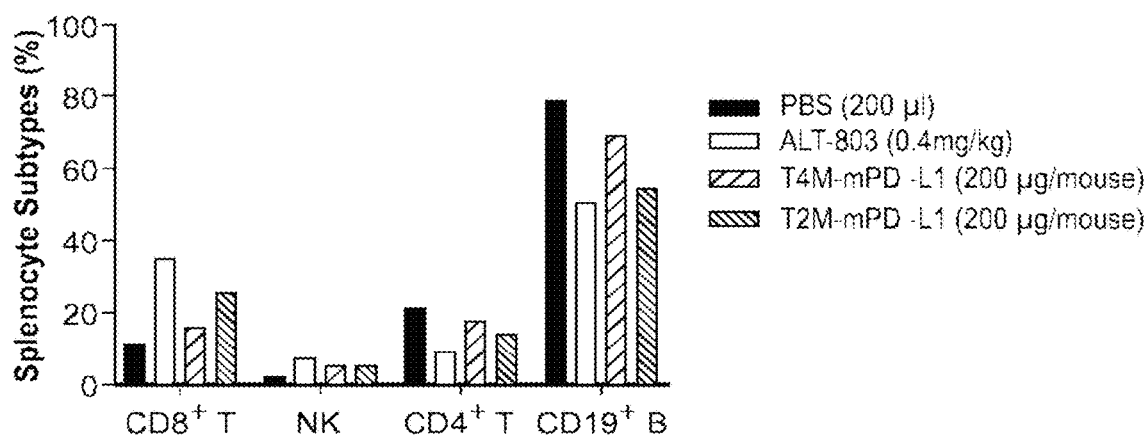
FIG. 15B and FIG.
Figure 15C:
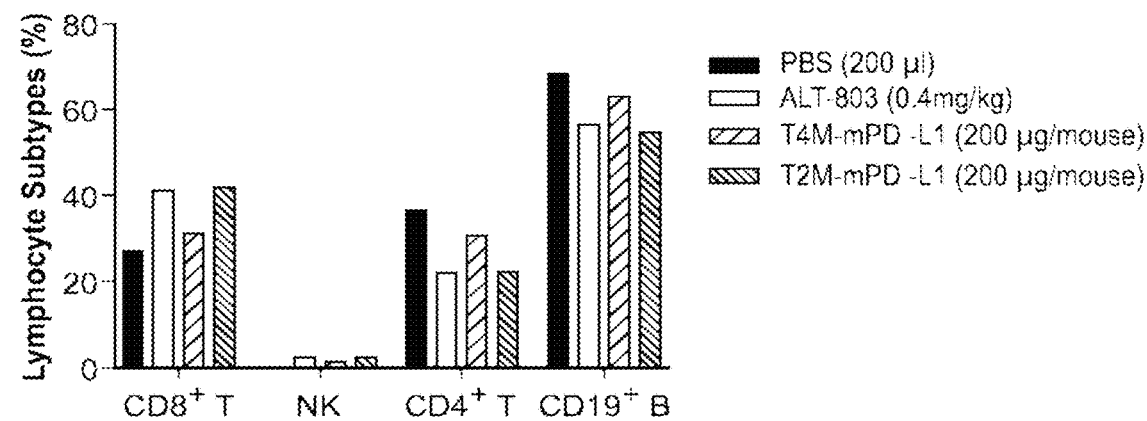

Example 3: Immunostimulatory and Anti-Tumor Activity of PD-L1 TxM In Vitro and In Vivo The ability of PD-L1 TxM to stimulate immune responses in vivo was assessed in mice. C57BL/6 mice were injected subcutaneously with 200 µl of PBS, ALT-803 (0.4 mg/kg, control), 4H mouse-specific PD-L1 TxM (200 µg, 2C2 (T4M-mPD-L1)), or 2H mouse-specific PD-L1 TxM (200 µg, PDN3 (T2M-mPD-L1)). Three days after treatment, spleens and lymph nodes were collected. Splenocytes and lymphocytes were prepared for flow cytometry following staining of immune cell subsets using anti-CD4, CD8, NK, and CD19 Abs. As shown in FIG. 15A, treatment with ALT-803, 2H PD-L1 TxM and 4H PD-L1 TxM induce an increase in spleen weights consistent with the immunostimulatory activities of these proteins. In particular, 2H PD-L1 TxM treatment induced a greater increase in spleen weights than 4H PD-L1 TxM, consistent with the difference in IL-15 activity observed with these complexes. Treatment with 2H PD-L1 TxM and 4H PD-L1 TxM also resulted in an increase in the percentage of CD8 T cells and NK cells in the spleen and lymph nodes of mice compared to the PBS control group (FIG. 15B and FIG. 15C). These immune responses are consistent with the IL-15 bioactivity of these TxM complexes.

Additionally, the ability of PD-L1 TxM to stimulate immune cell cytotoxicity against tumor cells was assessed in vitro. PD-L1-positive cells were labeled with CellTrace Violet (Invitrogen) according to the manufacturer's instructions, and cultured with immune effector cells (i.e. splenocytes) at effector:5T33P myeloma target ratio of 10:1 in R10 media (RPMI-1640 with 10% fetal calf serum) at 37° C. with 5% $CO_2$. The effector cells were prepared by stimulation of P-mel mice splenocytes for 3 days with anti-CD3 Ab (2C11: 4 µg/ml). The tumor and effector cells were incubated for 4 days with mouse specific PD-L1 TxM and then analyzed by flow cytometry to determine target cells survival. PBS served as a negative control and ALT-803 (IL-15N72D:IL-15Rα/Fc), anti-PD-L1 Ab and ALT-803+anti-PD-L1 Ab served as positive controls. As shown in FIG. 16, significant killing of 5T33P tumor cells was found in the group containing 2.1 µg of PD-L1 TxM compared to PBS treatment.

Similar in vitro anti-tumor activity was assessed using human-specific 2H PD-L1 TxM and 4H PD-L1 TxM complexes. Human NK cells from two different donors were purified from blood buffy coats with NK cell isolation kit from Stemcell Technologies and used as effector cells. PD-L1-positive human pancreatic tumor cells, SW1990, were labeled with Celltrace-violet and used as target cells. The human NK cells and SW1990 tumor cells were mixed at an E:T ratio of 5:1 in media alone or media containing 50 nM anti-human PD-L1 Ab (control), human-specific 2H PD-L1 TxM complex or 4H PD-L1 TxM complex. After 40 hrs, the percent of target cell death was assessed by flow cytometry based on propidium iodide staining of violet-labeled target cells. As shown in FIG. 17, human NK cells incubated with either human-specific 2H PD-L1 TxM or 4H PD-L1 TxM complexes were capable of mediating greater cytotoxicity against PD-L1-positive human tumor cells than untreated NK cells or NK cells treated with anti-human PD-L1 Ab (i.e., traditional ADCC). These results represent a significant improvement in immune cell-mediated targeted anti-tumor activity of the PD-L1 TxM complexes compared to anti-PD-L1 Abs.

An orthotopic 5T33P myeloma model was used to assess the efficacy of PD-L1 TxM in tumor bearing animals. Female C57BL/6NHsd mice (4 mice/group) were injected i.v. with 5T33P myeloma cells ($1\times10^7$/mouse) on day 0. Low dose PD-L1 TxM (0.11 mg/kg, a molar equivalent dose to 0.05 mg/kg ALT-803) or high dose PD-L1 TxM (52.5 μg/dose, a molar equivalent dose to 25 μg/dose anti-PD-L1 Ab) was then administered subcutaneously on days 7 and 14. ALT-803 (0.15 mg/kg) and ALT-803 (0.05 mg/kg)+anti-PD-L1 Ab (25 μg/dose) served as positive controls and PBS served as a negative control. Survival (or morbidity due to hind leg paralysis) was monitored as a study endpoint. Clearly, high dose PD-L1 TxM (52.5 μg/mouse) treatment was found to prolong survival of tumor-bearing mice compared to PBS treatment (FIG. 18). This effect was equivalent to that observed with the comparable ALT-803+anti-PD-L1 Ab combination therapy. No apparent toxicity was observed following PD-L1 TxM treatment of tumor bearing animals.

Additionally, the antitumor activity of PD-L1 TxM complexes was assessed in mice bearing orthotopic MB49luc tumor. C57BL/6NHsd mice (6 mice/group) were instilled intravesically into the bladder with MB49luc bladder tumor cells ($3\times10^4$/mouse) on day 0. Tumor bearing mice were treated subcutaneously with mouse-specific 2H PD-L1 TxM (2.8 mg/kg) on days 7, 11, 14 and 18. ALT-803 treatment (0.2 mg/kg, subQ) and ALT-803 (0.2 mg/kg, subQ)+anti-PD-L1 Ab (50 μg/dose, subQ) served as positive controls and PBS served as a negative control. Survival (or morbidity) was monitored as a study endpoint. As shown in FIG. 19, 2H PD-L1 TxM treatment was found to prolong survival of MB49luc tumor-bearing mice compared to PBS treatment. The anti-tumor effects of 2H PD-L1 TxM were as good or better than that observed with the ALT-803 and ALT-803+anti-PD-L1 Ab positive controls.

Example 4: Generation of IL-15-Based Fusion Protein Complexes Comprising Anti-CTLA4 Binding Domains (CTLA4 TxM) and Anti-PD-1 Binding Domains (PD-1 TxM)

Similar to the fusion protein complexes described in Examples 1-3, fusion protein complexes of the invention have been generated comprising binding domains that recognize CTLA4 and PD-1. Specifically, constructs were made linking a single-chain anti-CTLA4 antibody to the huIL-15N72D and IL-15RαSu/Fc chains. The anti-CTLA4 single chain antibody (anti-CTLA4scAb) sequence comprises the coding regions of the heavy and light chain V antibody domains antibody linked via a flexible linker sequence. The single chain antibody domain can be arranged in either the VH-linker-VL or VL-linker-VH format. In some cases, the anti-CTLA4scAb is linked to the C-terminus of the IL-15N72D and/or IL-15RαSu/Fc chains. In other cases, the anti-CTLA4 is linked to the N-terminus of IL-15N72D and/or IL-15RαSu/Fc chains. Anti-CTLA4scAbs specific to either the mouse or human CTLA4 molecules were used in these constructs.

The nucleic acid sequence of anti-human CTLA-4 scAb/huIL-15RαSu/huIgG1 Fc construct (including leader sequence) is as follows (SEQ ID NO: 13):

```
(Signal peptide)
ATGAAGTGGGTGACCTTTATCTCCCTGCTGTTCCTGTTTTCCTCCGCCTA

CAGC- (anti-human CTLA-4 scAh)
(VL)
ATCGTGATGACCCAGTCCCCTAGCTCCCTGAGCGCTAGCGTGGGAGACCG

GGTGACCATCACCTGTCGGGCCTCCCAGAGCATTTCCAGCTACCTGAACT

GGTACCAGCAGAAGCCCGGCAAGGCCCCTAAGCTGCTGATTTACGCTGCC

AGCAGCCTGCAGTCCGGAGTGCCTCCCAGGTTTAGCGGCTCCGGATCCGG

CACCGAGTTCACCCTGACCATCTCCTCCCTGCAGCCCGAGGACTTCGCCA

CCTACTACTGTCAGCAGGCCAACAGCTTTCCCCCCACCTTTGGCCAAGGA

ACCAAGGTGGACATCAAGAGGACCGTGGCC (Linker)
GGAGGCGGAGGCTCCGGCGGCGGCGGCTCCGGCGGCGGCGGCTCC (VH)
CTGGTGCAGTCCGGCGCTGAAGTGAAGAAGCCTGGCGCCTCCGTGAAGGT

GTCCTGCGAGGCCTCCGGCTACACCTTCACCAACTACTACATCCACTGGC

TGAGGCAGGCTCCTGGACAGGGCCTGGAGTGGATGGGCATCATCAACCCC

TCCGGAGGCTCCACCACCTACGCCCAGAAGTTCCAGGGCAGGATCACCAT

GACAAGGGACACCTCCACCAACACCCTGTACATGGAACTGTCCTCCCTCC

GGTCCGAGGACACCGCCATCTACTACTGCGCCAGGAGGGATTGCAGGGGC

CCTAGCTGCTACTTCGCTTACTGGGGCCAGGGAACCACCGTGACCGTGTC

CTCCGCCTCCACCAAGGGC (Human IL-15R a sushi domain)
ATCACGTGCCCTCCCCCCATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Human IgG1 CH2 CH3 (Fc) domain)
GAGCCGAAATCTTGTGACAAAACTCACACATGCCCACCGTGCCCAGCACC

TGAACTCCTGGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG
```

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCTGGTAAATAA

The amino acid sequence of the human CTLA-4 scAb/huIL-15RαSu/huIgG1 Fc protein (including leader sequence) is as follows (SEQ ID NO: 14):

(Signal peptide)
MKWVTFISLLFLFSSAYS-(anti-human CTLA-4 scAb)

(VL)
IVMTQSPSSLSASVGDRVTITCRASQSISSYLNWYQQKPGKAPKLLIYAA

SSLQSGVPPRFSGSGSGTEFTLTISSLQPEDFATYYCQQANSFPPTFGQG

TKVDIKRTVA (Linker)
GGGGSGGGGSGGGGS (VH)
LVQSGAEVKKPGASVKVSCEASGYTFTNYYIHWLRQAPGQGLEWMGIINP

SGGSTTYAQKFQGRITMTRDTSTNTLYMELSSLRSEDTAIYYCARRDCRG

PSCYFAYWGQGTTVTVSSASTKG (Human IL-15R a sushi domain)
ITCPPPMSVEHADIWVKSYSLYSRERYICNSGFKRKAGTSSLTECVLNKA

TNVAHWTTPSLKCIR (Human IgG1 CH2 CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some cases, the leader peptide is cleaved from the mature polypeptide.

Similarly, the nucleic acid sequence of anti-mouse CTLA-4 scAb/huIL-15RαSu/mIgG2a construct (including leader sequence) is as follows (SEQ ID NO: 15):

(Signal peptide)
ATGAAGTGGGTAACCTTTATTTCCCTTCTTTTTCTCTTTAGCTCGGCTTA

TTCC (anti-mouse CTLA-4 scAb)
(VL)
GACATCATGATGACCCAGTCCCCTTCCTCCCTGTCCGTGAGCGCTGGCGA

GAAGGCTACCATCAGCTGCAAGTCCTCCCAGTCCCTGTTCAACAGCAACG

CCAAGACCAACTACCTGAACTGGTACCTGCAGAAGCCCGGCCAGTCCCCC

AAGCTGCTGATCTATTACGCTAGCACCAGGCATACCGGCGTGCCCGACAG

GTTTAGGGGATCCGGCAGCGGCACCGACTTCACCCTGACCATCTCCAGCG

TGCAGGACGAGGACCTCGCTTTCTACTACTGCCAGCAATGGTACGATTAC

CCTTACACCTTCGGCGCTGGCACCAAGGTGGAGATTAAGAGG (Linker)
GGCGGAGGCGGATCCGGCGGCGGCGGCTCCGGCGGCGGAGGCTCC (VH)
CAGATTCAGCTGCAGGAGTCCGGCCCTGGACTGGTCAACCCTAGCCAGTC

CCTGAGCCTGTCCTGTTCCGTGACAGGCTATAGCATCACCAGCGGCTACG

GCTGGAACTGGATCAGGCAGTTTCCCGGCCAGAAAGTGGAGTGGATGGGC

TTCATCTACTACGAGGGCTCCACCTACTATAACCCCTCCATCAAGTCCCG

GATCAGCATCACCAGGGATACCTCCAAGAACCAGTTCTTCCTGCAAGTCA

ACTCCGTGACCACCGAAGACACCGCCACCTACTACTGCGCCAGGCAGACA

GGCTACTTCGACTACTGGGGCCAGGGCACAATGGTGACCGTCAGCAGCGC

C (Human IL-15R a sushi domain)
ATCACGTGCCCTCCCCCCATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Mouse IgG2a CH2 CH3 domain)
GAACCAAGAGGGCCCACAATCAAGCCCTGTCCTCCATGCAAATGCCCAGC

ACCTAACCTCTTGGGTGGACCATCCGTCTTCATCTTCCCTCCAAAGATCA

AGGATGTACTCATGATCTCCCTGAGCCCCATAGTCACATGTGTGGTGGTG

GATGTGAGCGAGGATGACCCAGATGTCCAGATCAGCTGGTTTGTGAACAA

CGTGGAAGTACACACAGCTCAGACACAAACCCATAGAGAGGATTACAACA

GTACTCTCCGGGTGGTCAGTGCCCTCCCCATCCAGCACCAGGACTGGATG

AGTGGCAAGGAGTTCAAATGCAAGGTCAACAACAAAGACCTCCCAGCGCC

CATCGAGAGAACCATCTCAAAACCCAAAGGGTCAGTAAGAGCTCCACAGG

TATATGTCTTGCCTCCACCAGAAGAAGAGATGACTAAGAAACAGGTCACT

CTGACCTGCATGGTCACAGACTTCATGCCTGAAGACATTTACGTGGAGTG

GACCAACAACGGGAAAACAGAGCTAAACTACAAGAACACTGAACCAGTCC

TGGACTCTGATGGTTCTTACTTCATGTACAGCAAGCTGAGAGTGGAAAAG

AAGAACTGGGTGGAAAGAAATAGCTACTCCTGTTCAGTGGTCCACGAGGG

TCTGCACAATCACCACACGACTAAGAGCTTCTCCCGGACTCCAGGTAAAT

AA

The amino acid sequence of the anti-mouse CTLA-4 scAb/huIL-15RαSu/mIgG2a fusion protein (including leader sequence) is as follows (SEQ ID NO: 16):

(Signal peptide)
MKWVTFISLLFLFSSAYS- (Anti-mouse CTLA-4 scAb)
(VL)
DIMMTQSPSSLSVSAGEKATISCKSSQSLFNSNAKTNYLNWYLQKPGQSP

KLLIYYASTRHTGVPDRFRGSGSGTDFTLTISSVQDEDLAFYYCQQWYDY

PYTFGAGTKVEIKR

-continued (Linker)
GGGGSGGGGSGGGGS (VH)
QIQLQESGPGLVNPSQSLSLSCSVTGYSITSGYGWNWIRQFPGQKVEWMG

FIYYEGSTYYNPSIKSRISITRDTSKNQFFLQVNSVTTEDTATYYCARQT

GYFDYWGQGTMVTVSSA- (Human IL-15R a sushi domain)
ITCPPPMSVEHADIWVKSYSLYSRERYICNSGFKRKAGTSSLTECVLNKA

TNVAHWTTPSLKCIR (Mouse IgG2a CH2 CH3 domain)
EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT

LTCMVTDFMPEDIYVEWTNNGKTELNYKNTEPVLDSDGSYFMYSKLRVEK

KNWVERNSYSCSVVHEGLHNHHTTKSFSRTPGK

In some cases, the leader peptide is cleaved from the mature polypeptide.

As indicated above, the anti-human and mouse CTLA4 scAb domains have also been generated as fusions to the IL-15N72D protein.

Similarly, the nucleic acid sequence of anti-human PD1 scAb/IL-15N72D construct (including signal peptide sequence and stop codon) is as follows (SEQ ID NO: 17):

(Signal peptide)
ATGGAATGGAGCTGGGTGTTCCTGTTCTTTCTGTCCGTGACCACCGGTGT

CCACTCC (Anti-human PDI scAb)
(VL)
CTGCCTGTGCTGACTCAACCACCCTCGGTGTCTGAAGTCCCCGGGCAGAG

GGTCACCATTTCCTGTTCTGGAGGCATCTCCAACATCGGAAGCAATGCTG

TAAACTGGTACCAGCACTTCCCAGGAAAGGCTCCCAAACTCCTCATCTAT

TATAATGATCTGCTGCCCTCAGGGGTCTCTGACCGATTCTCTGCCTCCAA

GTCTGGCACCTCAGCCTCCCTGGCCATCAGTGGGCTCCGGTCCGAGGATG

AGGCTGATTATTACTGTGCAGCATGGGATGACAATCTGAGTGCTTATGTC

TTCGCAACTGGGACCAAGGTCACCGTCCTGAGT (Linker)
GGAGGTGGCGGATCCGGAGGTGGAGGTTCTGGTGGAGGTGGGAGT (VH)
CAGGTTCAGCTGGTGCAGTCTGGGGCTGAGGTGAAGAAGCCTGGGGCCTC

AGTGAAGGTCTCCTGCAAGGCTTCTGGTTACACCTTTACCAGCTATGGTA

TCAGCTGGGTGCGACAGGCCCCTGGACAAGGGCTTGAGTGGATGGGATGG

ATCAGCGCTTACAATGGTAACACAAACTATGCACAGAAGCTCCAGGGCAG

AGTCACCATGACCACAGACACATCCACGAGCACAGCCTACATGGAGCTGA

GGAGCCTGAGATCTGACGACACGGCCGTGTATTACTGTGCGAGAGGGTTA

TACGGTGACGAGGACTACTGGGGCCAGGGAACCCTGGTCACCGTGAGCTC

A (Human IL-15N72D)
AACTGGGTTAACGTAATAAGTGATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT

CATCCTAGCAAACGACAGTTTGTCTTCTAATGGGAATGTAACAGAATCTG

GATGCAAAGAATGTGAGGAACTGGAGGAAAAAAATATTAAAGAATTTTTG

CAGAGTTTTGTACATATTGTCCAAATGTTCATCAACACTTCTTAA

The amino acid sequence of the anti-PD1 scAb-IL-15N72D fusion protein (including signal peptide sequence) is as follows (SEQ ID NO: 18):

(Signal peptide)
MEWSWVFLFFLSVTTGVHS- (Anti-human PD1 scAb)
(VL)
LPVLTQPPSVSEVPGQRVTISCSGGISNIGSNAVNWYQHFPGKAPKLLIY

YNDLLPSGVSDRFSASKSGTSASLAISGLRSEDEADYYCAAWDDNLSAYV

FATGTKVTVLS (Linker)
GGGGSGGGGSGGGGS (VH)
QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARGL

YGDEDYWGQGTLVTVSS (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

In some cases, the leader peptide is cleaved from the mature polypeptide. As indicated above, the anti-human PD-1 scAb domain has also been generated as fusions to the huIL-15RαSu/Fc construct.

The sequences were cloned into expression vectors as described in Example 1 and previously (U.S. Pat. No. 8,507,222, at Examples 1 and 2, incorporated herein by reference), and the expression vectors transfected into CHO cells. In some cases, the CHO cells were transfected with vectors encoding both huIL-15N72D and huIL-15RαSu/Fc fusion proteins with the same or different (i.e. anti-PD-L1 and anti-CTLA4 scAb) binding domains. The fusion protein complexes were purified from the CHO cell culture supernatant using Protein A affinity chromatography as described above.

In addition of anti-human PD-1 scAb/anti-human CTLA-4 scAb T×M complexes described above, an anti-human PD-L1 scAb/anti-human CTLA-4 scAb T×M complex was generated by co-transfecting CHO cells with expression vectors comprising the anti-human PD-L1 scAb/IL-15N72D (SEQ. ID NO: 1) and anti-human CTLA-4 scAb/huIL-15RαSu/huIgG1 Fc ((SEQ ID NO: 15) constructs. These fusion protein complexes were purified from the CHO cell culture supernatant using Protein A affinity chromatography as described above.

Example 5: Generation of IL-15-Based Fusion Protein Complexes Comprising Other Binding Domains Similar to the fusion protein complexes described in Examples 1-4, fusion protein complexes of the invention have been generated comprising binding domains that recognize CD47, GITR, ssDNA and other disease related targets (i.e., CD20, CD19, etc).

CD47 is a cell-surface molecule that promotes immune evasion by engaging signal-regulatory protein alpha (SIRPα), which serves as an inhibitory receptor on macrophages. This "don't eat me signal" can be disrupted by blocking the interaction of CD47 and SIRPα, thus restoring antibody-dependent cellular phagocytosis (ADCP) by macrophages. The IL-15 domains of the invention activate and expand NK and CD8+ cells while increasing their cytolytic activity. At high enough concentrations, the Fc region of the invention may interact with Fcγ receptors on NK cells and macrophages for ADCC or ADCP, respectively. This example describes the generation and initial characterization of a fusion protein complex that comprises a Vh region of a nanobody (NbVh; PNAS 2016 113 (19) E2646-E2654) to block the CD47/SIRPα pathway, activation of NK and CD8+ cells through the IL-15 domain, and allow for tumor clearance via Fc-mediated ADCC/ADCP. As described in detail below, a protein complex comprising an anti-mouse CD47 NbVh/huIL-15N72D and an anti-mouse CD47 NbVh/huIL-15RαSu/mIgG2a Fc was generated.

Specifically, constructs were made linking anti-mouse CD47 NbVh to the huIL-15N72D chains. The anti-mouse CD47 NbVh sequence comprises the coding regions of the heavy chain variable domain of an alpaca nanobody. The anti-mouse CD47 NbVh is linked to the N-terminus of huIL-15N72D. The nucleic acid and protein sequences of a construct comprising the anti-mouse CD47 NbVh linked to the N-terminus of the huIL-15N72D are shown below.

The nucleic acid sequence of the anti-mouse CD47 NbVh/huIL-15N72D construct (including signal peptide sequence) is as follows (SEQ ID NO: 19):

```
(Signal peptide)
ATGAAGTGGGTGACCTTCATCAGCCTGCTGTTCCTGTTCTCCAGCGCCTA
CTCC (Anti-mouse CD47 Vh chain of nanobody)
CAGGTGCAGCTGGTGGAGTCCGGAGGAGGCCTGGTGGAGCCTGGAGGATC

CCTGAGGCTGTCCTGTGCCGCCAGCGGCATCATCTTCAAGATCAACGACA

TGGGCTGGTATCGGCAGGCCCCTGGCAAAAGGAGGGAGTGGGTGGCCGCT

TCCACAGGAGGCGATGAGGCCATCTACAGGGACTCCGTGAAGGACAGGTT

CACCATCTCCAGGGACGCCAAGAACTCCGTGTTCCTGCAGATGAACTCCC

TGAAGCCCGAGGATACCGCCGTGTACTACTGCACCGCCGTGATCTCCACC

GATAGGGACGGCACCGAGTGGAGGAGGTACTGGGGCCAGGGCACACAGGT

GACTGTGTCCTCCGGCGGC (Human IL-15N72D)
AACTGGGTTAACGTAATAAGTGATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT
```

```
CATCCTAGCAAACGACAGTTTGTCTTCTAATGGGAATGTAACAGAATCTG

GATGCAAAGAATGTGAGGAACTGGAGGAAAAAAATATTAAAGAATTTTTG

CAGAGTTTTGTACATATTGTCCAAATGTTCATCAACACTTCTTAA
```

The amino acid sequence of the anti-mouse CD47 NbVh/IL-15N72D fusion protein (including signal peptide sequence) is as follows (SEQ ID NO: 20):

```
(Signal peptide)
MKWVTFISLLFLFSSAYS (Anti-mouse CD47 Vh chain of nanobody)
QVQLVESGGGLVEPGGSLRLSCAASGIIFKINDMGWYRQAPGKRREWVAA

STGGDEAIYRDSVKDRFTISRDAKNSVFLQMNSLKPEDTAVYYCTAVIST

DRDGTEWRRYWGQGTQVTVSSGG (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS
```

The nucleic acid sequence of the anti-mouse CD47 NbVh/huIL-15RaSu/mIgG2a Fc construct (including leader sequence) is as follows (SEQ ID NO: 21):

```
(Signal peptide)
ATGAAGTGGGTGACCTTCATCAGCCTGCTGTTCCTGTTCTCCAGCGCCTA
CTCC (Anti-mouse CD47 Vh chain of nanobody)
CAGGTGCAGCTGGTGGAGTCCGGAGGAGGCCTGGTGGAGCCTGGAGGATC

CCTGAGGCTGTCCTGTGCCGCCAGCGGCATCATCTTCAAGATCAACGACA

TGGGCTGGTATCGGCAGGCCCCTGGCAAAAGGAGGGAGTGGGTGGCCGCT

TCCACAGGAGGCGATGAGGCCATCTACAGGGACTCCGTGAAGGACAGGTT

CACCATCTCCAGGGACGCCAAGAACTCCGTGTTCCTGCAGATGAACTCCC

TGAAGCCCGAGGATACCGCCGTGTACTACTGCACCGCCGTGATCTCCACC

GATAGGGACGGCACCGAGTGGAGGAGGTACTGGGGCCAGGGCACACAGGT

GACTGTGTCCTCCGGCGGC (Human IL-15R a sushi domain)
ATCACGTGTCCTCCTCCTATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Mouse IgG2a CH2 CH3 (Fc) domain)
GAACCAAGAGGGCCCACAATCAAGCCCTGTCCTCCATGCAAATGCCCAGC

ACCTAACCTCTTGGGTGGACCATCCGTCTTCATCTTCCCTCCAAAGATCA

AGGATGTACTCATGATCTCCCTGAGCCCCATAGTCACATGTGTGGTGGTG

GATGTGAGCGAGGATGACCCAGATGTCCAGATCAGCTGGTTTGTGAACAA

CGTGGAAGTACACACAGCTCAGACACAAACCCATAGAGAGGATTACAACA

GTACTCTCCGGGTGGTCAGTGCCCTCCCCATCCAGCACCAGGACTGGATG

AGTGGCAAGGAGTTCAAATGCAAGGTCAACAACAAAGACCTCCCAGCGCC

CATCGAGAGAACCATCTCAAAACCCAAAGGGTCAGTAAGAGCTCCACAGG
```

-continued
TATATGTCTTGCCTCCACCAGAAGAAGAGATGACTAAGAAACAGGTCACT

CTGACCTGCATGGTCACAGACTTCATGCCTGAAGACATTTACGTGGAGTG

GACCAACAACGGGAAAACAGAGCTAAACTACAAGAACACTGAACCAGTCC

TGGACTCTGATGGTTCTTACTTCATGTACAGCAAGCTGAGAGTGGAAAAG

AAGAACTGGGTGGAAAGAAATAGCTACTCCTGTTCAGTGGTCCACGAGGG

TCTGCACAATCACCACACGACTAAGAGCTTCTCCCGGACTCCAGGTAAA

The amino acid sequence of the anti-mouse CD47 NbVh/huIL-15RαSu/mIgG2a Fc fusion protein (including leader sequence) is as follows (SEQ ID NO: 22):

(Signal peptide)
MKWVTFISLLFLFSSAYS (Anti-mouse CD47 Vh chain of nanobody)
QVQLVESGGGLVEPGGSLRLSCAASGIIFKINDMGWYRQAPGKRREWVAA

STGGDEAIYRDSVKDRFTISRDAKNSVFLQMNSLKPEDTAVYYCTAVIST

DRDGTEWRRYWGQGTQVTVSSGG (Human IL-15R a sushi domain)
ITCPPPMSVEHADIWVKSYSLYSRERYICNSGFKRKAGTSSLTECVLNKA

TNVAHWTTPSLKCIR (Mouse IgG2a CH2 CH3 (Fc) domain)
EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT

LTCMVTDFMPEDIYVEWTNNGKTELNYKNTEPVLDSDGSYFMYSKLRVEK

KNWVERNSYSCSVVHEGLHNHHTTKSFSRTPGK

As indicated above, in some cases, the leader peptide is cleaved from the mature polypeptide.

Similar constructs were generated using a single chain antibody domain derived from an antibody specific to human CD47. The nucleic acid sequence of the anti-human CD47 scAb/huIL-15N72D construct (including signal peptide sequence) is as follows (SEQ ID NO: 23):

(Signal peptide)
ATGAAGTGGGTGACCTTCATCAGCCTGCTGTTCCTGTTCTCCAGCGCCTA

CTCC (Anti-human CD47 scAb)
(VL)
AACATCCAGATGACCCAGTCCCCTTCCGCCATGAGCGCTTCCGTGGGCGA

CAGGGTGACCATCACCTGCAAGGCCTCCCAGGACATCCACAGGTACCTGT

CCTGGTTCCAGCAGAAGCCCGGCAAGGTGCCCAAGCACCTGATCTACAGG

GCTAACAGGCTGGTGTCCGGCGTGCCTTCCAGGTTTTCCGGCTCCGGCTC

CGGCACCGAGTTCACCCTGACCATCTCCAGCCTGCAGCCCGAGGACTTCG

CCACCTACTACTGCCTGCAGTACGACGAGTTCCCCTACACCTTCGGCGGC

GGCACCAAGGTGGAGATCAAG (Linker)
GGAGGTGGCGGATCCGGAGGTGGAGGTTCTGGTGGAGGTGGGAGT (VH)
CAGATGCAGCTGGTACAGTCCGGCGCCGAGGTGAAGAAGACCGGCTCCAG

CGTGAAGGTGTCCTGCAAGGCCTCCGGCTTCAACATCAAGGACTACTACC

TGCACTGGGTGAGGCAGGCCCCTGGACAAGCCCTGGAGTGGATGGGCTGG

ATCGACCCCGACAACGGCGACACCGAGTACGCCCAGAAGTTCCAGGACAG

GGTGACCATCACCAGGGACAGGTCCATGAGCACCGCCTACATGGAGCTGT

CCTCCCTGAGGTCCGAGGACACCGCCATGTACTACTGCAACGCCGCCTAC

GGCTCCTCCTCCTACCCCATGGACTACTGGGGCCAGGGCACCACCGTGAC

CGTG (Human IL-15N72D)
AACTGGGTTAACGTAATAAGTGATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT

CATCCTAGCAAACGACAGTTTGTCTTCTAATGGGAATGTAACAGAATCTG

GATGCAAAGAATGTGAGGAACTGGAGGAAAAAAATATTAAAGAATTTTTG

CAGAGTTTTGTACATATTGTCCAAATGTTCATCAACACTTCTTAA

The amino acid sequence of the anti-human CD47 scAb/huIL-15N72D fusion protein (including signal peptide sequence) is as follows (SEQ ID NO: 24):

(Signal peptide)
MKWVTFISLLFLFSSAYS (Anti-human CD47 scAb)
(VL)
NIQMTQSPSAMSASVGDRVTITCKASQDIHRYLSWFQQKPGKVPKHLIYR

ANRLVSGVPSRFSGSGSGTEFTLTISSLQPEDFATYYCLQYDEFPYTFGG

GTKVEIK (Linker)
GGGGSGGGGSGGGGS (VH)
QMQLVQSGAEVKKTGSSVKVSCKASGFNIKDYYLHWVRQAPGQALEWMGW

IDPDNGDTEYAQKFQDRVTITRDRSMSTAYMELSSLRSEDTAMYYCNAAY

GSSSYPMDYWGQGTTVTV (human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

The nucleic acid sequence of the anti-human CD47 scAb/huIL-15RαSu/hIgG1 Fc construct (including leader sequence) is as follows (SEQ ID NO: 25):

(Signal peptide)
ATGAAGTGGGTGACCTTCATCAGCCTGCTGTTCCTGTTCTCCAGCGCCTA
CTCC (Anti-human CD47 scAb)
(VL)
AACATCCAGATGACCCAGTCCCCTTCCGCCATGAGCGCTTCCGTGGGCGA

CAGGGTGACCATCACCTGCAAGGCCTCCCAGGACATCCACAGGTACCTGT

CCTGGTTCCAGCAGAAGCCCGGCAAGGTGCCCAAGCACCTGATCTACAGG

GCTAACAGGCTGGTGTCCGGCGTGCCTTCCAGGTTTTCCGGCTCCGGCTC

CGGCACCGAGTTCACCCTGACCATCTCCAGCCTGCAGCCCGAGGACTTCG

CCACCTACTACTGCCTGCAGTACGACGAGTTCCCCTACACCTTCGGCGGC

GGCACCAAGGTGGAGATCAAG (Linker)
GGAGGTGGCGGATCCGGAGGTGGAGGTTCTGGTGGAGGTGGGAGT (VH)
CAGATGCAGCTGGTACAGTCCGGCGCCGAGGTGAAGAAGACCGGCTCCAG

CGTGAAGGTGTCCTGCAAGGCCTCCGGCTTCAACATCAAGGACTACTACC

TGCACTGGGTGAGGCAGGCCCCTGGACAAGCCCTGGAGTGGATGGGCTGG

ATCGACCCCGACAACGGCGACACCGAGTACGCCCAGAAGTTCCAGGACAG

GGTGACCATCACCAGGGACAGGTCCATGAGCACCGCCTACATGGAGCTGT

CCTCCCTGAGGTCCGAGGACACCGCCATGTACTACTGCAACGCCGCCTAC

GGCTCCTCCTCCTACCCCATGGACTACTGGGGCCAGGGCACCACCGTGAC
CGTG (Human IL-15R α sushi domain)
ATCACGTGTCCTCCTCCTATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Human IgG1 CH2 CH3 (Fc) domain)
GAGCCGAAATCTTGTGACAAAACTCACACATGCCCACCGTGCCCAGCACC

TGAACTCCTGGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCTGGTAAATAA

The amino acid sequence of the anti-human CD47 scAb/ huIL-15RαSu/hIgG1 Fc fusion protein (including leader sequence) is as follows (SEQ ID NO: 26):

(Signal peptide)
MKWVTFISLLFLFSSAYS (Anti-human CD47 scAb)
(VL)
NIQMTQSPSAMSASVGDRVTITCKASQDIHRYLSWFQQKPGKVPKHLIYR

ANRLVSGVPSRFSGSGSGTEFTLTISSLQPEDFATYYCLQYDEFPYTFGG

GTKVEIK (Linker)
GGGGSGGGGSGGGGS (VH)
QMQLVQSGAEVKKTGSSVKVSCKASGFNIKDYYLHWVRQAPGQALEWMGW

IDPDNGDTEYAQKFQDRVTITRDRSMSTAYMELSSLRSEDTAMYYCNAAY

GSSSYPMDYWGQGTTVTV (Human IL-15R α sushi domain)
ITCPPPMSVEHADIWVKSYSLYSRERYICNSGFKRKAGTSSLTECVLNKA

TNVAHWTTPSLKCIR (Human IgG1 CH2–CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

Interactions between GITR ligand and GITR are known to provide stimulatory signaling to immune cells, thus GITR ligand (GITRL) is known to be an immune agonist molecule that could potentially act synergistically with the immune stimulatory activity of IL-15. Thus, constructs were made linking human GIRTL to the huIL-15N72D chains.

The nucleic acid sequence of the human GITRL/huIL-15N72D construct (including signal peptide sequence) is as follows (SEQ ID NO: 27):

(Signal peptide)
ATGAAGTGGGTGACCTTCATCAGCCTGCTGTTCCTGTTCTCCAGCGCCTA
CTCC (Human GITRL)
ACCGCCAAGGAGCCCTGCATGGCCAAGTTCGGCCCTCTGCCCTCCAAGTG

GCAGATGGCCTCCTCCGAGCCTCCCTGTGTGAACAAGGTGTCCGACTGGA

AGCTGGAGATCCTGCAGAACGGCCTGTACCTGATCTACGGCCAGGTGGCC

CCCAACGCCAACTACAACGACGTGGCCCCCTTCGAGGTGCGGCTGTACAA

GAACAAGGACATGATCCAGACCCTGACCAACAAGTCCAAGATCCAGAACG

TGGGCGGCACCTATGAGCTGCACGTGGGCGACACCATCGACCTGATCTTC

AACTCCGAGCACCAGGTGCTGAAGAACAACACCTACTGGGGCATC (Human IL-15N72D)
AACTGGGTTAACGTAATAAGTGATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT

CATCCTAGCAAACGACAGTTTGTCTTCTAATGGGAATGTAACAGAATCTG

-continued
GATGCAAAGAATGTGAGGAACTGGAGGAAAAAAATATTAAAGAATTTTTG

CAGAGTTTTGTACATATTGTCCAAATGTTCATCAACACTTCTTAA

The amino acid sequence of the human GITRL/IL-15N72D fusion protein (including signal peptide sequence) is as follows (SEQ ID NO: 28):

(Signal peptide)
MKWVTFISLLFLFSSAYS (Human GITRL)
TAKEPCMAKFGPLPSKWQMASSEPPCVNKVSDWKLEILQNGLYLIYGQVA

PNANYNDVAPFEVRLYKNKDMIQTLTNKSKIQNVGGTYELHVGDTIDLIF

NSEHQVLKNNTYWGI (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

The nucleic acid sequence of the human GITRL/huIL-15RαSu/hIgG1 Fc construct (including leader sequence) is as follows (SEQ ID NO: 29):

(Signal peptide)
ATGAAGTGGGTGACCTTCATCAGCCTGCTGTTCCTGTTCTCCAGCGCCTA

CTCC (Human GITRL)
ACCGCCAAGGAGCCCTGCATGGCCAAGTTCGGCCCTCTGCCCTCCAAGTG

GCAGATGGCCTCCTCCGAGCCTCCCTGTGTGAACAAGGTGTCCGACTGGA

AGCTGGAGATCCTGCAGAACGGCCTGTACCTGATCTACGGCCAGGTGGCC

CCCAACGCCAACTACAACGACGTGGCCCCCTTCGAGGTGCGGCTGTACAA

GAACAAGGACATGATCCAGACCCTGACCAACAAGTCCAAGATCCAGAACG

TGGGCGGCACCTATGAGCTGCACGTGGGCGACACCATCGACCTGATCTTC

AACTCCGAGCACCAGGTGCTGAAGAACAACACCTACTGGGGCATC (Human IL-15R a sushi domain)
ATCACGTGTCCTCCTCCTATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCAGTCTCAAATGCATTAGA (Human IgG1 CH2 CH3 (Fc) domain)
GAGCCGAAATCTTGTGACAAAACTCACACATGCCCACCGTGCCCAGCACC

TGAACTCCTGGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTG

-continued
ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCTGGTAAATAA

The amino acid sequence of the human GITRL/huIL-15RαSu/hIgG1 Fc fusion protein (including leader sequence) is as follows (SEQ ID NO: 30):

(Signal peptide)
MKWVTFISLLFLFSSAYS (Human GITRL)
TAKEPCMAKFGPLPSKWQMASSEPPCVNKVSDWKLEILQNGLYLIYGQVA

PNANYNDVAPFEVRLYKNKDMIQTLTNKSKIQNVGGTYELHVGDTIDLIF

NSEHQVLKNNTYWGI (Human IL-15R a sushi domain)
ITCPPPMSVEHADIWVKSYSLYSRERYICNSGFKRKAGTSSLTECVLNKA

TNVAHWTTPSLKCIR (Human IgG1 CH2 CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

Fusion protein complexes of the invention could also be generated comprising binding domains that target antigens expressed by diseased cells. Such antigens could comprise single stranded DNA (ssDNA) released by disease cells including tumor cells. Thus, fusion protein complexes of the invention were generated with single chain Ab domains that recognize ssDNA (TNT scAb from Hu51-4 antibody).

The nucleic acid sequence of the TNT scAb/huIL-15N72D construct (including signal peptide sequence) is as follows (SEQ ID NO: 31):

(Signal peptide)
ATGAAGTGGGTGACCTTCATCAGCCTGCTGTTCCTGTTCTCCAGCGCCTA

CTCC (TNT scAb)
(VL)
GAGATCGTGCTGACCCAGTCCCCTGCTACCCTGTCCCTGTCCCTGGCGA

GAGGGCTACCCTGTCCTGCAGGGCCAGGCAATCCATCTCCAACTACCTGC

ACTGGTACCAGCAGAAACCTGGCCAGGCCCCCAGGCTGCTGATCTACTAC

GCCTCCCAGTCCATCTCCGGCATCCCTGACAGGTTCAGCGGATCCGGCTC

CGGCACCGACTTCACCCTGACCATCTCCAGGCTGGAGCCTGAGGACTTCG

CCGTGTACTACTGCCAGCAGTCCAACTCCTGGCCTCTGACCTTCGGCCAG

GGCACCAAGGTGGAGATCAAGCGG (Linker)
GGAGGTGGCGGATCCGGAGGTGGAGGTTCTGGTGGAGGTGGGAGT (VH)
GAGGTGCAGCTGGTGCAGTCCGGCGCCGAAGTGAAGAAGCCCGGAGCCTC

CGTGAAGGTGTCCTGCAAGGCCTCCGGCTACACCTTCACCAGGTACTGGA

TGCACTGGGTGAGGCAGGCCCCTGGACAGGGACTGGAGTGGATCGGCGCC

ATCTACCCCGGCAACTCCGACACCTCCTACAACCAGAAGTTCAAGGGCAA

GGCCACCATCACCGCCGACACCTCCACCAACACCGCCTACATGGAGCTGT

CCTCCCTGAGGTCCGAGGACACCGCCGTGTACTACTGCGCTAGGGGCGAG

GAGATCGGCGTGAGGAGGTGGTTCGCCTACTGGGGACAGGGCACCCTGGT

GACCGTGTCCAGC (Human IL-15N72D)
AACTGGGTTAACGTAATAAGTGATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT

CATCCTAGCAAACGACAGTTTGTCTTCTAATGGGAATGTAACAGAATCTG

GATGCAAAGAATGTGAGGAACTGGAGGAAAAAAATATTAAAGAATTTTTG

CAGAGTTTTGTACATATTGTCCAAATGTTCATCAACACTTCTTAA

The amino acid sequence of the TNT scAb/IL-15N72D fusion protein (including signal peptide sequence) is as follows (SEQ ID NO: 32):

(Signal peptide)
MKWVTFISLLFLFSSAYS (TNT scAb)
(VL)
EIVLTQSPATLSLSPGERATLSCRARQSISNYLHWYQQKPGQAPRLLIYY

ASQSISGIPDRFSGSGSGTDFTLTISRLEPEDFAVYYCQQSNSWPLTFGQ

GTKVEIKR (Linker)
GGGGSGGGGSGGGGS (VH)
EVQLVQSGAEVKKPGASVKVSCKASGYTFTRYWMHWVRQAPGQGLEWIGA

IYPGNSDTSYNQKFKGKATITADTSTNTAYMELSSLRSEDTAVYYCARGE

EIGVRRWFAYWGQGTLVTVSS (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

The nucleic acid sequence of the TNT/huIL-15RαSu/hIgG1 Fc construct (including leader sequence) is as follows (SEQ ID NO: 33):

(Signal peptide)
ATGAAGTGGGTGACCTTCATCAGCCTGCTGTTCCTGTTCTCCAGCGCCTA

CTCC (TNT scAb)
(VL)
GAGATCGTGCTGACCCAGTCCCCTGCTACCCTGTCCCTGTCCCCTGGCGA

GAGGGCTACCCTGTCCTGCAGGGCCAGGCAATCCATCTCCAACTACCTGC

ACTGGTACCAGCAGAAACCTGGCCAGGCCCCCAGGCTGCTGATCTACTAC

GCCTCCCAGTCCATCTCCGGCATCCCTGACAGGTTCAGCGGATCCGGCTC

CGGCACCGACTTCACCCTGACCATCTCCAGGCTGGAGCCTGAGGACTTCG

CCGTGTACTACTGCCAGCAGTCCAACTCCTGGCCTCTGACCTTCGGCCAG

GGCACCAAGGTGGAGATCAAGCGG (Linker)
GGAGGTGGCGGATCCGGAGGTGGAGGTTCTGGTGGAGGTGGGAGT (VH)
GAGGTGCAGCTGGTGCAGTCCGGCGCCGAAGTGAAGAAGCCCGGAGCCTC

CGTGAAGGTGTCCTGCAAGGCCTCCGGCTACACCTTCACCAGGTACTGGA

TGCACTGGGTGAGGCAGGCCCCTGGACAGGGACTGGAGTGGATCGGCGCC

ATCTACCCCGGCAACTCCGACACCTCCTACAACCAGAAGTTCAAGGGCAA

GGCCACCATCACCGCCGACACCTCCACCAACACCGCCTACATGGAGCTGT

CCTCCCTGAGGTCCGAGGACACCGCCGTGTACTACTGCGCTAGGGGCGAG

GAGATCGGCGTGAGGAGGTGGTTCGCCTACTGGGGACAGGGCACCCTGGT

GACCGTGTCCAGC (Human IL-15R a sushi domain)
ATCACGTGTCCTCCTCCTATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Human IgG1 CH2 CH3 (Fc) domain)
GAGCCGAAATCTTGTGACAAAACTCACACATGCCCACCGTGCCCAGCACC

TGAACTCCTGGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCTGGTAAATAA

The amino acid sequence of the TNT scAb/huIL-15RαSu/hIgG1 Fc fusion protein (including leader sequence) is as follows (SEQ ID NO: 34):

(Signal peptide)
MKWVTFISLLFLFSSAYS (TNT scAb)
(VL)
EIVLTQSPATLSLSPGERATLSCRARQSISNYLHWYQQKPGQAPRLLIYY

ASQSISGIPDRFSGSGSGTDFTLTISRLEPEDFAVYYCQQSNSWPLTFGQ

GTKVEIKR (Linker)
GGGGSGGGGSGGGGS (VH)
EVQLVQSGAEVKKPGASVKVSCKASGYTFTRYWMHWVRQAPGQGLEWIGA

IYPGNSDTSYNQKFKGKATITADTSTNTAYMELSSLRSEDTAVYYCARGE

EIGVRRWFAYWGQGTLVTVSS (Human IL-15R a sushi domain)
ITCPPPMSVEHADIWVKSYSLYSRERYICNSGFKRKAGTSSLTECVLNKA

TNVAHWTTPSLKCIR (Human IgG1 CH2 CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

Fusion protein complexes of the invention could also be generated comprising binding domains that target other antigens expressed by diseased cells. Such antigens could comprise tissue factor or CD33 expressed on disease cells including tumor cells or checkpoint inhibitors expressed on immune cells.

Tissue Factor (TF) is a transmembrane glycoprotein reported to be overexpressed in several tumor cell types. Importantly, increased TF expression has been implicated in cancer cell signaling, tumor cell migration, and decreased apoptosis leading to enhanced prospect of metastasis. Therefore, targeting of TF may be beneficial in immunotherapeutic strategies against tumor cell types that overexpress this protein. A chimeric anti-tissue factor antibody, ALT-836, has been previously generated and clinically tested. Humanized variable chains of this antibody (hOAT) have also been characterized. Thus, fusion protein complexes of the invention were generated with single chain Ab domains that recognize human tissue factor (hOAT scAb).

The nucleic acid sequence of the hOAT scAb/huIL-15RαSu/hIgG1 Fc construct (including leader sequence) is as follows (SEQ ID NO: 35):

(Signal peptide)
ATGAAGTGGGTGACCTTCATCAGCCTGCTGTTCCTGTTCTCCAGCGCCTA

CTCC (hOAT scAb)
(VL)
GACATCCAGATGACCCAGTCCCCTGCTTCCCTGTCCGCTTCCGTGGGCGA

CAGGGTGACCATCACCTGCCTGGCCTCCCAGACCATCGACACCTGGCTGG

CCTGGTACCTGCAGAAGCCCGGCAAGTCCCCCCAGCTGCTGATCTACGCC

GCTACCAACCTGGCCGACGGCGTGCCTAGCAGGTTTTCCGGCTCCGGCTC

CGGCACCGACTTCTCCTTCACCATCTCCTCCCTGCAGCCCGAGGACTTCG

CCACCTACTACTGCCAGCAGGTGTACTCCTCCCCCTTCACCTTCGGCCAG

GGCACCAAGCTGGAGATCAAG (Linker)
GGAGGTGGCGGATCCGGAGGTGGAGGTTCTGGTGGAGGTGGGAGT (VH)
CAGATCCAGCTGGTGCAGTCCGGCGGCGAAGTGAAAAAGCCCGGCGCCAG

CGTGAGGGTGTCCTGTAAGGCCTCCGGCTACTCCTTCACCGACTACAACG

TGTACTGGGTGAGGCAGTCCCCCGGCAAGGGACTGGAGTGGATCGGCTAC

ATCGACCCCTACAACGGCATCACCATCTACGACCAGAACTTCAAGGGCAA

GGCCACCCTGACCGTGGACAAGTCCACCTCCACAGCCTACATGGAGCTGT

CCTCCCTGAGGTCCGAGGACACCGCCGTGTACTTCTGCGCCAGGGACGTG

ACCACCGCTCTGGACTTCTGGGGACAGGGCACCACCGTGACCGTGAGCTC

C (Human IL-15R a sushi domain)
ATCACGTGTCCTCCTCCTATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Human IgG1 CH2 CH3 (Fc) domain)
GAGCCGAAATCTTGTGACAAAACTCACACATGCCCACCGTGCCCAGCACC

TGAACTCCTGGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCTGGTAAA

The amino acid sequence of the hOAT scAb/huIL-15RαSu/hIgG1 Fc fusion protein (including signal peptide sequence) is as follows (SEQ ID NO: 36):

(Signal peptide)
MKWVTFISLLFLFSSAYS (hOATscAb)
(VL)
DIQMTQSPASLSASVGDRVTITCLASQTIDTWLAWYLQKPGKSPQLLIYA

ATNLADGVPSRFSGSGSGTDFSFTISSLQPEDFATYYCQQVYSSPFTFGQ

GTKLEIK (Linker)
GGGGSGGGGSGGGGS (VH)
QIQLVQSGGEVKKPGASVRVSCKASGYSFTDYNVYWVRQSPGKGLEWIGY

IDPYNGITIYDQNFKGKATLTVDKSTSTAYMELSSLRSEDTAVYFCARDV

TTALDFWGQGTTVTVSS (Human IL-15R a sushi domain)
ITCPPPMSVEHADIWVKSYSLYSRERYICNSGFKRKAGTSSLTECVLNKA

TNVAHWTTPSLKCIR (Human IgG1 CI12-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some cases, the leader peptide is cleaved from the mature polypeptide.

Similar constructs could be generated to express the hOAT scAb/huIL-15N72D fusion protein.

The sequences were cloned into expression vectors as described in Example 1 and previously (U.S. Pat. No. 8,507,222, at Examples 1 and 2, incorporated herein by reference), and the expression vectors transfected into CHO cells. In some cases, the CHO cells were transfected with vectors encoding both huIL-15N72D and huIL-15RαSu/Fc fusion proteins with the same or different binding domains of the invention. The fusion protein complexes were purified from the CHO cell culture supernatant using Protein A affinity chromatography as described above.

Fusion protein complexes of the invention were also generated with single chain Ab domains that recognize CD33 (CD33 scAb). The nucleic acid sequence of the CD33 scAb/huIL-15N72D construct (including signal peptide sequence) is as follows (SEQ ID NO: 37):

(Signal peptide)
ATGGATTTTCAGGTGCAGATTATCAGCTTCCTGCTAATCAGTGCTTCAGT

CATAATGTCAAGAGGA (CD33 scAb)
(VL)
CAGGTGCAGCTGGTTCAGAGCGGTGCGGAAGTTAAAAAGCCGGGCTCTTC

CGTGAAAGTTAGCTGCAAAGCGTCTGGTTATACCTTCACCGACTACAACA

TGCACTGGGTCCGCCAGGCCCCAGGCCAGGGTCTGGAATGGATCGGTTAT

ATTTACCCGTACAACGGTGGCACGGGATATAACCAGAAATTCAAATCCAA

AGCTACCATCACTGCGGACGAAAGCACCAACACCGCATATATGGAATTGT

CTTCTCTGCGTAGCGAAGATACCGCGGTTTACTATTGCGCTCGTGGTCGT

CCAGCGATGGATTACTGGGGTCAGGGCACCCTGGTGACCGTGAGCTCT (Linker)
GGCGGAGGCGGATCTGGTGGTGGCGGATCCGGTGGAGGCGGAAGC (VH)
GATATCCAGATGACCCAGTCCCCGAGCTCCCTGTCTGCCAGCGTGGGCGA

CCGCGTGACTATCACCTGCCGTGCGTCCGAAAGCGTGGATAACTACGGCA

TTTCCTTTATGAACTGGTTCCAGCAGAAACCGGGTAAAGCCCCGAAACTG

CTGATTTATGCGGCCTCTAACCAGGGCAGCGGTGTGCCGAGCCGCTTTTC

CGGCAGCGGTTCGGGGACCGATTTCACTCTGACCATTTCTAGCCTGCAGC

CAGATGACTTCGCGACCTACTACTGCCAACAGTCTAAAGAAGTTCCGTGG

ACCTTCGGTCAGGGTACCAAAGTTGAAATTAAA (Human IL-15N72D)
AACTGGGTTAACGTAATAAGTGATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT

CATCCTAGCAAACGACAGTTTGTCTTCTAATGGGAATGTAACAGAATCTG

GATGCAAAGAATGTGAGGAACTGGAGGAAAAAAATATTAAAGAATTTTTG

CAGAGTTTTGTACATATTGTCCAAATGTTCATCAACACTTCTTAA

The amino acid sequence of the CD33 scAb/IL-15N72D fusion protein (including signal peptide sequence) is as follows (SEQ ID NO: 38):

(Signal peptide)
MDFQVQIISFLLISASVIMSRG (CD33 scAb)
(VL)
QVQLVQSGAEVKKPGSSVKVSCKASGYTFTDYNMHWVRQAPGQGLEWIGY

IYPYNGGTGYNQKFKSKATITADESTNTAYMELSSLRSEDTAVYYCARGR

PAMDYWGQGTLVTVSS (Linker)
GGGGSGGGGSGGGGS (VH)
DIQMTQSPSSLSASVGDRVTITCRASESVDNYGISFMNWFQQKPGKAPKL

LIYAASNQGSGVPSRFSGSGSGTDFTLTISSLQPDDFATYYCQQSKEVPW

TFGQGTKVEIK (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

In some cases, the leader peptide is cleaved from the mature polypeptide.

The nucleic acid sequence of the CD33 scAb/huIL-15RαSu/hIgG1 Fc construct (including leader sequence) is as follows (SEQ ID NO: 39):

(Signal peptide)
ATGGATTTTCAGGTGCAGATTATCAGCTTCCTGCTAATCAGTGCTTCAGT

CATAATGTCAAGAGGA (CD33 scAb)
(VL)
CAGGTGCAGCTGGTTCAGAGCGGTGCGGAAGTTAAAAAGCCGGGCTCTTC

CGTGAAAGTTAGCTGCAAAGCGTCTGGTTATACCTTCACCGACTACAACA

TGCACTGGGTCCGCCAGGCCCCAGGCCAGGGTCTGGAATGGATCGGTTAT

```
ATTTACCCGTACAACGGTGGCACGGGATATAACCAGAAATTCAAATCCAA

AGCTACCATCACTGCGGACGAAAGCACCAACACCGCATATATGGAATTGT

CTTCTCTGCGTAGCGAAGATACCGCGGTTTACTATTGCGCTCGTGGTCGT

CCAGCGATGGATTACTGGGGTCAGGGCACCCTGGTGACCGTGAGCTCT (Linker)
GGCGGAGGCGGATCTGGTGGTGGCGGATCCGGTGGAGGCGGAAGC (VH)
GATATCCAGATGACCCAGTCCCCGAGCTCCCTGTCTGCCAGCGTGGGCGA

CCGCGTGACTATCACCTGCCGTGCGTCCGAAAGCGTGGATAACTACGGCA

TTTCCTTTATGAACTGGTTCCAGCAGAAACCGGGTAAAGCCCCGAAACTG

CTGATTTATGCGGCCTCTAACCAGGGCAGCGGTGTGCCGAGCCGCTTTTC

CGGCAGCGGTTCGGGGACCGATTTCACTCTGACCATTTCTAGCCTGCAGC

CAGATGACTTCGCGACCTACTACTGCCAACAGTCTAAAGAAGTTCCGTGG

ACCTTCGGTCAGGGTACCAAAGTTGAAATTAAA (Human IL-15R a sushi domain)
ATCACGTGTCCTCCTCCTATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Human IgG1 CH2 CH3 (Fc) domain)
GAGCCGAAATCTTGTGACAAAACTCACACATGCCCACCGTGCCCAGCACC

TGAACTCCTGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCTGGTAAATAA
```

The amino acid sequence of the CD33 scAb/huIL-15RαSu/hIgG1 Fc fusion protein (including leader sequence) is as follows (SEQ ID NO: 40):

(Signal peptide)
MDFQVQIISFLLISASVIMSRG (CD33 scAb)
(VL)
QVQLVQSGAEVKKPGSSVKVSCKASGYTFTDYNMHWVRQAPGQGLEWIGY

IYPYNGGTGYNQKFKSKATITADESTNTAYMELSSLRSEDTAVYYCARGR

PAMDYWGQGTLVTVSS (Linker)
GGGGSGGGGSGGGGS (VH)
DIQMTQSPSSLSASVGDRVTITCRASESVDNYGISFMNWFQQKPGKAPKL

LIYAASNQGSGVPSRFSGSGSGTDFTLTISSLQPDDFATYYCQQSKEVPW

TFGQGTKVEIK (Human IL-15R a sushi domain)
ITCPPPMSVEHADIWVKSYSLYSRERYICNSGFKRKAGTSSLTECVLNKA

TNVAHWTTPSLKCIR (Human IgG1 CH2 CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some cases, the leader peptide is cleaved from the mature polypeptide.

The sequences were cloned into expression vectors as described in Example 1 and previously (U.S. Pat. No. 8,507,222, at Examples 1 and 2, incorporated herein by reference), and the expression vectors transfected into CHO cells. In some cases, the CHO cells were transfected with vectors encoding both huIL-15N72D and huIL-15RαSu/Fc fusion proteins with the same or different binding domains of the invention. The fusion protein complexes were purified from the CHO cell culture supernatant using Protein A affinity chromatography as described above.

Intercellular adhesion molecule 1 (ICAM-1) is a cell surface glycoprotein in the immunoglobulin superfamily. It has been demonstrated that the level of ICAM-1 protein expression on the cell surface positively correlated with metastatic potential of various solid tumors. Lymphocyte function-associated antigen 1 (LFA-1) is found on all T-cells and on B-cells, macrophages, neutrophils, and NK cells. It is known to bind to ICAM-1, specifically through the "I domain", to sustain cellular adhesion (immunological/cytolytic synapse formation) or rolling (to slow the movement of cells in the bloodstream prior to extravasation). The I domain alone can support high affinity binding to ICAM-1 with the addition of two mutations: K287C and K294C. Therefore, a TxM was created comprising the LFA-1 I domain, along with the mutations, in order to target tumors and facilitate activation and localization of effector immune cells via the huIL-15N72D: huIL-15RαSu complex.

The nucleic acid sequence of the human LFA-1 I domain (K287C/K294C)/huIL-15RαSu/huIgG1 Fc construct (including leader sequence) is as follows (SEQ ID NO: 41):

```
(Signal peptide)
ATGAAGTGGGTGACCTTCATCAGCCTGCTGTTCCTGTTCTCCAGCGCCTAC

TCC (human LFA-1 I domain(K287C/K294C))
ATGAAGTGGGTGACCTTCATCAGCCTGCTGTTCCTGTTCTCCAGCGCCTAC

TCCGATTTAGTGTTTCTGTTCGACGGCTCCATGTCTTTACAGCCCGATGAG

TTCCAGAAGATTTTAGACTTCATGAAGGACGTGATGAAGAAACTGTCCAAC

ACCAGCTACCAGTTCGCTGCCGTGCAGTTCTCCACCTCCTACAAGACCGAG
```

```
TTCGACTTCTCCGACTACGTGAAGCGGAAGGACCCCGATGCTTTACTGAAG

CACGTCAAGCACATGCTGCTGCTCACCAACACCTTTGGCGCCATCAACTAC

GTGGCCACCGAGGTGTTTCGTGAGGAACTGGGAGCTCGGCCCGATGCCACC

AAGGTGCTGATTATCATCACCGACGGCGAAGCCACCGATAGCGGAAACATC

GATGCCGCCAAGGACATCATCCGGTACATTATCGGCATCGGCAAGCACTTC

CAGACCAAGGAGAGCCAAGAGACTTTACACAAGTTCGCCTCCAAGCCCGCT

TCCGAGTTCGTGTGCATTTTAGACACCTTCGAGTGTTTAAAGGATTTATTT

ACCGAGCTGCAGAAGAAGATCTACGTGATTGAGGGCACCAGCAAGCAAGAT

CTGACCTCCTTCAACATGGAGCTGTCCAGCAGCGGCATTTCCGCTGATTTA

TCTCGTGGCCACGCC (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Human IgG1 CH2-CH3 (Fc) domain)
GAGCCGAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG

GTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA
```

The amino acid sequence of the mature human LFA-1 I domain(K287C/K294C)/huIL-15RαSu/huIgG1 Fc fusion protein (including leader sequence) is as follows (SEQ ID NO: 42):

```
(Signal peptide)
MKWVTFISLLFLFSSAYS (human LFA-1 I domain(K287C/K294C)
DLVFLFDGSMSLQPDEFQKILDFMKDVMKKLSNTSYQFAAVQFSTSYKTEF

DFSDYVKRKDPDALLKHVKHMLLLTNTFGAINYVATEVFREELGARPDATK

VLIIITDGEATDSGNIDAAKDIIRYIIGIGKHFQTKESQETLHKFASKPAS

EFVCILDTFECLKDLFTELQKKIYVIEGTSKQDLTSFNMELSSSGISADLS

RGHA (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK
```

In some cases, the leader peptide is cleaved from the mature polypeptide.

Similar constructs could be generated to express the human LFA-1 I domain (K287C/K294C)/huIL-15N72D fusion protein.

The sequences were cloned into expression vectors as described in Example 1 and previously (U.S. Pat. No. 8,507,222, at Examples 1 and 2, incorporated herein by reference), and the expression vectors transfected into CHO cells. In some cases, the CHO cells were transfected with vectors encoding both huIL-15N72D and huIL-15RαSu/Fc fusion proteins with the same or different binding domains of the invention. The fusion protein complexes were purified from the CHO cell culture supernatant using Protein A affinity chromatography as described above.

For example. CHO cells were transfected with the huIL-15N72D expression vector. Cells were also transfected with vectors expressing the human LFA-1 I domain(K287C/K294C)/huIL-15RαSu/huIgG1 Fc construct. Co-expression of the two constructs in CHO cells allowed formation and secretion of a soluble huIL-15N72D: human LFA-1 I domain(K287C/K294C)/huIL-15RαSu/huIgG1 Fc complex (referred to as 2*hLFA1/TxM).

Notch1 is a member of the Type I transmembrane protein family, which shares structural characteristics including an extracellular domain consisting of multiple epidermal growth factor-like (EGF) repeats, and an intracellular domain consisting of multiple different domain types. Its overexpression has been demonstrated in several tumor types making it an attractive target for immunotherapy. Delta-like protein 4 (DLL4) is one several ligands for Notch1 and has been shown to have the highest affinity. Therefore, the extracellular domain of DLL4 (positions 27-529) was used for targeting of Notch1 in the creation of a TxM complex.

The nucleic acid sequence of the hDLL4/huIL-15RαSu/huIgG1 Fc construct (including leader sequence) is as follows (SEQ ID NO: 43):

```
(Signal peptide)
ATGAAGTGGGTGACCTTCATCAGCCTGCTGTTCCTGTTCTCCAGCGCCTAC

TCC (hDLL4)
AGCGGCGTGTTCCAGCTGCAGCTGCAAGAGTTTATCAACGAGAGGGCGTG

CTGGCTTCCGGTCGTCCTTGTGAGCCCGGTTGTAGGACCTTTTTCCGGGTG

TGTTTAAAGCATTTTCAAGCTGTGGTGTCCCCCGGACCTTGTACCTTCGGC

ACCGTGTCCACCCCCGTTCTGGGCACCAACTCCTTCGCCGTTCGTGACGAC

AGCTCCGGAGGAGGTCGTAATCCTTTACAGCTGCCTTTCAACTTTACTTGG
```

```
CCCGGCACCTTCTCCCTCATCATCGAAGCTTGGCATGCCCCCGGTGACGAT
CTGCGGCCCGAAGCTCTGCCCCCCGATGCTTTAATCAGCAAGATTGCCATT
CAAGGTTCTTTAGCCGTGGGCCAGAACTGGCTGCTGGACGAGCAGACCAGC
ACACTCACTCGTCTGAGGTACTCCTATCGTGTGATCTGCAGCGACAACTAC
TACGGCGACAATTGCAGCCGGCTGTGCAAGAAGAGGAACGACCACTTCGGC
CATTACGTCTGCCAGCCCGACGGCAATTTATCTTGTCTGCCCGGTTGGACC
GGCGAGTACTGTCAGCAGCCCATCTGTTTAAGCGGCTGCCACGAGCAGAAC
GGCTACTGCAGCAAGCCCGCTGAGTGTCTGTGTAGGCCCGGCTGGCAAGGT
AGGCTGTGCAACGAGTGCATCCCCCACAATGGCTGTCGGCACGGCACTTGT
TCCACCCCTTGGCAGTGCACTTGTGACGAGGGCTGGGGAGGTTTATTCTGC
GACCAAGATCTGAACTACTGCACCCACCACAGCCCTTGTAAGAACGGAGCT
ACTTGTTCCAACAGCGGCCAGAGGTCCTACACTTGTACTTGTAGGCCCGGT
TACACCGGCGTCGACTGCGAACTGGAACTGAGCGAATGCGATAGCAACCCT
TGTCGTAACGGCGGCAGCTGCAAGGACCAAGAAGACGGCTACCACTGTTTA
TGCCCTCCCGGATACTACGGTTTACACTGCGAGCACTCCACACTGTCTTGT
GCCGACTCCCCTTGTTTCAACGGCGGAAGCTGTCGTGAGAGGAACCAAGGT
GCCAACTACGCTTGTGAGTGCCCTCCCAACTTCACCGGCTCCAACTGCGAG
AAGAAGGTGGATCGTTGCACCTCCAACCCTTGCGCCAACGGCGGCCAGTGT
TTAAATAGGGGCCCTTCCCGGATGTGTCGTTGTCGTCCCGGTTTTACCGGC
ACCTACTGCGAGCTGCACGTCAGCGATTGCGCCCGGAATCCTTGCGCTCAC
GGCGGAACTTGTCACGATTTAGAGAACGGTTTAATGTGCACTTGTCCCGCT
GGATTCAGCGGTCGTAGGTGTGAGGTGAGGACCTCCATCGACGCTTGTGCC
AGCAGCCCTTGCTTCAATCGTGCCACTTGTTACACCGATTTATCCACCGAC
ACCTTCGTGTGCAACTGCCCCTACGGCTTCGTGGGATCTCGTTGCGAGTTC
CCCGTTGGCCTGCCTCCTAGCTTTCCCTGG
(Human IL-15R α sushi domain)
ATCACGTGTCCTCCTCCTATGTCCGTGGAACACGCAGACATCTGGGTCAAG
AGCTACAGCTTGTACTCCAGGGAGCGGTACATTTGTAACTCTGGTTTCAAG
CGTAAAGCCGGCACGTCCAGCCTGACGGAGTGCGTGTTGAACAAGGCCACG
AATGTCGCCCACTGGACAACCCCCAGTCTCAAATGCATTAGA
(Human IgG1 CH2-CH3 (Fc) domain)
GAGCCGAAATCTTGTGACAAAACTCACACATGCCCACCGTGCCCAGCACCT
GAACTCCTGGGGGGACCGTCAGTCTTCCTCTTCCCCCCAAAACCCAAGGAC
ACCCTCATGATCTCCCGGACCCCTGAGGTCACATGCGTGGTGGTGGACGTG
AGCCACGAAGACCCTGAGGTCAAGTTCAACTGGTACGTGGACGGCGTGGAG
GTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAA
ACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGG
CAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTAC
ACGCAGAAGAGCCTCTCCCTGTCTCCTGGTAAATAA
```

The amino acid sequence of the mature hDLL4/huIL-15RαSu/huIgG1 Fc fusion protein (including leader sequence) is as follows (SEQ ID NO: 44):

```
(Signal peptide)
MKWVTFISLLFLFSSAYS (hDLL4)
SGVFQLQLQEFINERGVLASGRPCEPGCRTFFRVCLKHFQAVVSPGPCTFG
TVSTPVLGTNSFAVRDDSSGGGRNPLQLPFNFTWPGTFSLIIEAWHAPGDD
LRPEALPPDALISKIAIQGSLAVGQNWLLDEQTSTLTRLRYSYRVICSDNY
YGDNCSRLCKKRNDHFGHYVCQPDGNLSCLPGWTGEYCQQPICLSGCHEQN
GYCSKPAECLCRPGWQGRLCNECIPHNGCRHGTCSTPWQCTCDEGWGGLFC
DQDLNYCTHHSPCKNGATCSNSGQRSYTCTCRPGYTGVDCELELSECDSNP
CRNGGSCKDQEDGYHCLCPPGYYGLHCEHSTLSCADSPCFNGGSCRERNQG
ANYACECPPNFTGSNCEKKVDRCTSNPCANGGQCLNRGPSRMCRCRPGFTG
TYCELHVSDCARNPCAHGGTCHDLENGLMCTCPAGFSGRRCEVRTSIDACA
SSPCFNRATCYTDLSTDTFVCNCPYGFVGSRCEFPVGLPPSFPW (Human IL-15R α sushi domain)
ITCPPPMSVEHADIWVKSYSLYSRERYICNSGFKRKAGTSSLTECVLNKAT
NVAHWTTPSLKCIR (Human IgG1 CH2-CH3 (Fc) domain)
EPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQ
GNVFSCSVMHEALHNHYTQKSLSLSPGK
```

In some cases, the leader peptide is cleaved from the mature polypeptide.

Similar constructs could be generated to express hDLL4 domain/huIL-15N72D fusion protein.

The sequences were cloned into expression vectors as described in Example 1 and previously (U.S. Pat. No. 8,507,222, at Examples 1 and 2, incorporated herein by reference), and the expression vectors transfected into CHO cells. In some cases, the CHO cells were transfected with vectors encoding both huIL-15N72D and huIL-15RαSu/Fc fusion proteins with the same or different binding domains of the invention. The fusion protein complexes were purified from the CHO cell culture supernatant using Protein A affinity chromatography as described above.

For example, co-expression of huIL-15N72D and hDLL4/huIL-15RαSu/huIgG1 Fc expression vectors in CHO cells allowed formation and secretion of a soluble T×M complex referred to as 2*hDLL4/T×M.

T-cell immunoglobulin and mucin-domain containing-3 (Tim-3) is an immune checkpoint receptor found on IFN-γ-producing CD4[+] T helper 1 (Th1) and CD8[+] T cytotoxic 1 (Tc1) T cells. Therefore, it is an attractive target for cancer immunotherapy. Thus, fusion protein complexes of the invention were generated with single chain Ab domains that recognize human Tim-3 (haTIM3scFv).

The nucleic acid sequence of the haTIM3scFv/huIL-15RαSu/huIgG1 Fc construct (including leader sequence) is as follows (SEQ ID NO: 45):

(Signal peptide)
ATGGAATGGAGCTGGGTCTTTCTCTTCTTCCTGTCAGTAACCACCGGTGTC

CACTCC (haTIM3scFv: VL-linker-VH scFv)
(VL)
TCCTATGTGCTGACTCAGCCTCCCTCCGCGTCCGGGTCTCCTGGACAGTCA

GTCACCATCTCCTGCACTGGAACCAGCAGTGACGTTGGTAATAATAACTAT

GTCTCCTGGTACCAACAGCACCCAGGCAAAGCCCCCAAACTCATGATTTAT

GATGTCAGTAATCGGCCCTCAGGGGTTTCTACTCGCTTCTCTGGCTCCAAG

TCTGGCAACACGGCCTCCCTGACCATCTCTGGGCTCCAGGCTGAGGACGAG

GCTGATTATTACTGCAGCTCATATACAACCAGCAGTACTTATGTCTTCGGA

ACTGGGACCAAGCTGACCGTCCTGGGGCAGCCAAAGGCG (linker)
GGAGGTGGCGGATCCGGAGGTGGAGGTTCTGGTGGAGGTGGGAGT (VH)
CTGGTGCAATCTGGGGCTGAGGTGAAGAAGCCTGGGGCCTCAGTGAAGGTC

TCCTGCAAGGCTTCTGGATACACCTTCACCGGCTACTATATGCACTGGGTG

CGACAGGCCCCTGGACAAGGGCTTGAGTGGATGGGATGGATCAACCCTAAC

AGTGGTGGCACAAACTATGCACAGAAGTTCCAGGGCAGAGTCACCATGACC

AGGAACACCTCCATAAGCACAGCCTACATGGAGTTGAGCAGCCTGAGATCT

GACGACACGGCCGTGTATTACTGTGCGAGAGAGATGTATTACTATGGTTCG

GGGTACAACTGGTTCGACCCCTGGGGCCAGGGAACCCTGGTCACCGTGAGC

TCA (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Human IgG1 CH2-CH3 (Fc) domain)
GAGCCGAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG

GTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA

The amino acid sequence of the mature haTIM3scFv/huIL-15RαSu/huIgG1 Fc fusion protein (including leader sequence) is as follows (SEQ ID NO: 46):

(Signal peptide)
MEWSWVFLFFLSVTTGVHS (haTIM3scFv: VL-linker-VH scFv)
(VL)
SYVLTQPPSASGSPGQSVTISCTGTSSDVGNNNYVSWYQQHPGKAPKLMIY

DVSNRPSGVSTRFSGSKSGNTASLTISGLQAEDEADYYCSSYTTSSTYVFG

TGTKLTVLGQPKA (linker)
GGGGSGGGGSGGGGS (VH)
LVQSGAEVKKPGASVKVSCKASGYTFTGYYMHWVRQAPGQGLEWMGWINPN

SGGTNYAQKFQGRVTMTRNTSISTAYMELSSLRSDDTAVYYCAREMYYGS

GYNWFDPWGQGTLVTVSS (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

In some cases, the leader peptide is cleaved from the mature polypeptide.

Similar constructs could be generated to express the haTIM3scFv/huIL-15N72D fusion protein.

The sequences were cloned into expression vectors as described in Example 1 and previously (U.S. Pat. No. 8,507,222, at Examples 1 and 2, incorporated herein by reference), and the expression vectors transfected into CHO cells. In some cases, the CHO cells were transfected with vectors encoding both huIL-15N72D and huIL-15RαSu/Fc fusion proteins with the same or different binding domains of the invention. The fusion protein complexes were purified from the CHO cell culture supernatant using Protein A affinity chromatography as described above.

For example. CHO cells were transfected with the huIL-15N72D expression vector. Cells were also transfected with vectors expressing the haTIM3scFv/huIL-15RαSu/huIgG1 Fc construct. Co-expression of the two constructs in CHO cells allowed formation and secretion of a soluble huIL-15N72D: haTIM3scFv/huIL-15RαSu/huIgG1 Fc complex (referred to as 2*haTIM3/TxM).

In addition to tumor targeting molecules, TxM complexes can be created that detect and act against virally infected cells. The recent discovery of highly potent, broadly neutralizing, HIV-specific monoclonal antibodies (bNAbs) provides a novel class of potential therapeutic agents. It has long been known that neutralizing antibodies can target the HIV envelope (Env) and effectively suppress viral replication in vitro. To combine this Ab mediated suppression with the "kick and kill" approach of waking up latent virus replication and killing it with activated effector cells (via IL-15 stimulation), TxM complexes have been created comprising single chain antibody domains (scFvs) of bNAbs. The creation and characterization of four different anti-HIV TxMs comprising scFvs from bNAbs N6, 2G12, VRC07 and 10-1074 are described below.

The nucleic acid sequence of N6scFv/huIL-15RαSu/huIgG1 Fc construct (including leader sequence) is as follows (SEQ ID NO: 47):

```
(Signal peptide)
ATGAAGTGGGTGACCTTCATCAGCCTGCTGTTCCTGTTCTCCAGCGCCTAC

TCC (N6 scFv: VL-linker-VH scFv)
(VL)
TACATCCACGTGACCCAGTCCCCCTCCTCTTTAAGCGTGAGCATCGGAGAT

CGTGTGACCATCAACTGCCAGACCTCCCAAGGTGTGGGCTCCGATTTACAC

TGGTACCAGCACAAGCCCGGTCGGGCCCCCAAGCTGCTGATCCACCACACC

AGCTCCGTGGAGGATGGCGTGCCCTCTCGTTTCTCCGGCTCCGGCTTCCAT

ACCTCCTTCAATTTAACCATCAGCGATTTACAAGCTGACGACATCGCCACC

TACTACTGCCAAGTTCTCCAGTTCTTCGGCCGGGGCTCTCGTCTGCATATC

AAG (linker)
GGAGGCGGCGGATCCGGCGGCGGAGGCAGCGGCGGAGGCGGATCT (VH)
CGTGCTCATCTGGTGCAGAGCGGAACCGCCATGAAGAAGCCCGGTGCTAGC

GTGCGGGTGTCTTGTCAGACCAGCGGATACACCTTCACCGCCCACATTTTA

TTCTGGTTTCGTCAAGCTCCCGGTCGTGGACTGGAATGGGTGGGCTGGATC

AAGCCCCAGTATGGCGCCGTGAACTTTGGCGGCGGCTTTCGTGATCGGGTG

ACTTTAACTCGTGACGTGTATCGGGAGATCGCCTACATGGACATTAGGGGT

TTAAAGCCCGACGATACCGCCGTGTACTACTGCGCTCGTGATCGTTCCTAC

GGCGATAGCAGCTGGGCTTTAGATGCTTGGGGCCAAGGTACCACAGTGTGG

TCCGCC (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Human IgG1 CH2-CH3 (Fc) domain)
GAGCCGAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG

GTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA
```

The nucleic acid sequence of 2G12scFv/huIL-15RαSu/huIgG1 Fc construct (including leader sequence) is as follows (SEQ ID NO: 48):

```
(Signal peptide)
ATGAAGTGGGTGACCTTCATCAGCCTGCTGTTCCTGTTCTCCAGCGCCTAC

TCC (2G12 scFv: VL-linker-VH scFv)
(VL)
GTGGTGATGACCCAGTCCCCCTTCCACCCTGTCCGCTTCCGTGGGCGACACC

ATCACCATCACCTGCAGGGCCTCCCAGTCCATCGAGACCTGGCTGGCCTGG

TACCAGCAGAAGCCCGGCAAGGCCCCCAAGCTGCTGATCTACAAGGCCTCC

ACCCTGAAGACCGGCGTGCCCTCCAGGTTTTCCGGATCCGGCTCCGGCACC

GAGTTCACCCTGACCATCAGCGGCCTGCAGTTCGACGACTTCGCCACCTAC

CACTGCCAGCACTACGCCGGCTACTCCGCCACCTTTGGACAGGGCACCAGG

GTGGAGATCAAG (linker)
GGAGGTGGCGGATCCGGAGGTGGAGGTTCTGGTGGAGGTGGGAGT (VH)
GAGGTGCAGCTGGTGGAATCCGGAGGCGGCCTGGTGAAAGCTGGCGGAAGC

CTGATCCTGAGCTGCGGCGTGTCCAACTTCAGGATCTCCGCCCACACCATG

AACTGGGTGAGGAGGGTGCCTGGAGGAGGACTGGAGTGGGTGGCCAGCATC

TCCACCTCCTCCACCTACAGGGACTACGCCGACGCCGTGAAGGGCAGGTTC

ACCGTGAGCAGGGACGACCTGGAGGACTTCGTGTACCTGCAGATGCACAAG

ATGCGGGTGGAGGACACCGCCATCTACTACTGCGCCAGGAAGGGCTCCGAC

AGGCTGTCCGACAACGACCCCTTTGACGCCTGGGGCCCTGGAACCGTGGTG

ACAGTGTCCCCC (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Human IgG1 CH2-CH3 (Fc) domain)
GAGCCGAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG

GTGCATAATGCCAAGACAAAGCCGCGGGAGGAGCAGTACAACAGCACGTAC
```

```
CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA
```

The nucleic acid sequence of VRC07(523)scFv/huIL-15RαSu/huIgG1 Fc construct (including leader sequence) is as follows (SEQ ID NO: 49):

```
(Signal peptide)
ATGAAGTGGGTGACCTTCATCAGCCTGCTGTTCCTGTTCTCCAGCGCCTAC

TCC (VRC07(523) scFv: VL-linker-VH scFv)
(VL)
TCCTCCCTGACCCAGAGCCCCGGAACACTCTCCCTCTCCCCCGGTGAGACC

GCTATCATCTCTTGTAGGACCAGCCAGTACGGCTCTTTAGCTTGGTATCAA

CAGAGGCCCGGCCAAGCTCCTAGGCTGGTCATTTACAGCGGCAGCACAAGG

GCCGCCGGCATCCCCGATAGGTTCTCCGGCTCCCGGTGGGGCCCCGATTAC

AATTTAACAATCTCCAATTTAGAGTCCGGAGACTTCGGCGTCTACTACTGC

CAGCAGTACGAGTTCTTCGGCAAGGTACCAAAGTGCAAGTTGATATCAAG (linker)
GGCGGCGGAGGCTCCGGCGGCGGCGGATCCGGCGGAGGAGGATCC (VH)
CAAGTTAGGCTGTCCCAGAGCGGAGGCCAGATGAAGAAGCCCGGTGACTCC

ATGCGGATCAGCTGTCGTGCCAGCGGCTACGAGTTCATCAACTGCCCCATC

AACTGGATTCGTCTGGCCCCCGGTAAGCGGCCCGAATGGATGGGCTGGATG

AAACCTCGTCACGGCGCTGTGTCCTACGCTCGTCAGCTGCAAGGTCGTGTG

ACCATGACTCGTGACATGTACAGCGAGACCGCCTTTTTAGAGCTGAGGTCT

TTAACCTCCGACGACACCGCTGTGTACTTCTGCACCCGGGGCAAGTACTGC

ACCGCTCGGGACTACTACAACTGGGACTTCGAGCACTGGGGCCAAGGTACA

CCCGTGACAGTGTCCTCC (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA (Human IgG1 CH2-CH3 (Fc) domain)
GAGCCGAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG
```

```
GTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA
```

The nucleic acid sequence of 10-1074scFv/huIL-15RαSu/huIgG1 Fc construct (including leader sequence) is as follows (SEQ ID NO: 50):

```
(Signal peptide)
ATGAAGTGGGTGACCTTCATCAGCCTGCTGTTCCTGTTCTCCAGCGCCTAC

TCC (10-1074 scFv: VL-linker-VH scFv)
(VL)
TCCAGCTACGTGAGGCCTCTCTCCGTGGCTCTGGGCGAAACAGCTCGTATC

AGCTGCGGTCGTCAAGCTCTGGGATCTCGTGCTGTGCAGGTACCAGCAC

CGGCCCGGTCAAGCTCCCATTTTACTGATCTACAACAACCAAGATCGGCCC

TCCGGCATCCCCGAAAGGTTTAGCGGCACCCCCGATATCAACTTCGGCACA

AGGGCCACTTTAACCATTAGCGGAGTGGAGGCCGGCGACGAGGCCGACTAC

TACTGCCACATGTGGGACTCCCGGTCCGGCTTTTCTTGGAGCTTTGGCGG

GCTACTCGTCTGACAGTGCTG (linker)
GGCGGAGGCGGCTCCGGAGGCGGCGGCAGCGGAGGAGGCGGATCC (VH)
CAAGTTCAGCTGCAAGAATCCGGACCCGGTTTAGTGAAGCCCAGCGAGACT

TTAAGCGTGACTTGTAGCGTGAGCGGCGACAGCATGAACAACTACTACTGG

ACTTGGATTCGTCAGAGCCCCGGTAAGGGTTTAGAGTGGATCGGCTACATC

TCCGACCGGGAGTCCGCCACCTACAACCCCTCTTTAAACTCCCGGGTGGTG

ATCTCTCGTGACACCTCCAAGAACCAGCTGTCTTTAAAGCTGAACTCCGTG

ACCCCCGCTGACACCGCCGTGTACTACTGCGCTACCGCTAGGCGGGGCCAG

AGGATCTACGCGTGGTGAGCTTCGGCGAGTTCTTCTACTACTACAGCATG

GACGTGTGGGCAAAGGCACCACCGTGACCGTGTCCTCC (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA
```

(Human IgG1 CH2-CH3 (Fc) domain)
GAGCCGAAATCTTGTGACAAAACTCACACATGCCCACCGTGCCCAGCACCT

GAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAG

GTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCTG

CCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTAC

ACGCAGAAGAGCCTCTCCCTGTCTCCTGGTAAATAA

The amino acid sequence of the mature N6scFv/huIL-15RαSu/huIgG1 Fc fusion protein (including leader sequence) is as follows (SEQ ID NO: 51):

(Signal peptide)
MKWVTFISLLFLFSSAYS (N6 scFv: VL-linker-VH scFv)
(VL)
YIHVTQSPSSLSVSIGDRVTINCQTSQGVGSDLHWYQHKPGRAPKLLIHHT

SSVEDGVPSRFSGSGFHTSFNLTISDLQADDIATYYCQVLQFFGRGSRLHI

K (linker)
GGGGSGGGGSGGGGS (VH)
RAHLVQSGTAMKKPGASVRVSCQTSGYTFTAHILFWFRQAPGRGLEWVGWI

KPQYGAVNFGGGFRDRVTLTRDVYREIAYMDIRGLKPDDTAVYYCARDRSY

GDSSWALDAWGQGTTVWSA (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

The amino acid sequence of the mature 2G12scFv/huIL-15RαSu/huIgG1 Fc fusion protein (including leader sequence) is as follows (SEQ ID NO: 52):

(Signal peptide)
MKWVTFISLLFLFSSAYS (2G12 scFv: VL-linker-VH scFv)
(VL)
VVMTQSPSTLSASVGDTITITCRASQSIETWLAWYQQKPGKAPKLLIYKAS

TLKTGVPSRFSGSGSGTEFTLTISGLQFDDFATYHCQHYAGYSATFGQGTR

VEIK (linker)
GGGGSGGGGSGGGGS (VH)
EVQLVESGGGLVKAGGSLILSCGVSNFRISAHTMNWVRRVPGGGLEWVASI

STSSTYRDYADAVKGRFTVSRDDLEDFVYLQMHKMRVEDTAIYYCARKGSD

RLSDNDPFDAWGPGTVVTVSP (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

The amino acid sequence of the mature VRC07(523)scFv/huIL-15RαSu/huIgG1 Fc fusion protein (including leader sequence) is as follows (SEQ ID NO: 53):

(Signal peptide)
MKWVTFISLLFLFSSAYS (VRC07(523) scFv: VL-linker-VH scFv)
(VL)
SSLTQSPGTLSLSPGETAIISCRTSQYGSLAWYQQRPGQAPRLVIYSGSTR

AAGIPDRFSGSRWGPDYNLTISNLESGDFGVYYCQQYEFFGQGTKVQVDIK (linker)
GGGGSGGGGSGGGGS (VH)
QVRLSQSGGQMKKPGDSMRISCRASGYEFINCPINWIRLAPGKRPEWMGWM

KPRHGAVSYARQLQGRVTMTRDMYSETAFLELRSLTSDDTAVYFCTRGKYC

TARDYYNWDFEHWGQGTPVTVSS (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

The amino acid sequence of the mature 10-1074scFv/huIL-15RαSu/huIgG1 Fc fusion protein (including leader sequence) is as follows (SEQ ID NO: 54):

(Signal peptide)
MKWVTFISLLFLFSSAYS (10-1074) scFv: VL-linker-VH scFv)
(VL)
SSYVRPLSVALGETARISCGRQALGSRAVQWYQHRPGQAPILLIYNNQDRP

SGIPERFSGTPDINFGTRATLTISGVEAGDEADYYCHMWDSRSGFSWSFGG

ATRLTVL (linker)
GGGGSGGGGSGGGGS (VH)
QVQLQESGPGLVKPSETLSVTCSVSGDSMNNYYWTWIRQSPGKGLEWIGYI

SDRESATYNPSLNSRVVISRDTSKNQLSLKLNSVTPADTAVYYCATARRGQ

RIYGVVSFGEFFYYYSMDVWGKGTTVTVSS (Human IL-15R α sushi domain)
ITCPPPMSVEHADIWVKSYSLYSRERYICNSGFKRKAGTSSLTECVLNKAT

NVAHWTTPSLKCIR (Human IgG1 CH2-CH3 (Fc) domain)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

In some cases, the leader peptide is cleaved from the mature polypeptide.

Similar constructs could be generated to express bNAb scFv/huIL-15N72D fusion proteins as described above.

The sequences were cloned into expression vectors as described in Example 1 and previously (U.S. Pat. No. 8,507,222, at Examples 1 and 2, incorporated herein by reference), and the expression vectors transfected into CHO cells. In some cases, the CHO cells were transfected with vectors encoding both huIL-15N72D and huIL-15RαSu/Fc fusion proteins with the same or different binding domains of the invention. The fusion protein complexes were purified from the CHO cell culture supernatant using Protein A affinity chromatography as described above.

For example, co-expression of the huIL-15N72D and N6scFv/huIL-15RαSu/huIgG1 Fc expression vectors in CHO cells allowed formation and secretion of a soluble TxM complex referred to as 2*hN6/TxM. Co-expression of the huIL-15N72D and 2G12scFv/huIL-15RαSu/huIgG1 Fc expression vectors in CHO cells allowed formation and secretion of a soluble TxM complex referred to as 2*h2G12/TxM. Co-expression of the huIL-15N72D and VRC07(523) scFv/huIL-15RαSu/huIgG1 Fc expression vectors in CHO cells allowed formation and secretion of a soluble TxM complex referred to as 2*hVRC07(523)/TxM. Co-expression of the huIL-15N72D and 10-1074scFv/huIL-15RαSu/huIgG1 Fc expression vectors in CHO cells allowed formation and secretion of a soluble TxM complex referred to as 2*h10-1074/TxM.

As indicated above, the TxM proteins can be purified from CHO cell supernatants by Protein A chromatography and other separation methods (i.e., ion exchange, hydrophobic, and/or size exclusion chromatography, and filtration methods). Furthermore, the purified proteins can be characterized by gel, chromatography, and other analytical methods. For example, FIG. 20 shows size exclusion chromatography analysis of various TxM complexes including those with 2 scAb or binding domains (i.e. 2 headed (2H) IL-15N72D:anti-PD-L1 scAb/IL-15RαSu/Fc complexes) or 4 scAb or binding domains (i.e. 4 headed (4H) anti-PD-L1 scAb/IL-15N72D:anti-PD-L1 scAb/IL-15RαSu/Fc complexes) or combinations of different targeting domains (i.e., tumor targeting domains/anti-PDL1scAb TxM complexes). The SEC chromatographs indicate that the Protein A-purified TxM proteins are primarily comprised of a major protein peak with a migration pattern consistent with the IL-15N72D:IL-15RαSu/Fc complex.

Similar TxM constructs comprising scAb or binding domains could be readily generated with antibody sequences specific to other CD antigens, cytokines or chemokine receptors or ligands, growth factor receptors or ligands, cell adhesion molecules, MHC/MHC-like molecules, Fc receptors, Toll-like receptors, NK receptors, TCRs, BCRs, positive/negative co-stimulatory receptors or ligands, death receptors or ligands, tumor associated antigens, virus-encoded and bacterial-encoded antigens, and bacterial-specific. Of particular interest are TxM with disease specific binding domains (e.g. scAbs) to antigens of CD4, CD19, CD20, CD21, CD22, CD23, CD25, CD30, CD33, CD38, CD40, CD44, CD51, CD52, CD70, CD74, CD80, CD123, CD152, CD147, CD221, EGFR, HER-2/neu, HER-1, HER-3, HER-4, CEA, OX40 ligand, cMet, tissue factor, Nectin-4, PSA, PSMA, EGFL7, FGFR, IL-6 receptor, IGF-1 receptor, GD2, CA-125, EpCam, death receptor 5, MUC1, VEGFR1, VEGFR2, PDGFR, Trail R2, folate receptor, angiopoietin-2, alphavbeta3 integrin receptor, HLA-DR antigens and other disease targets described herein. Antibody domains against viral antigens from HIV, HCV, HBC, CMV, HTLV, HPV, EBV, RSV and other virus are also of interest, particularly those recognizing the HIV envelope spike and/or gp120 and gp41 epitopes. Such antibody domains can be generated from sequences known in the art or isolated de novo from a variety of sources (i.e., vertebrate hosts or cells, combinatorial libraries, random synthetic libraries, computational modeling, etc.) know in the art.

Example 6: Characterization of Activities of Other TxM

The binding activities of CTLA-4 TxM were assessed using CTLA-4-positive immune cells. In studies on mouse specific CTLA-4 TxM, the expression of CTLA-4 in mouse lymphocytes was first induced by anti-CD3 Ab (2C11, 4 μg/ml) for 4 days. CTLA-4 expression was assessed by staining with PE anti-mouse CTLA-4 antibody (clone UC10-4B9) or PE Armenian Hamster IgG isotype control. As shown in FIG. 21A, flow cytometry analysis demonstrated that mouse CTLA-4 was markedly induced. Addition of mouse specific CTLA-4 TxM (100 μl sup) was capable of blocking anti-mouse CTLA-4 antibody binding as did a positive control anti-mCTLA-4 antibody (clone HB304). For studies with human specific CTLA-4 TxM, the expression of CTLA-4 in human PBMC was induced by anti-CD3 Ab (OKT3:4 μg/ml) for 3 days. Cells were then stained with PE anti-human CTLA-4 antibody (clone BNI3, Biolegend) or PE mouse IgG2a, K isotype control. Consistent with the results described above, human specific CTLA-4 TxM (CL-8-100 ul) was capable of blocking CTLA-4 on the surface of human immune cells (FIG. 21B). These results demonstrate the specificity of the CTLA-4 TxM complex.

Similarly, the binding activity of a mouse specific PD-L1/CTLA-4 TxM complex was assessed on PD-L1-positive 5T33 myeloma tumor cells (per methods described in Example 2) and CTLA-4-positive immune cells. As shown in FIG. 22A and FIG. 22B, the PD-L1/CTLA-4 T×M (sup) was capable of blocking binding to both PD-L1 and CTLA-4 expressed on the cell surface. This also indicates that multispecific T×M complexes retain reactivity of each of the linked binding domains.

Direct binding of the CD47 T×M constructs was assessed using CD47-positive cells. As shown in FIG. 23A and FIG. 23B, mouse and human specific CD47 T×M complexes were able to stain mouse B16F10 melanoma and human Jurkat T cells, respectively. These results indicate that these complexes retained CD47 binding activity.

A single stranded DNA ELISA method (ALPCO ssDNA ELISA kit 35-SSSHU-E01) was used to assess binding of T×M complexes comprising the TNT scAb domain. Briefly, purified T×M protein comprising TNT scAb domains were serially diluted and 100 µL was added to ELISA wells coated with human recombinant single stranded DNA. After 30 min incubation, the wells were washed and 100 µL of HRP-anti-human IgG antibody was added. After additional incubation and wash steps, the bound T×M protein was detected with TMB substrate. Absorbance of the wells was read at 450 nM. As shown in FIG. 24A and FIG. 24B, TNT scAb T×M and TNT scAb/anti-human PD-L1 scAb T×M complexes were capable of binding single stranded DNA, with TNT scAb T×M having a lower Kd (188 pM) compare to that of TNT scAb/anti-human PD-L1 scAb T×M (10279 pM), potentially because of the higher avidity of the 4H TNT scAb in TNT scAb T×M compared to 2H TNT scAb in TNT scAb/anti-human PD-L1 scAb T×M.

The ability of TNT scAb T×M complexes to bind tumor cells was also evaluated, exposing the tumor cell DNA by fixing and permeabilizing the cells. In the initial study, MB231 breast cancer cells were first fixed with 1.5% paraformaldehyde and permeabilized with 0.1% saponin and then $10^5$ cells ($10^6$ cells/mL) were incubated for 30 min at room temperature with 0.01-100 nM of TNT scAb T×M, TNT scAb/anti-human PD-L1 scAb T×M or 2H-anti-human PD-L1 scAb T×M (negative control). The cells were washed and stained with anti-human IgG Fc-APC and then were analyzed by flow cytometry. FIG. 25A shows the mean fluorescence intensity (MFI) of MB231 cell staining at different T×M concentrations, confirming specific and concentration dependent binding of TNT scAb T×M and TNT scAb/anti-human PD-L1 scAb T×M to permeabilized breast tumor cells. Minimal binding was seen with the negative control PD-L1 scAb T×M complex, consistent with low level expression of PD-L1 on the MB231 cell line. A similar study was conducted with fixed and permeabilized PD-L1-negative A549 human lung tumor cells. Again, the results (FIG. 25B) confirm specific and concentration dependent binding of TNT scAb T×M and TNT scAb/anti-human PD-L1 scAb T×M to permeabilized lung tumor cells.

Furthermore, the ability of T×M complexes comprising hOAT scAb and/or anti-human PD-L1 scAb domains to bind tumor cells was assessed. The SW1990 human pancreatic cancer cell line expresses high levels of human TF and low levels of human PD-L1. In this study, $10^5$ SW1990 cells ($10^6$ cells/mL) were incubated for 30 min at room temperature with 0.01-100 nM of 2 headed (h2) hOATscAb/T×M, anti-human PD-L1scAb/hOATscAb/T×M, h2*anti-human PD-L1scAb/T×M or control hOAT Ab or control anti-human PD-L1 Ab (Avelumab). The cells were washed and stained with anti-human IgG Fc-APC and then were analyzed by flow cytometry. FIG. 26 shows the mean fluorescence intensity (MFI) of SW1990 cell staining at different protein concentrations. The results confirm that the T×M complexes comprising hOAT scAb (h2*hOATscAb/T×M and anti-human PD-L1scAb/hOATscAb/T×M) exhibit similar high-level staining of human TF on SW1990 tumor cells as the control hOAT Ab. T×M complexes comprising anti-human PD-L1 scAb (h2*anti-human PD-L1scAb/T×M) exhibit lower level staining of human PD-L1 on SW1990 tumor cells similar to the control anti-human PD-L1 Ab (Avelumab).

ELISA-based methods were used to confirm the formation of the huIL-15N72D: human LFA-1 I domain(K287C/K294C)/huIL-15RαSu/huIgG1 Fc complex. Binding activity was assessed in culture supernatant from CHO cells co-transfected with the huIL-15N72D and human LFA-1 I domain(K287C/K294C)/huIL-15RαSu/huIgG1 Fc expression vectors. In FIG. 27A, the fusion protein complexes were detected using a huIL15/huIgG1-specific ELISA with a capture antibody, anti-human IL-15 antibody (R&D Systems) and a detection antibody, anti-human IgG antibody (Jackson ImmunoResearch). This binding was compared to a control sample using only the supernatant of media containing untransfected CHO cells. The results indicate production and proper complex formation for the 2*hLFA1/T×M.

Additionally, 2*hLFA1/T×M binding to ICAM-1 was assessed by ELISA (FIG. 27B). Wells of an immunoplate were coated with 1 µg of human ICAM-1-Fc (Biolegend). After wash steps, CHO culture supernatant containing 2*hLFA1/T×M was added to the cells. Following incubation and additional wash steps, binding of the fusion protein complexes was detected using an HRP-conjugated anti-human IL-15 antibody (R&D Systems). The absorbance in the wells was read at 405 nm after incubation with ABTS. The results in FIG. 27B indicate that this complex recognizes ICAM-1.

Similar ELISA-based methods confirmed the formation of a huIL-15N72D: hDLL4/huIL-15RαSu/huIgG1 Fc complex in the transfected CHO cell culture supernatant. In FIG. 28, the fusion protein complexes in the culture supernatant were detected using a huIL15/huIgG1-specific ELISA with a capture antibody, anti-human IL-15 antibody (R&D Systems) and a detection antibody, anti-human IgG antibody (Jackson ImmunoResearch). The sample is compared to a control sample using only the supernatant of media containing untransfected CHO cells. The results indicate production and proper complex formation of the 2*hDLL4/T×M complexes.

ELISA-based methods also confirmed the formation of the huIL-15N72D: haTIM3scFv/huIL-15RαSu/huIgG1 Fc complex. In FIG. 29, the fusion protein complexes in the transfected CHO culture supernatant were detected using a huIL15/huIgG1-specific ELISA with a capture antibody, anti-human IL-15 antibody (R&D Systems) and a detection antibody, anti-human IgG antibody (Jackson ImmunoResearch). This binding was compared to a control sample using only the supernatant of media containing untransfected CHO cells. The results indicate production and proper complex formation of 2*haTIM3/T×M complexes.

Supernatant from CHO cells co-transfected with bNAb scFv T×M expression vectors was used to determine the expression and binding capabilities of the T×M complexes. ELISA-based methods confirmed the formation of the bNAb scFv T×M complexes. In FIG. 30A and FIG. 30B, the fusion protein complexes in the transfected CHO culture supernatant were detected using a huIL15/huIgG1-specific ELISA with a capture antibody, anti-human IL-15 antibody (R&D Systems) and a detection antibody, anti-human IgG antibody (Jackson ImmunoResearch). The positive control T×M is one that recognizes hCD20. The results indicate production and proper complex formation for four different bNAb scFv TxM complexes.

Additionally, bNAb scFv TxM binding to HIV protein targets (gp120(SF162.LS) and gp140 (SF162.LS)) was assessed by ELISA. For this study, wells of an immunoplate were coated with 0.1 µg of HIV 120(SF162.LS) or gp140 (SF162.LS) (ProtTech, Inc.). After wash steps, CHO culture supernatants containing bNAb scFv TxMs were added to the cells. The negative control TxM is one that recognizes hCD20. Following incubation and additional wash steps, binding of the fusion protein complexes was detected using an HRP-conjugated anti-human IgG antibody (Jackson ImmunoResearch). The absorbance in the wells was read at 405 nm after incubation with ABTS. The results in FIG. 30C to FIG. 30F indicate that the bNAb scFv TxM complexes recognizes HIV protein targets.

Overall these results demonstrate that TxM complexes with binding domains specific to a variety of immune checkpoint and signaling molecules can be generated and provide enhanced binding activities to target molecules. These complexes exhibit IL-15 immunostimulatory activity and are capable of directing immune mediated cytotoxicity against target antigens on cells. These complexes also are highly efficacious in animal tumor models.

Example 7: Immunostimulatory and Anti-Tumor Activities of TxM Complexes

As indicated in Example 2, the IL-15 immunostimulatory activity of TxM complexes has been assessed based on proliferation of IL-2Rβ/γ-bearing immune cells such as the 32Dβ cell line. Briefly, increasing concentrations of purified TxM proteins were added to 32Dβ cells ($10^4$ cells/well) in 200 µL IMDM:10% FBS media and cells were incubated for 3 days at 37° C. PrestoBlue cell viability reagent (20 µL/well) then was added. After 4 hours, absorbance was measured at 570 nm (with a 600-nm reference wavelength for normalization) to determine cell proliferation based on reduction of PrestoBlue, a resazurin-based solution, by metabolically active cells. The half maximal effective concentration (EC50) of IL-15 bioactivity for the TxM complexes was then determined based on the relationship between absorbance and TxM protein concentration. Table 1 show the IL-15 EC50 values for various TxM complexes comprising binding domains of the invention. The results confirm the immunostimulatory activity of various purified TxM complexes including those with two scAb/binding domains (i.e., 2 headed (2H) anti-PD-L1 scAb/IL-15N72D: anti-PD-L1 scAb/IL-15RαSu/Fc complexes) or four scAb/binding domains (i.e., 4 headed (4H) anti-PD-L1 scAb/IL-15N72D:anti-PD-L1 scAb/IL-15RαSu/Fc complexes) or combinations of different targeting domains (i.e., tumor targeting domains/anti-PDL1scAb TxM complexes).

TABLE 1

| IL-15 Activity of TxM Complexes | |
|---|---|
| | EC50 (pM TxM) |
| 2H-anti-human PD-L1 scAb TxM | 14 |
| 4H-anti-human PD-L1 scAb TxM | 220 |
| 2H-anti-mouse PD-L1 scAb TxM | 58 |

TABLE 1-continued

| IL-15 Activity of TxM Complexes | |
|---|---|
| | EC50 (pM TxM) |
| anti-human CTLA-4 scAb/anti-human PD-L1 scAb TxM | 73 |
| TNT scAb TxM | 1013 |
| TNT scAb/anti-human PD-L1 scAb TxM | 8498 |
| 2H-hOAT TxM | 115 |
| hOAT/anti-human PD-L1 scAb TxM | 202 |

The ability of hOAT scAb TxM to stimulate immune cell cytotoxicity against tumor cells was assessed in vitro. Human NK cells were purified from blood buffy coats with NK cell isolation kit from Stemcell Technologies and used as effector cells. TF-positive human pancreatic tumor cells, SW1990, were labeled with Celltrace-violet and used as target cells. The human NK cells and SW1990 tumor cells were mixed at an E:T ratio of 1:1 in media alone or media containing 10 nM hOAT Ab (control) or 2H hOAT scAb TxM complex. After 40 hrs, the percent of target cell death was assessed by flow cytometry based on propidium iodide staining of violet-labeled target cells. As shown in FIG. 31, human NK cells incubated with 2H hOAT scAb TxM complex were capable of mediating greater cytotoxicity against TF-positive human tumor cells than untreated NK cells or NK cells treated with hOAT Ab (i.e., traditional ADCC). These results represent a significant improvement in immune cell-mediated targeted anti-tumor activity of the anti-TF TxM complexes compared to anti-TF Abs.

The ability of TxM complexes to overcome checkpoint-mediated inhibition of T cell activity is assessed in previously described in vitro assays (Steward, R, et al Cancer Immunol Res 2015 3(9):1052-1062). For example, freshly isolated primary human T cells are cultured together with anti-CD3 and anti-CD28-coated beads to demonstrate increased immune cell proliferation (measured by BrDU incorporation) and IFNγ release (measured by ELISA). Addition of PD-L1 antibody on the beads significantly reduces T cell proliferation and IFNγ release due inhibitory signaling of PD-L1/PD-1 interactions. Addition of soluble PD-L1 TxM or PD-1 TxM in the context of anti-CD3, anti-CD28, PD-L1-coated beads and T cells increases T cell proliferation and IFNγ release due to blockade of PD-L1/PD-1 interactions. Similar assays with CTLA-4 TxM in the context of anti-CD3, anti-CD28, anti-CTLA-4-coated beads and T cells also demonstrate the immune checkpoint inhibitory activity of CTLA-4 TxM.

The anti-tumor activity of these complexes is assessed in mouse xenograft models using human tumor cell lines and patient derived tumor cells (Morton, J. J., et al. Cancer Research 2016 doi: 10.1158/0008-5472). Commercially available humanized mouse models (i.e., Hu-CD34 NSG™, Jackson laboratory) have been developed to assess the activity of immunotherapies on human immune cell responses against tumors derived from human tumor cell lines and patient derived tumor cells. For example, Hu-CD34 NSG™ mice bearing PD-L1-positive subcutaneous human MDA-MB-231 breast cancer tumors is treated with PBS or increasing dose levels of PD-L1 TxM or PD-1 TxM (i.e., subcutaneous administration twice weekly for 2 weeks) and tumor growth is assessed. Dose dependent decreases in tumor volume provides evidence of the therapeutic activity of PD-L1 TxM and/or PD-1 TxM against PD-L1-positive human tumors. Solid tumor mouse models are also available using patient derived PD-L1-positive tumor cells (i.e., BR1126(TM00098), LG1306(TM00302)). The activity of PD-L1 T×M and/or PD-1 T×M in BR1126 tumor-bearing Hu-CD34 NSG™ mice is assessed by evaluating tumor growth or mouse survival post-treatment. In addition, treatment dependent changes in T cell responses in the blood and tumor microenvironment is evaluated in these models. An increase in T cells levels or activity (i.e., IFNγ-positive cells) in the blood or tumor post PD-L1 T×M and/or PD-1 T×M treatment provide evidences of immunostimulatory activity of these complexes in tumor-bearing mice. Together, these studies demonstrate the immune cell-mediated activity of PD-L1 T×M and/or PD-1 T×M against human tumors in vivo.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts, and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated soluble fusion protein complex comprising at least two soluble proteins, wherein
a first soluble protein comprises an interleukin-15 (IL-15) polypeptide domain and a second
soluble protein comprises a soluble IL-15 receptor alpha sushi-binding domain (IL-15RαSu) fused to an immunoglobulin Fc domain,
wherein the second soluble protein is substantially identical to SEQ ID NO:14 or SEQ ID NO:16, and
wherein the IL-15 domain of the first soluble protein binds to the IL-15RαSu domain of the second soluble protein to form a soluble fusion protein complex.

2. The soluble fusion protein complex of claim 1, wherein one of the first or second soluble protein further comprises a second binding domain that specifically binds to a disease antigen, immune checkpoint molecule, or immune signaling molecule.

3. The soluble fusion protein complex of claim 1, wherein the IL-15 polypeptide is an IL-15 variant comprising an N72D mutation (IL-15N72D).

4. The soluble fusion protein complex of claim 1, wherein the first soluble protein comprises the amino acid sequence set forth in one of SEQ ID NOs: 2, 6, 10, 18, 20, 24, 28, 32, or 38 and wherein the second soluble protein is substantially identical to SEQ ID NO:14 or SEQ ID NO:16.

5. A method for treating a neoplasia in a subject in need thereof comprising administering to the subject an effective amount of the soluble fusion protein complex of claim 1.

6. The method of claim 5, wherein the subject is suffering a neoplasia selected from the group consisting of a glioblastoma, prostate cancer, hematological cancer, B-cell neoplasms, multiple myeloma, B-cell lymphoma, B cell non-Hodgkin lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, prostate cancer, pancreatic cancer, colorectal cancer, ovarian cancer, non-small cell lung carcinoma, and squamous cell head and neck carcinoma.

7. The method of claim 5, wherein the effective amount is between about 1 and 100 μg/kg said fusion protein complex.

8. The method of claim 5, wherein the fusion protein complex is administered at least one time per week.

9. The method of claim 5, wherein the fusion protein complex is administered systemically, locally, intravenously, subcutaneously or intratumorally.

10. The method of claim 5, wherein said fusion protein complex increases immune cell proliferation.

11. The method of claim 5, wherein the fusion protein complex stimulates immune cell responses against cells associated with the neoplasia.

12. An isolated soluble fusion protein complex comprising at least:
a first soluble protein having at least 85% sequence identity to SEQ ID NO:2; and
a second soluble protein comprising an interleukin-15 (IL-15) receptor alpha sushi-binding
domain (IL-15RαSu) fused to an immunoglobulin Fc domain,
wherein the first soluble protein is bound to the second soluble protein to form a soluble fusion protein complex.

13. The soluble fusion protein complex of claim 12, wherein the first soluble protein lacks the signal peptide of amino acids 1-18 of SEQ ID NO:2.

14. The soluble fusion protein complex of claim 13, wherein the second soluble protein has at least 85% sequence identity to SEQ ID NO:4, and wherein the second soluble protein lacks the signal peptide of amino acids 1-18 of SEQ ID NO:4.

15. An isolated soluble fusion protein complex comprising at least:
a first soluble protein comprising an interleukin-15 (IL-15) polypeptide domain; and
a second soluble protein having at least 85% sequence identity to SEQ ID NO:4,
wherein the first soluble protein is bound to the second soluble protein to form a soluble fusion protein complex.

16. The soluble fusion protein complex of claim 15, wherein the second soluble protein lacks the signal peptide of amino acids 1-18 of SEQ ID NO:4.

* * * * *